(12) United States Patent
Burlew et al.

(10) Patent No.: US 9,371,547 B2
(45) Date of Patent: *Jun. 21, 2016

(54) EXTRACTION SOLVENTS DERIVED FROM OIL FOR ALCOHOL REMOVAL IN EXTRACTIVE FERMENTATION

(71) Applicant: BUTAMAX ADVANCED BIOFUELS LLC, Wilmington, DE (US)

(72) Inventors: Keith H. Burlew, Middletown, DE (US); Robert Dicosimo, Chadds Ford, PA (US); Michael Charles Grady, Oaklyn, NJ (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/481,950

(22) Filed: Sep. 10, 2014

(65) Prior Publication Data

US 2015/0010975 A1    Jan. 8, 2015

Related U.S. Application Data

(63) Continuation of application No. 13/894,894, filed on May 15, 2013, now Pat. No. 8,865,443, which is a continuation of application No. 13/692,254, filed on Dec. 3, 2012, now Pat. No. 8,476,047, which is a continuation of application No. 13/162,643, filed on Jun. 17, 2011, now Pat. No. 8,409,834.

(60) Provisional application No. 61/356,290, filed on Jun. 18, 2010, provisional application No. 61/368,451, filed on Jul. 28, 2010, provisional application No. 61/368,436, filed on Jul. 28, 2010, provisional application No. 61/368,444, filed on Jul. 28, 2010, provisional application No. 61/368,429, filed on Jul. 28, 2010, provisional application No. 61/379,546, filed on Sep. 2, 2010, provisional application No. 61/440,034, filed on Feb. 7, 2011.

(51) Int. Cl.

| | | |
|---|---|---|
| *C12P 7/16* | (2006.01) |
| *C12N 1/14* | (2006.01) |
| *C12N 15/00* | (2006.01) |
| *B01D 3/00* | (2006.01) |
| *B01D 21/26* | (2006.01) |
| *C07C 29/86* | (2006.01) |
| *C11B 1/02* | (2006.01) |
| *C11B 13/00* | (2006.01) |
| *C12M 1/00* | (2006.01) |
| *C12P 7/64* | (2006.01) |
| *C12P 7/18* | (2006.01) |

(52) U.S. Cl.
CPC . *C12P 7/16* (2013.01); *B01D 3/002* (2013.01); *B01D 21/26* (2013.01); *C07C 29/86* (2013.01); *C11B 1/025* (2013.01); *C11B 13/00* (2013.01); *C12M 1/00* (2013.01); *C12M 21/12* (2013.01); *C12M 45/04* (2013.01); *C12M 45/09* (2013.01); *C12N 1/14* (2013.01); *C12N 15/00* (2013.01); *C12P 7/18* (2013.01); *C12P 7/6418* (2013.01); *B01D 21/262* (2013.01); *Y02E 50/10* (2013.01); *Y02E 50/16* (2013.01); *Y02E 50/17* (2013.01); *Y02W 30/74* (2015.05)

(58) Field of Classification Search
None
See application file for complete search history.

(56) References Cited

U.S. PATENT DOCUMENTS

| | | | |
|---|---|---|---|
| 5,221,357 A | 6/1993 | Brink | |
| 6,646,146 B1 | 11/2003 | Sinnema et al. | |
| 7,851,188 B2 | 12/2010 | Donaldson et al. | |
| 7,932,063 B2 | 4/2011 | Dunson et al. | |
| 8,409,834 B2* | 4/2013 | Burlew et al. | 435/155 |
| 8,476,047 B2* | 7/2013 | Burlew et al. | 435/155 |
| 8,865,443 B2* | 10/2014 | Burlew et al. | 435/183 |
| 2007/0014905 A1 | 1/2007 | Chen et al. | |
| 2007/0077635 A1 | 4/2007 | Brunner et al. | |
| 2008/0176298 A1 | 7/2008 | Randhava et al. | |

(Continued)

FOREIGN PATENT DOCUMENTS

| | | |
|---|---|---|
| GB | 2146638 | 4/1985 |
| JP | 1986192291 | 8/1986 |

(Continued)

OTHER PUBLICATIONS

Ban et al., Whole cell biocatalyst for biodiesel fuel production utilizing Rhizopus oryzae cells immobilized within biomass support particles, Biochem. Eng. J. 8:39-43, 2001.

(Continued)

*Primary Examiner* — Nashaat Nashed

(57) ABSTRACT

In an alcohol fermentation process, oil derived from biomass is hydrolyzed into an extractant available for in situ removal of a product alcohol such as butanol from a fermentation broth. The glycerides in the oil can be catalytically (e.g., enzymatically) hydrolyzed into free fatty acids, which form a fermentation product extractant having a partition coefficient for a product alcohol greater than a partition coefficient of the oil of the biomass for the product alcohol. Oil derived from a feedstock of an alcohol fermentation process can be hydrolyzed by contacting the feedstock including the oil with one or more enzymes whereby at least a portion of the oil is hydrolyzed into free fatty acids forming a fermentation product extractant, or the oil can be separated from the feedstock prior to the feedstock being fed to a fermentation vessel, and the separated oil can be contacted with the enzymes to form the fermentation product extractant. The fermentation product extractant can be contacted with a fermentation broth for in situ removal of a product alcohol.

20 Claims, 9 Drawing Sheets

(56) References Cited

U.S. PATENT DOCUMENTS

| | | |
|---|---|---|
| 2008/0182308 A1 | 7/2008 | Donaldson et al. |
| 2009/0017164 A1 | 1/2009 | Schisler et al. |
| 2009/0163376 A1 | 6/2009 | Li et al. |
| 2009/0171129 A1 | 7/2009 | Evanko et al. |
| 2009/0181153 A1 | 7/2009 | Bendorf et al. |
| 2009/0269823 A1 | 10/2009 | Bramucci et al. |
| 2009/0305363 A1 | 12/2009 | Anthony et al. |
| 2009/0305370 A1 | 12/2009 | Grady et al. |
| 2010/0081154 A1 | 4/2010 | Flint et al. |
| 2010/0092603 A1 | 4/2010 | Bruinsma et al. |
| 2010/0124773 A1 | 5/2010 | Yang |
| 2010/0159551 A1 | 6/2010 | Redford |
| 2011/0008863 A1 | 1/2011 | Zhu et al. |
| 2011/0124060 A1 | 5/2011 | Anthony et al. |
| 2011/0244536 A1 | 10/2011 | Nagarajan et al. |
| 2011/0312044 A1 | 12/2011 | Anton et al. |
| 2011/0312053 A1 | 12/2011 | Burlew et al. |
| 2012/0015416 A1 | 1/2012 | Anthony et al. |
| 2012/0156738 A1 | 6/2012 | Anton et al. |
| 2012/0164302 A1 | 6/2012 | Roesch et al. |

FOREIGN PATENT DOCUMENTS

| | | |
|---|---|---|
| WO | WO2009015333 | 1/2009 |
| WO | WO2009026706 | 3/2009 |
| WO | WO2009149270 | 12/2009 |
| WO | WO2010049491 | 5/2010 |
| WO | WO2010059919 | 5/2010 |
| WO | WO2011063402 | 5/2011 |
| WO | WO2012036857 | 3/2012 |

OTHER PUBLICATIONS

Barros et al., Integration of Enzyme Catalysis in an Extraction Fermentation Process, Studies in Organic Chemistry 29, 1986.

Bellion et al., Microb. Growth C1 Compd., [Int. Symp.], 7th (1993), 415 32, Editor(s): Murrell, J. Collin; Kelly, Don P. Publisher: Intercept, Andover, UK.

Bligh et al., A Rapid Method of Total Lipid Extraction and Purification, Can. J. Biochem. Physiol. 37:911-917, 1959.

Gupta et al., Bacterial lipases: an overview of production, purification and biochemical properties, Appl. Microbiol. Biotechnol. 64:763-781, 2004.

Horton et al., Engineering hybrid genes without the use of restriction enzymes: gene splicing by overlap extension, Gene, 77:61-68, 1989.

Kim et al., Extractive Recovery of Products from Fermentation Broths, Biotechnol. Bioprocess. Eng. 4:1-11, 1999.

Kohlhase et al., Catalytic Effects in the Ammonolysis of Vegetable Oils, The Journal of the American Oil Chemists' Society 48:265-270, 1971.

Lynd et al., Microbial Cellulose Utilization: Fundamentals of Biotechnology, Microbiology and Molecular Biology Reviews 66:506-577, 2002.

Ma et al., Plasmid construction by homologous recombination in yeast, Gene, 58:201-216, 1987.

Malinowski, Two-phase partitioning bioreactors in fermentation technology, Biotechnology Advances 19:525-538, 2001.

Amberg, et al. Methods in Yeast Genetics, 2005, Cold Spring Harbor Laboratory Press, Cold Spring Harbor, NY, pp. 201-202.

Oliveira et al., Production and Extractive Biocatalysis of Ethanol Using Microencapsulated Yeast Cells and Lipase System, J Chem Technol Biotechnol 52:219-225, 1991.

Oliveira et al., Immobilization of Saccharomyces cerevisiae Cells and Rhizomucor miehi Lipase for the Production and Extractive Biocatalysis of Ethanol, Bioprocess Eng 16:349-353, 1997.

Oliveira et al., Improvement of Alcoholic Fermentations by Simultaneous Extraction and Enzymatic Esterification of Ethanol, J Mol Catal B: Enzym 5:29-33, 1998.

Oliveira et al., Effect of extraction and Enzymatic Esterification of Ethanol on Glucose Consumption by Two Saccharomyces strains: a Comparative Study, J Chem Technol Biotechnol 76:285-290, 2001.

Oudshoorn et al., Assessment of Options for Selective 1-Butanol Recovery from Aqueous Solution, Industrial and Engineering Chemistry Research 48:7325-7336, 2009.

Roe et al., Fatty Acid Amides. IV. Reaction of Fats With Ammonia and Amines, The Journal of the American Oil Chemists' Society 29:18-22, 1952.

Roffler, Steve Ronald: Extractive fermentation—lactic acid and acetone/butanol production, 1986, pp. 1-289, PhD. Dissertation in Chemical Engineering, UC Berkeley.

Sulter et al., Proliferation and metabolic significance of peroxisomes in candida boidinii during growth on D-alanine or oleic acid . . . , Arch Microbiol 153:485-489, 1990.

Yoo et al., Enzymatic Synthesis of Sugar Fatty Acid Esters, Journal of Industrial Engineering Chemistry 13:1-5, 2007.

International Search Report and Written Opinion dated Oct. 14, 2011, International Application No. PCT/US2011/040806.

U.S. Appl. No. 13/193,147, filed Jul. 28, 2011.

U.S. Appl. No. 61/440,034, filed Feb. 7, 2011.

U.S. Appl. No. 13/163,243, filed Jun. 17, 2011.

\* cited by examiner

SEQUENCE LISTING

<160> NUMBER OF SEQ ID NOS: 145

<210> SEQ ID NO 1
<211> LENGTH: 11844
<212> TYPE: DNA
<213> ORGANISM: Artificial Sequence
<220> FEATURE:
<223> OTHER INFORMATION: Plasmid

<400> SEQUENCE: 1

```
tcccattacc gacatttggg cgctatacgt gcatatgttc atgtatgtat ctgtatttaa      60
aacacttttg tattattttt cctcatatat gtgtataggt ttatacggat gatttaatta     120
ttacttcacc acccttattt tcaggctgat atcttagcct tgttactagt tagaaaaaga     180
cattttgct gtcagtcact gtcaagagat tcttttgctg gcatttcttc tagaagcaaa     240
aagagcgatg cgtctttttcc gctgaaccgt tccagcaaaa aagactacca acgcaatatg     300
gattgtcaga atcatataaa agagaagcaa ataactcctt gtcttgtatc aattgcatta     360
taatatcttc ttgttagtgc aatatcatat agaagtcatc gaaatagata ttaagaaaaa     420
caaactgtac aatcaatcaa tcaatcatcg ctgaggatgt tgacaaaagc aacaaaagaa     480
caaaaatccc ttgtgaaaaa cagaggggcg gagcttgttg ttgattgctt agtggagcaa     540
ggtgtcacac atgtatttgg cattccaggt gcaaaaattg atgcggtatt tgacgcttta     600
caagataaag gacctgaaat tatcgttgcc cggcacgaac aaaacgcagc attcatggcc     660
caagcagtcg gccgtttaac tggaaaaccg ggagtcgtgt tagtcacatc aggaccgggt     720
gcctctaact tggcaacagg cctgctgaca gcgaacactg aaggagaccc tgtcgttgcg     780
cttgctggaa acgtgatccg tgcagatcgt ttaaaacgga cacatcaatc tttggataat     840
gcggcgctat tccagccgat tacaaaatac agtgtagaag ttcaagatgt aaaaaatata     900
ccggaagctg ttacaaatgc atttaggata gcgtcagcag ggcaggctgg ggccgctttt     960
gtgagctttc cgcaagatgt tgtgaatgaa gtcacaaata cgaaaaacgt gcgtgctgtt    1020
gcagcgccaa aactcggtcc tgcagcagat gatgcaatca gtgcggccat agcaaaaatc    1080
caaacagcaa aacttcctgt cgttttggtc ggcatgaaag gcggaagacc ggaagcaatt    1140
aaagcggttc gcaagctttt gaaaaaggtt cagcttccat tgttgaaac atatcaagct    1200
gccggtaccc tttctagaga tttagaggat caatattttg gccgtatcgg tttgttccgc    1260
aaccagcctg gcgatttact gctagagcag gcagatgttg ttctgacgat cggctatgac    1320
ccgattgaat atgatccgaa attctggaat atcaatggag accggacaat tatccattta    1380
gacgagatta tcgctgacat tgatcatgct taccagcctg atcttgaatt gatcggtgac    1440
attccgtcca cgatcaatca tatcgaacac gatgctgtga agtggaatt tgcagagcgt    1500
gagcagaaaa tccttttctga tttaaaacaa tatatgcatg aaggtgagca ggtgcctgca    1560
gattggaaat cagacagagc gcaccctctt gaaatcgtta agagttgcg taatgcagtc    1620
gatgatcatg ttacagtaac ttgcgatatc ggttcgcacg ccatttggat gtcacgttat    1680
ttccgcagct acgagccgtt aacattaatg atcagtaacg gtatgcaaac actcggcgtt    1740
gcgcttcctt gggcaatcgg cgcttcattg gtgaaaccgg gagaaaaagt ggtttctgtc    1800
tctggtgacg gcggtttctt attctcagca atggaattag agacagcagt tcgactaaaa    1860
gcaccaattg tacacattgt atggaacgac agcacatatg acatggttgc attccagcaa    1920
ttgaaaaaat ataaccgtac atctgcggtc gatttcggaa atatcgatat cgtgaaatat    1980
gcggaaagct tcggagcaac tggcttgcgc gtagaatcac cagaccagct ggcagatgtt    2040
ctgcgtcaag gcatgaacgc tgaaggtcct gtcatcatcg atgtcccggt tgactacagt    2100
gataacatta atttagcaag tgacaagctt ccgaaagaat tcggggaact catgaaaacg    2160
aaagctctct agttaattaa tcatgtaatt agttatgtca cgcttacatt cacgccctcc    2220
ccccacatcc gctctaaccg aaaaggaagg agttagacaa cctgaagtct aggtccctat    2280
```

```
ttatttttttt atagttatgt tagtattaag aacgttattt atatttcaaa ttttctttt      2340 ttttctgtac agacgcgtgt acgcatgtaa cattatactg aaaaccttgc ttgagaaggt      2400
tttgggacgc tcgaaggctt taatttgcgg gcggccgcac ctggtaaaac ctctagtgga      2460
gtagtagatg taatcaatga agcggaagcc aaaagaccag agtagaggcc tatagaagaa      2520
actgcgatac cttttgtgat ggctaaacaa acagacatct ttttatatgt ttttacttct      2580
gtatatcgtg aagtagtaag tgataagcga atttggctaa gaacgttgta agtgaacaag      2640
ggacctcttt tgcctttcaa aaaggattaa aatggagtta atcattgaga tttagttttc      2700
gttagattct gtatccctaa ataactccct tacccgacgg gaaggcacaa aagacttgaa      2760
taatagcaaa cggccagtag ccaagaccaa ataatactag agttaactga tggtcttaaa      2820
caggcattac gtggtgaact ccaagaccaa tatacaaaat atcgataagt tattcttgcc      2880
caccaattta aggagcctac atcaggacag tagtaccatt cctcagagaa gaggtataca      2940
taacaagaaa atcgcgtgaa caccttatat aacttagccc gttattgagc taaaaaacct      3000
tgcaaaattt cctatgaata agaatacttc agacgtgata aaaatttact ttctaactct      3060
tctcacgctg cccctatctg ttcttccgct ctaccgtgag aaataaagca tcgagtacgg      3120
cagttcgctg tcactgaact aaaacaataa ggctagttcg aatgatgaac ttgcttgctg      3180
tcaaacttct gagttgccgc tgatgtgaca ctgtgacaat aaattcaaac cggttatagc      3240
ggtctcctcc ggtaccggtt ctgccacctc caatagagct cagtaggagt cagaacctct      3300
gcggtggctg tcagtgactc atccgcgttt cgtaagttgt gcgcgtgcac atttcgcccg      3360
ttcccgctca tcttgcagca ggcggaaatt ttcatcacgc tgtaggacgc aaaaaaaaaa      3420
taattaatcg tacaagaatc ttggaaaaaa aattgaaaaa ttttgtataa aagggatgac      3480
ctaacttgac tcaatggctt ttacacccag tattttccct ttccttgttt gttacaatta      3540
tagaagcaag acaaaaacat atagacaacc tattcctagg agttatattt ttttacccta      3600
ccagcaatat aagtaaaaaa ctgtttaaac agtatggcag ttacaatgta ttatgaagat      3660
gatgtagaag tatcagcact tgctggaaag caaattgcag taatcggtta tggttcacaa      3720
ggacatgctc acgcacagaa tttgcgtgat tctggtcaca acgttatcat tggtgtgcgc      3780
cacggaaaat cttttgataa agcaaaagaa gatggctttg aaacatttga agtaggagaa      3840
gcagtagcta aagctgatgt tattatggtt ttggcaccag atgaacttca acaatccatt      3900
tatgaagagg acatcaaacc aaacttgaaa gcaggttcag cacttggttt tgctcacgga      3960
tttaatatcc attttggcta tattaaagta ccagaagacg ttgacgtctt tatggttgcg      4020
cctaaggctc caggtcacct tgtccgtcgg acttatactg aaggttttgg tacaccagct      4080
ttgtttgttt cacaccaaaa tgcaagtggt catgcgcgtg aaatcgcaat ggattgggcc      4140
aaaggaattg gttgtgctcg agtgggaatt attgaaacaa ctttttaaaga agaaacagaa      4200 gaagatttgt ttggagaaca agctgttcta tgtggaggtt tgacagcact tgttgaagcc      4260
ggttttgaaa cactgacaga agctggatac gctggcgaat tggcttactt tgaagttttg      4320
cacgaaatga aattgattgt tgacctcatg tatgaaggtg ttttactaa aatgcgtcaa      4380 tccatctcaa atactgctga gtttggcgat tatgtgactg tccacggat tattactgac      4440 gaagttaaaa agaatatgaa gcttgttttg gctgatattc aatctggaaa atttgctcaa      4500
gatttcgttg atgacttcaa agcggggcgt ccaaaattaa tagcctatcg cgaagctgca      4560
aaaaatcttg aaattgaaaa aattggggca gagctacgtc aagcaatgcc attcacacaa      4620
tctggtgatg acgatgcctt taaaatctat cagtaaggcc ctgcaggcct atcaagtgct      4680
```

```
ggaaactttt tctcttggaa tttttgcaac atcaagtcat agtcaattga attgacccaa    4740
tttcacattt aagattttt ttttttcatc cgacatacat ctgtacacta ggaagccctg    4800
tttttctgaa gcagcttcaa atatatatat tttttacata tttattatga ttcaatgaac    4860
aatctaatta aatcgaaaac aagaaccgaa acgcgaataa ataatttatt tagatggtga    4920
caagtgtata agtcctcatc gggacagcta cgatttctct ttcggttttg gctgagctac    4980
tggttgctgt gacgcagcgg cattagcgcg gcgttatgag ctaccctcgt ggcctgaaag    5040
atggcgggaa taaagcggaa ctaaaaatta ctgactgagc catattgagg tcaatttgtc    5100
aactcgtcaa gtcacgtttg gtggacggcc cctttccaac gaatcgtata tactaacatg    5160
cgcgcgcttc ctatatacac atatacatat atatatatat atatatgtgt gcgtgtatgt    5220
gtacacctgt atttaatttc cttactcgcg ggttttctt ttttctcaat tcttggcttc    5280
ctctttctcg agcggaccgg atcctccgcg gtgccggcag atctatttaa atggcgcgcc    5340
gacgtcaggt ggcacttttc ggggaaatgt gcgcggaacc cctatttgtt tatttttcta    5400
aatacattca aatatgtatc cgctcatgag acaataaccc tgataaatgc ttcaataata    5460
ttgaaaaagg aagagtatga gtattcaaca tttccgtgtc gcccttattc ccttttttgc    5520
ggcattttgc cttcctgttt ttgctcaccc agaaacgctg gtgaaagtaa aagatgctga    5580
agatcagttg ggtgcacgag tgggttacat cgaactggat ctcaacagcg gtaagatcct    5640
tgagagtttt cgccccgaag aacgttttcc aatgatgagc acttttaaag ttctgctatg    5700
tggcgcggta ttatcccgta ttgacgccgg gcaagagcaa ctcggtcgcc gcatacacta    5760
ttctcagaat gacttggttg agtactcacc agtcacagaa aagcatctta cggatggcat    5820
gacagtaaga gaattatgca gtgctgccat aaccatgagt gataacactg cggccaactt    5880
acttctgaca acgatcggag gaccgaagga gctaaccgct tttttgcaca acatggggga    5940
tcatgtaact cgccttgatc gttgggaacc ggagctgaat gaagccatac caaacgacga    6000
gcgtgacacc acgatgcctg tagcaatggc aacaacgttg cgcaaactat taactggcga    6060
actacttact ctagcttccc ggcaacaatt aatagactgg atggaggcgg ataaagttgc    6120
aggaccactt ctgcgctcgg cccttccggc tggctggttt attgctgata aatctggagc    6180
cggtgagcgt gggtctcgcg gtatcattgc agcactgggg ccagatggta agccctcccg    6240
tatcgtagtt atctacacga cggggagtca ggcaactatg gatgaacgaa atagacagat    6300
cgctgagata ggtgcctcac tgattaagca ttggtaactg tcagaccaag tttactcata    6360
tatactttag attgatttaa aacttcattt ttaatttaaa aggatctagg tgaagatcct    6420
ttttgataat ctcatgacca aaatccctta acgtgagttt tcgttccact gagcgtcaga    6480
ccccgtagaa aagatcaaag gatcttcttg agatcctttt tttctgcgcg taatctgctg    6540
cttgcaaaca aaaaaaccac cgctaccagc ggtggtttgt ttgccggatc aagagctacc    6600
aactcttttt ccgaaggtaa ctggcttcag cagagcgcag ataccaaata ctgttcttct    6660
agtgtagccg tagttaggcc accacttcaa gaactctgta gcaccgccta catacctcgc    6720
tctgctaatc ctgttaccag tggctgctgc cagtggcgat aagtcgtgtc ttaccgggtt    6780
ggactcaaga cgatagttac cggataaggc gcagcggtcg ggctgaacgg ggggttcgtg    6840
cacacagccc agcttggagc gaacgaccta ccgaactg agataccta agcgtgagct    6900 atgagaaagc gccacgcttc ccgaagggag aaaggcggac aggtatccgg taagcggcag    6960
ggtcggaaca ggagagcgca cgagggagct tccagggga aacgcctggt atctttatag    7020
```

```
tcctgtcggg tttcgccacc tctgacttga gcgtcgattt ttgtgatgct cgtcaggggg    7080
gcggagccta tggaaaaacg ccagcaacgc ggccttttta cggttcctgg ccttttgctg    7140
gccttttgct cacatgttct ttcctgcgtt atccctgat  tctgtggata accgtattac    7200
cgcctttgag tgagctgata ccgctcgccg cagccgaacg accgagcgca gcgagtcagt    7260
gagcgaggaa gcggaagagc gcccaatacg caaaccgcct ctccccgcgc gttggccgat    7320
tcattaatgc agctggcacg acaggtttcc cgactggaaa gcgggcagtg agcgcaacgc    7380
aattaatgtg agttagctca ctcattaggc accccaggct ttacacttta tgcttccggc    7440
tcgtatgttg tgtggaattg tgagcggata acaatttcac acaggaaaca gctatgacca    7500
tgattacgcc aagcttttc  tttccaattt ttttttttc  gtcattataa aaatcattac    7560
gaccgagatt cccgggtaat aactgatata attaaattga agctctaatt tgtgagttta    7620
gtatacatgc atttacttat aatacagttt tttagttttg ctggccgcat cttctcaaat    7680
atgcttccca gcctgctttt ctgtaacgtt caccctctac cttagcatcc cttccctttg    7740
caaatagtcc tcttccaaca ataataatgt cagatcctgt agagaccaca tcatccacgg    7800
ttctatactg ttgacccaat gcgtctccct tgtcatctaa acccacaccg ggtgtcataa    7860
tcaaccaatc gtaaccttca tctcttccac ccatgtctct ttgagcaata aagccgataa    7920
caaaatcttt gtcgctcttc gcaatgtcaa cagtacccct agtatattct ccagtagata    7980
gggagccctt gcatgacaat tctgctaaca tcaaaaggcc tctaggttcc tttgttactt    8040
cttctgccgc ctgcttcaaa ccgctaacaa tacctgggcc caccacaccg tgtgcattcg    8100
taatgtctgc ccattctgct attctgtata cacccgcaga gtactgcaat ttgactgtat    8160
taccaatgtc agcaaatttt ctgtcttcga agagtaaaaa attgtacttg gcggataatg    8220
cctttagcgg cttaactgtg ccctccatgg aaaaatcagt caagatatcc acatgtgttt    8280
ttagtaaaca aattttggga cctaatgctt caactaactc cagtaattcc ttggtggtac    8340
gaacatccaa tgaagcacac aagtttgttt gcttttcgtg catgatatta aatagcttgg    8400
cagcaacagg actaggatga gtagcagcac gttccttata tgtagctttc gacatgattt    8460
atcttcgttt cctgcaggtt tttgttctgt gcagttgggt taagaatact gggcaatttc    8520
atgtttcttc aacactacat atgcgtatat ataccaatct aagtctgtgc tccttccttc    8580
gttcttcctt ctgttcggag attaccgaat caaaaaaatt tcaaggaaac cgaaatcaaa    8640
aaaaagaata aaaaaaaaat gatgaattga aaagcttgca tgcctgcagg tcgactctag    8700
tatactccgt ctactgtacg atacacttcc gctcaggtcc ttgtccttta acgaggcctt    8760
accactcttt tgttactcta ttgatccagc tcagcaaagg cagtgtgatc taagattcta    8820
tcttcgcgat gtagtaaaac tagctagacc gagaaagaga ctagaaatgc aaaaggcact    8880
tctacaatgg ctgccatcat tattatccga tgtgacgctg catttttttt tttttttttt    8940
tttttttttt tttttttttt tttttttttt ttttgtacaa atatcataaa aaagagaat     9000
ctttttaagc aaggattttc ttaacttctt cggcgacagc atcaccgact cggtggtac     9060
tgttggaacc acctaaatca ccagttctga tacctgcatc caaaaccttt ttaactgcat    9120
cttcaatggc tttaccttct tcaggcaagt tcaatgacaa tttcaacatc attgcagcag    9180
acaagatagt ggcgataggg ttgaccttat tctttggcaa atctggagcg gaaccatggc    9240
atggttcgta caaaccaaat gcggtgttct tgtctggcaa agaggccaag gacgcagatg    9300
gcaacaaacc caaggagcct gggataacgg aggcttcatc ggagatgata tcaccaaaca    9360
tgttgctggt gattataata ccatttaggt gggttgggtt cttaactagg atcatggcgg    9420
```

```
cagaatcaat caattgatgt tgaactttca atgtagggaa ttcgttcttg atggtttcct   9480
ccacagtttt tctccataat cttgaagagg ccaaaacatt agctttatcc aaggaccaaa   9540
taggcaatgg tggctcatgt tgtagggcca tgaaagcggc cattcttgtg attctttgca   9600
cttctggaac ggtgtattgt tcactatccc aagcgcacac atcaccatcg tcttcctttc   9660
tcttaccaaa gtaaatacct cccactaatt ctctaacaac aacgaagtca gtacctttag   9720
caaattgtgg cttgattgga gataagtcta aagagagtc ggatgcaaag ttacatggtc   9780
ttaagttggc gtacaattga agttctttac ggattttag taaaccttgt tcaggtctaa   9840
cactaccggt accccattta ggaccaccca cagcaccta caaaacggca tcagccttct   9900
tggaggcttc cagcgcctca tctggaagtg aacacctgt agcatcgata gcagcaccac   9960
caattaaatg attttcgaaa tcgaacttga cattggaacg aacatcagaa atagctttaa  10020
gaaccttaat ggcttcggct gtgatttctt gaccaacgtg gtcacctggc aaaacgacga  10080
tcttcttagg ggcagacatt acaatggtat atccttgaaa tatatataaa aaaaaaaaa   10140
aaaaaaaaa aaaaaaatgc agcttctcaa tgatattcga atacgctttg aggagataca  10200
gcctaatatc cgacaaactg ttttacagat ttacgatcgt acttgttacc catcattgaa  10260
ttttgaacat ccgaacctgg gagttttccc tgaaacagat agtatatttg aacctgtata  10320
ataatatata gtctagcgct ttacggaaga caatgtatgt atttcggttc ctggagaaac  10380
tattgcatct attgcatagg taatcttgca cgtcgcatcc ccggttcatt ttctgcgttt  10440
ccatcttgca cttcaatagc atatctttgt taacgaagca tctgtgcttc attttgtaga  10500
acaaaaatgc aacgcgagag cgctaatttt tcaaacaaag aatctgagct gcattttac  10560
agaacagaaa tgcaacgcga aagcgctatt ttaccaacga agaatctgtg cttcattttt  10620
gtaaaacaaa aatgcaacgc gagagcgcta attttcaaa caaagaatct gagctgcatt  10680
tttacagaac agaaatgcaa cgcgagagcg ctattttacc aacaaagaat ctatacttct  10740
tttttgttct acaaaaatgc atcccgagag cgctattttt ctaacaaagc atcttagatt  10800
acttttttc tcctttgtgc gctctataat gcagtctctt gataacttt tgcactgtag   10860
gtccgttaag gttagaagaa ggctactttg gtgtctattt tctcttccat aaaaaaagcc  10920
tgactccact tcccgcgttt actgattact agcgaagctg cgggtgcatt ttttcaagat  10980
aaaggcatcc ccgattatat tctataccga tgtggattgc gcatactttg tgaacagaaa  11040
gtgatagcgt tgatgattct tcattggtca gaaaattatg aacggtttct tctattttgt  11100
ctctatatac tacgtatagg aaatgtttac attttcgtat tgttttcgat tcactctatg  11160
aatagttctt actacaattt ttttgtctaa agagtaatac tagagataaa cataaaaaat  11220
gtagaggtcg agtttagatg caagttcaag gagcgaaagg tggatgggta ggttatatag  11280
ggatatagca cagagatata tagcaaagag atactttga gcaatgtttg tggaagcggt   11340
attcgcaata ttttagtagc tcgttacagt ccggtgcgtt tttggttttt tgaaagtgcg  11400
tcttcagagc gcttttggtt ttcaaaagcg ctctgaagtt cctatacttt ctagagaata  11460
ggaacttcgg aataggaact tcaaagcgtt tccgaaaacg agcgcttccg aaaatgcaac  11520
gcgagctgcg cacatacagc tcactgttca cgtcgcacct atatctgcgt gttgcctgta  11580
tatatatata catgagaaga acggcatagt gcgtgtttat gcttaaatgc gtacttatat  11640
gcgtctattt atgtaggatg aaaggtagtc tagtacctcc tgtgatatta tcccattcca  11700
tgcggggtat cgtatgcttc cttcagcact accctttagc tgttctatat gctgccactc  11760
```

-continued

```
ctcaattgga ttagtctcat ccttcaatgc tatcatttcc tttgatattg gatcatatgc  11820
atagtaccga gaaactagag gatc                                          11844
```

<210> SEQ ID NO 2
<211> LENGTH: 15539
<212> TYPE: DNA
<213> ORGANISM: Artificial Sequence
<220> FEATURE:
<223> OTHER INFORMATION: Plasmid

<400> SEQUENCE: 2

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accataaatt cccgttttaa gagcttggtg agcgctagga gtcactgcca ggtatcgttt   240
gaacacggca ttagtcaggg aagtcataac acagtccttt cccgcaattt tctttttcta   300
ttactcttgg cctcctctag tacactctat attttttat gcctcggtaa tgattttcat   360 ttttttttt ccacctagcg gatgactctt tttttttctt agcgattggc attatcacat   420
aatgaattat acattatata aagtaatgtg atttcttcga agaatatact aaaaaatgag   480
caggcaagat aaacgaaggc aaagatgaca gagcagaaag ccctagtaaa gcgtattaca   540
aatgaaacca agattcagat tgcgatctct ttaaagggtg tcccctagc gatagagcac   600 tcgatcttcc cagaaaaaga ggcagaagca gtagcagaac aggccacaca atcgcaagtg   660
attaacgtcc acacaggtat agggtttctg gaccatatga tacatgctct ggccaagcat   720
tccggctggt cgctaatcgt tgagtgcatt ggtgacttac acatagacga ccatcacacc   780
actgaagact gcgggattgc tctcggtcaa gcttttaaag gggcctagg ggccgtgcgt   840 ggagtaaaaa ggtttggatc aggatttgcg cctttggatg aggcactttc cagagcggtg   900
gtagatcttt cgaacaggcc gtacgcagtt gtcgaacttg gtttgcaaag ggagaaagta   960
ggagatctct cttgcgagat gatcccgcat tttcttgaaa gctttgcaga ggctagcaga  1020
attaccctcc acgttgattg tctgcgaggc aagaatgatc atcaccgtag tgagagtgcg  1080
ttcaaggctc ttgcggttgc cataagagaa gccacctcgc ccaatggtac caacgatgtt  1140
ccctccacca aagtgttct tatgtagtga caccgattat ttaaagctgc agcatacgat  1200
atatatacat gtgtatatat gtataccact gaatgtcagt aagtatgtat acgaacagta  1260
tgatactgaa gatgacaagg taatgcatca ttctatacgt gtcattctga acgaggcgcg  1320 cttcctttt tctttttgc ttttctttt tttctctt gaactcgacg gatctatgcg  1380
gtgtgaaata ccgcacagat gcgtaaggag aaaataccgc atcaggaaat tgtaagcgtt  1440
aatattttgt taaaattcgc gttaaatttt tgttaaatca gctcatttt taaccaatag  1500 gccgaaatcg gcaaaatccc ttataaatca aagaataga ccgagatagg gttgagtgtt  1560
gttccagttt ggaacaagag tccactatta agaacgtgg actccaacgt caagggcga  1620 aaaccgtct atcagggcga tggcccacta cgtgaaccat cacctaatc aagttttttg  1680 gggtcgaggt gccgtaaagc actaaatcgg aaccctaaag ggagccccg atttagagct  1740 tgacggggaa agccggcgaa cgtggcgaga aggaaggga agaaagcgaa aggagcgggc  1800
gctagggcgc tggcaagtgt agcggtcacg ctgcgcgtaa ccaccacacc cgccgcgctt  1860
aatgcgccgc tacagggcgc gtccattcgc cattcaggct gcgcaactgt tgggaagggc  1920
gcggtgcggg cctcttcgct attacgccag ctggcgaaag gggatgtgc tgcaaggcga  1980
```

```
ttaagttggg taacgccagg gttttcccag tcacgacgtt gtaaaacgac ggccagtgag    2040
cgcgcgtaat acgactcact atagggcgaa ttgggtaccg ggcccccct cgaggtcgac     2100
ggcgcgccac tggtagagag cgactttgta tgccccaatt gcgaaacccg cgatatcctt    2160
ctcgattctt tagtacccga ccaggacaag gaaaaggagg tcgaaacgtt tttgaagaaa    2220
caagaggaac tacacggaag ctctaaagat ggcaaccagc cagaaactaa gaaaatgaag    2280
ttgatggatc caactggcac cgctggcttg aacaacaata ccagccttcc aacttctgta    2340
aataacggcg gtacgccagt gccaccagta ccgttacctt tcggtatacc tccttccccc    2400
atgtttccaa tgcccttcat gcctccaacg gctactatca caaatcctca tcaagctgac    2460
gcaagcccta agaaatgaat aacaatactg acagtactaa ataattgcct acttggcttc    2520
acatacgttg catacgtcga tatagataat aatgataatg acagcaggat tatcgtaata    2580
cgtaatagct gaaaatctca aaaatgtgtg ggtcattacg taaataatga taggaatggg    2640
attcttctat ttttccttt tccattctag cagccgtcgg gaaaacgtgg catcctctct     2700
ttcgggctca attggagtca cgctgccgtg agcatcctct ctttccatat ctaacaactg    2760
agcacgtaac caatggaaaa gcatgagctt agcgttgctc caaaaagta ttggatggtt     2820
aataccattt gtctgttctc ttctgacttt gactcctcaa aaaaaaaat ctacaatcaa     2880
cagatcgctt caattacgcc ctcacaaaaa cttttttcct tcttcttcgc ccacgttaaa    2940
ttttatccct catgttgtct aacggatttc tgcacttgat ttattataaa aagacaaaga    3000
cataatactt ctctatcaat ttcagttatt gttcttcctt gcgttattct tctgttcttc    3060
ttttcttttt gtcatatata accataacca agtaatacat attcaaacta gtatgactga    3120
caaaaaaact cttaaagact taagaaatcg tagttctgtt tacgattcaa tggttaaatc    3180
acctaatcgt gctatgttgc gtgcaactgg tatgcaagat gaagactttg aaaaacctat    3240
cgtcggtgtc atttcaactt gggctgaaaa cacaccttgt aatatccact tacatgactt    3300
tggtaaacta gccaaagtcg gtgttaagga agctggtgct tggccagttc agttcggaac    3360
aatcacggtt tctgatggaa tcgccatggg aacccaagga atgcgtttct ccttgacatc    3420
tcgtgatatt attgcagatt ctattgaagc agccatggga ggtcataatg cggatgcttt    3480
tgtagccatt ggcggttgtg ataaaaacat gcccggttct gttatcgcta tggctaacat    3540
ggatatccca gccatttttg cttacggcgg aacaattgca cctggtaatt tagacggcaa    3600
agatatcgat ttagtctctg tctttgaagg tgtcggccat tggaaccacg gcgatatgac    3660
caaagaagaa gttaaagctt tggaatgtaa tgcttgtccc ggtcctggag gctgcggtgg    3720
tatgtatact gctaacacaa tggcgacagc tattgaagtt ttgggactta gccttccggg    3780
ttcatcttct caccggctg aatccgcaga aagaaagca gatattgaag aagctggtcg      3840
cgctgttgtc aaaatgctcg aaatgggctt aaaaccttct gacattttaa cgcgtgaagc    3900
ttttgaagat gctattactg taactatggc tctgggaggg tcaaccaact caaccccttca   3960
cctcttagct attgcccatg ctgctaatgt ggaattgaca cttgatgatt tcaatacttt    4020
ccaagaaaaa gttcctcatt tggctgattt gaaaccttct ggtcaatatg tattccaaga    4080
cctttacaag gtcggagggg taccagcagt tatgaaatat ctccttaaaa atggcttcct    4140
tcatggtgac cgtatcactt gtactggcaa aacagtcgct gaaaatttga aggcttttga    4200
tgatttaaca cctggtcaaa aggttattat gccgcttgaa aatcctaaac gtgaagatgg    4260
tccgctcatt attctccatg gtaacttggc tccagacggt gccgttgcca aagtttctgg    4320
```

```
tgtaaaagtg cgtcgtcatg tcggtcctgc taaggtcttt aattctgaag aagaagccat    4380
tgaagctgtc ttgaatgatg atattgttga tggtgatgtt gttgtcgtac gttttgtagg    4440
accaaagggc ggtcctggta tgcctgaaat gctttccctt tcatcaatga ttgttggtaa    4500
agggcaaggt gaaaaagttg cccttctgac agatggccgc ttctcaggtg gtacttatgg    4560
tcttgtcgtg ggtcatatcg ctcctgaagc acaagatggc ggtccaatcg cctacctgca    4620
aacaggagac atagtcacta ttgaccaaga cactaaggaa ttacactttg atatctccga    4680
tgaagagtta aaacatcgtc aagagaccat tgaattgcca ccgctctatt cacgcggtat    4740
ccttggtaaa tatgctcaca tcgtttcgtc tgcttctagg ggagccgtaa cagacttttg    4800
gaagcctgaa gaaactggca aaaatgttg tcctggttgc tgtggttaag cggccgcgtt     4860
aattcaaatt aattgatata gttttttaat gagtattgaa tctgtttaga ataatggaa     4920
tattattttt atttatttat ttatattatt ggtcggctct tttcttctga aggtcaatga    4980
caaaatgata tgaaggaaat aatgattct aaaattttac aacgtaagat attttacaa     5040
aagcctagct catcttttgt catgcactat tttactcacg cttgaaatta acggccagtc    5100
cactgcggag tcatttcaaa gtcatcctaa tcgatctatc gttttgata gctcattttg     5160
gagttcgcga ttgtcttctg ttattcacaa ctgttttaat ttttatttca ttctggaact    5220
cttcgagttc tttgtaaagt ctttcatagt agcttacttt atcctccaac atatttaact    5280
tcatgtcaat ttcggctctt aaattttcca catcatcaag ttcaacatca tcttttaact    5340
tgaatttatt ctctagctct tccaaccaag cctcattgct ccttgattta ctggtgaaaa    5400
gtgatacact ttgcgcgcaa tccaggtcaa aacttcctg caagaattc accaatttct       5460
cgacatcata gtacaatttg ttttgttctc ccatcacaat ttaatatacc tgatggattc    5520
ttatgaagcg ctgggtaatg gacgtgtcac tctacttcgc cttttccct actccttta      5580
gtacggaaga caatgctaat aaataagagg gtaataataa tattattaat cggcaaaaaa    5640
gattaaacgc caagcgttta attatcagaa agcaaacgtc gtaccaatcc ttgaatgctt    5700
cccaattgta tattaagagt catcacagca acatattctt gttattaaat taattattat    5760
tgattttga tattgtataa aaaaaccaaa tatgtataaa aaaagtgaat aaaaaatacc      5820
aagtatggag aaatatatta gaagtctata cgttaaacca cccgggcccc cctcgaggt     5880
cgacggtatc gataagcttg atatcgaatt cctgcagccc ggggatcca ctagttctag     5940
agcggccgct ctagaactag taccacaggt gttgtcctct gaggacataa aatacacacc    6000
gagattcatc aactcattgc tggagttagc atatctacaa ttgggtgaaa tggggagcga    6060
tttgcaggca tttgctcggc atgccggtag aggtgtggtc aataagagcg acctcatgct    6120
atacctgaga aagcaacctg acctacagga aagagttact caagaataag aattttcgtt    6180
ttaaaaccta agagtcactt taaaatttgt atacacttat ttttttata acttatttaa     6240
taataaaaat cataaatcat aagaaattcg cttactctta attaatcaaa aagttaaaat    6300
tgtacgaata gattcaccac ttcttaacaa atcaaaccct tcattgattt tctcgaatgg    6360
caatacatgt gtaattaaag gatcaagagc aaacttcttc gccataaagt cggcaacaag    6420
ttttggaaca ctatccttgc tcttaaaacc gccaaatata gctcccttcc atgtacgacc    6480
gcttagcaac agcataggat tcatcgacaa attttgtgaa tcaggaggaa cacctacgat    6540
cacactgact ccatatgcct cttgacagca ggacaacgca gttaccatag tatcaagacg    6600
gcctataact tcaaaagaga aatcaactcc accgtttgac atttcagtaa ggacttcttg    6660
tattggtttc ttataatctt gagggttaac acattcagta gccccgacct ccttagcttt    6720
```

```
tgcaaatttg tccttattga tgtctacacc tataatcctc gctgcgcctg cagctttaca    6780
ccccataata acgcttagtc ctactcctcc taaaccgaat actgcacaag tcgaaccctg    6840
tgtaaccttt gcaactttaa ctgcggaacc gtaaccggtg gaaaatccgc accctatcaa    6900
gcaaactttt tccagtggtg aagctgcatc gattttagcg acagatatct cgtccaccac    6960
tgtgtattgg gaaaatgtag aagtaccaag gaaatggtgt ataggtttcc ctctgcatgt    7020
aaatctgctt gtaccatcct gcatagtacc tctaggcata gacaaatcat ttttaaggca    7080
gaaattaccc tcaggatgtt tgcagactct acacttacca cattgaggag tgaacagtgg    7140
gatcacttta tcaccaggac gaacagtggt aacaccttca cctatggatt caacgattcc    7200
ggcagcctcg tgtcccgcga ttactggcaa aggagtaact agagtgccac tcaccacatg    7260
gtcgtcggat ctacagattc cggtggcaac catcttgatt ctaacctcgt gtgcttttgg    7320
tggcgctact tctacttctt ctatgctaaa cggcttttc tcttcccaca aaactgccgc     7380
tttacactta ataactttac cggctgttga catcctcagc tagctattgt aatatgtgtg    7440
tttgtttgga ttattaagaa gaataattac aaaaaaaatt acaaaggaag gtaattacaa    7500
cagaattaag aaaggacaag aaggaggaag agaatcagtt cattatttct tctttgttat    7560
ataacaaacc caagtagcga tttggccata cattaaaagt tgagaaccac cctccctggc    7620
aacagccaca actcgttacc attgttcatc acgatcatga aactcgctgt cagctgaaat    7680
ttcacctcag tggatctctc ttttattct tcatcgttcc actaaccttt ttccatcagc     7740
tggcagggaa cggaaagtgg aatcccattt agcgagcttc ctcttttctt caagaaaaga    7800
cgaagcttgt gtgtgggtgc gcgcgctagt atctttccac attaagaaat ataccataaa    7860
ggttacttag acatcactat ggctatatat atatatatat atatatgtaa cttagccacca    7920
tcgcgcgtgc atcactgcat gtgttaaccg aaaagtttgg cgaacacttc accgacacgg    7980
tcatttagat ctgtcgtctg cattgcacgt cccttagcct taaatcctag gcgggagcat    8040
tctcgtgtaa ttgtgcagcc tgcgtagcaa ctcaacatag cgtagtctac ccagttttc     8100
aagggtttat cgttagaaga ttctcccttt tcttcctgct cacaaatctt aaagtcatac    8160
attgcacgac taaatgcaag catgcggatc ccccgggctg caggaattcg atatcaagct    8220
tatcgatacc gtcgactggc cattaatctt tcccatatta gatttcgcca agccatgaaa    8280
gttcaagaaa ggtcttttaga cgaattaccc ttcatttctc aaactggcgt caagggatcc    8340
tggtatggtt ttatcgtttt atttctggtt cttatagcat cgttttggac ttctctgttc    8400
ccattaggcg gttcaggagc cagcgcagaa tcattctttg aaggatactt atcctttcca    8460
attttgattg tctgttacgt tggacataaa ctgtatacta gaaattggac tttgatggtg    8520
aaactagaag atatggatct tgataccggc agaaaacaag tagatttgac tcttcgtagg    8580
gaagaaatga ggattgagcg agaaacatta gcaaaaagat ccttcgtaac aagattttta    8640
catttctggt gttgaaggga agatatgag ctatacagcg gaatttccat atcactcaga    8700
ttttgttatc taattttttc cttcccacgt ccgcgggaat ctgtgtatat tactgcatct    8760
agatatatgt tatcttatct tggcgcgtac atttaatttt caacgtattc tataagaaat    8820
tgcgggagtt ttttcatgt agatgatact gactgcacgc aaatataggc atgatttata    8880
ggcatgattt gatggctgta ccgataggaa cgctaagagt aacttcagaa tcgttatcct    8940
ggcggaaaaa attcatttgt aaactttaaa aaaaaagcc aatatcccca aaattattaa     9000
gagcgcctcc attattaact aaaatttcac tcagcatcca caatgtatca ggtatctact    9060
```

```
acagatatta catgtggcga aaaagacaag aacaatgcaa tagcgcatca agaaaaaaca    9120
caaagctttc aatcaatgaa tcgaaaatgt cattaaaata gtatataaat tgaaactaag    9180
tcataaagct ataaaaagaa aatttattta aatgcaagat ttaaagtaaa ttcacggccc    9240
tgcaggcctc agctcttgtt ttgttctgca aataacttac ccatctttt caaaacttta    9300 ggtgcaccct cctttgctag aataagttct atccaataca tcctatttgg atctgcttga    9360
gcttctttca tcacggatac gaattcattt tctgttctca caattttgga cacaactctg    9420
tcttccgttg ccccgaaact ttctggcagt tttgagtaat tccacatagg aatgtcatta    9480
taactctggt tcggaccatg aatttccctc tcaaccgtgt aaccatcgtt attaatgata    9540
aagcagattg ggtttatctt ctctctaatg gctagtccta attcttggac agtcagttgc    9600
aatgatccat ctccgataaa caataaatgt ctagattctt tatctgcaat ttggctgcct    9660
agagctgcgg ggaaagtgta tcctatagat ccccacaagg gttgaccaat aaaatgtgat    9720
ttcgatttca gaaatataga tgaggcaccg aagaaagaag tgccttgttc agccacgatc    9780
gtctcattac tttgggtcaa attttcgaca gcttgccaca gtctatcttg tgacaacagc    9840
gcgttagaag gtacaaaatc ttcttgcttt ttatctatgt acttgccttt atattcaatt    9900
tcggacaagt caagaagaga tgatatcagg gattcgaagt cgaaattttg gattctttcg    9960
ttgaaaattt taccttcatc gatattcaag gaaatcattt tattttcatt aagatggtga   10020
gtaaatgcac ccgtactaga atcggtaagc tttacaccca acataagaat aaaatcagca   10080
gattccacaa attccttcaa gtttggctct gacagagtac cgttgtaaat ccccaaaaat   10140
gagggcaatg cttcatcaac agatgattta ccaaagttca aagtagtaat aggtaactta   10200
gtctttgaaa taaactgagt aacagtcttc tctaggccga acgatataat ttcatggcct   10260
gtgattacaa ttggtttctt ggcattcttc agactttcct gtattttgtt cagaatctct   10320
tgatcagatg tattcgacgt ggaattttcc ttcttaagag gcaaggatgg tttttcagcc   10380
ttagcggcag ctacatctac aggtaaattg atgtaaaccg gctttctttc ctttagtaag   10440
gcagacaaca ctctatcaat ttcaacagtt gcattctcgg ctgtcaataa agtcctggca   10500
gcagtaaccg gttcgtgcat cttcataaag tgcttgaaat caccatcagc caacgtatgg   10560
tgaacaaact taccttcgtt ctgcactttc gaggtaggag atcccacgat ctcaacaaca   10620
ggcaggttct cagcataggg gcccgctaag ccattaactg cggataattc gccaacacca   10680
aatgtagtca agaatgccgc agcctttttc gttcttgcgt acccgtcggc catataggag   10740
gcatttaact cattagcatt tcccacccat ttcatatctt tgtgtgaaat aatttgatct   10800
agaaattgca aattgtagtc acctggtact ccgaatattt cttctatacc taattcgtgt   10860
aatctgtcca acagatagtc acctactgta tacattttgt ttactagttt atgtgtgttt   10920
attcgaaact aagttcttgg tgttttaaaa ctaaaaaaaa gactaactat aaaagtagaa   10980
tttaagaagt ttaagaaata gatttacaga attacaatca ataccaccg tctttatata   11040 cttattagtc aagtagggga ataatttcag ggaactggtt tcaacctttt ttttcagctt   11100
tttccaaatc agagagagca gaaggtaata gaaggtgtaa gaaaatgaga tagatacatg   11160
cgtgggtcaa ttgccttgtg tcatcattta ctccaggcag gttgcatcac tccattgagg   11220
ttgtgcccgt ttttgcctg tttgtgcccc tgttctctgt agttgcgcta agagaatgga   11280
cctatgaact gatggttggt gaagaaaaca atatttggt gctgggattc tttttttttc   11340
tggatgccag cttaaaaagc gggctccatt atatttagtg gatgccagga ataaactgtt   11400
cacccagaca cctacgatgt tatatattct gtgtaacccg cccctatttt tgggcatgta   11460
```

```
cgggttacag cagaattaaa aggctaattt tttgactaaa taaagttagg aaaatcacta   11520
ctattaatta tttacgtatt ctttgaaatg gcagtattga taatgataaa ctcgaactga   11580
aaaagcgtgt tttttattca aaatgattct aactccctta cgtaatcaag gaatctttt    11640 gccttggcct ccgcgtcatt aaacttcttg ttgttgacgc taacattcaa cgctagtata   11700
tattcgtttt tttcaggtaa gttcttttca acgggtctta ctgatgaggc agtcgcgtct   11760
gaacctgtta agaggtcaaa tatgtcttct tgaccgtacg tgtcttgcat gttattagct   11820
ttgggaattt gcatcaagtc ataggaaaat ttaaatcttg gctctcttgg gctcaaggtg   11880
acaaggtcct cgaaaatagg gcgcgcccca ccgcggtgga gctccagctt ttgttccctt   11940
tagtgagggt taattgcgcg cttggcgtaa tcatggtcat agctgtttcc tgtgtgaaat   12000
tgttatccgc tcacaattcc acacaacata cgagccggaa gcataaagtg taaagcctgg   12060
ggtgcctaat gagtgagcta actcacatta attgcgttgc gctcactgcc cgctttccag   12120
tcgggaaacc tgtcgtgcca gctgcattaa tgaatcggcc aacgcgcggg gagaggcggt   12180
ttgcgtattg ggcgctcttc cgcttcctcg ctcactgact cgctgcgctc ggtcgttcgg   12240
ctgcggcgag cggtatcagc tcactcaaag gcggtaatac ggttatccac agaatcaggg   12300
gataacgcag gaaagaacat gtgagcaaaa ggccagcaaa aggccaggaa ccgtaaaaag   12360
gccgcgttgc tggcgttttt ccataggctc cgcccccctg acgagcatca caaaaatcga   12420
cgctcaagtc agaggtggcg aaacccgaca ggactataaa gataccaggc gtttccccct   12480
ggaagctccc tcgtgcgctc tcctgttccg accctgccgc ttaccggata cctgtccgcc   12540
tttctccctt cgggaagcgt ggcgctttct catagctcac gctgtaggta tctcagttcg   12600
gtgtaggtcg ttcgctccaa gctgggctgt gtgcacgaac ccccgttca gcccgaccgc   12660 tgcgccttat ccggtaacta tcgtcttgag tccaacccgg taagacacga cttatcgcca   12720
ctggcagcag ccactggtaa caggattagc agagcgaggt atgtaggcgg tgctacagag   12780
ttcttgaagt ggtggcctaa ctacggctac actagaagaa cagtatttgg tatctgcgct   12840
ctgctgaagc cagttacctt cggaaaaaga gttggtagct cttgatccgg caaacaaacc   12900
accgctggta gcggtggttt ttttgtttgc aagcagcaga ttacgcgcag aaaaaaagga   12960
tctcaagaag atccttttgat ctttctacg gggtctgacg ctcagtggaa cgaaaactca   13020
cgttaaggga ttttggtcat gagattatca aaaaggatct tcacctagat ccttttaaat   13080
taaaaatgaa gttttaaatc aatctaaagt atatatgagt aaacttggtc tgacagttac   13140
caatgcttaa tcagtgaggc acctatctca gcgatctgtc tatttcgttc atccatagtt   13200
gcctgactcc ccgtcgtgta gataactacg atacgggagg gcttaccatc tggccccagt   13260
gctgcaatga taccgcgaga cccacgctca ccggctccag atttatcagc aataaaccag   13320
ccagccggaa gggccgagcg cagaagtggt cctgcaactt tatccgcctc catccagtct   13380
attaattgtt gccgggaagc tagagtaagt agttcgccag ttaatagttt gcgcaacgtt   13440
gttgccattg ctacaggcat cgtggtgtca cgctcgtcgt ttggtatggc ttcattcagc   13500
tccggttccc aacgatcaag gcgagttaca tgatccccca tgttgtgcaa aaaagcggtt   13560
agctccttcg gtcctccgat cgttgtcaga agtaagttgg ccgcagtgtt atcactcatg   13620
gttatggcag cactgcataa ttctcttact gtcatgccat ccgtaagatg cttttctgtg   13680
actggtgagt actcaaccaa gtcattctga gaatagtgta gcggcgacc gagttgctct   13740 tgcccggcgt caatacggga taataccgcg ccacatagca gaactttaaa agtgctcatc   13800
```

```
attggaaaac gttcttcggg gcgaaaactc tcaaggatct taccgctgtt gagatccagt    13860
tcgatgtaac ccactcgtgc acccaactga tcttcagcat cttttacttt caccagcgtt    13920
tctgggtgag caaaaacagg aaggcaaaat gccgcaaaaa agggaataag ggcgacacgg    13980
aaatgttgaa tactcatact cttccttttt caatattatt gaagcattta tcagggttat    14040
tgtctcatga gcggatacat atttgaatgt atttagaaaa ataaacaaat aggggttccg    14100
cgcacatttc cccgaaaagt gccacctgaa cgaagcatct gtgcttcatt ttgtagaaca    14160
aaaatgcaac gcgagagcgc taatttttca aacaagaat ctgagctgca tttttacaga    14220
acagaaatgc aacgcgaaag cgctatttta ccaacgaaga atctgtgctt cattttgtga    14280
aaacaaaaat gcaacgcgag agcgctaatt tttcaaacaa agaatctgag ctgcattttt    14340
acagaacaga aatgcaacgc gagagcgcta ttttaccaac aaagaatcta tacttctttt    14400
ttgttctaca aaaatgcatc ccgagagcgc tatttttcta caaagcatc ttagattact    14460
tttttttctcc tttgtgcgct ctataatgca gtctcttgat aacttttgc actgtaggtc    14520
cgttaaggtt agaagaaggc tactttggtg tctattttct cttccataaa aaagcctga    14580
ctccacttcc cgcgtttact gattactagc gaagctgcgg gtgcattttt tcaagataaa    14640
ggcatcccg attatattct ataccgatgt ggattgcgca tactttgtga acagaaagtg    14700
atagcgttga tgattcttca ttggtcagaa aattatgaac ggtttcttct attttgtctc    14760
tatatactac gtataggaaa tgtttacatt ttcgtattgt tttcgattca ctctatgaat    14820
agttcttact acaatttttt tgtctaaaga gtaatactag agataaacat aaaaaatgta    14880
gaggtcgagt ttagatgcaa gttcaaggag cgaaaggtgg atgggtaggt tatataggga    14940
tatagcacag agatatatag caaagagata cttttgagca atgtttgtgg aagcggtatt    15000
cgcaatattt tagtagctcg ttacagtccg gtgcgttttt ggttttttga aagtgcgtct    15060
tcagagcgct tttggttttc aaaagcgctc tgaagttcct atactttcta gagaatagga    15120
acttcggaat aggaacttca aagcgtttcc gaaaacgagc gcttccgaaa atgcaacgcg    15180
agctgcgcac atacagctca ctgttcacgt cgcacctata tctgcgtgtt gcctgtatat    15240
atatatacat gagaagaacg gcatagtgcg tgtttatgct taaatgcgta cttatatgcg    15300
tctatttatg taggatgaaa ggtagtctag tacctcctgt gatattatcc cattccatgc    15360
ggggtatcgt atgcttcctt cagcactacc ctttagctgt tctatatgct gccactcctc    15420
aattggatta gtctcatcct tcaatgctat catttccttt gatattggat catactaaga    15480
aaccattatt atcatgacat taacctataa aaataggcgt atcacgaggc cctttcgtc    15539
```

<210> SEQ ID NO 3
<211> LENGTH: 4586
<212> TYPE: DNA
<213> ORGANISM: Artificial Sequence
<220> FEATURE:
<223> OTHER INFORMATION: pLA54 plasmid

<400> SEQUENCE: 3

```
gggtaccgag ctcgaattca ctggccgtcg ttttacaacg tcgtgactgg gaaaaccctg      60
gcgttaccca acttaatcgc cttgcagcac atccccctttt cgccagctgg cgtaatagcg     120
aagaggcccg caccgatcgc ccttcccaac agttgcgcag cctgaatggc gaatggcgcc     180
tgatgcggta ttttctcctt acgcatctgt gcggtatttc acaccgcata tggtgcactc     240
tcagtacaat ctgctctgat gccgcatagt taagccagcc ccgacacccg ccaacacccg     300
ctgacgcgcc ctgacgggct tgtctgctcc cggcatccgc ttacagacaa gctgtgaccg     360
```

```
tctccgggag ctgcatgtgt cagaggtttt caccgtcatc accgaaacgc gcgagacgaa     420
agggcctcgt gatacgccta tttttatagg ttaatgtcat gataataatg gtttcttaga     480
cgtcaggtgg cacttttcgg ggaaatgtgc gcggaacccc tatttgttta tttttctaaa     540
tacattcaaa tatgtatccg ctcatgagac aataaccctg ataaatgctt caataatatt     600
gaaaaaggaa gagtatgagt attcaacatt tccgtgtcgc ccttattccc ttttttgcgg     660 catttttgcct tcctgttttt gctcacccag aaacgctggt gaaagtaaaa gatgctgaag     720
atcagttggg tgcacgagtg ggttacatcg aactggatct caacagcggt aagatccttg     780
agagttttcg ccccgaagaa cgttttccaa tgatgagcac ttttaaagtt ctgctatgtg     840
gcgcggtatt atcccgtatt gacgccgggc aagagcaact cggtcgccgc atacactatt     900
ctcagaatga cttggttgag tactcaccag tcacagaaaa gcatcttacg gatggcatga     960
cagtaagaga attatgcagt gctgccataa ccatgagtga taacactgcg gccaacttac    1020
ttctgacaac gatcggagga ccgaaggagc taaccgcttt tttgcacaac atgggggatc    1080
atgtaactcg ccttgatcgt tgggaaccgg agctgaatga agccatacca aacgacgagc    1140
gtgacaccac gatgcctgta gcaatggcaa caacgttgcg caaactatta actggcgaac    1200
tacttactct agcttcccgg caacaattaa tagactggat ggaggcggat aaagttgcag    1260
gaccacttct gcgctcggcc cttccggctg gctggtttat tgctgataaa tctggagccg    1320
gtgagcgtgg gtctcgcggt atcattgcag cactggggcc agatggtaag ccctcccgta    1380
tcgtagttat ctacacgacg gggagtcagg caactatgga tgaacgaaat agacagatcg    1440
ctgagatagg tgcctcactg attaagcatt ggtaactgtc agaccaagtt tactcatata    1500
tactttagat tgatttaaaa cttcattttt aatttaaaag gatctaggtg aagatccttt    1560
ttgataatct catgaccaaa atcccttaac gtgagttttc gttccactga gcgtcagacc    1620
ccgtagaaaa gatcaaagga tcttcttgag atccttttttt tctgcgcgta atctgctgct    1680
tgcaaacaaa aaaaccaccg ctaccagcgg tggtttgttt gccggatcaa gagctaccaa    1740 ctcttttttcc gaaggtaact ggcttcagca gagcgcagat accaaatact gtccttctag    1800
tgtagccgta gttaggccac cacttcaaga actctgtagc accgcctaca tacctcgctc    1860
tgctaatcct gttaccagtg gctgctgcca gtggcgataa gtcgtgtctt accgggttgg    1920
actcaagacg atagttaccg gataaggcgc agcggtcggg ctgaacgggg gttcgtgca    1980 cacagcccag cttggagcga acgacctaca ccgaactgag atacctacag cgtgagctat    2040
gagaaagcgc cacgcttccc gaagggagaa aggcggacag gtatccggta agcggcaggg    2100
tcggaacagg agagcgcacg agggagcttc caggggggaaa cgcctggtat ctttatagtc    2160
ctgtcgggtt tcgccacctc tgacttgagc gtcgattttt gtgatgctcg tcagggggc     2220 ggagcctatg gaaaaacgcc agcaacgcgg cctttttacg gttcctggcc ttttgctggc    2280
cttttgctca catgttcttt cctgcgttat cccctgattc tgtggataac cgtattaccg    2340
cctttgagtg agctgatacc gctcgccgca gccgaacgac cgagcgcagc gagtcagtga    2400
gcgaggaagc ggaagagcgc ccaatacgca aaccgcctct ccccgcgcgt tggccgattc    2460
attaatgcag ctggcacgac aggtttcccg actggaaagc gggcagtgag cgcaacgcaa    2520
ttaatgtgag ttagctcact cattaggcac cccaggcttt acactttatg cttccggctc    2580
gtatgttgtg tggaattgtg agcggataac aatttcacac aggaaacagc tatgaccatg    2640
attacgccaa gcttgcatgc ctgcaggtcg actctagagg atccccgcat tgcggattac    2700
```

```
gtattctaat gttcagataa cttcgtatag catacattat acgaagttat ctagggattc    2760
ataaccattt tctcaatcga attacacaga acacaccgta caaacctctc tatcataact    2820
acttaatagt cacacacgta ctcgtctaaa tacacatcat cgtcctacaa gttcatcaaa    2880
gtgttggaca dacaactata ccagcatgga tctcttgtat cggttctttt ctcccgctct    2940
ctcgcaataa caatgaacac tgggtcaatc atagcctaca caggtgaaca gagtagcgtt    3000
tatacagggt ttatacggtg attcctacgg caaaaatttt tcatttctaa aaaaaaaag     3060 aaaaatttt ctttccaacg ctagaaggaa aagaaaaatc taattaaatt gatttggtga     3120
ttttctgaga gttcccttt tcatatatcg aattttgaat ataaaaggag atcgaaaaaa     3180
tttttctatt caatctgttt tctggttta tttgatagtt ttttttgtgta ttattattat    3240 ggattagtac tggtttatat gggtttttct gtataacttc ttttattt agtttgttta     3300 atcttatttt gagttacatt atagttccct aactgcaaga gaagtaacat taaaactcga    3360
gatgggtaag gaaaagactc acgtttcgag gccgcgatta aattccaaca tggatgctga    3420
tttatatggg tataaatggg ctcgcgataa tgtcgggcaa tcaggtgcga caatctatcg    3480
attgtatggg aagcccgatg cgccagagtt gtttctgaaa catggcaaag gtagcgttgc    3540
caatgatgtt acagatgaga tggtcagact aaactggctg acggaattta tgcctcttcc    3600
gaccatcaag cattttatcc gtactcctga tgatgcatgg ttactcacca ctgcgatccc    3660
cggcaaaaca gcattccagg tattagaaga atatcctgat tcaggtgaaa atattgttga    3720
tgcgctggca gtgttcctgc gccggttgca ttcgattcct gtttgtaatt gtccttttaa    3780
cagcgatcgc gtatttcgtc tcgctcaggc gcaatcacga atgaataacg gtttggttga    3840
tgcgagtgat tttgatgacg agcgtaatgg ctggcctgtt gaacaagtct ggaaagaaat    3900
gcataagctt ttgccattct caccggattc agtcgtcact catggtgatt tctcacttga    3960
taaccttatt tttgacgagg ggaaattaat aggttgtatt gatgttggac gagtcggaat    4020
cgcagaccga taccaggatc ttgccatcct atggaactgc ctcggtgagt tttctccttc    4080
attacagaaa cggctttttc aaaaatatgg tattgataat cctgatatga ataaattgca    4140
gtttcatttg atgctcgatg agtttttcta agtttaactt gatactacta gattttttct    4200
cttcatttat aaaattttg gttataattg aagctttaga agtatgaaaa atccttttt     4260 tttcattctt tgcaaccaaa ataagaagct tctttattc attgaaatga tgaatataaa    4320
cctaacaaaa gaaaagact cgaatatcaa acattaaaaa aaaataaaag aggttatctg    4380
ttttcccatt tagttggagt ttgcattttc taatagatag aactctcaat taatgtggat    4440
ttagtttctc tgttcgtttt tttttgtttt gttctcactg tatttacatt tctatttagt    4500
atttagttat tcatataatc tataacttcg tatagcatac attatacgaa gttatccagt    4560
gatgatacaa cgagttagcc aaggtg                                         4586

<210> SEQ ID NO 4
<211> LENGTH: 80
<212> TYPE: DNA
<213> ORGANISM: Artificial Sequence
<220> FEATURE:
<223> OTHER INFORMATION: Primer

<400> SEQUENCE: 4
ttccggtttc tttgaaattt ttttgattcg gtaatctccg agcagaagga gcattgcgga      60
ttacgtattc taatgttcag                                                 80
```

<210> SEQ ID NO 5
<211> LENGTH: 81
<212> TYPE: DNA
<213> ORGANISM: Artificial Sequence
<220> FEATURE:
<223> OTHER INFORMATION: Primer

<400> SEQUENCE: 5
gggtaataac tgatataatt aaattgaagc tctaatttgt gagtttagta caccttggct    60
aactcgttgt atcatcactg g                                              81

<210> SEQ ID NO 6
<211> LENGTH: 38
<212> TYPE: DNA
<213> ORGANISM: Artificial Sequence
<220> FEATURE:
<223> OTHER INFORMATION: Primer

<400> SEQUENCE: 6
gcctcgagtt ttaatgttac ttctcttgca gttaggga                            38

<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
gctaaattcg agtgaaacac aggaagacca g                                   31

<210> SEQ ID NO 8
<211> LENGTH: 90
<212> TYPE: DNA
<213> ORGANISM: Artificial Sequence
<220> FEATURE:
<223> OTHER INFORMATION: Primer

<400> SEQUENCE: 8
gtattttggt agattcaatt ctctttccct ttccttttcc ttcgctcccc ttccttatca    60
gcattgcgga ttacgtattc taatgttcag                                     90

<210> SEQ ID NO 9
<211> LENGTH: 90
<212> TYPE: DNA
<213> ORGANISM: Artificial Sequence
<220> FEATURE:
<223> OTHER INFORMATION: Primer

<400> SEQUENCE: 9
ttggttgggg gaaaaagagg caacaggaaa gatcagaggg ggaggggggg ggagagtgtc    60
accttggcta actcgttgta tcatcactgg                                     90

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
tcggtgcggg cctcttcgct a                                              21

<210> SEQ ID NO 11

```
<211> LENGTH: 21
<212> TYPE: DNA
<213> ORGANISM: Artificial Sequence
<220> FEATURE:
<223> OTHER INFORMATION: Primer

<400> SEQUENCE: 11
aatgtgagtt agctcactca t                                              21

<210> SEQ ID NO 12
<211> LENGTH: 57
<212> TYPE: DNA
<213> ORGANISM: Artificial Sequence
<220> FEATURE:
<223> OTHER INFORMATION: Primer

<400> SEQUENCE: 12
aattggatcc ggcgcgccgt ttaaacggcc ggccaatgtg ctgtggttt cagggtc       57

<210> SEQ ID NO 13
<211> LENGTH: 49
<212> TYPE: DNA
<213> ORGANISM: Artificial Sequence
<220> FEATURE:
<223> OTHER INFORMATION: Primer

<400> SEQUENCE: 13
aatttctaga ttaattaagc ggccgcaagg ccatgaagct ttttctttc                49

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
ttctcgacgt gggccttttt cttg                                           24

<210> SEQ ID NO 15
<211> LENGTH: 49
<212> TYPE: DNA
<213> ORGANISM: Artificial Sequence
<220> FEATURE:
<223> OTHER INFORMATION: Primer

<400> SEQUENCE: 15
tgcagcttta ataatcggt gtcactactt tgccttcgtt tatcttgcc                 49

<210> SEQ ID NO 16
<211> LENGTH: 49
<212> TYPE: DNA
<213> ORGANISM: Artificial Sequence
<220> FEATURE:
<223> OTHER INFORMATION: Primer

<400> SEQUENCE: 16
gagcaggcaa gataaacgaa ggcaaagtag tgacaccgat tatttaaag                49

<210> SEQ ID NO 17
<211> LENGTH: 49
<212> TYPE: DNA
<213> ORGANISM: Artificial Sequence
<220> FEATURE:
<223> OTHER INFORMATION: Primer

<400> SEQUENCE: 17
```

```
tatggaccct gaaaccacag ccacattgta accaccacga cggttgttg          49

<210> SEQ ID NO 18
<211> LENGTH: 49
<212> TYPE: DNA
<213> ORGANISM: Artificial Sequence
<220> FEATURE:
<223> OTHER INFORMATION: Primer

<400> SEQUENCE: 18
tttagcaaca accgtcgtgg tggttacaat gtggctgtgg tttcagggt           49

<210> SEQ ID NO 19
<211> LENGTH: 49
<212> TYPE: DNA
<213> ORGANISM: Artificial Sequence
<220> FEATURE:
<223> OTHER INFORMATION: Primer

<400> SEQUENCE: 19
ccagaaaccc tatacctgtg tggacgtaag gccatgaagc ttttctttt          49

<210> SEQ ID NO 20
<211> LENGTH: 49
<212> TYPE: DNA
<213> ORGANISM: Artificial Sequence
<220> FEATURE:
<223> OTHER INFORMATION: Primer

<400> SEQUENCE: 20
attggaaaga aaagcttca tggccttacg tccacacagg tatagggtt           49

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
cataagaaca cctttggtgg ag                                       22

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
aggattatca ttcataagtt tc                                       22

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
ttcttggagc tgggacatgt ttg                                      23

<210> SEQ ID NO 24
<211> LENGTH: 22
<212> TYPE: DNA
```

```
<213> ORGANISM: Artificial Sequence
<220> FEATURE:
<223> OTHER INFORMATION: Primer

<400> SEQUENCE: 24
tgatgatatt tcataaataa tg                                          22

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
atgcgtccat ctttacagtc ctg                                         23

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
tacgtacgga ccaatcgaag tg                                          22

<210> SEQ ID NO 27
<211> LENGTH: 49
<212> TYPE: DNA
<213> ORGANISM: Artificial Sequence
<220> FEATURE:
<223> OTHER INFORMATION: Primer

<400> SEQUENCE: 27
aattcgtttg agtacactac taatggcttt gttggcaata tgttttgc              49

<210> SEQ ID NO 28
<211> LENGTH: 49
<212> TYPE: DNA
<213> ORGANISM: Artificial Sequence
<220> FEATURE:
<223> OTHER INFORMATION: Primer

<400> SEQUENCE: 28
atatagcaaa aacatattgc caacaaagcc attagtagtg tactcaaac             49

<210> SEQ ID NO 29
<211> LENGTH: 49
<212> TYPE: DNA
<213> ORGANISM: Artificial Sequence
<220> FEATURE:
<223> OTHER INFORMATION: Primer

<400> SEQUENCE: 29
tatggaccct gaaaccacag ccacattctt gttatttata aaaagacac             49

<210> SEQ ID NO 30
<211> LENGTH: 49
<212> TYPE: DNA
<213> ORGANISM: Artificial Sequence
<220> FEATURE:
<223> OTHER INFORMATION: Primer

<400> SEQUENCE: 30
ctcccgtgtc ttttataaa taacaagaat gtggctgtgg tttcagggt              49
```

-continued

<210> SEQ ID NO 31
<211> LENGTH: 49
<212> TYPE: DNA
<213> ORGANISM: Artificial Sequence
<220> FEATURE:
<223> OTHER INFORMATION: Primer

<400> SEQUENCE: 31
taccgtaggc gtccttagga aagatagaag gccatgaagc ttttctttt         49

<210> SEQ ID NO 32
<211> LENGTH: 49
<212> TYPE: DNA
<213> ORGANISM: Artificial Sequence
<220> FEATURE:
<223> OTHER INFORMATION: Primer

<400> SEQUENCE: 32
attggaaaga aaagcttca tggccttcta tctttcctaa ggacgccta          49

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
ttattgtttg gcatttgtag c                                        21

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
ccaagcatct cataaaccta tg                                       22

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
tgtgcagatg cagatgtgag ac                                       22

<210> SEQ ID NO 36
<211> LENGTH: 17
<212> TYPE: DNA
<213> ORGANISM: Artificial Sequence
<220> FEATURE:
<223> OTHER INFORMATION: Primer

<400> SEQUENCE: 36
agttattgat accgtac                                             17

<210> SEQ ID NO 37
<211> LENGTH: 19
<212> TYPE: DNA
<213> ORGANISM: Artificial Sequence
<220> FEATURE:

<223> OTHER INFORMATION: Primer

<400> SEQUENCE: 37
cgagataccg taggcgtcc                                          19

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
ttatgtatgc tcttctgact tttc                                    24

<210> SEQ ID NO 39
<211> LENGTH: 49
<212> TYPE: DNA
<213> ORGANISM: Artificial Sequence
<220> FEATURE:
<223> OTHER INFORMATION: Primer

<400> SEQUENCE: 39
aataattaga gattaaatcg ctcattttt gccagtttct tcaggcttc          49

<210> SEQ ID NO 40
<211> LENGTH: 49
<212> TYPE: DNA
<213> ORGANISM: Artificial Sequence
<220> FEATURE:
<223> OTHER INFORMATION: Primer

<400> SEQUENCE: 40
agcctgaaga aactggcaaa aaatgagcga tttaatctct aattattag         49

<210> SEQ ID NO 41
<211> LENGTH: 49
<212> TYPE: DNA
<213> ORGANISM: Artificial Sequence
<220> FEATURE:
<223> OTHER INFORMATION: Primer

<400> SEQUENCE: 41
tatggaccct gaaccacag ccacattttt caatcattgg agcaatcat          49

<210> SEQ ID NO 42
<211> LENGTH: 49
<212> TYPE: DNA
<213> ORGANISM: Artificial Sequence
<220> FEATURE:
<223> OTHER INFORMATION: Primer

<400> SEQUENCE: 42
taaaatgatt gctccaatga ttgaaaaatg tggctgtggt ttcagggtc         49

<210> SEQ ID NO 43
<211> LENGTH: 49
<212> TYPE: DNA
<213> ORGANISM: Artificial Sequence
<220> FEATURE:
<223> OTHER INFORMATION: Primer

<400> SEQUENCE: 43
accgtaggtg ttgtttggga aagtggaagg ccatgaagct ttttctttc         49

```
<210> SEQ ID NO 44
<211> LENGTH: 49
<212> TYPE: DNA
<213> ORGANISM: Artificial Sequence
<220> FEATURE:
<223> OTHER INFORMATION: Primer

<400> SEQUENCE: 44
ttggaaagaa aaagcttcat ggccttccac tttcccaaac aacacctac         49

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
ttattgctta gcgttggtag cag                                    23

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
tttttggtgg ttccggcttc c                                      21

<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47
aaagttggca tagcggaaac tt                                     22

<210> SEQ ID NO 48
<211> LENGTH: 16
<212> TYPE: DNA
<213> ORGANISM: Artificial Sequence
<220> FEATURE:
<223> OTHER INFORMATION: Primer

<400> SEQUENCE: 48
gtcattgaca ccatct                                            16

<210> SEQ ID NO 49
<211> LENGTH: 19
<212> TYPE: DNA
<213> ORGANISM: Artificial Sequence
<220> FEATURE:
<223> OTHER INFORMATION: Primer

<400> SEQUENCE: 49
agagataccg taggtgttg                                         19

<210> SEQ ID NO 50
<211> LENGTH: 33
<212> TYPE: DNA
<213> ORGANISM: Artificial Sequence
<220> FEATURE:
<223> OTHER INFORMATION: Primer
```

```
<400> SEQUENCE: 50
aattggcgcg ccatgaaagc tctggtttat cac                                33

<210> SEQ ID NO 51
<211> LENGTH: 49
<212> TYPE: DNA
<213> ORGANISM: Artificial Sequence
<220> FEATURE:
<223> OTHER INFORMATION: Primer

<400> SEQUENCE: 51
tgaatcatga gttttatgtt aattagctca ggcagcgcct gcgttcgag               49

<210> SEQ ID NO 52
<211> LENGTH: 49
<212> TYPE: DNA
<213> ORGANISM: Artificial Sequence
<220> FEATURE:
<223> OTHER INFORMATION: Primer

<400> SEQUENCE: 52
atcctctcga acgcaggcgc tgcctgagct aattaacata aaactcatg               49

<210> SEQ ID NO 53
<211> LENGTH: 34
<212> TYPE: DNA
<213> ORGANISM: Artificial Sequence
<220> FEATURE:
<223> OTHER INFORMATION: Primer

<400> SEQUENCE: 53
aattgtttaa acaagtaaat aaattaatca gcat                               34

<210> SEQ ID NO 54
<211> LENGTH: 49
<212> TYPE: DNA
<213> ORGANISM: Artificial Sequence
<220> FEATURE:
<223> OTHER INFORMATION: Primer

<400> SEQUENCE: 54
acacaataca ataacaagaa gaacaaaatg aaagctctgg tttatcacg               49

<210> SEQ ID NO 55
<211> LENGTH: 49
<212> TYPE: DNA
<213> ORGANISM: Artificial Sequence
<220> FEATURE:
<223> OTHER INFORMATION: Primer

<400> SEQUENCE: 55
agcgtataca tctgttggga aagtagaagg ccatgaagct ttttctttc               49

<210> SEQ ID NO 56
<211> LENGTH: 49
<212> TYPE: DNA
<213> ORGANISM: Artificial Sequence
<220> FEATURE:
<223> OTHER INFORMATION: Primer

<400> SEQUENCE: 56
ttggaaagaa aaagcttcat ggccttctac tttcccaaca gatgtatac               49

<210> SEQ ID NO 57
<211> LENGTH: 22
```

```
<212> TYPE: DNA
<213> ORGANISM: Artificial Sequence
<220> FEATURE:
<223> OTHER INFORMATION: Primer

<400> SEQUENCE: 57
ttattgttta gcgttagtag cg                                              22

<210> SEQ ID NO 58
<211> LENGTH: 72
<212> TYPE: DNA
<213> ORGANISM: Artificial Sequence
<220> FEATURE:
<223> OTHER INFORMATION: Primer

<400> SEQUENCE: 58
cataatcaat ctcaaagaga acaacacaat acaataacaa gaagaacaaa atgaaagctc     60
tggtttatca cg                                                         72

<210> SEQ ID NO 59
<211> LENGTH: 21
<212> TYPE: DNA
<213> ORGANISM: Artificial Sequence
<220> FEATURE:
<223> OTHER INFORMATION: Primer

<400> SEQUENCE: 59
taggcataat caccgaagaa g                                               21

<210> SEQ ID NO 60
<211> LENGTH: 21
<212> TYPE: DNA
<213> ORGANISM: Artificial Sequence
<220> FEATURE:
<223> OTHER INFORMATION: Primer

<400> SEQUENCE: 60
aaaatggtaa gcagctgaaa g                                               21

<210> SEQ ID NO 61
<211> LENGTH: 17
<212> TYPE: DNA
<213> ORGANISM: Artificial Sequence
<220> FEATURE:
<223> OTHER INFORMATION: Primer

<400> SEQUENCE: 61
agttgttaga actgttg                                                    17

<210> SEQ ID NO 62
<211> LENGTH: 19
<212> TYPE: DNA
<213> ORGANISM: Artificial Sequence
<220> FEATURE:
<223> OTHER INFORMATION: Primer

<400> SEQUENCE: 62
gacgatagcg tatacatct                                                  19

<210> SEQ ID NO 63
<211> LENGTH: 22
<212> TYPE: DNA
<213> ORGANISM: Artificial Sequence
<220> FEATURE:
<223> OTHER INFORMATION: Primer
```

<400> SEQUENCE: 63
cttagcctct agccatagcc at                                             22

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
ttagttttgc tggccgcatc ttc                                            23

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
cccattaata tactattgag a                                              21

<210> SEQ ID NO 66
<211> LENGTH: 7523
<212> TYPE: DNA
<213> ORGANISM: Artificial Sequence
<220> FEATURE:
<223> OTHER INFORMATION: Plasmid

<400> SEQUENCE: 66
ccagcttttg ttcccttag tgagggttaa ttgcgcgctt ggcgtaatca tggtcatagc      60
tgtttcctgt gtgaaattgt tatccgctca caattccaca caacatagga gccggaagca   120
taaagtgtaa agcctggggt gcctaatgag tgaggtaact cacattaatt gcgttgcgct   180
cactgcccgc tttccagtcg ggaaacctgt cgtgccagct gcattaatga atcggccaac   240
gcgcggggag aggcggtttg cgtattgggc gctcttccgc ttcctcgctc actgactcgc   300
tgcgctcggt cgttcggctg cggcgagcgg tatcagctca ctcaaaggcg gtaatacggt   360
tatccacaga atcaggggat aacgcaggaa agaacatgtg agcaaaaggc cagcaaaagg   420
ccaggaaccg taaaaaggcc gcgttgctgg cgttttttcca taggctccgc ccccctgacg   480
agcatcacaa aaatcgacgc tcaagtcaga ggtggcgaaa cccgacagga ctataaagat   540
accaggcgtt tccccctgga agctccctcg tgcgctctcc tgttccgacc ctgccgctta   600
ccggatacct gtccgccttt ctcccttcgg gaagcgtggc gctttctcat agctcacgct   660
gtaggtatct cagttcggtg taggtcgttc gctccaagct gggctgtgtg cacgaacccc   720
ccgttcagcc cgaccgctgc gccttatccg gtaactatcg tcttgagtcc aacccggtaa   780
gacacgactt atcgccactg gcagcagcca ctggtaacag gattagcaga gcgaggtatg   840
taggcggtgc tacagagttc ttgaagtggt ggcctaacta cggctacact agaaggacag   900
tatttggtat ctgcgctctg ctgaagccag ttaccttcgg aaaaagagtt ggtagctctt   960
gatccggcaa acaaaccacc gctggtagcg gtggtttttt tgtttgcaag cagcagatta  1020
cgcgcagaaa aaaaggatct caagaagatc ctttgatctt ttctacgggg tctgacgctc  1080
agtggaacga aaactcacgt taagggattt tggtcatgag attatcaaaa aggatcttca  1140
cctagatcct tttaaattaa aaatgaagtt ttaaatcaat ctaaagtata tatgagtaaa  1200
cttggtctga cagttaccaa tgcttaatca gtgaggcacc tatctcagcg atctgtctat  1260

```
ttcgttcatc catagttgcc tgactccccg tcgtgtagat aactacgata cgggagggct      1320
taccatctgg ccccagtgct gcaatgatac cgcgagaccc acgctcaccg gctccagatt      1380
tatcagcaat aaaccagcca gccggaaggg ccgagcgcag aagtggtcct gcaactttat      1440
ccgcctccat ccagtctatt aattgttgcc gggaagctag agtaagtagt tcgccagtta      1500
atagtttgcg caacgttgtt gccattgcta caggcatcgt ggtgtcacgc tcgtcgtttg      1560
gtatggcttc attcagctcc ggttcccaac gatcaaggcg agttacatga tcccccatgt      1620
tgtgcaaaaa agcggttagc tccttcggtc ctccgatcgt tgtcagaagt aagttggccg      1680
cagtgttatc actcatggtt atggcagcac tgcataattc tcttactgtc atgccatccg      1740
taagatgctt ttctgtgact ggtgagtact caaccaagtc attctgagaa tagtgtatgc      1800
ggcgaccgag ttgctcttgc ccggcgtcaa tacgggataa taccgcgcca catagcagaa      1860
ctttaaaagt gctcatcatt ggaaaacgtt cttcggggcg aaaactctca aggatcttac      1920
cgctgttgag atccagttcg atgtaaccca ctcgtgcacc caactgatct tcagcatctt      1980
ttactttcac cagcgtttct gggtgagcaa aaacaggaag gcaaaatgcc gcaaaaaagg      2040
gaataagggc gacacggaaa tgttaatac tcatactctt ccttttcaa tattattgaa       2100 gcatttatca gggttattgt ctcatgagcg gatacatatt tgaatgtatt tagaaaaata     2160
aacaaatagg ggttccgcgc acatttcccc gaaaagtgcc acctgaacga agcatctgtg     2220
cttcattttg tagaacaaaa atgcaacgcg agagcgctaa ttttcaaac aaagaatctg      2280 agctgcattt ttacagaaca gaaatgcaac gcgaaagcgc tattttacca acgaagaatc     2340
tgtgcttcat ttttgtaaaa caaaaatgca acgcgagagc gctaattttt caaacaaaga    2400
atctgagctg catttttaca gaacagaaat gcaacgcgag agcgctattt taccaacaaa     2460
gaatctatac ttcttttttg ttctacaaaa atgcatcccg agagcgctat ttttctaaca    2520
aagcatctta gattactttt tttctccttt gtgcgctcta atgcagtc tcttgataac       2580 tttttgcact gtaggtccgt taaggttaga agaaggctac tttggtgtct attttctctt     2640
ccataaaaaa agcctgactc cacttcccgc gtttactgat tactagcgaa gctgcgggtg    2700 catttttca agataaaggc atccccgatt atattctata ccgatgtgga ttgcgcatac    2760
tttgtgaaca gaaagtgata gcgttgatga ttcttcattg gtcagaaaat tatgaacggt   2820
ttcttctatt ttgtctctat atactacgta taggaaatgt ttacatttc gtattgtttt   2880 cgattcactc tatgaatagt tcttactaca attttttgt ctaaagagta atactagaga    2940
taaacataaa aaatgtagag gtcgagttta gatgcaagtt caaggagcga aaggtggatg    3000
ggtaggttat ataggatat agcacagaga tatatagcaa agagatactt ttgagcaatg    3060
tttgtggaag cggtattcgc aatattttag tagctcgtta cagtccggtg cgttttggt    3120 tttttgaaag tgcgtcttca gagcgctttt ggttttcaaa agcgctctga agttcctata    3180
ctttctagag aataggaact tcggaatagg aacttcaaag cgtttccgaa aacgagcgct    3240
tccgaaaatg caacgcgagc tgcgcacata cagctcactg ttcacgtcgc acctatatct    3300
gcgtgttgcc tgtatatata tatacatgag aagaacggca tagtgcgtgt ttatgcttaa    3360
atgcgtactt atatgcgtct atttatgtag gatgaaaggt agtctagtac ctcctgtgat    3420
attatcccat tccatgcggg gtatcgtatg cttccttcag cactacccct tagctgttct    3480
atatgctgcc actcctcaat tggattagtc tcatccttca atgctatcat ttcctttgat    3540
attggatcat ctaagaaacc attattatca tgacattaac ctataaaaat aggcgtatca    3600
```

```
cgaggccctt tcgtctcgcg cgtttcggtg atgacggtga aaacctctga cacatgcagc    3660
tcccggagac ggtcacagct tgtctgtaag cggatgccgg gagcagacaa gcccgtcagg    3720
gcgcgtcagc gggtgttggc gggtgtcggg gctggcttaa ctatgcggca tcagagcaga    3780
ttgtactgag agtgcaccat aaattcccgt tttaagagct tggtgagcgc taggagtcac    3840
tgccaggtat cgtttgaaca cggcattagt cagggaagtc ataacacagt cctttcccgc    3900
aattttcttt ttctattact cttggcctcc tctagtacac tctatatttt tttatgcctc    3960
ggtaatgatt ttcattttt tttttcccct agcggatgac tcttttttttt tcttagcgat    4020 tggcattatc acataatgaa ttatacatta tataaagtaa tgtgatttct tcgaagaata    4080
tactaaaaaa tgagcaggca agataaacga aggcaaagat gacagagcag aaagccctag    4140
taaagcgtat tacaaatgaa accaagattc agattgcgat ctctttaaag ggtggtcccc    4200
tagcgataga gcactcgatc ttcccagaaa aagaggcaga agcagtagca gaacaggcca    4260
cacaatcgca agtgattaac gtccacacag gtatagggtt tctggaccat atgatacatg    4320
ctctggccaa gcattccggc tggtcgctaa tcgttgagtg cattggtgac ttacacatag    4380
acgaccatca caccactgaa gactgcggga ttgctctcgg tcaagctttt aaagaggccc    4440
tactggcgcg tggagtaaaa aggtttggat caggatttgc gcctttggat gaggcacttt    4500
ccagagcggt ggtagatctt tcgaacaggc cgtacgcagt tgtcgaactt ggtttgcaaa    4560
gggagaaagt aggagatctc tcttgcgaga tgatcccgca ttttcttgaa agctttgcag    4620
aggctagcag aattaccctc cacgttgatt gtctgcgagg caagaatgat catcaccgta    4680
gtgagagtgc gttcaaggct cttgcggttg ccataagaga agccacctcg cccaatggta    4740
ccaacgatgt tccctccacc aaaggtgttc ttatgtagtg acaccgatta tttaaagctg    4800
cagcatacga tatatataca tgtgtatata tgtataccta tgaatgtcag taagtatgta    4860
tacgaacagt atgatactga agatgacaag gtaatgcatc attctatacg tgtcattctg    4920
aacgaggcgc gctttccttt tttcttttg cttttctttt ttttttctct tgaactcgac    4980
ggatctatgc ggtgtgaaat accgcacaga tgcgtaagga gaaataccg catcaggaaa    5040 ttgtaaacgt taatatttg ttaaaattcg cgttaaattt tgttaaaatc agctcatttt    5100
ttaaccaata ggccgaaatc ggcaaaatcc cttataaatc aaaagaatag accgagatag    5160
ggttgagtgt tgttccagtt tggaacaaga gtccactatt aaagaacgtg gactccaacg    5220
tcaaagggcg aaaaccgtc tatcagggcg atggcccact acgtgaacca tcaccctaat    5280
caagtttttt ggggtcgagg tgccgtaaag cactaaatcg gaaccctaaa gggagccccc    5340
gatttagagc ttgacgggga agccggcga acgtggcgag aaaggaaggg aagaaagcga    5400
aaggagcggg cgctagggcg ctggcaagtg tagcggtcac gctgcgcgta accaccacac    5460
ccgccgcgct taatgcgccg ctacagggcg cgtcgcgcca ttcgccattc aggctgcgca    5520
actgttggga agggcgatcg gtgcgggcct cttcgctatt acgccagctg gcgaaagggg    5580
gatgtgctgc aaggcgatta agttgggtaa cgccagggtt ttcccagtca cgacgttgta    5640
aaacgacggc cagtgagcgc gcgtaatacg actcactata gggcgaattg ggtaccgggc    5700 ccccctcga ggtattagaa gccgccgagc gggcgacagc cctccgacgg aagactctcc    5760
tccgtgcgtc ctcgtcttca ccggtcgcgt tcctgaaacg cagatgtgcc tcgcgccgca    5820
ctgctccgaa caataaagat tctacaatac tagcttttat ggttatgaag aggaaaaatt    5880
ggcagtaacc tggcccccaca aaccttcaaa ttaacgaatc aaattaacaa ccataggatg    5940
ataatgcgat tagtttttta gccttatttc tggggtaatt aatcagcgaa gcgatgattt    6000
```

```
ttgatctatt aacagatata taaatggaaa agctgcataa ccactttaac taatactttc    6060
aacattttca gtttgtatta cttcttattc aaatgtcata aaagtatcaa caaaaaattg    6120
ttaatatacc tctatacttt aacgtcaagg agaaaaatgt ccaatttact gcccgtacac    6180
caaaatttgc ctgcattacc ggtcgatgca acgagtgatg aggttcgcaa gaacctgatg    6240
gacatgttca gggatcgcca ggcgttttct gagcatacct ggaaaatgct tctgtccgtt    6300
tgccggtcgt gggcggcatg gtgcaagttg aataaccgga atggttttcc cgcagaacct    6360
gaagatgttc gcgattatct tctatatctt caggcgcgcg gtctggcagt aaaaactatc    6420
cagcaacatt tgggccagct aaacatgctt catcgtcggt ccgggctgcc acgaccaagt    6480
gacagcaatg ctgtttcact ggttatgcgg cggatccgaa agaaaacgt tgatgccggt    6540 gaacgtgcaa acaggctct agcgttcgaa cgcactgatt tcgaccaggt tcgttcactc    6600
atggaaaata gcgatcgctg ccaggatata cgtaatctgg catttctggg gattgcttat    6660
aacaccctgt tacgtatagc cgaaattgcc aggatcaggg ttaaagatat ctcacgtact    6720
gacggtggga gaatgttaat ccatattggc agaacgaaaa cgctggttag caccgcaggt    6780
gtagagaagg cacttagcct gggggtaact aaactggtcg agcgatggat ttccgtctct    6840
ggtgtagctg atgatccgaa taactacctg ttttgccggg tcagaaaaaa tggtgttgcc    6900
gcgccatctg ccaccagcca gctatcaact cgcgccctgg aagggatttt tgaagcaact    6960
catcgattga tttacggcgc taaggatgac tctggtcaga gatacctggc ctggtctgga    7020
cacagtgccc gtgtcggagc cgcgcgagat atggcccgcg ctggagtttc aataccggag    7080
atcatgcaag ctggtggctg gaccaatgta atatattgtca tgaactatat ccgtaacctg    7140
gatagtgaaa caggggcaat ggtgcgcctg ctggaagatg gcgattagga gtaagcgaat    7200
ttcttatgat ttatgatttt tattattaaa taagttataa aaaaaataag tgtatacaaa    7260
ttttaaagtg actcttaggt tttaaaacga aaattcttat tcttgagtaa ctctttcctg    7320
taggtcaggt tgcttcctca ggtatagcat gaggtcgctc ttattgacca cacctctacc    7380
ggcatgccga gcaaatgcct gcaaatcgct ccccatttca cccaattgta gatatgctaa    7440
ctccagcaat gagttgatga atctcggtgt gtattttatg tcctcagagg acaacacctg    7500
tggtccgcca ccgcggtgga gct                                            7523
```

<210> SEQ ID NO 67
<211> LENGTH: 15456
<212> TYPE: DNA
<213> ORGANISM: Artificial Sequence
<220> FEATURE:
<223> OTHER INFORMATION: Template

<400> SEQUENCE: 67

```
aaagagtaat actagagata aacataaaaa atgtagaggt cgagtttaga tgcaagttca      60
aggagcgaaa ggtggatggg taggttatat agggatatag cacagagata tatagcaaag    120
agatactttt gagcaatgtt tgtggaagcg gtattcgcaa tattttagta gctcgttaca    180
gtccggtgcg ttttggttt tttgaaagtg cgtcttcaga gcgcttttgg ttttcaaaag    240
cgctctgaag ttcctatact ttctagagaa taggaacttc ggaataggaa cttcaaagcg    300
tttccgaaaa cgagcgcttc cgaaaatgca acgcgagctg cgcacataca gctcactgtt    360
cacgtcgcac ctatatctgc gtgttgcctg tatatatata tacatgagaa gaacggcata    420
gtgcgtgttt atgcttaaat gcgtactat atgcgtctat ttatgtagga tgaaaggtag    480
```

```
tctagtacct cctgtgatat tatcccattc catgcgggt atcgtatgct tccttcagca    540
ctacccttta gctgttctat atgctgccac tcctcaattg gattagtctc atccttcaat   600
gctatcattt cctttgatat tggatcatac taagaaacca ttattatcat gacattaacc   660
tataaaaata ggcgtatcac gaggccctt cgtctcgcgc gtttcggtga tgacggtgaa    720
aacctctgac acatgcagct cccggagacg gtcacagctt gtctgtaagc ggatgccggg   780
agcagacaag cccgtcaggg cgcgtcagcg ggtgttggcg ggtgtcgggg ctggcttaac   840
tatgcggcat cagagcagat tgtactgaga gtgcaccata aattcccgtt ttaagagctt   900
ggtgagcgct aggagtcact gccaggtatc gtttgaacac ggcattagtc agggaagtca   960
taacacagtc ctttcccgca attttctttt tctattactc ttggcctcct ctagtacact  1020
ctatatttt ttatgcctcg gtaatgattt tcatttttt ttttccacct agcggatgac    1080
tctttttttt tcttagcgat tggcattatc acataatgaa ttatacatta tataaagtaa  1140
tgtgatttct tcgaagaata tactaaaaaa tgagcaggca agataaacga aggcaaagat  1200
gacagagcag aaagccctag taaagcgtat tacaaatgaa accaagattc agattgcgat  1260
ctctttaaag ggtggtcccc tagcgataga gcactcgatc ttcccagaaa agaggcaga   1320
agcagtagca gaacaggcca cacaatcgca agtgattaac gtccacacag gtataggt   1380
tctggaccat atgatacatg ctctggccaa gcattccggc tggtcgctaa tcgttgagtg  1440
cattggtgac ttacacatag acgaccatca caccactgaa gactgcggga ttgctctcgg  1500
tcaagctttt aaagaggccc taggggccgt gcgtggagta aaaaggtttg gatcaggatt  1560
tgcgcctttg gatgaggcac tttccagagc ggtggtagat ctttcgaaca ggccgtacgc  1620
agttgtcgaa cttggttttgc aaagggagaa agtaggagat ctctcttgcg agatgatccc  1680
gcattttctt gaaagctttg cagaggctag cagaattacc ctccacgttg attgtctgcg  1740
aggcaagaat gatcatcacc gtagtgagag tgcgttcaag gctcttgcgg ttgccataag  1800
agaagccacc tcgcccaatg gtaccaacga tgttccctcc accaaggtg ttcttatgta   1860
gtgacaccga ttatttaaag ctgcagcata cgatatatat acatgtgtat atatgtatac  1920
ctatgaatgt cagtaagtat gtatacgaac agtatgatac tgaagatgac aaggtaatgc  1980
atcattctat acgtgtcatt ctgaacgagg cgcgctttcc ttttttcttt ttgcttttc   2040
ttttttttc tcttgaactc gacggatcta tgcggtgtga ataccgcac agatgcgtaa    2100
ggagaaaata ccgcatcagg aaattgtaag cgttaatatt ttgttaaaat tcgcgttaaa  2160
tttttgttaa atcagctcat tttttaacca ataggccgaa atcggcaaaa tcccttataa  2220
atcaaaagaa tagaccgaga taggtgag tgttgttcca gtttgaaaca agagtccact   2280
attaaagaac gtggactcca acgtcaaagg gcgaaaaacc gtctatcagg gcgatggccc  2340
actacgtgaa ccatcaccct aatcaagttt tttggggtcg aggtgccgta aagcactaaa  2400
tcggaacct aaagggagcc cccgatttag agcttgacgg ggaaagccgg cgaacgtggc    2460
gagaaaggaa gggaagaaag cgaaaggagc gggcgctagg gcgctggcaa gtgtagcggt  2520
cacgctgcgc gtaaccacca cacccgccgc gcttaatgcg ccgctacagg gcgcgtccat  2580
tcgccattca ggctgcgcaa ctgttgggaa gggcgcggtg cgggcctctt cgctattacg  2640
ccagctggcg aaagggggat gtgctgcaag gcgattaagt tgggtaacgc cagggttttc  2700
ccagtcacga cgttgtaaaa cgacggccag tgagcgcgcg taatacgact cactataggg  2760
cgaattgggt accgggcccc cctcgaggt cgacggcgcg ccactggtag agagcgactt   2820
tgtatgcccc aattgcgaaa cccgcgatat ccttctcgat tctttagtac ccgaccagga  2880
```

```
caaggaaaag gaggtcgaaa cgtttttgaa gaaacaagag gaactacacg gaagctctaa    2940
agatggcaac cagccagaaa ctaagaaaat gaagttgatg gatccaactg gcaccgctgg    3000
cttgaacaac aataccagcc ttccaacttc tgtaaataac ggcggtacgc cagtgccacc    3060
agtaccgtta cctttcggta tacctccttt ccccatgttt ccaatgccct tcatgcctcc    3120
aacggctact atcacaaatc ctcatcaagc tgacgcaagc cctaagaaat gaataacaat    3180
actgacagta ctaaataatt gcctacttgg cttcacatac gttgcatacg tcgatatatga   3240
taataatgat aatgacagca ggattatcgt aatacgtaat agctgaaaat ctcaaaaatg    3300
tgtgggtcat tacgtaaata atgataggaa tgggattctt ctattttttcc tttttccatt   3360
ctagcagccg tcgggaaaac gtggcatcct ctctttcggg ctcaattgga gtcacgctgc    3420
cgtgagcatc ctctctttcc atatctaaca actgagcacg taaccaatgg aaaagcatga    3480
gcttagcgtt gctccaaaaa agtattggat ggttaatacc atttgtctgt tctcttctga    3540
ctttgactcc tcaaaaaaaa aaatctcaaa tcaacagatc gcttcaatta cgccctcaca    3600
aaaactttttt tccttcttct tcgcccacgt taaatttttat ccctcatgtt gtctaacgga   3660
tttctgcact tgatttatta taaaaagaca aagacataat acttctctat caatttcagt    3720
tattgttcctt ccttgcgtta ttcttctgtt cttcttttttc ttttgtcata tataaccata   3780
accaagtaat acatattcaa actagtatga ctgacaaaaa actcttaaa gacttaagaa     3840
atcgtagttc tgtttacgat tcaatggtta aatcacctaa tcgtgctatg ttgcgtgcaa    3900
ctggtatgca agatgaagac tttgaaaaac ctatcgtcgg tgtcatttca acttgggctg    3960
aaaacacacc ttgtaatatc cacttacatg actttggtaa actagccaaa gtcggtgtta    4020
aggaagctgg tgcttggcca gttcagttcg gaacaatcac ggtttctgat ggaatcgcca    4080
tgggaacccca aggaatgcgt ttctccttga catctcgtga tattattgca gattctattg   4140
aagcagccat gggaggtcat aatgcggatg cttttgtagc cattggcggt tgtgataaaa    4200
acatgcccgg ttctgttatc gctatggcta acatggatat cccagccatt tttgcttacg    4260
gcggaacaat tgcacctggt aatttagacg gcaaagatat cgatttagtc tctgtctttg    4320
aaggtgtcgg ccattggaac cacggcgata tgaccaaaga agaagttaaa gctttggaat    4380
gtaatgcttg tcccggtcct ggaggctgcg gtggtatgta tactgctaac acaatggcga    4440
cagctattga agttttggga cttagccttc cgggttcatc ttctcacccg gctgaatccg    4500
cagaaaagaa agcagatatt gaagaagctg gtcgcgctgt tgtcaaaatg ctcgaaatgg    4560
gcttaaaacc ttctgacatt ttaacgcgtg aagcttttga agatgctatt actgtaacta    4620
tggctctggg aggttcaacc aactcaaccc ttcacctctt agctattgcc catgctgcta    4680
atgtggaatt gacacttgat gatttcaata ctttccaaga aaaagttcct catttggctg    4740
atttgaaacc ttctggtcaa tatgtattcc aagacctttta caaggtcgga ggggtaccag   4800
cagttatgaa atatctcctt aaaaatggct tccttcatgg tgaccgtatc acttgtactg    4860
gcaaaacagt cgctgaaaat ttgaaggctt ttgatgattt aacacctggt caaaaggtta    4920
ttatgccgct tgaaaatcct aaacgtgaag atggtccgct cattattctc catggtaact    4980
tggctccaga cggtgccgtt gccaaagttt ctggtgtaaa agtgcgtcgt catgtcggtc    5040
ctgctaaggt cttttaattct gaagaagaag ccattgaagc tgtcttgaat gatgatattg   5100
ttgatggtga tgttgttgtc gtacgttttg taggaccaaa gggcggtcct ggtatgcctg    5160
aaatgctttc cctttcatca atgattgttg gtaaggggca aggtgaaaaa gttgcccttc    5220
```

```
tgacagatgg ccgcttctca ggtggtactt atggtcttgt cgtgggtcat atcgctcctg    5280
aagcacaaga tggcggtcca atcgcctacc tgcaaacagg agacatagtc actattgacc    5340
aagacactaa ggaattacac tttgatatct ccgatgaaga gttaaaacat cgtcaagaga    5400
ccattgaatt gccaccgctc tattcacgcg gtatccttgg taaatatgct cacatcgttt    5460
cgtctgcttc taggggagcc gtaacagact tttggaagcc tgaagaaact ggcaaaaaat    5520
gttgtcctgg ttgctgtggt taagcggccg cgttaattca aattaattga tatagttttt    5580
taatgagtat tgaatctgtt tagaaataat ggaatattat ttttatttat ttatttatat    5640
tattggtcgg ctcttttctt ctgaaggtca atgacaaaat gatatgaagg aaataatgat    5700
ttctaaaatt ttacaacgta agatatttt acaaaagcct agctcatctt ttgtcatgca    5760
ctattttact cacgcttgaa attaacggcc agtccactgc ggagtcattt caaagtcatc    5820
ctaatcgatc tatcgttttt gatagctcat tttggagttc gcgattgtct tctgttattc    5880
acaactgttt taatttttat ttcattctgg aactcttcga gttctttgta aagtctttca    5940
tagtagctta ctttatcctc caacatattt aacttcatgt caatttcggc tcttaaattt    6000
tccacatcat caagttcaac atcatctttt aacttgaatt tattctctag ctcttccaac    6060
caagcctcat tgctccttga tttactggtg aaaagtgata cactttgcgc gcaatccagg    6120
tcaaaacttt cctgcaaaga attcaccaat ttctcgacat catagtacaa tttgttttgt    6180
tctcccatca caatttaata tacctgatgg attcttatga agcgctgggt aatggacgtg    6240
tcactctact tcgcctttt ccctactcct tttagtacgg aagacaatgc taataaataa    6300
gagggtaata ataatattat taatcggcaa aaaagattaa acgccaagcg tttaattatc    6360
agaaagcaaa cgtcgtacca atccttgaat gcttcccaat tgtatattaa gagtcatcac    6420
agcaacatat tcttgttatt aaattaatta ttattgattt ttgatattgt ataaaaaaac    6480
caaatatgta taaaaaaagt gaataaaaaa taccaagtat ggagaaatat attagaagtc    6540
tatacgttaa accacccggg cccccccctcg aggtcgacgg tatcgataag cttgatatcg    6600
aattcctgca gcccggggga tccactagtt ctagagcggc cgctctagaa ctagtaccac    6660
aggtgttgtc ctctgaggac ataaaataca caccgagatt catcaactca ttgctggagt    6720
tagcatatct acaattgggt gaaatgggga gcgatttgca ggcatttgct cggcatgccg    6780
gtagaggtgt ggtcaataag agcgacctca tgctatacct gagaaagcaa cctgacctac    6840
aggaaagagt tactcaagaa taagaatttt cgttttaaaa cctaagagtc actttaaaat    6900
ttgtatacac ttatttttt tataacttat ttaataataa aaatcataaa tcataagaaa    6960
ttcgcttact cttaattaat caggcagcgc ctgcgttcga gaggatgatc ttcatcgcct    7020
tctccttggc gccattgagg aatacctgat aggcgtgctc gatctcggcc agctcgaagc    7080
gatgggtaat catcttcttc aacggaagct tgtcggtcga ggcgaccttc atcagcatgg    7140
gcgtcgtgtt cgtgttcacc agtcccgtgg tgatcgtcag gttcttgatc cagagcttct    7200
gaatctcgaa gtcaaccttg acgccatgca cgccgacgtt ggcgatgtgc gcgccgggct    7260
tgacgatctc ctggcagatg tcccaagtcg ccggtatgcc caccgcctcg atcgcaacat    7320
cgactccctc tgccgcaatc ctatgcacgg cttcgacaac gttctccgtg ccggagttga    7380
tggtgtgcgt tgccccgagc tccttggcga gctggaggcg attctcgtcc atgtcgatca    7440
cgatgatggt cgaggggag tagaactggg cggtcaacag tacggacatg ccgacggggc    7500
ccgcgccgac aatagccacc gcatcgcccg gctggacatt cccatactgg acgccgattt    7560
cgtggccggt gggcaggatg tcgctcagca ggacggcgat ttcgtcgtca attgtctggg    7620
```

```
ggatcttgta gaggctgttg tcggcatgcg ggatgcggac gtattcggcc tgcacgccat    7680
cgatcatgta acccaggatc cacccgccgt cgcggcaatg ggagtaaagc tgcttcttgc    7740
agtagtcgca cgagccgcaa gaagtgacgc aggaaatcag gaccttgtcg cctttcttga    7800
actgcgtgac actctcgccc acttcctcga tgacgcctac cccttcatgg cccaggatgc    7860
gcccgtcggc gacctctgga ttcttgcctt tgtagatgcc gagatccgtg ccgcagatcg    7920
tggtcttcaa aacccgtact actacatccg tgggcttttg aagggtgggc ttgggcttgt    7980
cttcaagcga gatcttgtgg tcaccgtgat aaaccagagc tttcatcctc agctattgta    8040
atatgtgtgt ttgtttggat tattaagaag aataattaca aaaaaaatta caaaggaagg    8100
taattacaac agaattaaga aaggacaaga aggaggaaga gaatcagttc attatttctt    8160
ctttgttata taacaaaccc aagtagcgat ttggccatac attaaaagtt gagaaccacc    8220
ctccctggca acagccacaa ctcgttacca ttgttcatca cgatcatgaa actcgctgtc    8280
agctgaaatt tcacctcagt ggatctctct ttttattctt catcgttcca ctaacctttt    8340
tccatcagct ggcagggaac ggaaagtgga atcccattta gcgagcttcc tcttttcttc    8400
aagaaaagac gaagcttgtg tgtgggtgcg cgcgctagta tctttccaca ttaagaaata    8460
taccataaag gttacttaga catcactatg gctatatata tatatatata tatatatgta    8520
acttagcacc atcgcgcgtg catcactgca tgtgttaacc gaaaagtttg gcgaacactt    8580
caccgacacg gtcatttaga tctgtcgtct gcattgcacg tcccttagcc ttaaatccta    8640
ggcgggagca ttctcgtgta attgtgcagc ctgcgtagca actcaacata gcgtagtcta    8700
cccagttttt caagggttta tcgttagaag attctcccct tcttcctgc tcacaaatct     8760 taaagtcata cattgcacga ctaaatgcaa gcatgcggat cccccgggct gcaggaattc    8820
gatatcaagc ttatcgatac cgtcgactgg ccattaatct ttcccatatt agatttcgcc    8880
aagccatgaa agttcaagaa aggtctttag acgaattacc cttcatttct caaactggcg    8940
tcaagggatc ctggtatggt tttatcgttt tatttctggt tcttatagca tcgttttgga    9000
cttctctgtt cccattaggc ggttcaggag ccagcgcaga atcattcttt gaaggatact    9060 tatccttttcc aattttgatt gtctgttacg ttggacataa actgtatact agaaattgga    9120
ctttgatggt gaaactagaa gatatggatc ttgataccgg cagaaaacaa gtagatttga    9180
ctcttcgtag ggaagaaatg aggattgagc gagaaacatt agcaaaaaga tccttcgtaa    9240
caagattttt acatttctgg tgttgaaggg aaagatatga gctatacagc ggaatttcca    9300
tatcactcag attttgttat ctaatttttt ccttcccacg tccgcgggaa tctgtgtata    9360
ttactgcatc tagatatatg ttatcttatc ttggcgcgta catttaattt tcaacgtatt    9420
ctataagaaa ttgcgggagt ttttttcatg tagatgatac tgactgcacg caaatatagg    9480
catgatttat aggcatgatt tgatggctgt accgatagga acgctaagag taacttcaga    9540
atcgttatcc tggcggaaaa aattcatttg taaacttta aaaaaaaagc caatatcccc    9600
aaaattatta agagcgcctc cattattaac taaaatttca ctcagcatcc acaatgtatc    9660
aggtatctac tacagatatt acatgtggcg aaaaagacaa gaacaatgca atagcgcatc    9720
aagaaaaaac acaaagcttt caatcaatga atcgaaaatg tcattaaaat agtatataaa    9780
ttgaaactaa gtcataaagc tataaaaaga aaatttattt aaatgcaaga tttaaagtaa    9840
attcacggcc ctgcaggcct cagctcttgt tttgttctgc aaataactta cccatctttt    9900
tcaaaacttt aggtgcaccc tcctttgcta gaataagttc tatccaatac atcctatttg    9960
```

```
gatctgcttg agcttctttc atcacggata cgaattcatt ttctgttctc acaatttttgg   10020
acacaactct gtcttccgtt gccccgaaac tttctggcag ttttgagtaa ttccacatag    10080
gaatgtcatt ataactctgg ttcggaccat gaatttccct ctcaaccgtg taaccatcgt    10140
tattaatgat aaagcagatt gggtttatct tctctctaat ggctagtcct aattcttgga    10200
cagtcagttg caatgatcca tctccgataa acaataaatg tctagattct ttatctgcaa    10260
tttggctgcc tagagctgcg gggaaagtgt atcctataga tccccacaag ggttgaccaa    10320
taaaatgtga tttcgatttc agaaatatag atgaggcacc gaagaaagaa gtgccttgtt    10380
cagccacgat cgtctcatta ctttgggtca aattttcgac agcttgccac agtctatctt    10440
gtgacaacag cgcgttagaa ggtacaaaat cttcttgctt tttatctatg tacttgcctt    10500
tatattcaat ttcggacaag tcaagaagag atgatatcag ggattcgaag tcgaaatttt    10560
ggattctttc gttgaaaatt ttaccttcat cgatattcaa ggaaatcatt ttattttcat    10620
taagatggtg agtaaatgca cccgtactag aatcggtaag ctttacaccc aacataagaa    10680
taaaatcagc agattccaca aattccttca gtttggctc tgacagagta ccgttgtaaa     10740
tccccaaaaa tgagggcaat gcttcatcaa cagatgattt accaaagttc aaagtagtaa    10800
taggtaactt agtctttgaa ataaactgag taacagtctt ctctaggccg aacgatataa    10860
tttcatggcc tgtgattaca attggtttct ggcattctt cagactttcc tgtattttgt     10920
tcagaatctc ttgatcagat gtattcgacg tggaattttc cttcttaaga ggcaaggatg    10980
gttttttcagc cttagcggca gctacatcta caggtaaatt gatgtaaacc ggctttcttt   11040
cctttagtaa ggcagacaac actctatcaa tttcaacagt tgcattctcg gctgtcaata    11100
aagtcctggc agcagtaacc ggttcgtgca tcttcataaa gtgcttgaaa tcaccatcag    11160
ccaacgtatg gtgaacaaac ttaccttcgt tctgcacttt cgaggtagga gatcccacga    11220
tctcaacaac aggcaggttc tcagcatagg agcccgctaa gccattaact gcggataatt    11280
cgccaacacc aaatgtagtc aagaatgccg cagcctttt cgttcttgcg tacccgtcgg     11340
ccatatagga ggcatttaac tcattagcat ttcccaccca tttcatatct ttgtgtgaaa    11400
taatttgatc tagaaattgc aaattgtagt cacctggtac tccgaatatt tcttctatac    11460
ctaattcgtg taatctgtcc aacagatagt cacctactgt atacatttg tttactagtt     11520
tatgtgtgtt tattcgaaac taagttcttg gtgttttaaa actaaaaaaa agactaacta    11580
taaaagtaga atttaagaag tttaagaaat agatttacag aattacaatc aatacctacc    11640
gtctttatat acttattagt caagtagggg aataatttca gggaactggt ttcaacctt     11700
ttttttcagct ttttccaaat cagagagagc agaaggtaat agaaggtgta agaaaatgag   11760
atagatacat gcgtgggtca attgccttgt gtcatcattt actccaggca ggttgcatca    11820
ctccattgag gttgtgcccg ttttttgcct gtttgtgccc ctgttctctg tagttgcgct    11880
aagagaatgg acctatgaac tgatggttgg tgaagaaaac aatatttgg tgctgggatt     11940
ctttttttt ctggatgcca gcttaaaaag cgggctccat tatatttagt ggatgccagg     12000
aataaactgt tcacccagac acctacgatg ttatatattc tgtgtaaccc gccccctatt    12060
ttgggcatgc acgggttaca gcagaattaa aaggctaatt ttttgactaa ataaagttag    12120
gaaaatcact actattaatt atttacgtat tctttgaaat ggcagtattg ataatgataa    12180
actcgaactg aaaaagcgtg ttttttattc aaaatgattc taactcccctt acgtaatcaa   12240
ggaatctttt tgccttggcc tccgcgtcat taaacttctt gttgttgacg ctaacattca    12300
acgctagtat atattcgttt ttttcaggta agttctttc aacgggtctt actgatgagg     12360
```

```
cagtcgcgtc tgaacctgtt aagaggtcaa atatgtcttc ttgaccgtac gtgtcttgca    12420
tgttattagc tttgggaatt tgcatcaagt cataggaaaa tttaaatctt ggctctcttg    12480
ggctcaaggt gacaaggtcc tcgaaaatag ggcgcgcccc accgcggtgg agctccagct    12540
tttgttccct ttagtgaggg ttaattgcgc gcttggcgta atcatggtca tagctgtttc    12600
ctgtgtgaaa ttgttatccg ctcacaattc cacacaacat acgagccgga agcataaagt    12660
gtaaagcctg gggtgcctaa tgagtgagct aactcacatt aattgcgttg cgctcactgc    12720
ccgctttcca gtcgggaaac ctgtcgtgcc agctgcatta tgaatcggc caacgcgcgg    12780 ggagaggcgg tttgcgtatt gggcgctctt ccgcttcctc gctcactgac tcgctgcgct    12840
cggtcgttcg gctgcggcga gcggtatcag ctcactcaaa ggcggtaata cggttatcca    12900
cagaatcagg ggataacgca ggaaagaaca tgtgagcaaa aggccagcaa aaggccagga    12960
accgtaaaaa ggccgcgttg ctggcgtttt tccataggct ccgcccccct gacgagcatc    13020
acaaaaatcg acgctcaagt cagaggtggc gaaacccgac aggactataa agataccagg    13080
cgtttccccc tggaagctcc ctcgtgcgct ctcctgttcc gaccctgccg cttaccggat    13140
acctgtccgc ctttctccct tcgggaagcg tggcgctttc tcatagctca cgctgtaggt    13200
atctcagttc ggtgtaggtc gttcgctcca agctgggctg tgtgcacgaa ccccccgttc    13260
agcccgaccg ctgcgcctta tccggtaact atcgtcttga gtccaacccg gtaagacacg    13320
acttatcgcc actggcagca gccactggta acaggattag cagagcgagg tatgtaggcg    13380
gtgctacaga gttcttgaag tggtggccta actacggcta cactagaaga acagtatttg    13440
gtatctgcgc tctgctgaag ccagttacct tcggaaaaag agttggtagc tcttgatccg    13500
gcaaacaaac caccgctggt agcggtggtt tttttgtttg caagcagcag attacgcgca    13560
gaaaaaaagg atctcaagaa gatcctttga tcttttctac ggggtctgac gctcagtgga    13620
acgaaaactc acgttaaggg attttggtca tgagattatc aaaaaggatc ttcacctaga    13680
tccttttaaa ttaaaaatga agttttaaat caatctaaag tatatatgag taaacttggt    13740
ctgacagtta ccaatgctta atcagtgagg cacctatctc agcgatctgt ctatttcgtt    13800
catccatagt tgcctgactc cccgtcgtgt agataactac gatacgggag ggcttaccat    13860
ctggccccag tgctgcaatg ataccgcgag acccacgctc accggctcca gatttatcag    13920
caataaacca gccagccgga agggccgagc gcagaagtgg tcctgcaact ttatccgcct    13980
ccatccagtc tattaattgt tgccgggaag ctagagtaag tagttcgcca gttaatagtt    14040
tgcgcaacgt tgttgccatt gctacaggca tcgtggtgtc acgctcgtcg tttggtatgg    14100
cttcattcag ctccggttcc caacgatcaa ggcgagttac atgatccccc atgttgtgca    14160
aaaaagcggt tagctccttc ggtcctccga tcgttgtcag aagtaagttg gccgcagtgt    14220
tatcactcat ggttatggca gcactgcata attctcttac tgtcatgcca tccgtaagat    14280
gcttttctgt gactggtgag tactcaacca agtcattctg agaatagtgt atgcggcgac    14340
cgagttgctc ttgcccggcg tcaatacggg ataataccgc gccacatagc agaactttaa    14400
aagtgctcat cattggaaaa cgttcttcgg ggcgaaaact ctcaaggatc ttaccgctgt    14460
tgagatccag ttcgatgtaa cccactcgtg cacccaactg atcttcagca tcttttactt    14520
tcaccagcgt ttctgggtga gcaaaaacag gaaggcaaaa tgccgcaaaa aagggaataa    14580
gggcgacacg gaaatgttga atactcatac tcttcctttt tcaatattat tgaagcattt    14640
atcagggtta ttgtctcatg agcggataca tatttgaatg tatttagaaa aataaacaaa    14700
```

```
tagggggttcc gcgcacattt ccccgaaaag tgccacctga acgaagcatc tgtgcttcat    14760
tttgtagaac aaaaatgcaa cgcgagagcg ctaattttc aaacaaagaa tctgagctgc    14820
atttttacag aacagaaatg caacgcgaaa gcgctatttt accaacgaag aatctgtgct    14880 tcattttgt aaaacaaaaa tgcaacgcga gagcgctaat ttttcaaaca agaatctga     14940 gctgcatttt tacagaacag aaatgcaacg cgagagcgct attttaccaa caaagaatct   15000
atacttcttt tttgttctac aaaaatgcat cccgagagcg ctattttct aacaaagcat    15060 cttagattac ttttttctc ctttgtgcgc tctataatgc agtctcttga taacttttg     15120 cactgtaggt ccgttaaggt tagaagaagg ctactttggt gtctatttc tcttccataa    15180 aaaaagcctg actccacttc ccgcgtttac tgattactag cgaagctgcg ggtgcatttt   15240
ttcaagataa aggcatcccc gattatattc tataccgatg tggattgcgc atactttgtg   15300
aacagaaagt gatagcgttg atgattcttc attggtcaga aaattatgaa cggtttcttc   15360
tattttgtct ctatatacta cgtataggaa atgtttacat tttcgtattg ttttcgattc    15420
actctatgaa tagttcttac tacaattttt ttgtct                              15456

<210> SEQ ID NO 68
<211> LENGTH: 1559
<212> TYPE: DNA
<213> ORGANISM: Artificial Sequence
<220> FEATURE:
<223> OTHER INFORMATION: Template

<400> SEQUENCE: 68
gcattgcgga ttcgtattc taatgttcag taccgttcgt ataatgtatg ctatacgaag        60
ttatgcagat tgtactgaga gtgcaccata ccacctttc aattcatcat ttttttttta       120
ttcttttttt tgatttcggt ttccttgaaa ttttttgat tcggtaatct ccgaacagaa       180
ggaagaacga aggaaggagc acagacttag attggtatat atacgcatat gtagtgttga       240
agaaacatga aattgcccag tattcttaac ccaactgcac agaacaaaaa cctgcaggaa       300
acgaagataa atcatgtcga aagctacata taaggaacgt gctgctactc atcctagtcc       360
tgttgctgcc aagctattta atatcatgca cgaaaagcaa acaaacttgt gtgcttcatt       420
ggatgttcgt accaccaagg aattactgga gttagttgaa gcattaggtc ccaaaatttg       480
tttactaaaa acacatgtgg atatcttgac tgattttcc atggagggca cagttaagcc       540
gctaaaggca ttatccgcca agtacaattt tttactcttc gaagacagaa atttgctga      600 cattggtaat acagtcaaat tgcagtactc tgcgggtgta tacagaatag cagaatgggc      660
agacattacg aatgcacacg gtgtggtggg cccaggtatt gttagcggtt tgaagcaggc     720
ggcagaagaa gtaacaaagg aacctagagg cctttttgatg ttagcagaat tgtcatgcaa     780
gggctcccta tctactggag aatatactaa gggtactgtt gacattgcga agagcgacaa     840
agattttgtt atcggcttta ttgctcaaag agacatgggt ggaagagatg aaggttacga     900
ttggttgatt atgacacccg gtgtgggttt agatgacaag ggagacgcat gggtcaaca     960 gtatagaacc gtggatgatg tggtctctac aggatctgac attattattg ttggaagagg    1020
actatttgca aagggaaggg atgctaaggt agagggtgaa cgttacagaa aagcaggctg    1080
ggaagcatat ttgagaagat gcggccagca aaactaaaaa actgtattat aagtaaatgc    1140
atgtatacta aactcacaaa ttagagcttc aatttaatta tatcagttat tacccctatgc    1200 ggtgtgaaat accgcacaga tgcgtaagga gaaaataccg catcaggaaa ttgtaaacgt    1260
taatattttg ttaaaattcg cgttaaattt ttgttaaatc agctcatttt ttaaccaata    1320
```

```
ggccgaaatc ggcaaaatcc cttataaatc aaaagaatag accgagatag ggttgagtgt    1380
tgttccagtt tggaacaaga gtccactatt aaagaacgtg gactccaacg tcaaagggcg    1440
aaaaaccgtc tatcagggcg atggcccact acgtgaacca tcaccctaat caagataact    1500
tcgtataatg tatgctatac gaacggtacc agtgatgata caacgagtta gccaaggtg     1559

<210> SEQ ID NO 69
<211> LENGTH: 1047
<212> TYPE: DNA
<213> ORGANISM: Alcaligenes xylosoxydans

<400> SEQUENCE: 69
atgaaagctc tggtttatca cggtgaccac aagatctcgc ttgaagacaa gcccaagccc      60
acccttcaaa agcccacgga tgtagtagta cgggttttga agaccacgat ctgcggcacg     120
gatctcggca tctacaaagg caagaatcca gaggtcgccg acgggcgcat cctgggccat     180 gaagggg tag cgtcatcga ggaagtgggc gagagtgtca cgcagttcaa gaaaggcgac     240
aaggtcctga tttcctgcgt cacttcttgc ggctcgtgcg actactgcaa gaagcagctt     300
tactcccatt gccgcgacgg cggggtggat cctgggttaca tgatcgatgg cgtgcaggcc     360
gaatacgtcc gcatcccgca tgccgacaac agcctctaca gatcccccca gacaattgac     420
gacgaaatcg ccgtcctgct gagcgacatc ctgcccaccg ccacgaaaat cggcgtccag     480
tatgggaatg tccagccggg cgatgcggtg gctattgtcg gcgcgggccc cgtcggcatg     540
tccgtactgt tgaccgccca gttctactcc ccctcgacca tcatcgtgat cgacatggac     600
gagaatcgcc tccagctcgc caaggagctc ggggcaacgc acaccatcaa ctccggcacg     660
gagaacgttg tcgaagccgt gcataggatt gcggcagagg gagtcgatgt tgcgatcgag     720
gcggtgggca taccggcgac ttgggacatc tgccaggaga tcgtcaagcc cggcgcgcac     780
atcgccaacg tcggcgtgca tggcgtcaag gttgacttcg agattcagaa gctctggatc     840
aagaacctga cgatcaccac gggactggtg aacacgaaca cgacgcccat gctgatgaag     900
gtcgcctcga ccgacaagct tccgttgaag aagatgatta cccatcgctt cgagctggcc     960
gagatcgagc acgcctatca ggtattcctc aatggcgcca aggagaaggc gatgaagatc    1020
atcctctcga acgcaggcgc tgcctga                                      1047

<210> SEQ ID NO 70
<211> LENGTH: 348
<212> TYPE: PRT
<213> ORGANISM: Alcaligenes xylosoxydans

<400> SEQUENCE: 70

Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Arg Val
            20                  25                  30

Leu Lys Thr Thr Ile Cys Gly Thr Asp Leu Gly Ile Tyr Lys Gly Lys
        35                  40                  45

Asn Pro Glu Val Ala Asp Gly Arg Ile Leu Gly His Glu Gly Val Gly
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95
```

```
Lys Lys Gln Leu Tyr Ser His Cys Arg Asp Gly Gly Trp Ile Leu Gly
            100                 105                 110
Tyr Met Ile Asp Gly Val Gln Ala Glu Tyr Val Arg Ile Pro His Ala
        115                 120                 125
Asp Asn Ser Leu Tyr Lys Ile Pro Gln Thr Ile Asp Asp Glu Ile Ala
    130                 135                 140
Val Leu Leu Ser Asp Ile Leu Pro Thr Gly His Glu Ile Gly Val Gln
145                 150                 155                 160
Tyr Gly Asn Val Gln Pro Gly Asp Ala Val Ala Ile Val Gly Ala Gly
                165                 170                 175
Pro Val Gly Met Ser Val Leu Leu Thr Ala Gln Phe Tyr Ser Pro Ser
            180                 185                 190
Thr Ile Ile Val Ile Asp Met Asp Glu Asn Arg Leu Gln Leu Ala Lys
        195                 200                 205
Glu Leu Gly Ala Thr His Thr Ile Asn Ser Gly Thr Glu Asn Val Val
    210                 215                 220
Glu Ala Val His Arg Ile Ala Ala Glu Gly Val Asp Val Ala Ile Glu
225                 230                 235                 240
Ala Val Gly Ile Pro Ala Thr Trp Asp Ile Cys Gln Glu Ile Val Lys
                245                 250                 255
Pro Gly Ala His Ile Ala Asn Val Gly Val His Gly Val Lys Val Asp
            260                 265                 270
Phe Glu Ile Gln Lys Leu Trp Ile Lys Asn Leu Thr Ile Thr Thr Gly
        275                 280                 285
Leu Val Asn Thr Asn Thr Thr Pro Met Leu Met Lys Val Ala Ser Thr
    290                 295                 300
Asp Lys Leu Pro Leu Lys Lys Met Ile Thr His Arg Phe Glu Leu Ala
305                 310                 315                 320
Glu Ile Glu His Ala Tyr Gln Val Phe Leu Asn Gly Ala Lys Glu Lys
                325                 330                 335
Ala Met Lys Ile Ile Leu Ser Asn Ala Gly Ala Ala
            340                 345

<210> SEQ ID NO 71
<211> LENGTH: 1644
<212> TYPE: DNA
<213> ORGANISM: Artificial Sequence
<220> FEATURE:
<223> OTHER INFORMATION: codon optimized L. lactis kivD coding region
      for S. cerevisiae expression

<400> SEQUENCE: 71
atgtatacag taggtgacta tctgttggac agattacacg aattaggtat agaagaaata    60 ttcgagtac caggtgacta caatttgcaa tttctagatc aaattatttc acacaaagat    120
atgaaatggg tgggaaatgc taatgagtta atgcctcct atatggccga cgggtacgca    180
agaacgaaaa aggctgcggc attcttgact acatttggtg ttggcgaatt atccgcagtt    240
aatggcttag cgggctccta tgctgagaac ctgcctgttg ttgagatcgt gggatctcct    300
acctcgaaag tgcagaacga aggtaagttt gttcaccata cgttggctga tggtgatttc    360
aagcacttta tgaagatgca cgaaccggtt actgctgcca ggactttatt gacagccgag    420
aatgcaactg ttgaaattga tagtgttgtg tctgccttac taaggaaag aaagccggtt    480 tacatcaatt tacctgtaga gtagctgcc gctaaggctg aaaaaccatc cttgcctctt    540
aagaaggaaa attccacgtc gaatacatct gatcaagaga ttctgaacaa atacaggaa    600
```

| | |
|---|---|
| agtctgaaga atgccaagaa accaattgta atcacaggcc atgaaattat atcgttcggc | 660 |
| ctagagaaga ctgttactca gtttatttca aagactaagt tacctattac tactttgaac | 720 |
| tttggtaaat catctgttga tgaagcattg ccctcatttt tggggattta caacggtact | 780 |
| ctgtcagagc caaacttgaa ggaatttgtg gaatctgctg attttattct tatgttgggt | 840 |
| gtaaagctta ccgattctag tacgggtgca tttactcacc atcttaatga aaataaaatg | 900 |
| atttccttga atatcgatga aggtaaaatt ttcaacgaaa gaatccaaaa tttcgacttc | 960 |
| gaatccctga tatcatctct tcttgacttg tccgaaattg aatataaagg caagtacata | 1020 |
| gataaaaagc aagaagattt tgtaccttct aacgcgctgt tgtcacaaga tagactgtgg | 1080 |
| caagctgtcg aaaatttgac ccaaagtaat gagacgatcg tggctgaaca aggcacttct | 1140 |
| ttcttcggtg cctcatctat atttctgaaa tcgaaatcac attttattgg tcaacccttg | 1200 |
| tggggatcta taggatacac tttccccgca gctctaggca gccaaattgc agataaagaa | 1260 |
| tctagacatt tattgtttat cggagatgga tcattgcaac tgactgtcca agaattagga | 1320 |
| ctagccatta gagagaagat aaacccaatc tgctttatca ttaataacga tggttacacg | 1380 |
| gttgagaggg aaattcatgg tccgaaccag agttataatg acattcctat gtggaattac | 1440 |
| tcaaaactgc cagaaagttt cggggcaacg gaagacagag ttgtgtccaa aattgtgaga | 1500 |
| acagaaaatg aattcgtatc cgtgatgaaa gaagctcaag cagatccaaa taggatgtat | 1560 |
| tggatagaac ttattctagc aaaggagggt gcacctaaag ttttgaaaaa gatgggtaag | 1620 |
| ttatttgcag aacaaaacaa gagc | 1644 |

<210> SEQ ID NO 72
<211> LENGTH: 753
<212> TYPE: DNA
<213> ORGANISM: Saccharomyces cerevisiae

<400> SEQUENCE: 72

| | |
|---|---|
| gcatgcttgc atttagtcgt gcaatgtatg actttaagat tgtgagcag gaagaaaagg | 60 |
| gagaatcttc taacgataaa cccttgaaaa actgggtaga ctacgctatg ttgagttgct | 120 |
| acgcaggctg cacaattaca cgagaatgct cccgcctagg atttaaggct aagggacgtg | 180 |
| caatgcagac gacagatcta aatgaccgtg tcggtgaagt gttcgccaaa cttttcggtt | 240 |
| aacacatgca gtgatgcacg cgcgatgtg ctaagttaca tatatatata tatagccata | 300 |
| gtgatgtcta agtaaccttt atggtatatt tcttaatgtg gaaagatact agcgcgcgca | 360 |
| cccacacaca agcttcgtct tttcttgaag aaaagaggaa gctcgctaaa tgggattcca | 420 |
| cttttccgttc cctgccagct gatggaaaaa ggttagtgga acgatgaaga ataaaagag | 480 |
| agatccactg aggtgaaatt tcagctgaca gcgagtttca tgatcgtgat gaacaatggt | 540 |
| aacgagttgt ggctgttgcc agggagggtg gttctcaact tttaatgtat ggccaaatcg | 600 |
| ctacttgggt tgttatata acaaagaaga ataatgaac tgattctctt cctccttctt | 660 |
| gtcctttctt aattctgttg taattacctt cctttgtaat ttttttgta attattcttc | 720 |
| ttaataatcc aaacaaacac acatattaca ata | 753 |

<210> SEQ ID NO 73
<211> LENGTH: 316
<212> TYPE: DNA
<213> ORGANISM: Saccharomyces cerevisiae

<400> SEQUENCE: 73

| | |
|---|---|
| gagtaagcga atttcttatg atttatgatt tttattatta aataagttat aaaaaaaata | 60 |

```
agtgtataca aattttaaag tgactcttag gttttaaaac gaaaattctt attcttgagt    120
aactctttcc tgtaggtcag gttgctttct caggtatagc atgaggtcgc tcttattgac    180
cacacctcta ccggcatgcc gagcaaatgc ctgcaaatcg ctccccattt cacccaattg    240
tagatatgct aactccagca atgagttgat gaatctcggt gtgtatttta tgtcctcaga    300
ggacaacacc tgtggt                                                     316
```

<210> SEQ ID NO 74
<211> LENGTH: 30
<212> TYPE: DNA
<213> ORGANISM: Artificial Sequence
<220> FEATURE:
<223> OTHER INFORMATION: primer

<400> SEQUENCE: 74

```
ggaattcaca catgaaagct ctggtttatc                                       30
```

<210> SEQ ID NO 75
<211> LENGTH: 28
<212> TYPE: DNA
<213> ORGANISM: Artificial Sequence
<220> FEATURE:
<223> OTHER INFORMATION: Primer

<400> SEQUENCE: 75

```
gcgtccaggg cgtcaaagat caggcagc                                         28
```

<210> SEQ ID NO 76
<211> LENGTH: 55
<212> TYPE: DNA
<213> ORGANISM: Artificial Sequence
<220> FEATURE:
<223> OTHER INFORMATION: Primer

<400> SEQUENCE: 76

```
aaacaaacac acatattaca atagctgagg atgaaagctc tggtttatca cggtg           55
```

<210> SEQ ID NO 77
<211> LENGTH: 55
<212> TYPE: DNA
<213> ORGANISM: Artificial Sequence
<220> FEATURE:
<223> OTHER INFORMATION: primer

<400> SEQUENCE: 77

```
atcataagaa attcgcttac tcttaattaa tcaggcagcg cctgcgttcg agagg           55
```

<210> SEQ ID NO 78
<211> LENGTH: 8994
<212> TYPE: DNA
<213> ORGANISM: Artificial Sequence
<220> FEATURE:
<223> OTHER INFORMATION: constructed plasmid

<400> SEQUENCE: 78

```
ctagttctag agcggccgcc accgcggtgg agctccagct tttgttccct ttagtgaggg     60
ttaattgcgc gcttggcgta atcatggtca tagctgtttc ctgtgtgaaa ttgttatccg    120
ctcacaattc cacacaacat aggagccgga agcataaagt gtaaagcctg gggtgcctaa    180
tgagtgaggt aactcacatt aattgcgttg cgctcactgc ccgctttcca gtcgggaaac    240
ctgtcgtgcc agctgcatta atgaatcggc caacgcgcgg ggagaggcgg tttgcgtatt    300
```

```
gggcgctctt ccgcttcctc gctcactgac tcgctgcgct cggtcgttcg gctgcggcga    360
gcggtatcag ctcactcaaa ggcggtaata cggttatcca cagaatcagg ggataacgca    420
ggaaagaaca tgtgagcaaa aggccagcaa aaggccagga accgtaaaaa ggccgcgttg    480
ctggcgtttt tccataggct ccgcccccct gacgagcatc acaaaaatcg acgctcaagt    540
cagaggtggc gaaacccgac aggactataa agataccagg cgtttccccc tggaagctcc    600
ctcgtgcgct ctcctgttcc gaccctgccg cttaccggat acctgtccgc ctttctccct    660
tcgggaagcg tggcgctttc tcatagctca cgctgtaggt atctcagttc ggtgtaggtc    720
gttcgctcca agctgggctg tgtgcacgaa ccccccgttc agcccgaccg ctgcgcctta    780
tccggtaact atcgtcttga gtccaacccg gtaagacacg acttatcgcc actggcagca    840
gccactggta acaggattag cagagcgagg tatgtaggcg gtgctacaga gttcttgaag    900
tggtggccta actacggcta cactagaagg acagtatttg gtatctgcgc tctgctgaag    960
ccagttacct tcggaaaaag agttggtagc tcttgatccg gcaaacaaac caccgctggt   1020
agcggtggtt tttttgtttg caagcagcag attacgcgca gaaaaaaagg atctcaagaa   1080
gatcctttga tcttttctac ggggtctgac gctcagtgga acgaaaactc acgttaaggg   1140
attttggtca tgagattatc aaaaaggatc ttcacctaga tccttttaaa ttaaaaatga   1200
agttttaaat caatctaaag tatatatgag taaacttggt ctgacagtta ccaatgctta   1260
atcagtgagg cacctatctc agcgatctgt ctatttcgtt catccatagt tgcctgactc   1320
cccgtcgtgt agataactac gatacgggag ggcttaccat ctggccccag tgctgcaatg   1380
ataccgcgag acccacgctc accggctcca gatttatcag caataaacca gccagccgga   1440
agggccgagc gcagaagtgg tcctgcaact ttatccgcct ccatccagtc tattaattgt   1500
tgccgggaag ctagagtaag tagttcgcca gttaatagtt tgcgcaacgt tgttgccatt   1560
gctacaggca tcgtggtgtc acgctcgtcg tttggtatgg cttcattcag ctccggttcc   1620
caacgatcaa ggcgagttac atgatccccc atgttgtgca aaaaagcggt tagctccttc   1680
ggtcctccga tcgttgtcag aagtaagttg gccgcagtgt tatcactcat ggttatggca   1740
gcactgcata attctcttac tgtcatgcca tccgtaagat gcttttctgt gactggtgag   1800
tactcaacca agtcattctg agaatagtgt atgcggcgac cgagttgctc ttgcccggcg   1860
tcaatacggg ataataccgc gccacatagc agaactttaa aagtgctcat cattggaaaa   1920
cgttcttcgg ggcgaaaact ctcaaggatc ttaccgctgt tgagatccag ttcgatgtaa   1980
cccactcgtg cacccaactg atcttcagca tcttttactt tcaccagcgt ttctgggtga   2040
gcaaaaacag gaaggcaaaa tgccgcaaaa aagggaataa gggcgacacg gaaatgttga   2100
atactcatac tcttcctttt tcaatattat tgaagcattt atcagggtta ttgtctcatg   2160
agcggataca tatttgaatg tatttagaaa aataaacaaa taggggttcc gcgcacattt   2220
ccccgaaaag tgccacctga cgaagcatc tgtgcttcat tttgtagaac aaaaatgcaa   2280
cgcgagagcg ctaattttc aaacaaagaa tctgagctgc attttacag aacagaaatg   2340
caacgcgaaa gcgctatttt accaacgaag aatctgtgct tcattttgt aaaacaaaaa   2400
tgcaacgcga gagcgctaat ttttcaaaca agaatctga gctgcatttt tacagaacag   2460
aaatgcaacg cgagagcgct attttaccaa caaagaatct atacttcttt tttgttctac   2520
aaaaatgcat cccgagagcg ctattttttct aacaaagcat cttagattac ttttttttctc   2580
ctttgtgcgc tctataatgc agtctcttga taacttttg cactgtaggt ccgttaaggt   2640
tagaagaagg ctactttggt gtctattttc tcttccataa aaaaagcctg actccacttc   2700
```

```
ccgcgtttac tgattactag cgaagctgcg ggtgcatttt ttcaagataa aggcatcccc   2760
gattatattc tataccgatg tggattgcgc atactttgtg aacagaaagt gatagcgttg   2820
atgattcttc attggtcaga aaattatgaa cggtttcttc tattttgtct ctatatacta   2880
cgtataggaa atgtttacat tttcgtattg ttttcgattc actctatgaa tagttcttac   2940
tacaattttt ttgtctaaag agtaatacta gagataaaca taaaaaatgt agaggtcgag   3000
tttagatgca agttcaagga gcgaaaggtg gatgggtagg ttatataggg atatagcaca   3060
gagatatata gcaaagagat acttttgagc aatgtttgtg gaagcggtat tcgcaatatt   3120
ttagtagctc gttacagtcc ggtgcgtttt tggttttttg aaagtgcgtc ttcagagcgc   3180
ttttggtttt caaaagcgct ctgaagttcc tatactttct agagaatagg aacttcggaa   3240
taggaacttc aaagcgtttc cgaaaacgag cgcttccgaa aatgcaacgc gagctgcgca   3300
catacagctc actgttcacg tcgcacctat atctgcgtgt tgcctgtata tatatataca   3360
tgagaagaac ggcatagtgc gtgtttatgc ttaaatgcgt acttatatgc gtctatttat   3420
gtaggatgaa aggtagtcta gtacctcctg tgatattatc ccattccatg cggggtatcg   3480
tatgcttcct tcagcactac cctttagctg ttctatatgc tgccactcct caattggatt   3540
agtctcatcc ttcaatgcta tcatttcctt tgatattgga tcatactaag aaaccattat   3600
tatcatgaca ttaacctata aaaataggcg tatcacgagg cccttttcgtc tcgcgcgttt   3660 cggtgatgac ggtgaaaacc tctgacacat gcagctcccg gagacggtca cagcttgtct   3720
gtaagcggat gccgggagca gacaagcccg tcagggcgcg tcagcgggtg ttggcgggtg   3780
tcggggctgg cttaactatg cggcatcaga gcagattgta ctgagagtgc accatatcga   3840
ctacgtcgta aggccgtttc tgacagagta aaattcttga gggaactttc accattatgg   3900
gaaatgcttc aagaaggtat tgacttaaac tccatcaaat ggtcaggtca ttgagtgttt   3960
tttatttgtt gtattttttt tttttagag aaaatcctcc aatatcaaat taggaatcgt   4020
agtttcatga ttttctgtta cacctaactt tttgtgtggt gccctcctcc ttgtcaatat   4080
taatgttaaa gtgcaattct ttttccttat cacgttgagc cattagtatc aatttgctta   4140
cctgtattcc tttactatcc tccttttct ccttcttgat aaatgtatgt agattgcgta   4200
tatagtttcg tctaccctat gaacatattc cattttgtaa tttcgtgtcg tttctattat   4260
gaatttcatt tataaagttt atgtacaaat atcataaaaa aagagaatct ttttaagcaa   4320 ggatttctt aacttcttcg gcgacagcat caccgacttc ggtggtactg ttggaaccac   4380
ctaaatcacc agttctgata cctgcatcca aaaccttttt aactgcatct tcaatggcct   4440
taccttcttc aggcaagttc aatgacaatt tcaacatcat tgcagcagac aagatagtgg   4500
cgatagggtc aaccttattc tttggcaaat ctggagcaga accgtggcat ggttcgtaca   4560
aaccaaatgc ggtgttcttg tctggcaaag aggccaagga cgcagatggc aacaaaccca   4620
aggaacctgg gataacggag gcttcatcgg agatgatatc accaaacatg ttgctggtga   4680
ttataatacc atttaggtgg gttgggttct taactaggat catggcggca gaatcaatca   4740
attgatgttg aaccttcaat gtagggaatt cgttcttgat ggtttcctcc acagtttttc   4800
tccataatct tgaagaggcc aaaagattag ctttatccaa ggaccaaata ggcaatggtg   4860
gctcatgttg tagggccatg aaagcggcca ttcttgtgat tctttgcact tctggaacgg   4920
tgtattgttc actatcccaa gcgacaccat caccatcgtc ttcctttctc ttaccaaagt   4980
aaatacctcc cactaattct ctgacaacaa cgaagtcagt acctttagca aattgtggct   5040
```

```
tgattggaga taagtctaaa agagagtcgg atgcaaagtt acatggtctt aagttggcgt    5100
acaattgaag ttctttacgg attttttagta aaccttgttc aggtctaaca ctaccggtac    5160
cccatttagg accagccaca gcacctaaca aaacggcatc aaccttcttg gaggcttcca    5220
gcgcctcatc tggaagtggg acacctgtag catcgatagc agcaccacca attaaatgat    5280
tttcgaaatc gaacttgaca ttggaacgaa catcagaaat agctttaaga accttaatgg    5340
cttcggctgt gatttcttga ccaacgtggt cacctggcaa aacgacgatc ttcttagggg    5400
cagacatagg ggcagacatt agaatggtat atccttgaaa tatatatata tattgctgaa    5460
atgtaaaagg taagaaaagt tagaaagtaa gacgattgct aaccacctat tggaaaaaac    5520
aataggtcct taaataatat tgtcaacttc aagtattgtg atgcaagcat ttagtcatga    5580
acgcttctct attctatatg aaaagccggt tccggcctct cacctttcct ttttctccca    5640
attttttcagt tgaaaaaggt atatgcgtca ggcgacctct gaaattaaca aaaaatttcc    5700
agtcatcgaa tttgattctg tgcgatagcg ccctgtgtg ttctcgttat gttgaggaaa    5760
aaaataatgg ttgctaagag attcgaactc ttgcatctta cgatacctga gtattcccac    5820
agttaactgc ggtcaagata tttcttgaat caggcgcctt agaccgctcg gccaaacaac    5880
caattacttg ttgagaaata gagtataatt atcctataaa tataacgttt ttgaacacac    5940
atgaacaagg aagtacagga caattgattt tgaagagaat gtggattttg atgtaattgt    6000
tgggattcca tttttaataa ggcaataata ttaggtatgt ggatatacta gaagttctcc    6060
tcgaccgtcg atatgcggtg tgaaataccg cacagatgcg taaggagaaa ataccgcatc    6120
aggaaattgt aaacgttaat attttgttaa aattcgcgtt aaattttgt taaatcagct    6180
catttttttaa ccataggcc gaaatcggca aaatccctta taaatcaaaa gaatagaccg    6240
agatagggtt gagtgttgtt ccagtttgga acaagagtcc actattaaag aacgtggact    6300
ccaacgtcaa agggcgaaaa accgtctatc agggcgatgg cccactacgt gaaccatcac    6360
cctaatcaag ttttttgggg tcgaggtgcc gtaaagcact aaatcggaac cctaaaggga    6420
gcccccgatt tagagcttga cggggaaagc cggcgaacgt ggcgagaaag gaagggaaga    6480
aagcgaaagg agcgggcgct agggcgctgg caagtgtagc ggtcacgctg cgcgtaacca    6540
ccacacccgc cgcgcttaat gcgccgctac agggcgcgtc gcgccattcg ccattcaggc    6600
tgcgcaactg ttgggaaggg cgatcggtgc gggcctcttc gctattacgc cagctggcga    6660
aaggggatg tgctgcaagg cgattaagtt gggtaacgcc agggttttcc cagtcacgac    6720
gttgtaaaac gacggccagt gagcgcgcgt aatacgactc actataggc gaattgggta    6780
ccgggcccc cctcgaggtc gacggtatcg ataagcttga tatcgaattc ctgcagcccg    6840
ggggatccgc atgcttgcat ttagtcgtgc aatgtatgac tttaagattt gtgagcagga    6900
agaaaaggga gaatcttcta acgataaacc cttgaaaaac tgggtagact acgctatgtt    6960
gagttgctac gcaggctgca caattacacg agaatgctcc cgcctaggat ttaaggctaa    7020
gggacgtgca atgcagacga cagatctaaa tgaccgtgtc ggtgaagtgt tcgccaaact    7080
tttcggttaa cacatgcagt gatgcacgcg cgatggtgct aagttacata tatatatata    7140
tatatatata tagccatagt gatgtctaag taacctttat ggtatatttc ttaatgtgga    7200
aagatactag cgcgcgcacc cacacacaag cttcgtcttt tcttgaagaa agaggaagc    7260
tcgctaaatg ggattccact ttccgttccc tgccagctga tggaaaaagg ttagtggaac    7320
gatgaagaat aaaaagagag atccactgag gtgaaatttc agctgacagc gagtttcatg    7380
atcgtgatga acaatggtaa cgagttgtgg ctgttgccag ggagggtggt tctcaacttt    7440
```

```
taatgtatgg ccaaatcgct acttgggttt gttatataac aaagaagaaa taatgaactg   7500
attctcttcc tccttcttgt cctttcttaa ttctgttgta attaccttcc tttgtaattt   7560
tttttgtaat tattcttctt aataatccaa acaaacacac atattacaat agctagctga   7620
ggatgaaggc attagtttat catggggatc acaaaatttc gttagaagac aaaccaaaac   7680
ccactctgca gaaaccaaca gacgttgtgg ttagggtgtt gaaaacaaca atttgcggta   7740
ctgacttggg aatatacaaa ggtaagaatc ctgaagtggc agatggcaga atcctgggtc   7800
atgagggcgt tggcgtcatt gaagaagtgg gcgaatccgt gacacaattc aaaaagggg   7860 ataaagttt aatctcctgc gttactagct gtggatcgtg tgattattgc aagaagcaac    7920
tgtattcaca ctgtagagac ggtggctgga ttttaggtta catgatcgac ggtgtccaag   7980
ccgaatacgt cagaatacca catgctgaca attcattgta taagatcccg caaactatcg   8040
atgatgaaat tgcagtacta ctgtccgata ttttacctac tggacatgaa attggtgttc   8100
aatatggtaa cgttcaacca ggcgatgctg tagcaattgt aggagcaggt cctgttggaa   8160
tgtcagtttt gttaactgct caattttact cgcctagtac cattattgtt atcgacatgg   8220
acgaaaaccg tttacaatta gcgaaggagc ttggggccac acacactatt aactccggta   8280
ctgaaaatgt tgtcgaagct gtgcatcgta tagcagccga aggagtggat gtagcaatag   8340
aagctgttgg tatacccgca acctgggaca tctgtcagga aattgtaaaa cccgcgctc    8400 atattgccaa cgtgggagtt catggtgtta aggtggactt tgaaattcaa aagttgtgga   8460
ttaagaatct aaccatcacc actggtttgg ttaacactaa tactacccca atgttgatga   8520
aggtagcctc tactgataaa ttgcctttaa agaaaatgat tactcacagg tttgagttag   8580
ctgaaatcga acacgcatat caggttttct tgaatggcgc taagaaaaaa gctatgaaga   8640
ttattctatc taatgcaggt gccgcctaat taattaagag taagcgaatt tcttatgatt   8700
tatgattttt attattaaat aagttataaa aaaataagt gtatacaaat tttaaagtga    8760
ctcttaggtt ttaaaacgaa aattcttatt cttgagtaac tctttcctgt aggtcaggtt   8820
gctttctcag gtatagcatg aggtcgctct tattgaccac acctctaccg gcatgccgag   8880
caaatgcctg caaatcgctc cccatttcac ccaattgtag atatgctaac tccagcaatg   8940
agttgatgaa tctcggtgtg tatttatgt cctcagagga caacacctgt ggta           8994
```

<210> SEQ ID NO 79
<211> LENGTH: 2145
<212> TYPE: DNA
<213> ORGANISM: Artificial Sequence
<220> FEATURE:
<223> OTHER INFORMATION: constructed chimeric gene

<400> SEQUENCE: 79

```
gcatgcttgc atttagtcgt gcaatgtatg actttaagat ttgtgagcag gaagaaaagg     60
gagaatcttc taacgataaa cccttgaaaa actgggtaga ctacgctatg ttgagttgct    120
acgcaggctg cacaattaca cgagaatgct cccgcctagg atttaaggct aagggacgtg    180
caatgcagac gacagatcta aatgaccgtg tcggtgaagt gttcgccaaa cttttcggtt    240
aacacatgca gtgatgcacg cgcgatggtg ctaagttaca tatatatata tatatatata    300
tatagccata gtgatgtcta agtaaccttt atggtatatt tcttaatgtg gaaagatact    360
agcgcgcgca cccacacaca agcttcgtct tttcttgaag aaaagaggaa gctcgctaaa    420
tgggattcca ctttccgttc cctgccagct gatggaaaaa ggttagtgga acgatgaaga    480
```

```
ataaaaagag agatccactg aggtgaaatt tcagctgaca gcgagtttca tgatcgtgat    540
gaacaatggt aacgagttgt ggctgttgcc agggagggtg gttctcaact tttaatgtat    600
ggccaaatcg ctacttgggt tgttatata acaaagaaga aataatgaac tgattctctt     660
cctccttctt gtcctttctt aattctgttg taattaccett cctttgtaat tttttttgta   720
attattcttc ttaataatcc aaacaaacac acatattaca atagctagct gaggatgaag    780
gcattagttt atcatgggga tcacaaaatt tcgttagaag acaaaccaaa acccactctg    840
cagaaaccaa cagacgttgt ggttagggtg ttgaaaacaa caatttgcgg tactgacttg    900
ggaatataca aaggtaagaa tcctgaagtg gcagatggca gaatcctggg tcatgagggc    960
gttggcgtca ttgaagaagt gggcgaatcc gtgacacaat tcaaaaaggg ggataaagtt   1020
ttaatctcct gcgttactag ctgtggatcg tgtgattatt gcaagaagca actgtattca   1080
cactgtagag acggtggctg gatttttaggt tacatgatcg acggtgtcca agccgaatac  1140
gtcagaatac cacatgctga caattcattg tataagatcc cgcaaactat cgatgatgaa   1200
attgcagtac tactgtccga tattttacct actggacatg aaattggtgt tcaatatggt   1260
aacgttcaac caggcgatgc tgtagcaatt gtaggagcag gtcctgttgg aatgtcagtt   1320
ttgttaactg ctcaattta ctcgcctagt accattattg ttatcgacat ggacgaaaac    1380
cgtttacaat agcgaagga gcttgggggcc acacacacta ttaactccgg tactgaaaat   1440
gttgtcgaag ctgtgcatcg tatagcagcc gaaggagtgg atgtagcaat agaagctgtt   1500
ggtatacccg caacctggga catctgtcag gaaattgtaa acccggcgc tcatattgcc    1560
aacgtgggag ttcatggtgt taaggtggac tttgaaattc aaaagttgtg gattaagaat   1620
ctaaccatca ccactggttt ggttaacact aatactaccc caatgttgat gaaggtagcc   1680
tctactgata aattgccttt aaagaaaatg attactcaca ggtttgagtt agctgaaatc   1740
gaacacgcat atcaggtttt cttgaatggc gctaaagaaa aagctatgaa gattattcta   1800
tctaatgcag gtgccgccta attaattaag agtaagcgaa tttcttatga tttatgatttt  1860
ttattattaa ataagttata aaaaaaataa gtgtatacaa attttaaagt gactcttagg   1920
ttttaaaacg aaaattctta ttcttgagta actctttcct gtaggtcagg ttgctttctc    1980
aggtatagca tgaggtcgct cttattgacc acacctctac cggcatgccg agcaaatgcc   2040
tgcaaatcgc tccccatttc acccaattgt agatatgcta actccagcaa tgagttgatg   2100
aatctcggtg tgtattttat gtcctcagag gacaacacct gtggt                   2145

<210> SEQ ID NO 80
<211> LENGTH: 4280
<212> TYPE: DNA
<213> ORGANISM: Artificial Sequence
<220> FEATURE:
<223> OTHER INFORMATION: vector

<400> SEQUENCE: 80
ggggatcctc tagagtcgac ctgcaggcat gcaagcttgg cgtaatcatg gtcatagctg     60
tttcctgtgt gaaattgtta tccgctcaca attccacaca acatacgagc cggaagcata    120
aagtgtaaag cctggggtgc ctaatgagtg agctaactca cattaattgc gttgcgctca    180
ctgcccgctt tccagtcggg aaacctgtcg tgccagctgc attaatgaat cggccaacgc    240
gcggggagag gcggtttgcg tattgggcgc tcttccgctt cctcgctcac tgactcgctg    300
cgctcggtcg ttcggctgcg gcgagcggta tcagctcact caaaggcggt aatacggtta    360
tccacagaat caggggataa cgcaggaaag aacatgtgag caaaaggcca gcaaaaggcc    420
```

```
aggaaccgta aaaaggccgc gttgctggcg ttttccata ggctccgccc ccctgacgag    480
catcacaaaa atcgacgctc aagtcagagg tggcgaaacc cgacaggact ataaagatac    540
caggcgtttc ccctggaag ctccctcgtg cgctctcctg ttccgaccct gccgcttacc     600
ggatacctgt ccgcctttct ccttcggga agcgtggcgc tttctcatag ctcacgctgt     660
aggtatctca gttcggtgta ggtcgttcgc tccaagctgg gctgtgtgca cgaacccccc    720
gttcagcccg accgctgcgc cttatccggt aactatcgtc ttgagtccaa cccggtaaga    780
cacgacttat cgccactggc agcagccact ggtaacagga ttagcagagc gaggtatgta    840
ggcggtgcta cagagttctt gaagtggtgg cctaactacg gctacactag aaggacagta    900
tttggtatct gcgctctgct gaagccagtt accttcggaa aaagagttgg tagctcttga    960
tccggcaaac aaaccaccgc tggtagcggt ggtttttttg tttgcaagca gcagattacg   1020
cgcagaaaaa aaggatctca agaagatcct ttgatctttt ctacggggtc tgacgctcag   1080
tggaacgaaa actcacgtta agggattttg gtcatgagat tatcaaaaag gatcttcacc   1140
tagatccttt taaattaaaa atgaagtttt aaatcaatct aaagtatata tgagtaaact   1200
tggtctgaca gttaccaatg cttaatcagt gaggcaccta tctcagcgat ctgtctattt   1260
cgttcatcca tagttgcctg actccccgtc gtgtagataa ctacgatacg ggagggctta   1320
ccatctggcc ccagtgctgc aatgataccg cgagacccac gctcaccggc tccagattta   1380
tcagcaataa accagccagc cggaagggcc gagcgcagaa gtggtcctgc aactttatcc   1440
gcctccatcc agtctattaa ttgttgccgg gaagctagag taagtagttc gccagttaat   1500
agtttgcgca acgttgttgc cattgctaca ggcatcgtgg tgtcacgctc gtcgtttggt   1560
atggcttcat tcagctccgg ttcccaacga tcaaggcgag ttacatgatc ccccatgttg   1620
tgcaaaaaag cggttagctc cttcggtcct ccgatcgttg tcagaagtaa gttggccgca   1680
gtgttatcac tcatggttat ggcagcactg cataattctc ttactgtcat gccatccgta   1740
agatgctttt ctgtgactgg tgagtactca accaagtcat tctgagaata gtgtatgcgg   1800
cgaccgagtt gctcttgccc ggcgtcaata cgggataata ccgcgccaca tagcagaact   1860
ttaaaagtgc tcatcattgg aaaacgttct tcggggcgaa aactctcaag gatcttaccg   1920
ctgttgagat ccagttcgat gtaacccact cgtgcaccca actgatcttc agcatctttt   1980
actttcacca gcgtttctgg gtgagcaaaa acaggaaggc aaaatgccgc aaaaaaggga   2040 ataaggcga cacggaaatg ttgaatactc atactcttcc ttttcaata ttattgaagc     2100 atttatcagg gttattgtct catgagcgga tacatatttg aatgtattta gaaaaataaa   2160
caaatagggg ttccgcgcac atttccccga aaagtgccac ctgacgtcta agaaaccatt   2220
attatcatga cattaaccta taaaaatagg cgtatcacga ggccctttcg tctcgcgcgt   2280
ttcggtgatg acggtgaaaa cctctgacac atgcagctcc cggagacggt cacagcttgt   2340
ctgtaagcga tgccgggag cagacaagcc cgtcagggcg cgtcagcggg tgttggcggg    2400
tgtcggggct ggcttaacta tgcggcatca gagcagattg tactgagagt gcaccatatg   2460
cggtgtgaaa taccgcacag atgcgtaagg agaaaatacc gcatcaggcg ccattcgcca   2520
ttcaggctgc gcaactgttg ggaagggcga tcggtgcggg cctcttcgct attacgccag   2580
ctggcgaaag ggggatgtgc tgcaaggcga ttaagttggg taacgccagg gttttcccag   2640
tcacgacgtt gtaaaacgac ggccagtgaa ttcgagctcg gtaccccggg ctctgagaca   2700
gtagtaggtt agtcatcgct ctaccgacgc gcaggaaaag aaagaagcat tgcggattac   2760
```

-continued

```
gtattctaat gttcagcccg cggaacgcca gcaaatcacc acccatgcgc atgatactga    2820
gtcttgtaca cgctgggctt ccagtgtact gagagtgcac cataccacag ctttcaatt     2880 caattcatca tttttttttt attctttttt ttgatttcgg tttctttgaa attttttga     2940 ttcggtaatc tccgaacaga aggaagaacg aaggaaggag cacagactta gattggtata    3000
tatacgcata tgtagtgttg aagaaacatg aaattgccca gtattcttaa cccaactgca    3060
cagaacaaaa acctgcagga aacgaagata aatcatgtcg aaagctacat ataaggaacg    3120
tgctgctact catcctagtc ctgttgctgc caagctattt aatatcatgc acgaaaagca    3180
aacaaacttg tgtgcttcat tggatgttcg taccaccaag gaattactgg agttagttga    3240
agcattaggt cccaaaattt gtttactaaa aacacatgtg gatatcttga ctgattttc     3300 catggagggc acagttaagc cgctaaaggc attatccgcc aagtacaatt ttttactctt    3360
cgaagacaga aaatttgctg acattggtaa tacagtcaaa ttgcagtact ctgcgggtgt    3420
atacagaata gcagaatggg cagacattac gaatgcacac ggtgtggtgg gcccaggtat    3480
tgttagcggt ttgaagcagg cggcagaaga agtaacaaag gaacctagag gccttttgat    3540
gttagcagaa ttgtcatgca agggctccct atctactgga gaatatacta agggtactgt    3600
tgacattgcg aagagcgaca aagattttgt tatcggcttt attgctcaaa gagacatggg    3660
tggaagagat gaaggttacg attggttgat tatgacaccc ggtgtgggtt tagatgacaa    3720
gggagacgca ttgggtcaac agtatagaac cgtggatgat gtggtctcta caggatctga    3780
cattattatt gttggaagag gactatttgc aaagggaagg gatgctaagg tagagggtga    3840
acgttacaga aaagcaggct gggaagcata tttgagaaga tgcggccagc aaaactaaaa    3900
aactgtatta taagtaaatg catgtatact aaactcacaa attagagctt caatttaatt    3960
atatcagtta ttaccctatg cggtgtgaaa taccgcacag atgcgtaagg agaaaatacc    4020
gcatcaggaa attgtaaacg ttaatatttt gttaaaattc gcgttaaatt tttgttaaat    4080
cagctcattt tttaaccaat aggccgaaat cggcaaaatc ttcagcccgc ggaacgccag    4140
caaatcacca cccatgcgca tgatactgag tcttgtacac gctgggcttc cagtgatgat    4200
acaacgagtt agccaaggtg agcacggatg tctaaattag aattacgttt taatatcttt    4260
ttttccatat ctagggctag                                                4280
```

<210> SEQ ID NO 81
<211> LENGTH: 30
<212> TYPE: DNA
<213> ORGANISM: Artificial Sequence
<220> FEATURE:
<223> OTHER INFORMATION: primer

<400> SEQUENCE: 81

```
gcatgcttgc atttagtcgt gcaatgtatg                                       30
```

<210> SEQ ID NO 82
<211> LENGTH: 54
<212> TYPE: DNA
<213> ORGANISM: Artificial Sequence
<220> FEATURE:
<223> OTHER INFORMATION: primer

<400> SEQUENCE: 82

```
gaacattaga atacgtaatc cgcaatgcac tagtaccaca ggtgttgtcc tctg             54
```

<210> SEQ ID NO 83
<211> LENGTH: 54

```
<212> TYPE: DNA
<213> ORGANISM: Artificial Sequence
<220> FEATURE:
<223> OTHER INFORMATION: primer

<400> SEQUENCE: 83
cagaggacaa cacctgtggt actagtgcat tgcggattac gtattctaat gttc         54

<210> SEQ ID NO 84
<211> LENGTH: 28
<212> TYPE: DNA
<213> ORGANISM: Artificial Sequence
<220> FEATURE:
<223> OTHER INFORMATION: primer

<400> SEQUENCE: 84
caccttggct aactcgttgt atcatcac                                      28

<210> SEQ ID NO 85
<211> LENGTH: 100
<212> TYPE: DNA
<213> ORGANISM: Artificial Sequence
<220> FEATURE:
<223> OTHER INFORMATION: primer

<400> SEQUENCE: 85
ttttaagccg aatgagtgac agaaaaagcc cacaacttat caagtgatat tgaacaaagg   60
gcgaaacttc gcatgcttgc atttagtcgt gcaatgtatg                         100

<210> SEQ ID NO 86
<211> LENGTH: 98
<212> TYPE: DNA
<213> ORGANISM: Artificial Sequence
<220> FEATURE:
<223> OTHER INFORMATION: primer

<400> SEQUENCE: 86
cccaattggt aaatattcaa caagagacgc gcagtacgta acatgcgaat tgcgtaattc   60
acggcgataa caccttggct aactcgttgt atcatcac                           98

<210> SEQ ID NO 87
<211> LENGTH: 29
<212> TYPE: DNA
<213> ORGANISM: Artificial Sequence
<220> FEATURE:
<223> OTHER INFORMATION: primer

<400> SEQUENCE: 87
caaaagccca tgtcccacac caaaggatg                                     29

<210> SEQ ID NO 88
<211> LENGTH: 26
<212> TYPE: DNA
<213> ORGANISM: Artificial Sequence
<220> FEATURE:
<223> OTHER INFORMATION: primer

<400> SEQUENCE: 88
caccatcgcg cgtgcatcac tgcatg                                        26

<210> SEQ ID NO 89
<211> LENGTH: 28
<212> TYPE: DNA
<213> ORGANISM: Artificial Sequence
<220> FEATURE:
```

<223> OTHER INFORMATION: primer

<400> SEQUENCE: 89
tcggtttttg caatatgacc tgtgggcc                                          28

<210> SEQ ID NO 90
<211> LENGTH: 22
<212> TYPE: DNA
<213> ORGANISM: Artificial Sequence
<220> FEATURE:
<223> OTHER INFORMATION: primer

<400> SEQUENCE: 90
gagaagatgc ggccagcaaa ac                                                22

<210> SEQ ID NO 91
<211> LENGTH: 2745
<212> TYPE: DNA
<213> ORGANISM: Artificial Sequence
<220> FEATURE:
<223> OTHER INFORMATION: constructed coding region-terminator segment

<400> SEQUENCE: 91
atgactgaca aaaaaactct taaagactta agaaatcgta gttctgttta cgattcaatg        60
gttaaatcac ctaatcgtgc tatgttgcgt gcaactggta tgcaagatga agactttgaa       120
aaacctatcg tcggtgtcat ttcaacttgg gctgaaaaca caccttgtaa tatccactta       180
catgactttg gtaaactagc caaagtcggt gttaaggaag ctggtgcttg gccagttcag       240
ttcggaacaa tcacggtttc tgatggaatc gccatgggaa cccaaggaat gcgtttctcc       300
ttgacatctc gtgatattat tgcagattct attgaagcag ccatgggagg tcataatgcg       360
gatgcttttg tagccattgg cggttgtgat aaaaacatgc ccggttctgt tatcgctatg       420
gctaacatgg atatcccagc catttttgct tacggcggaa caattgcacc tggtaattta       480
gacggcaaag atatcgattt agtctctgtc tttgaaggtg tcggccattg gaaccacggc       540
gatatgacca agaagaagt taaagctttg gaatgtaatg cttgtcccgg tcctggaggc       600
tgcggtggta tgtatactgc taacacaatg gcgacagcta ttgaagtttt gggacttagc       660
cttccgggtt catcttctca cccggctgaa tccgcagaaa agaaagcaga tattgaagaa       720 ctggtcgcg ctgttgtcaa aatgctcgaa atgggcttaa aaccttctga catttttaacg      780 cgtgaagctt ttgaagatgc tattactgta actatggctc tgggaggttc aaccaactca       840 accctcacc tcttagctat tgcccatgct gctaatgtgg aattgacact tgatgatttc       900
aatactttcc aagaaaaagt tcctcatttg gctgatttga accttctgg tcaatatgta       960 ttccaagacc tttacaaggt cggaggggta ccagcagtta tgaaatatct ccttaaaaat      1020
ggcttccttc atggtgaccg tatcacttgt actggcaaaa cagtcgctga aaatttgaag      1080 cttttgatg atttaacacc tggtcaaaag gttattatgc cgcttgaaaa tcctaaacgt      1140
gaagatggtc cgctcattat tctccatggt aacttggctc agacggtgc cgttgccaaa      1200 gtttctggtg taaaagtgcg tcgtcatgtc ggtcctgcta aggtctttaa ttctgaagaa      1260
gaagccattg aagctgtctt gaatgatgat attgttgatg gtgatgttgt tgtcgtacgt      1320
tttgtaggac caaagggcgg tcctggtatg cctgaaatgc tttcccttttc atcaatgatt      1380 gttggtaaag ggcaaggtga aaagttgcc cttctgacag atggccgctt ctcaggtggt      1440
acttatggtc ttgtcgtggg tcatatcgct cctgaagcac aagatggcgg tccaatcgcc      1500
tacctgcaaa caggagacat agtcactatt gaccaagaca ctaaggaatt acactttgat      1560

-continued

```
atctccgatg aagagttaaa acatcgtcaa gagaccattg aattgccacc gctctattca    1620
cgcggtatcc ttggtaaata tgctcacatc gtttcgtctg cttctagggg agccgtaaca    1680
gactttggaa agcctgaaga aactggcaaa aaatgttgtc ctggttgctg tggttaagcg    1740
gccgcgttaa ttcaaattaa ttgatatagt tttttaatga gtattgaatc tgtttagaaa    1800
taatggaata ttattttat ttatttattt atattattgg tcggctcttt tcttctgaag    1860
gtcaatgaca aaatgatatg aaggaaataa tgatttctaa aattttacaa cgtaagatat    1920
ttttacaaaa gcctagctca tcttttgtca tgcactattt tactcacgct tgaaattaac    1980
ggccagtcca ctgcggagtc atttcaaagt catcctaatc gatctatcgt ttttgatagc    2040
tcattttgga gttcgcgatt gtcttctgtt attcacaact gttttaattt ttatttcatt    2100
ctggaactct tcgagttctt tgtaaagtct ttcatagtag cttactttat cctccaacat    2160
atttaacttc atgtcaattt cggctcttaa attttccaca tcatcaagtt caacatcatc    2220
ttttaacttg aatttattct ctagctcttc caaccaagcc tcattgctcc ttgatttact    2280
ggtgaaaagt gatacacttt gcgcgcaatc caggtcaaaa cttcctgca aagaattcac     2340 caatttctcg acatcatagt acaatttgtt ttgttctccc atcacaattt aatatacctg    2400
atggattctt atgaagcgct gggtaatgga cgtgtcactc tacttcgcct ttttccctac    2460
tccttttagt acgaagaca atgctaataa ataagagggt aataataata ttattaatcg     2520 gcaaaaaga ttaaacgcca agcgtttaat tatcagaaag caaacgtcgt accaatcctt     2580
gaatgcttcc caattgtata ttaagagtca tcacagcaac atattcttgt tattaaatta    2640
attattattg attttgata ttgtataaaa aaaccaaata tgtataaaaa aagtgaataa     2700
aaaataccaa gtatggagaa atatattaga agtctatacg ttaaa                    2745
```

<210> SEQ ID NO 92
<211> LENGTH: 27
<212> TYPE: DNA
<213> ORGANISM: Artificial Sequence
<220> FEATURE:
<223> OTHER INFORMATION: primer

<400> SEQUENCE: 92
gacttttgga agcctgaaga aactggc                                         27

<210> SEQ ID NO 93
<211> LENGTH: 20
<212> TYPE: DNA
<213> ORGANISM: Artificial Sequence
<220> FEATURE:
<223> OTHER INFORMATION: primer

<400> SEQUENCE: 93
cttggcagca acaggactag                                                 20

<210> SEQ ID NO 94
<211> LENGTH: 26
<212> TYPE: DNA
<213> ORGANISM: Artificial Sequence
<220> FEATURE:
<223> OTHER INFORMATION: primer

<400> SEQUENCE: 94
ccaggccaat tcaacagact gtcggc                                          26

<210> SEQ ID NO 95

<211> LENGTH: 2347
<212> TYPE: DNA
<213> ORGANISM: Artificial Sequence
<220> FEATURE:
<223> OTHER INFORMATION: constructed URA3 marker with flanking
      homologous repeat sequences for HIS gene replacement and marker
      excision

<400> SEQUENCE: 95

| | | | | | |
|---|---|---|---|---|---|
| gcattgcgga | ttacgtattc | taatgttcag | gtgctggaag | aagagctgct | taaccgccgc | 60 |
| gcccagggtg | aagatccacg | ctactttacc | ctgcgtcgtc | tggatttcgg | cggctgtcgt | 120 |
| ctttcgctgg | caacgccggt | tgatgaagcc | tgggacggtc | cgctctcctt | aaacggtaaa | 180 |
| cgtatcgcca | cctcttatcc | tcacctgctc | aagcgttatc | tcgaccagaa | aggcatctct | 240 |
| tttaaatcct | gcttactgaa | cggttctgtt | gaagtcgccc | cgcgtgccgg | actggcggat | 300 |
| gcgatttgcg | atctggtttc | caccggtgcc | acgctggaag | ctaacggcct | gcgcgaagtc | 360 |
| gaagttatct | atcgctcgaa | agcctgcctg | attcaacgcg | atggcgaaat | ggaagaatcc | 420 |
| aaacagcaac | tgatcgacaa | actgctgacc | cgtattcagg | gtgtgatcca | ggcgcgcgaa | 480 |
| tcaaaataca | tcatgatgca | cgcaccgacc | gaacgtctgg | atgaagtcat | ggtacctact | 540 |
| gagagtgcac | ataccacag | cttttcaatt | caattcatca | tttttttttt | attctttttt | 600 |
| ttgatttcgg | tttctttgaa | attttttttga | ttcggtaatc | tccgaacaga | aggaagaacg | 660 |
| aaggaaggag | cacagactta | gattggtata | tatacgcata | tgtagtgttg | aagaaacatg | 720 |
| aaattgccca | gtattcttaa | cccaactgca | cagaacaaaa | acctgcagga | aacgaagata | 780 |
| aatcatgtcg | aaagctacat | ataaggaacg | tgctgctact | catcctagtc | ctgttgctgc | 840 |
| caagctatt | aatatcatgc | acgaaaagca | aacaaacttg | tgtgcttcat | tggatgttcg | 900 |
| taccaccaag | gaattactgg | agttagttga | agcattaggt | cccaaaattt | gtttactaaa | 960 |
| aacacatgtg | gatatcttga | ctgattttc | catggagggc | acagttaagc | cgctaaaggc | 1020 |
| attatccgcc | aagtacaatt | ttttactctt | cgaagacaga | aaatttgctg | acattggtaa | 1080 |
| tacagtcaaa | ttgcagtact | ctgcgggtgt | atacagaata | gcagaatggg | cagacattac | 1140 |
| gaatgcacac | ggtgtggtgg | gcccaggtat | tgttagcggt | ttgaagcagg | cggcagaaga | 1200 |
| agtaacaaag | gaacctagag | gccttttgat | gttagcagaa | ttgtcatgca | agggctccct | 1260 |
| atctactgga | gaatatacta | agggtactgt | tgacattgcg | aagagcgaca | agatttttgt | 1320 |
| tatcggcttt | attgctcaaa | gagacatggg | tggaagagat | gaaggttacg | attggttgat | 1380 |
| tatgacaccc | ggtgtgggtt | tagatgacaa | gggagacgca | ttgggtcaac | agtatagaac | 1440 |
| cgtggatgat | gtggtctcta | caggatctga | cattattatt | gttggaagag | gactatttgc | 1500 |
| aaagggaagg | gatgctaagg | tagagggtga | acgttacaga | aaagcaggct | gggaagcata | 1560 |
| tttgagaaga | tgcggccagc | aaaactaaaa | aactgtatta | taagtaaatg | catgtatact | 1620 |
| aaactcacaa | attagagctt | caatttaatt | atatcagtta | ttaccctatg | cggtgtgaaa | 1680 |
| taccgcacag | atgcgtaagg | agaaaatacc | gcatcaggaa | attgtaaacg | ttaatatttt | 1740 |
| gttaaaattc | gcgttaaatt | tttgttaaat | cagctcattt | tttaaccaat | aggccgaaat | 1800 |
| cggcaaaatc | tctagagtgc | tggaagaaga | gctgcttaac | cgccgcgccc | agggtgaaga | 1860 |
| tccacgctac | tttaccctgc | gtcgtctgga | tttcggcggc | tgtcgtcttt | cgctggcaac | 1920 |
| gccggttgat | gaagcctggg | acggtccgct | ctccttaaac | ggtaaacgta | tcgccacctc | 1980 |
| ttatcctcac | ctgctcaagc | gttatctcga | ccagaaaggc | atctctttta | aatcctgctt | 2040 |
| actgaacggt | tctgttgaag | tcgccccgcg | tgccggactg | gcggatgcga | tttgcgatct | 2100 |

```
ggtttccacc ggtgccacgc tggaagctaa cggcctgcgc gaagtcgaag ttatctatcg    2160
ctcgaaagcc tgcctgattc aacgcgatgg cgaaatggaa gaatccaaac agcaactgat    2220
cgacaaactg ctgacccgta ttcagggtgt gatccaggcg cgcgaatcaa aatacatcat    2280
gatgcacgca ccgaccgaac gtctggatga agtcatccag tgatgataca acgagttagc    2340
caaggtg                                                              2347

<210> SEQ ID NO 96
<211> LENGTH: 80
<212> TYPE: DNA
<213> ORGANISM: Artificial Sequence
<220> FEATURE:
<223> OTHER INFORMATION: primer

<400> SEQUENCE: 96
cttcgaagaa tatactaaaa aatgagcagg caagataaac gaaggcaaag gcattgcgga    60
ttacgtattc taatgttcag                                                80

<210> SEQ ID NO 97
<211> LENGTH: 81
<212> TYPE: DNA
<213> ORGANISM: Artificial Sequence
<220> FEATURE:
<223> OTHER INFORMATION: primer

<400> SEQUENCE: 97
tatacacatg tatatatatc gtatgctgca gctttaaata atcggtgtca caccttggct    60
aactcgttgt atcatcactg g                                              81

<210> SEQ ID NO 98
<211> LENGTH: 26
<212> TYPE: DNA
<213> ORGANISM: Artificial Sequence
<220> FEATURE:
<223> OTHER INFORMATION: primer

<400> SEQUENCE: 98
gacttgaata atgcagcggc gcttgc                                         26

<210> SEQ ID NO 99
<211> LENGTH: 30
<212> TYPE: DNA
<213> ORGANISM: Artificial Sequence
<220> FEATURE:
<223> OTHER INFORMATION: primer

<400> SEQUENCE: 99
ccaccctctt caattagcta agatcatagc                                     30

<210> SEQ ID NO 100
<211> LENGTH: 25
<212> TYPE: DNA
<213> ORGANISM: Artificial Sequence
<220> FEATURE:
<223> OTHER INFORMATION: primer

<400> SEQUENCE: 100
aaaaattgat tctcatcgta aatgc                                          25

<210> SEQ ID NO 101
<211> LENGTH: 20
<212> TYPE: DNA
```

<213> ORGANISM: Artificial Sequence
<220> FEATURE:
<223> OTHER INFORMATION: primer

<400> SEQUENCE: 101
ctgcagcgag gagccgtaat                                          20

<210> SEQ ID NO 102
<211> LENGTH: 90
<212> TYPE: DNA
<213> ORGANISM: Artificial Sequence
<220> FEATURE:
<223> OTHER INFORMATION: primer

<400> SEQUENCE: 102
atggttcatt taggtccaaa aaaaccacaa gccagaaagg gttccatggc cgatgtgcca    60
gcattgcgga ttacgtattc taatgttcag                                    90

<210> SEQ ID NO 103
<211> LENGTH: 91
<212> TYPE: DNA
<213> ORGANISM: Artificial Sequence
<220> FEATURE:
<223> OTHER INFORMATION: primer

<400> SEQUENCE: 103
ttaagcaccg atgataccaa cggacttacc ttcagcaatt cttttttggg ccaaagcagc    60
caccttggct aactcgttgt atcatcactg g                                  91

<210> SEQ ID NO 104
<211> LENGTH: 24
<212> TYPE: DNA
<213> ORGANISM: Artificial Sequence
<220> FEATURE:
<223> OTHER INFORMATION: primer

<400> SEQUENCE: 104
ctaggatgag tagcagcacg ttcc                                          24

<210> SEQ ID NO 105
<211> LENGTH: 26
<212> TYPE: DNA
<213> ORGANISM: Artificial Sequence
<220> FEATURE:
<223> OTHER INFORMATION: primer

<400> SEQUENCE: 105
ccaattccgt gatgtctctt tgttgc                                        26

<210> SEQ ID NO 106
<211> LENGTH: 20
<212> TYPE: DNA
<213> ORGANISM: Artificial Sequence
<220> FEATURE:
<223> OTHER INFORMATION: primer

<400> SEQUENCE: 106
gtgaacgagt tcacaaccgc                                              20

<210> SEQ ID NO 107
<211> LENGTH: 22
<212> TYPE: DNA
<213> ORGANISM: Artificial Sequence
<220> FEATURE:
<223> OTHER INFORMATION: primer

<400> SEQUENCE: 107
gttcgttcca gaattatcac gc                                           22

<210> SEQ ID NO 108
<211> LENGTH: 28
<212> TYPE: DNA
<213> ORGANISM: Artificial Sequence
<220> FEATURE:
<223> OTHER INFORMATION: primer

<400> SEQUENCE: 108
ggatccgcat gcttgcattt agtcgtgc                                     28

<210> SEQ ID NO 109
<211> LENGTH: 20
<212> TYPE: DNA
<213> ORGANISM: Artificial Sequence
<220> FEATURE:
<223> OTHER INFORMATION: primer

<400> SEQUENCE: 109
gggatgcgga cgtattcggc                                              20

<210> SEQ ID NO 110
<211> LENGTH: 4506
<212> TYPE: DNA
<213> ORGANISM: Saccharomyces cerevisiae

<400> SEQUENCE: 110
atgtcgaata ccccttataa ttcatctgtg ccttccattg catccatgac ccagtcttcg    60
gtctcaagaa gtcctaacat gcatacagca actacgcccg gtgccaacac cagctctaac   120 tctccacccct tgcacatgtc ttcagattcg tccaagatca agaggaagcg taacagaatt   180
ccgctcagtt gcaccatttg tcggaaaagg aaagtcaaat gtgacaaact cagaccacac   240
tgccagcagt gcactaaaac tggggtagcc catctctgcc actacatgga acagacctgg   300
gcagaagagg cagagaaaga attgctgaag acaacgaat taagaagct tagggagcgc   360 gtaaaatctt tagaaaagac tctttctaag gtgcactctt ctccttcgtc taactccttg   420
aaaagttaca acactcccga gagcagcaac ctgtttatgg gtagcgatga acacaccacc   480
cttgttaatg caaatacagg ctctgcttcc tctgcctcgc atatgcatca gcaacaacag   540
caacagcagc aacaggaaca acaacaagac ttttccagaa gtgcgaacgc caacgcgaat   600
tcctcgtccc tttctatctc aaataaatat gacaacgatg agctggactt aactaaggac   660
tttgatcttt tgcatatcaa agtaacggaa accatccact taggtgccac ccactggttg   720
tctatcatga aggtgaccc gtacctaaaa ctttttgtggg gtcatatctt cgctatgagg   780
gaaaagttaa atgaatggta ctaccaaaaa aattcgtact ctaagctgaa gtcaagcaaa   840
tgtcccatca atcacgcgca agcgccgcct tctgccgctg ccgccgctac agaaaatgt    900 cctgttgatc actccgcgtt ttcgtctggc atggtggccc caaggagga gactcctctt   960 cctaggaaat gtccagttga ccacaccatg ttctcttcgg gaatgattcc tcccagagag  1020
gacacttcgt cccagaagag gtgtcccgtt gaccacacca tgtattccgc aggaatgatg  1080
ccgcccaagg acgagacacc ttccccattt tccactaaag ctatgataga ccataacaag  1140
catacaatga atccgcctca gtcaaaatgt cctgtggacc atagaaacta tatgaaggat  1200
tatccctctg acatggcaaa ttcttcttcg aacccggcaa gtcgttgccc cattgaccat  1260

```
tcaagcatga aaaatacagc ggccttacca gcttcaacgc acaataccat cccacaccac     1320
caaccacagt ccggatctca tgctcgttcg catcccgcac aaagcaggaa acatgattcc     1380
tacatgacag aatctgaagt cctcgcaaca ctttgtgaga tgttgccacc aaagcgcgtc     1440
atcgcattat tcatcgagaa attcttcaaa catttatacc ctgccattcc aatcttagat     1500
gaacagaatt tcaaaaatca cgtgaatcaa atgctttcgt tgtcttcgat gaatcccaca     1560
gttaacaact tggtatgag catgccatct tcatctacac tagagaacca acccataaca     1620
caaatcaatc ttccaaaact ttccgattct tgtaacttag gtattctgat aataatcttg     1680
agattgacat ggctatccat accttctaat tcctgcgaag tcgacctggg agaagaaagt     1740
ggctcatttt tagtgcccaa cgaatctagc aatatgtctg catctgcatt gacctcgatg     1800
gctaaagaag aatcacttct gctaaagcat gagacaccgg tcgaggcact ggagctatgt     1860
caaaaatact tgattaaatt cgatgaactt tctagtattt ccaataacaa cgttaattta     1920
accacggtgc agtttgccat ttttttacaac ttctatatga aaagtgcctc taatgatttg     1980
actaccttga caaataccaa caacactggc atggccaatc ctggtcacga ttccgagtct     2040
caccagatcc tattgtccaa tattactcaa atggccttta gttgtgggtt acacagagac     2100
cctgataatt ttcctcaatt aaacgctacc attccagcaa ccagccagga cgtgtctaac     2160
aacgggagca aaaaggcaaa ccctagcacc aatccaactt gaataacaa catgtctgct     2220
gccactacca acagcagtag cagatctggc agtgctgatt caagaagtgg ttctaaccct     2280
gtgaacaaga aggaaaatca ggttagtatc gaaagattta acacacttg gaggaaaatt     2340
tggtattaca ttgttagcat ggatgttaac caatctcttt ccctggggag ccctcgacta     2400
ctaagaaatc tgagggattt cagcgataca aagctaccaa gtgcgtcaag gattgattat     2460
gttcgcgata tcaaagagtt aatcattgtg aagaattta ctcttttttt ccaaattgat     2520
ttgtgtatta ttgctgtatt aaatcacatt ttgaatgttt cttttagcaag aagcgtgaga     2580
aaatttgaac tggattcatt gattaatta ttgaaaaatc tgacctatgg tactgagaat     2640
gtcaatgatg tagtgagctc cttgatcaac aaagggttat taccaacttc ggaaggtggt     2700
tctgtagatt caaataatga tgaaatttac ggtctaccga aactaccga tattctaaac     2760
catggtcaac ataaccaaaa cttgtatgct gatggaagaa atacttctag tagtgatata     2820
gataagaaat tggaccttcc tcacgaatct acaacgagag ctctattctt ttccaagcat     2880
atgacaatta gaatgttgct gtacttattg aactacattt tgtttactca ttatgaacca     2940
atgggcagtg aagatcctgg tactaatatc ctagctaagg agtacgctca agaggcatta     3000
aattttgcca tggatggcta cagaaactgc atgattttct tcaacaatat cagaaacacc     3060
aattcactat tcgattacat gaatgttatc ttgtcttacc cttgtttgga cattggacat     3120
cgttctttac aatttatcgt ttgtttgatc ctgagagcta aatgtggccc attgactggt     3180
atgcgtgaat catcgatcat tactaatggt acatcaagtg gatttaatag ttcggtagaa     3240
gatgaggacg tcaaagttaa acaagaatct tctgatgaat tgaaaaaaga cgatttcatg     3300
aaagatgtaa atttggattc aggcgattca ttagcagaga ttctaatgtc aagaatgctg     3360
ctatttcaaa aactaacaaa acaactatca aagaagtaca actacgctat tcgtatgaac     3420
aaatccactg gattctttgt ctctttacta gatacacctt caaagaaatc agactcgaaa     3480
tcgggtggta gttcattcat gttgggtaat tggaaacatc caaaggtttc aaacatgagc     3540
ggatttcttg ctggtgacaa agaccaatta cagaaatgcc ccgtgtacca agatgcgctc     3600
gggtttgtta gtccaaccgg tgctaatgaa ggttctgctc cgatgcaagg catgtcctta     3660
```

```
cagggctcta ctgctaggat gggagggacc cagttgccac caattagatc atacaaacct    3720
atcacgtaca caagtagtaa tctacgtcgt atgaatgaaa cgggtgaggc agaagctaag    3780
agaagaagat ttaatgatgg ctatattgat aataatagta acaacgatat acctagagga    3840
atcagcccaa aaccttcaaa tgggctatca tcggtgcagc cactattatc gtcatttttcc   3900 atgaaccagc taaacggggg taccattcca acggttccat cgttaaccaa cattacttca    3960
caaatgggag ctttaccatc tttagatagg atcaccacta atcaaataaa tttgccagac    4020
ccatctagag atgaagcatt tgacaactcc atcaagcaaa tgacgcctat gacaagtgca    4080
ttcatgaatg ctaatactac aattccaagt tcaactttaa acgggaatat gaacatgaat    4140
ggagctggaa ctgcgaatac agatacaagt gccaacggca gtgctttatc gacactgaca    4200
agcccacaag gctcagactt agcatccaat tctgctacac agtataaacc tgacttagaa    4260 gacttttttga tgcaaaattc taactttaat gggctaatga taaatccttc cagtctggta   4320
gaagttgttg gtggatacaa cgatcctaat aaccttggaa gaaatgacgc ggttgatttt    4380
ctacccgttg ataatgttga aattgatggt gttggaataa aaatcaacta tcatctacta    4440
actagtattt acgttactag tatattatca tatacggtgt tagaagatga cgcaaatgat    4500
gagaaa                                                                4506

<210> SEQ ID NO 111
<211> LENGTH: 99
<212> TYPE: DNA
<213> ORGANISM: Artificial Sequence
<220> FEATURE:
<223> OTHER INFORMATION: primer

<400> SEQUENCE: 111
tcctttctca attattattt tctactcata acctcacgca aaataacaca gtcaaatcaa    60
tcaaagtatg actgacaaaa aaactcttaa agacttaag                           99

<210> SEQ ID NO 112
<211> LENGTH: 77
<212> TYPE: DNA
<213> ORGANISM: Artificial Sequence
<220> FEATURE:
<223> OTHER INFORMATION: primer

<400> SEQUENCE: 112
gaacattaga atacgtaatc cgcaatgctt ctttcttttc cgtttaacgt atagacttct    60
aatatatttc tccatac                                                    77

<210> SEQ ID NO 113
<211> LENGTH: 45
<212> TYPE: DNA
<213> ORGANISM: Artificial Sequence
<220> FEATURE:
<223> OTHER INFORMATION: primer

<400> SEQUENCE: 113
aaacggaaaa gaaagaagca ttgcggatta cgtattctaa tgttc                     45

<210> SEQ ID NO 114
<211> LENGTH: 88
<212> TYPE: DNA
<213> ORGANISM: Artificial Sequence
<220> FEATURE:
<223> OTHER INFORMATION: primer
```

<400> SEQUENCE: 114

| | |
|---|---|
| tattttcgt tacataaaaa tgcttataaa actttaacta ataattagag attaaatcgc | 60 |
| caccttggct aactcgttgt atcatcac | 88 |

<210> SEQ ID NO 115
<211> LENGTH: 1713
<212> TYPE: DNA
<213> ORGANISM: Streptococcus mutans

<400> SEQUENCE: 115

| | |
|---|---|
| atgactgaca aaaaaactct taaagactta agaaatcgta gttctgttta cgattcaatg | 60 |
| gttaaatcac ctaatcgtgc tatgttgcgt gcaactggta tgcaagatga agactttgaa | 120 |
| aaacctatcg tcggtgtcat ttcaacttgg gctgaaaaca caccttgtaa tatccactta | 180 |
| catgactttg gtaaactagc caaagtcggt gttaaggaag ctggtgcttg gccagttcag | 240 |
| ttcggaacaa tcacggtttc tgatggaatc gccatgggaa cccaaggaat gcgtttctcc | 300 |
| ttgacatctc gtgatattat tgcagattct attgaagcag ccatgggagg tcataatgcg | 360 |
| gatgcttttg tagccattgg cggttgtgat aaaaacatgc ccggttctgt tatcgctatg | 420 |
| gctaacatgg atatcccagc catttttgct tacgcggaa caattgcacc tggtaattta | 480 |
| gacggcaaag atatcgattt agtctctgtc tttgaaggtg tcggccattg gaaccacggc | 540 |
| gatatgacca agaagaagt taagctttg gaatgtaatg cttgtcccgg tcctggaggc | 600 |
| tgcggtggta tgtatactgc taacacaatg gcgacagcta ttgaagtttt gggacttagc | 660 |
| cttccgggtt catcttctca cccggctgaa tccgcagaaa agaaagcaga tattgaagaa | 720 |
| gctggtcgcg ctgttgtcaa atgctcgaa atgggcttaa accttctga cattttaacg | 780 |
| cgtgaagctt ttgaagatgc tattactgta actatggctc tgggaggttc aaccaactca | 840 |
| acccttcacc tcttagctat tgcccatgct gctaatgtgg aattgacact tgatgatttc | 900 |
| aatactttcc aagaaaaagt tcctcatttg gctgatttga accttctgg tcaatatgta | 960 |
| ttccaagacc tttacaaggt cggagggggta ccagcagtta tgaaatatct ccttaaaaat | 1020 |
| ggcttccttc atggtgaccg tatcacttgt actggcaaaa cagtcgctga aaatttgaag | 1080 |
| gcttttgatg atttaacacc tggtcaaaag gttattatgc cgcttgaaaa tcctaaacgt | 1140 |
| gaagatggtc cgctcattat tctccatggt aacttggctc cagacggtgc cgttgccaaa | 1200 |
| gtttctggtg taaaagtgcg tcgtcatgtc ggtcctgcta aggtctttaa ttctgaagaa | 1260 |
| gaagccattg aagctgtctt gaatgatgat attgttgatg gtgatgttgt tgtcgtacgt | 1320 |
| tttgtaggac caaagggcgg tcctggtatg cctgaaatgc tttcccttc atcaatgatt | 1380 |
| gttggtaaag ggcaaggtga aaagttgcc cttctgacag atggccgctt ctcaggtggt | 1440 |
| acttatggtc ttgtcgtggg tcatatcgct cctgaagcac aagatggcgg tccaatcgcc | 1500 |
| tacctgcaaa caggagacat agtcactatt gaccaagaca ctaaggaatt acactttgat | 1560 |
| atctccgatg aagagttaaa acatcgtcaa gagaccattg aattgccacc gctctattca | 1620 |
| cgcggtatcc ttggtaaata tgctcacatc gtttcgtctg cttctagggg agccgtaaca | 1680 |
| gacttttgga agcctgaaga aactggcaaa aaa | 1713 |

<210> SEQ ID NO 116
<211> LENGTH: 571
<212> TYPE: PRT
<213> ORGANISM: Streptococcus mutans

<400> SEQUENCE: 116

-continued

```
Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
                20                  25                  30

Gly Met Gln Asp Glu Asp Phe Glu Lys Pro Ile Val Gly Val Ile Ser
            35                  40                  45

Thr Trp Ala Glu Asn Thr Pro Cys Asn Ile His Leu His Asp Phe Gly
        50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
                100                 105                 110

Ala Ala Met Gly Gly His Asn Ala Asp Ala Phe Val Ala Ile Gly Gly
            115                 120                 125

Cys Asp Lys Asn Met Pro Gly Ser Val Ile Ala Met Ala Asn Met Asp
    130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
                180                 185                 190

Asn Ala Cys Pro Gly Pro Gly Cys Gly Gly Met Tyr Thr Ala Asn
            195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
            245                 250                 255

Asp Ile Leu Thr Arg Glu Ala Phe Glu Asp Ala Ile Thr Val Thr Met
            260                 265                 270

Ala Leu Gly Gly Ser Thr Asn Ser Thr Leu His Leu Leu Ala Ile Ala
            275                 280                 285

His Ala Ala Asn Val Glu Leu Thr Leu Asp Asp Phe Asn Thr Phe Gln
    290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
        355                 360                 365

Gln Lys Val Ile Met Pro Leu Glu Asn Pro Lys Arg Glu Asp Gly Pro
370                 375                 380

Leu Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415
```

-continued

```
Asn Ser Glu Glu Glu Ala Ile Glu Ala Val Leu Asn Asp Asp Ile Val
            420                 425                 430

Asp Gly Asp Val Val Val Arg Phe Val Gly Pro Lys Gly Gly Pro
            435                 440                 445

Gly Met Pro Glu Met Leu Ser Leu Ser Ser Met Ile Val Gly Lys Gly
    450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Leu Lys His
        515                 520                 525

Arg Gln Glu Thr Ile Glu Leu Pro Pro Leu Tyr Ser Arg Gly Ile Leu
    530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
            565                 570

<210> SEQ ID NO 117
<211> LENGTH: 548
<212> TYPE: PRT
<213> ORGANISM: Lactococcus lactis

<400> SEQUENCE: 117

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220
```

```
Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
        290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
            405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
        450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
        530                 535                 540

Gln Asn Lys Ser
545
```

<210> SEQ ID NO 118
<211> LENGTH: 1125
<212> TYPE: DNA
<213> ORGANISM: Artificial Sequence
<220> FEATURE:
<223> OTHER INFORMATION: horse ADH coding region codon optimized for S.
      cerevisiae expression

<400> SEQUENCE: 118
atgtcaacag ccggtaaagt tattaagtgt aaagcggcag ttttgtggga agagaaaaag    60
ccgtttagca tagaagaagt agaagtagcg ccaccaaaag cacacgaggt tagaatcaag   120

```
atggttgcca ccggaatctg tagatccgac gaccatgtgg tgagtggcac tctagttact     180
cctttgccag taatcgcggg acacgaggct gccggaatcg ttgaatccat aggtgaaggt     240
gttaccactg ttcgtcctgg tgataaagtg atcccactgt tcactcctca atgtggtaag     300
tgtagagtct gcaaacatcc tgagggtaat ttctgcctta aaatgatttt gtctatgcct     360
agaggtacta tgcaggatgg tacaagcaga tttacatgca gagggaaacc tatacaccat     420
ttccttggta cttctacatt tcccaatac acagtggtgg acgagatatc tgtcgctaaa      480
atcgatgcag cttcaccact ggaaaaagtt tgcttgatag ggtgcggatt ttccaccggt     540
tacggttccg cagttaaagt tgcaaaggtt acacagggtt cgacttgtgc agtattcggt     600
ttaggaggag taggactaag cgttattatg gggtgtaaag ctgcaggcgc agcgaggatt     660
ataggtgtag acatcaataa ggacaaattt gcaaaagcta aggaggtcgg ggctactgaa     720
tgtgttaacc ctcaagatta taagaaacca atacaagaag tccttactga aatgtcaaac     780
ggtggagttg atttctcttt tgaagttata ggccgtcttg tactatggt aactgcgttg      840 tcctgctgtc aagaggcata tggagtcagt gtgatcgtag tgttcctcc tgattcacaa      900 aatttgtcga tgaatcctat gctgttgcta agcggtcgta catggaaggg agctatattt     960 ggcggttttta agagcaagga tagtgttcca aaacttgttg ccgactttat ggcgaagaag    1020
tttgctcttg atcctttaat tacacatgta ttgccattcg agaaaatcaa tgaagggttt    1080
gatttgttaa gaagtggtga atctattcgt acaattttaa ctttt                     1125
```

<210> SEQ ID NO 119
<211> LENGTH: 375
<212> TYPE: PRT
<213> ORGANISM: Equus caballus

<400> SEQUENCE: 119

```
Met Ser Thr Ala Gly Lys Val Ile Lys Cys Lys Ala Ala Val Leu Trp
1               5                   10                  15

Glu Glu Lys Lys Pro Phe Ser Ile Glu Glu Val Glu Val Ala Pro Pro
            20                  25                  30

Lys Ala His Glu Val Arg Ile Lys Met Val Ala Thr Gly Ile Cys Arg
        35                  40                  45

Ser Asp Asp His Val Val Ser Gly Thr Leu Val Thr Pro Leu Pro Val
    50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Thr Pro
                85                  90                  95

Gln Cys Gly Lys Cys Arg Val Cys Lys His Pro Glu Gly Asn Phe Cys
            100                 105                 110

Leu Lys Asn Asp Leu Ser Met Pro Arg Gly Thr Met Gln Asp Gly Thr
        115                 120                 125

Ser Arg Phe Thr Cys Arg Gly Lys Pro Ile His Phe Leu Gly Thr
    130                 135                 140

Ser Thr Phe Ser Gln Tyr Thr Val Val Asp Glu Ile Ser Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Lys Val Ala Lys Val Thr Gln
            180                 185                 190

Gly Ser Thr Cys Ala Val Phe Gly Leu Gly Gly Val Gly Leu Ser Val
```

```
                195                 200                 205
Ile Met Gly Cys Lys Ala Ala Gly Ala Ala Arg Ile Ile Gly Val Asp
    210                 215                 220

Ile Asn Lys Asp Lys Phe Ala Lys Ala Lys Glu Val Gly Ala Thr Glu
225                 230                 235                 240

Cys Val Asn Pro Gln Asp Tyr Lys Lys Pro Ile Gln Glu Val Leu Thr
                245                 250                 255

Glu Met Ser Asn Gly Val Asp Phe Ser Phe Glu Val Ile Gly Arg
            260                 265                 270

Leu Asp Thr Met Val Thr Ala Leu Ser Cys Cys Gln Glu Ala Tyr Gly
                275                 280                 285

Val Ser Val Ile Val Gly Val Pro Pro Asp Ser Gln Asn Leu Ser Met
    290                 295                 300

Asn Pro Met Leu Leu Leu Ser Gly Arg Thr Trp Lys Gly Ala Ile Phe
305                 310                 315                 320

Gly Gly Phe Lys Ser Lys Asp Ser Val Pro Lys Leu Val Ala Asp Phe
                325                 330                 335

Met Ala Lys Lys Phe Ala Leu Asp Pro Leu Ile Thr His Val Leu Pro
            340                 345                 350

Phe Glu Lys Ile Asn Glu Gly Phe Asp Leu Leu Arg Ser Gly Glu Ser
        355                 360                 365

Ile Arg Thr Ile Leu Thr Phe
    370                 375

<210> SEQ ID NO 120
<211> LENGTH: 643
<212> TYPE: DNA
<213> ORGANISM: Saccharomyces cerevisiae

<400> SEQUENCE: 120
gaaatgaata acaatactga cagtactaaa taattgccta cttggcttca catacgttgc      60
atacgtcgat atagataata atgataatga cagcaggatt atcgtaatac gtaatagttg    120
aaaatctcaa aaatgtgtgg gtcattacgt aaataatgat aggaatggga ttcttctatt    180
tttccttttt ccattctagc agccgtcggg aaaacgtggc atcctctctt tcgggctcaa    240
ttggagtcac gctgccgtga gcatcctctc tttccatatc taacaactga gcacgtaacc    300
aatgaaaaag catgagctta gcgttgctcc aaaaaagtat tggatggtta ataccatttg    360
tctgttctct tctgactttg actcctcaaa aaaaaaaaat ctacaatcaa cagatcgctt    420
caattacgcc ctcacaaaaa cttttttcct tcttcttcgc ccacgttaaa ttttatccct    480
catgttgtct aacggatttc tgcacttgat ttattataaa aagacaaaga cataatactt    540
ctctatcaat ttcagttatt gttcttcctt gcgttattct tctgttcttc ttttctttt    600 gtcatatata accataacca agtaatacat attcaaatct aga                      643

<210> SEQ ID NO 121
<211> LENGTH: 9089
<212> TYPE: DNA
<213> ORGANISM: Artificial Sequence
<220> FEATURE:
<223> OTHER INFORMATION: constructed plasmid

<400> SEQUENCE: 121
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
```

```
ttggcgggtg tcgggctgg cttaactatg cggcatcaga gcagattgta ctgagagtgc    180
accataccac agcttttcaa ttcaattcat cattttttt ttattcttt ttttgatttc    240
ggtttctttg aaattttttt gattcggtaa tctccgaaca gaaggaagaa cgaaggaagg    300
agcacagact tagattggta tatatacgca tatgtagtgt tgaagaaaca tgaaattgcc    360
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa ttttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa ttttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact ataggggcgaa ttgggtaccg gccccccct cgaggtcgac tggccattaa   2040
tctttcccat attagatttc gccaagccat gaaagttcaa gaaaggtctt tagacgaatt   2100
accccttcatt tctcaaactg gcgtcaaggg atcctggtat ggttttatcg ttttatttct   2160
ggttcttata gcatcgtttt ggacttctct gttcccatta ggcggttcag gagccagcgc   2220
agaatcattc tttgaaggat acttatcctt tccaattttg attgtctgtt acgttggaca   2280
taaactgtat actagaaatt ggactttgat ggtgaaacta aagatatgg atcttgatac   2340
cggcagaaaa caagtagatt tgactcttcg tagggaagaa atgaggattg agcgagaaac   2400
attagcaaaa agatccttcg taacaagatt tttacatttc tggtgttgaa gggaaagata   2460
tgagctatac agcggaattt ccatatcact cagattttgt tatctaattt tttccttccc   2520
```

```
acgtccgcgg gaatctgtgt atattactgc atctagatat atgttatctt atcttggcgc    2580
gtacatttaa ttttcaacgt attctataag aaattgcggg agttttttc atgtagatga     2640 tactgactgc acgcaaatat aggcatgatt tataggcatg atttgatggc tgtaccgata    2700
ggaacgctaa gagtaacttc agaatcgtta tcctggcgga aaaaattcat ttgtaaactt    2760
taaaaaaaaa agccaatatc cccaaaatta ttaagagcgc ctccattatt aactaaaatt    2820
tcactcagca tccacaatgt atcaggtatc tactacagat attacatgtg gcgaaaaaga    2880
caagaacaat gcaatagcgc atcaagaaaa acacaaagc tttcaatcaa tgaatcgaaa     2940
atgtcattaa aatagtatat aaattgaaac taagtcataa agctataaaa agaaaattta    3000
tttaaatgca agatttaaag taaattcacg gccctgcagg ccctaacctg ctaggacaca    3060
acgtctttgc ctggtaaagt ttctagctga cgtgattcct tcacctgtgg atccggcaat    3120
tgtaaaggtt gtgaaaccct cagcttcata accgacacct gcaaatgact ttgcattctt    3180
aacaaagata gttgtatcaa tttcacgttc gaatctatta aggttatcga tgttcttaga    3240
ataaatgtag gcggaatgtt ttctattctg ctcagctatc ttggcgtatt taatggcttc    3300
atcaatgtcc ttcactctaa ctataggcaa aattggcatc atcaactccg tcataacgaa    3360
cggatggttt gcgttgactt cacaaataat acactttaca ttacttggtg actctacatc    3420
tatttcatcc aaaaacagtt tagcgtcctt accaacccac ttcttattaa tgaaatattc    3480
ttgagtttca ttgttctttt gaagaacaag gtctatcagc ttggatactt ggtcttcatt    3540
gataatgacg gcgttgtttt tcaacatgtt agagatcaga tcatctgcaa cgttttcaaa    3600
cacgaacact tcttttttccg cgatacaagg aagattgttg tcaaacgaac aaccttcaat   3660
aatgcttctg ccggccttct cgatatctgc tgtatcgtct acaataaccg gaggattacc    3720
cgcgccagct ccgatggcct ttttaccaga attaagaagg gttttttacca tacccgggcc   3780 accgtaccg cacaacaatt ttatggatgg atgtttgata atagcgtcta aactttccat    3840
agttgggttc tttatagtag tgacaaggtt ttcaggtcca ccacagctaa ttatggcttt    3900
gtttatcatt tctactgcga aagcgacaca cttttttggcg catgggtgac cattaaatac    3960
aactgcattc cccgcagcta tcatacctat agaattgcag ataacggttt ctgttggatt    4020
cgtgcttgga gttatagcgc cgataactcc gtatggactc atttcaacca ctgttagtcc    4080
attatcgccg gaccatgctg ttgttgtcag atcttcagtg cctggggtat acttggccac    4140
taattcatgt ttcaagattt tatcctcata ccttcccatg tgggtttcct ccaggatcat    4200
tgtggctaag acctctttat tctgtaatgc ggcttttctt atttcggtga ttattttctc    4260
tctttgttcc tttgtgtagt gtagggaaag aatcttttgt gcatgtactg cagaagaaat    4320
ggcattctca acattttcaa atactccaaa acatgaagag ttatctttgt aattcttttaa   4380 gttgatgttt tcaccattag tcttcacttt caagtctttg gtggttggga ttaaggtatc    4440
tttatccatg gtgtttgttt atgtgtgttt attcgaaact aagttcttgg tgttttaaaa    4500
ctaaaaaaaa gactaactat aaaagtagaa tttaagaagt ttaagaaata gatttacaga    4560
attacaatca atacctaccg tctttatata cttattagtc aagtaggga ataatttcag     4620 ggaactggtt tcaaccttttt ttttcagctt tttccaaatc agagagagca gaaggtaata   4680
gaaggtgtaa gaaaatgaga tagatacatg cgtgggtcaa ttgccttgtg tcatcattta    4740
ctccaggcag gttgcatcac tccattgagg ttgtgcccgt ttttttgcctg tttgtgcccc   4800 tgttctctgt agttgcgcta agagaatgga cctatgaact gatggttggt gaagaaaaca    4860
```

```
atattttggt gctgggattc tttttttttc tggatgccag cttaaaaagc gggctccatt    4920
atatttagtg gatgccagga ataaactgtt cacccagaca cctacgatgt tatatattct    4980
gtgtaacccg cccctattt tgggcatgta cgggttacag cagaattaaa aggctaattt    5040
tttgactaaa taaagttagg aaaatcacta ctattaatta tttacgtatt ctttgaaatg    5100
gcagtattga taatgataaa ctcgaactga aaaagcgtgt tttttattca aaatgattct    5160
aactcccta cgtaatcaag gatcttttt gccttggcct ccgcgtcatt aaacttcttg    5220
ttgttgacgc taacattcaa cgctagtata tattcgtttt tttcaggtaa gttcttttca    5280
acgggtctta ctgatgaggc agtcgcgtct gaacctgtta agaggtcaaa tatgtcttct    5340
tgaccgtacg tgtcttgcat gttattagct ttgggaattt gcatcaagtc ataggaaaat    5400
ttaaatcttg gctctcttgg gctcaaggtg acaaggtcct cgaaaatagg gcgcgcccca    5460
ccgcggtgga gctccagctt tgttccctt tagtgagggt taattgcgcg cttggcgtaa    5520
tcatggtcat agctgtttcc tgtgtgaaat tgttatccgc tcacaattcc acacaacata    5580
ggagccggaa gcataaagtg taaagcctgg ggtgcctaat gagtgaggta actcacatta    5640
attgcgttgc gctcactgcc cgcttttccag tcgggaaacc tgtcgtgcca gctgcattaa    5700
tgaatcggcc aacgcgcggg gagaggcggt ttgcgtattg ggcgctcttc cgcttcctcg    5760
ctcactgact cgctgcgctc ggtcgttcgg ctgcggcgag cggtatcagc tcactcaaag    5820
gcggtaatac ggttatccac agaatcaggg gataacgcag gaaagaacat gtgagcaaaa    5880
ggccagcaaa aggccaggaa ccgtaaaaag gccgcgttgc tggcgttttt ccataggctc    5940
cgcccccctg acgagcatca caaaaatcga cgctcaagtc agaggtggcg aaacccgaca    6000
ggactataaa gataccaggc gtttccccct ggaagctccc tcgtgcgctc tcctgttccg    6060
accctgccgc ttaccggata cctgtccgcc tttctccctt cgggaagcgt ggcgctttct    6120
catagctcac gctgtaggta tctcagttcg gtgtaggtcg ttcgctccaa gctgggctgt    6180
gtgcacgaac ccccgttca gcccgaccgc tgcgccttat ccggtaacta tcgtcttgag    6240
tccaacccgg taagacacga cttatcgcca ctggcagcag ccactggtaa caggattagc    6300
agagcgaggt atgtaggcgg tgctacagag ttcttgaagt ggtggcctaa ctacggctac    6360
actagaagga cagtatttgg tatctgcgct ctgctgaagc cagttacctt cggaaaaaga    6420
gttggtagct cttgatccgg caaacaaacc accgctggta gcggtggttt ttttgtttgc    6480
aagcagcaga ttacgcgcag aaaaaaagga tctcaagaag atcctttgat cttttctacg    6540
gggtctgacg ctcagtggaa cgaaaactca cgttaaggga ttttggtcat gagattatca    6600
aaaaggatct tcacctagat ccttttaaat taaaaatgaa gttttaaatc aatctaaagt    6660
atatatgagt aaacttggtc tgacagttac caatgcttaa tcagtgaggc acctatctca    6720
gcgatctgtc tatttcgttc atccatagtt gcctgactcc ccgtcgtgta gataactacg    6780
atacgggagg gcttaccatc tggccccagt gctgcaatga taccgcgaga cccacgctca    6840
ccggctccag atttatcagc aataaaccag ccagccggaa gggccgagcg cagaagtggt    6900
cctgcaactt tatccgcctc catccagtct attaattgtt gccgggaagc tagagtaagt    6960
agttcgccag ttaatagttt gcgcaacgtt gttgccattg ctacaggcat cgtggtgtca    7020
cgctcgtcgt ttggtatggc ttcattcagc tccggttccc aacgatcaag gcgagttaca    7080
tgatccccca tgttgtgcaa aaaagcggtt agctccttcg gtcctccgat cgttgtcaga    7140
agtaagttgg ccgcagtgtt atcactcatg gttatggcag cactgcataa ttctcttact    7200
gtcatgccat ccgtaagatg cttttctgtg actggtgagt actcaaccaa gtcattctga    7260
```

```
gaatagtgta tgcggcgacc gagttgctct tgcccggcgt caatacggga taataccgcg   7320
ccacatagca gaactttaaa agtgctcatc attggaaaac gttcttcggg gcgaaaactc   7380
tcaaggatct taccgctgtt gagatccagt tcgatgtaac ccactcgtgc acccaactga   7440
tcttcagcat cttttacttt caccagcgtt tctgggtgag caaaaacagg aaggcaaaat   7500
gccgcaaaaa agggaataag ggcgacacgg aaatgttgaa tactcatact cttcctttt    7560 caatattatt gaagcattta tcagggttat tgtctcatga gcggatacat atttgaatgt   7620
atttagaaaa ataaacaaat aggggttccg cgcacatttc cccgaaaagt gccacctgaa   7680
cgaagcatct gtgcttcatt tgtagaaca aaaatgcaac gcgagagcgc taattttttca   7740 aacaaagaat ctgagctgca ttttacaga acagaaatgc aacgcgaaag cgctatttta    7800
ccaacgaaga atctgtgctt cattttgta aacaaaaat gcaacgcgag agcgctaatt    7860
tttcaaacaa gaatctgag ctgcatttt acagaacaga atgcaacgc gagagcgcta    7920 ttttaccaac aaagaatcta tacttctttt ttgttctaca aaaatgcatc ccgagagcgc   7980
tatttttcta acaaagcatc ttagattact tttttctcc tttgtgcgct ctataatgca    8040
gtctcttgat aacttttgc actgtaggtc cgttaaggtt agaagaaggc tactttggtg   8100 tctatttct cttccataaa aaagcctga ctccacttcc cgcgttact gattactagc      8160 gaagctgcgg gtgcattttt tcaagataaa ggcatccccg attatattct ataccgatgt   8220
ggattgcgca tactttgtga acagaaagtg atagcgttga tgattcttca ttggtcagaa   8280
aattatgaac ggtttcttct attttgtctc tatatactac gtataggaaa tgtttacatt    8340
ttcgtattgt tttcgattca ctctatgaat agttcttact acaatttttt tgtctaaaga   8400
gtaatactag agataaacat aaaaaatgta gaggtcgagt ttagatgcaa gttcaaggag   8460
cgaaaggtgg atgggtaggt tatataggga tatagcacag agatatatag caaagagata   8520
cttttgagca atgtttgtgg aagcggtatt cgcaatattt tagtagctcg ttacagtccg   8580
gtgcgttttt ggttttttga aagtgcgtct tcagagcgct tttggttttc aaaagcgctc   8640
tgaagttcct atactttcta gagaatagga acttcggaat aggaacttca aagcgtttcc   8700
gaaaacgagc gcttccgaaa atgcaacgcg agctgcgcac atacagctca ctgttcacgt   8760
cgcacctata tctgcgtgtt gcctgtatat atatatacat gagaagaacg gcatagtgcg   8820
tgtttatgct taaatgcgta cttatatgcg tctatttatg taggatgaaa ggtagtctag   8880
tacctcctgt gatattatcc cattccatgc ggggtatcgt atgcttcctt cagcactacc   8940
ctttagctgt tctatatgct gccactcctc aattggatta gtctcatcct tcaatgctat   9000
catttccttt gatattggat catactaaga aaccattatt atcatgacat taacctataa   9060
aaataggcgt atcacgaggc cctttcgtc                                     9089

<210> SEQ ID NO 122
<211> LENGTH: 1023
<212> TYPE: DNA
<213> ORGANISM: Saccharomyces cerevisiae

<400> SEQUENCE: 122
caccgcggtg gggcgcgccc tattttcgag gaccttgtca ccttgagccc aagagagcca    60
agatttaaat tttcctatga cttgatgcaa attcccaaag ctaataacat gcaagacacg   120
tacggtcaag aagacatatt tgacctctta acaggttcag acgcgactgc ctcatcagta   180
agacccgttg aaaagaactt acctgaaaaa aacgaatata tactagcgtt gaatgttagc   240
```

-continued

```
gtcaacaaca agaagtttaa tgacgcggag gccaaggcaa aaagattcct tgattacgta      300
agggagttag aatcattttg aataaaaaac acgcttttc agttcgagtt tatcattatc      360
aatactgcca tttcaaagaa tacgtaaata attaatagta gtgattttcc taactttatt      420
tagtcaaaaa attagccttt taattctgct gtaacccgta catgcccaaa atagggggcg      480
ggttacacag aatatataac atcgtaggtg tctgggtgaa cagtttattc ctggcatcca      540
ctaaatataa tggagcccgc ttttaagct ggcatccaga aaaaaaaga atcccagcac       600 caaaatattg ttttcttcac caaccatcag ttcataggtc cattctctta gcgcaactac      660
agagaacagg ggcacaaaca ggcaaaaaac gggcacaacc tcaatggagt gatgcaacct      720
gcctggagta aatgatgaca caaggcaatt gacccacgca tgtatctatc tcattttctt      780
acaccttcta ttccttctg ctctctctga tttggaaaaa gctgaaaaaa aaggttgaaa       840
ccagttccct gaaattattc ccctacttga ctaataagta tataaagacg gtaggtattg      900
attgtaattc tgtaaatcta tttcttaaac ttcttaaatt ctactttat agttagtctt       960 ttttttagtt ttaaaacacc aagaacttag tttcgaataa acacacataa actagtaaac     1020
aaa                                                                   1023
```

<210> SEQ ID NO 123
<211> LENGTH: 21
<212> TYPE: DNA
<213> ORGANISM: Artificial Sequence
<220> FEATURE:
<223> OTHER INFORMATION: primer

<400> SEQUENCE: 123
caaaagctga gctccaccgc g                                                21

<210> SEQ ID NO 124
<211> LENGTH: 44
<212> TYPE: DNA
<213> ORGANISM: Artificial Sequence
<220> FEATURE:
<223> OTHER INFORMATION: primer

<400> SEQUENCE: 124
gtttactagt ttatgtgtgt ttattcgaaa ctaagttctt ggtg                       44

<210> SEQ ID NO 125

<400> SEQUENCE: 125

000

<210> SEQ ID NO 126
<211> LENGTH: 39
<212> TYPE: DNA
<213> ORGANISM: Artificial Sequence
<220> FEATURE:
<223> OTHER INFORMATION: primer

<400> SEQUENCE: 126
cacacatatt acaatagcta gctgaggatg aaagctctg                             39

<210> SEQ ID NO 127
<211> LENGTH: 39
<212> TYPE: DNA
<213> ORGANISM: Artificial Sequence
<220> FEATURE:
<223> OTHER INFORMATION: primer

<400> SEQUENCE: 127
cagagctttc atcctcagct agctattgta atatgtgtg            39

<210> SEQ ID NO 128
<211> LENGTH: 9491
<212> TYPE: DNA
<213> ORGANISM: Artificial Sequence
<220> FEATURE:
<223> OTHER INFORMATION: constructed plasmid

<400> SEQUENCE: 128

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accataaatt cccgttttaa gagcttggtg agcgctagga gtcactgcca ggtatcgttt   240
gaacacggca ttagtcaggg aagtcataac acagtccttt cccgcaattt tcttttctta   300
ttactcttgg cctcctctag tacactctat atttttttat gcctcggtaa tgattttcat   360
tttttttttt cccctagcgg atgactcttt ttttttctta gcgattggca ttatcacata   420
atgaattata cattatataa agtaatgtga tttcttcgaa gaatatacta aaaaatgagc   480
aggcaagata aacgaaggca aagatgacag agcagaaagc cctagtaaag cgtattacaa   540
atgaaaccaa gattcagatt gcgatctctt taaagggtgg tcccctagcg atagagcact   600
cgatcttccc agaaaaagag gcagaagcag tagcagaaca ggccacacaa tcgcaagtga   660
ttaacgtcca cacaggtata gggtttctgg accatatgat acatgctctg gccaagcatt   720
ccggctggtc gctaatcgtt gagtgcattg gtgacttaca catagacgac catcacacca   780
ctgaagactg cgggattgct ctcggtcaag cttttaaaga ggccctactg gcgcgtggag   840
taaaaaggtt tggatcagga tttgcgcctt tggatgaggc actttccaga gcggtggtag   900
atctttcgaa caggccgtac gcagttgtcg aacttggttt gcaaagggag aaagtaggag   960
atctctcttg cgagatgatc ccgcattttc ttgaaagctt gcagaggct agcagaatta  1020
ccctccacgt tgattgtctg cgaggcaaga atgatcatca ccgtagtgag agtgcgttca  1080
aggctcttgc ggttgccata agagaagcca cctcgcccaa tggtaccaac gatgttccct  1140
ccaccaaagg tgttcttatg tagtgacacc gattatttaa agctgcagca tacgatatat  1200
atacatgtgt atatatgtat acctatgaat gtcagtaagt atgtatacga acagtatgat  1260
actgaagatg acaaggtaat gcatcattct atacgtgtca ttctgaacga ggcgcgcttt  1320
cctttttttct ttttgctttt tcttttttttt tctcttgaac tcgacggatc tatgcggtgt  1380
gaaataccgc acagatgcgt aaggagaaaa taccgcatca ggaaattgta acgttaata  1440
ttttgttaaa attcgcgtta aattttttgtt aaatcagctc attttttaac caataggccg  1500
aaatcggcaa aatcccttat aaatcaaaag aatagaccga gatagggttg agtgttgttc  1560
cagtttggaa caagagtcca ctattaaaga acgtggactc caacgtcaaa gggcgaaaaa  1620
ccgtctatca gggcgatggc ccactacgtg aaccatcacc ctaatcaagt ttttttgggt  1680
cgaggtgccg taaagcacta aatcggaacc ctaaagggag cccccgattt agagcttgac  1740
ggggaaagcc ggcgaacgtg cgagaaagg aagggaagaa agcgaaagga gcgggcgcta  1800
gggcgctggc aagtgtagcg gtcacgctgc gcgtaaccac cacacccgcc gcgcttaatg  1860
cgccgctaca gggcgcgtcg cgccattcgc cattcaggct gcgcaactgt tgggaagggc  1920
gatcggtgcg ggcctcttcg ctattacgcc agctggcgaa aggggatgt gctgcaaggc  1980
```

```
gattaagttg ggtaacgcca gggttttccc agtcacgacg ttgtaaaacg acggccagtg    2040
agcgcgcgta atacgactca ctatagggcg aattgggtac cgggccccc ctcgaggtcg     2100 acggcgcgcc actggtagag agcgactttg tatgccccaa ttgcgaaacc cgcgatatcc    2160
ttctcgattc tttagtaccc gaccaggaca aggaaaagga ggtcgaaacg tttttgaaga    2220
aacaagagga actacacgga agctctaaag atggcaacca gccagaaact aagaaaatga    2280
agttgatgga tccaactggc accgctggct gaacaacaa taccagcctt ccaacttctg     2340
taaataacgg cggtacgcca gtgccaccag taccgttacc tttcggtata cctcctttcc    2400
ccatgtttcc aatgcccttc atgcctccaa cggctactat cacaaatcct catcaagctg    2460
acgcaagccc taagaaatga ataacaatac tgacagtact aaataattgc ctacttggct    2520
tcacatacgt tgcatacgtc gatatagata ataatgataa tgacagcagg attatcgtaa    2580
tacgtaatag ttgaaaatct caaaaatgtg tgggtcatta cgtaaataat gataggaatg    2640
ggattcttct atttttcctt tttccattct agcagccgtc gggaaaacgt ggcatcctct    2700
ctttcgggct caattggagt cacgctgccg tgagcatcct ctctttccat atctaacaac    2760
tgagcacgta accaatggaa aagcatgagc ttagcgttgc tccaaaaaag tattggatgg    2820
ttaataccat ttgtctgttc tcttctgact ttgactcctc aaaaaaaaaa aatctacaat    2880
caacagatcg cttcaattac gccctcacaa aaacttttt ccttcttctt cgcccacgtt     2940
aaattttatc cctcatgttg tctaacggat ttctgcactt gatttattat aaaaagacaa    3000
agacataata cttctctatc aatttcagtt attgttcttc cttgcgttat tcttctgttc    3060
ttctttttct tttgtcatat ataaccataa ccaagtaata catattcaaa ctagtatgac    3120
tgacaaaaaa actcttaaag acttaagaaa tcgtagttct gtttacgatt caatggttaa    3180
atcacctaat cgtgctatgt tgcgtgcaac tggtatgcaa gatgaagact ttgaaaaacc    3240
tatcgtcggt gtcatttcaa cttgggctga aacacacct tgtaatatcc acttacatga     3300
ctttggtaaa ctagccaaag tcggtgttaa ggaagctggt gcttggccag ttcagttcgg    3360
aacaatcacg gtttctgatg gaatcgccat gggaacccaa ggaatgcgtt ctccttgac     3420 atctcgtgat attattgcag attctattga agcagccatg ggaggtcata atgcggatgc    3480
ttttgtagcc attggcggtt gtgataaaaa catgcccggt tctgttatcg ctatggctaa    3540 catgatatc ccagccattt ttgcttacgg cggaacaatt gcacctggta atttagacgg     3600
caaagatatc gatttagtct ctgtctttga aggtgtcggc cattggaacc acggcgatat    3660
gaccaaagaa gaagttaaag ctttggaatg taatgcttgt cccggtcctg gaggctgcgg    3720
tggtatgtat actgctaaca caatggcgac agctattgaa gttttgggac ttagccttcc    3780
gggttcatct tctcacccgg ctgaatccgc agaaagaaa gcagatattg aagaagctgg     3840
tcgcgctgtt gtcaaaatgc tcgaaatggg cttaaaacct tctgacattt taacgcgtga    3900
agcttttgaa gatgctatta ctgtaactat ggctctggga ggttcaacca actcaaccct    3960
tcacctctta gctattgccc atgctgctaa tgtggaattg acacttgatg atttcaatac    4020
tttccaagaa aaagttcctc atttggctga tttgaaacct tctggtcaat atgtattcca    4080 agaccttac aaggtcggag gggtaccagc agttatgaaa tatctcctta aaaatggctt    4140
ccttcatggt gaccgtatca cttgtactgg caaaacagtc gctgaaaatt tgaaggcttt    4200
tgatgattta acacctggtc aaaaggttat tatgccgctt gaaaatccta acgtgaaga     4260 tggtccgctc attattctcc atggtaactt ggctccagac ggtgccgttg ccaaagtttc    4320
```

```
tggtgtaaaa gtgcgtcgtc atgtcggtcc tgctaaggtc tttaattctg aagaagaagc    4380
cattgaagct gtcttgaatg atgatattgt tgatggtgat gttgttgtcg tacgttttgt    4440
aggaccaaag ggcggtcctg gtatgcctga aatgctttcc ctttcatcaa tgattgttgg    4500
taaagggcaa ggtgaaaaag ttgcccttct gacagatggc cgcttctcag gtggtactta    4560
tggtcttgtc gtgggtcata tcgctcctga agcacaagat ggcggtccaa tcgcctacct    4620
gcaaacagga gacatagtca ctattgacca agacactaag gaattacact ttgatatctc    4680
cgatgaagag ttaaaacatc gtcaagagac cattgaattg ccaccgctct attcacgcgg    4740
tatccttggt aaatatgctc acatcgtttc gtctgcttct aggggagccg taacagactt    4800
ttggaagcct gaagaaactg gcaaaaaatg ttgtcctggt tgctgtggtt aagcggccgc    4860
gttaattcaa attaattgat atagtttttt aatgagtatt gaatctgttt agaaataatg    4920 gaatatatt tttatttatt tatttatatt attggtcggc tcttttcttc tgaaggtcaa    4980
tgacaaaatg atatgaagga ataatgatt tctaaaattt tacaacgtaa gatatttta    5040 caaaagccta gctcatcttt tgtcatgcac tattttactc acgcttgaaa ttaacggcca    5100
gtccactgcg gagtcatttc aaagtcatcc taatcgatct atcgttttg atagctcatt    5160 ttggagttcg cgattgtctt ctgttattca caactgtttt aatttttatt tcattctgga    5220
actcttcgag ttctttgtaa agtctttcat agtagcttac tttatcctcc aacatattta    5280
acttcatgtc aatttcggct cttaaatttt ccacatcatc aagttcaaca tcatctttta    5340
acttgaattt attctctagc tcttccaacc aagcctcatt gctccttgat ttactggtga    5400
aaagtgatac actttgcgcg caatccaggt caaaactttc ctgcaaagaa ttcaccaatt    5460
tctcgacatc atagtacaat ttgtttgtt ctcccatcac aatttaatat acctgatgga    5520
ttcttatgaa gcgctgggta atggacgtgt cactctactt cgccttttc cctactcctt    5580 ttagtacgga agacaatgct aataaataag agggtaataa taatattatt aatcggcaaa    5640
aaagattaaa cgccaagcgt ttaattatca gaaagcaaac gtcgtaccaa tccttgaatg    5700
cttcccaatt gtatattaag agtcatcaca gcaacatatt cttgttatta aattaattat    5760
tattgatttt tgatattgta taaaaaaacc aaatatgtat aaaaaaagtg aataaaaaat    5820
accaagtatg gagaaatata ttagaagtct atacgttaaa ccaccgcggt ggagctccag    5880
cttttgttcc ctttagtgag ggttaattgc gcgcttggcg taatcatggt catagctgtt    5940
tcctgtgtga aattgttatc cgctcacaat tccacacaac ataggagccg aagcataaa    6000 gtgtaaagcc tggggtgcct aatgagtgag gtaactcaca ttaattgcgt tgcgctcact    6060
gcccgctttc cagtcgggaa acctgtcgtg ccagctgcat taatgaatcg gccaacgcgc    6120
ggggagaggc ggtttgcgta ttgggcgctc ttccgcttcc tcgctcactg actcgctgcg    6180
ctcggtcgtt cggctgcggc gagcggtatc agctcactca aaggcggtaa tacggttatc    6240
cacagaatca ggggataacg caggaaagaa catgtgagca aaaggccagc aaaaggccag    6300
gaaccgtaaa aaggccgcgt tgctggcgtt tttccatagg ctccgccccc ctgacgagca    6360
tcacaaaaat cgacgctcaa gtcagaggtg gcgaaacccg acaggactat aaagatacca    6420
ggcgtttccc cctggaagct ccctcgtgcg ctctcctgtt ccgaccctgc cgcttaccgg    6480
atacctgtcc gcctttctcc cttcgggaag cgtggcgctt tctcatagct cacgctgtag    6540
gtatctcagt tcggtgtagg tcgttcgctc caagctgggc tgtgtgcacg aaccccccgt    6600
tcagcccgac cgctgcgcct tatccggtaa ctatcgtctt gagtccaacc cggtaagaca    6660
cgacttatcg ccactggcag cagccactgg taacaggatt agcagagcga ggtatgtagg    6720
```

```
cggtgctaca gagttcttga agtggtggcc taactacggc tacactagaa ggacagtatt    6780
tggtatctgc gctctgctga agccagttac cttcggaaaa agagttggta gctcttgatc    6840
cggcaaacaa accaccgctg gtagcggtgg ttttttttgtt tgcaagcagc agattacgcg    6900
cagaaaaaaa ggatctcaag aagatccttt gatcttttct acggggtctg acgctcagtg    6960
gaacgaaaac tcacgttaag ggattttggt catgagatta tcaaaaagga tcttcaccta    7020 gatccttttta aattaaaaat gaagttttaa atcaatctaa agtatatatg agtaaacttg    7080
gtctgacagt taccaatgct taatcagtga ggcacctatc tcagcgatct gtctatttcg    7140
ttcatccata gttgcctgac tccccgtcgt gtagataact acgatacggg agggcttacc    7200
atctggcccc agtgctgcaa tgataccgcg agacccacgc tcaccggctc cagatttatc    7260
agcaataaac cagccagccg gaagggccga gcgcagaagt ggtcctgcaa ctttatccgc    7320
ctccatccag tctattaatt gttgccggga agctagagta agtagttcgc cagttaatag    7380
tttgcgcaac gttgttgcca ttgctacagg catcgtggtg tcacgctcgt cgtttggtat    7440
ggcttcattc agctccggtt cccaacgatc aaggcgagtt acatgatccc ccatgttgtg    7500
caaaaaagcg gttagctcct tcggtcctcc gatcgttgtc agaagtaagt tggccgcagt    7560
gttatcactc atggttatgg cagcactgca taattctctt actgtcatgc catccgtaag    7620
atgcttttct gtgactggtg agtactcaac caagtcattc tgagaatagt gtatgcggcg    7680
accgagttgc tcttgcccgg cgtcaatacg ggataatacc gcgccacata gcagaacttt    7740
aaaagtgctc atcattggaa aacgttcttc ggggcgaaaa ctctcaagga tcttaccgct    7800
gttgagatcc agttcgatgt aacccactcg tgcacccaac tgatcttcag catcttttac    7860
tttcaccagc gtttctgggt gagcaaaaac aggaaggcaa aatgccgcaa aaaagggaat    7920
aagggcgaca cggaaatgtt gaatactcat actcttcctt tttcaatatt attgaagcat    7980
ttatcagggt tattgtctca tgagcggata catatttgaa tgtatttaga aaaataaaca    8040
aataggggtt ccgcgcacat ttccccgaaa agtgccacct gaacgaagca tctgtgcttc    8100
attttgtaga acaaaaatgc aacgcgagag cgctaatttt tcaaacaaag aatctgagct    8160
gcatttttac agaacagaaa tgcaacgcga aagcgctatt ttaccaacga agaatctgtg    8220
cttcattttt gtaaaacaaa aatgcaacgc gagagcgcta attttcaaa caaagaatct    8280 gagctgcatt tttacagaac agaaatgcaa cgcgagagcg ctattttacc aacaaagaat    8340
ctatacttct ttttgttct acaaaaatgc atcccgagag cgctattttt ctaacaaagc    8400
atcttagatt acttttttc tcctttgtgc gctctataat gcagtctctt gataactttt    8460
tgcactgtag gtccgttaag gttagaagaa ggctactttg gtgtctattt tctcttccat    8520
aaaaaaagcc tgactccact tcccgcgttt actgattact agcgaagctg cgggtgcatt    8580
ttttcaagat aaaggcatcc ccgattatat tctataccga tgtggattgc gcatactttg    8640
tgaacagaaa gtgatagcgt tgatgattct tcattggtca gaaaattatg aacgtttct    8700 tctattttgt ctctatatac tacgtatagg aaatgtttac attttcgtat tgttttcgat    8760
tcactctatg aatagttctt actacaattt ttttgtctaa agagtaatac tagagataaa    8820
cataaaaaat gtagaggtcg agtttagatg caagttcaag gagcgaaagg tggatgggta    8880
ggttatatag ggatatagca cagagatata tagcaaagag atactttttga gcaatgtttg    8940 tggaagcggt attcgcaata ttttagtagc tcgttacagt ccggtgcgtt ttggttttt    9000 tgaaagtgcg tcttcagagc gcttttggtt ttcaaaagcg ctctgaagtt cctatacttt    9060
```

```
ctagagaata ggaacttcgg aataggaact tcaaagcgtt tccgaaaacg agcgcttccg    9120
aaaatgcaac gcgagctgcg cacatacagc tcactgttca cgtcgcacct atatctgcgt    9180
gttgcctgta tatatatata catgagaaga acggcatagt gcgtgtttat gcttaaatgc    9240
gtacttatat gcgtctattt atgtaggatg aaaggtagtc tagtacctcc tgtgatatta    9300
tcccattcca tgcggggtat cgtatgcttc cttcagcact acccttagc tgttctatat     9360 gctgccactc ctcaattgga ttagtctcat ccttcaatgc tatcatttcc tttgatattg    9420
gatcatctaa gaaaccatta ttatcatgac attaacctat aaaaataggc gtatcacgag    9480
gccctttcgt c                                                         9491
```

<210> SEQ ID NO 129
<211> LENGTH: 1000
<212> TYPE: DNA
<213> ORGANISM: Saccharomyces cerevisiae

<400> SEQUENCE: 129

```
gttaattcaa attaattgat atagtttttt aatgagtatt gaatctgttt agaaataatg     60
gaatattatt tttatttatt tatttatatt attggtcggc tcttttcttc tgaaggtcaa    120
tgacaaaatg atatgaagga ataatgatt tctaaaattt tacaacgtaa gatatttta    180 caaaagccta gctcatcttt tgtcatgcac tattttactc acgcttgaaa ttaacggcca    240
gtccactgcg gagtcatttc aaagtcatcc taatcgatct atcgttttg atagctcatt    300 ttggagttcg cgattgtctt ctgttattca caactgtttt aatttttatt tcattctgga    360
actcttcgag ttctttgtaa agtctttcat agtagcttac tttatcctcc aacatattta    420
acttcatgtc aatttcggct cttaaatttt ccacatcatc aagttcaaca tcatcttta    480 acttgaattt attctctagc tcttccaacc aagcctcatt gctccttgat ttactggtga    540
aaagtgatac actttgcgcg caatccaggt caaaactttc ctgcaaagaa ttcaccaatt    600
tctcgacatc atagtacaat ttgttttgtt ctcccatcac aatttaatat acctgatgga    660
ttcttatgaa gcgctgggta atggacgtgt cactctactt cgccttttc cctactcctt     720 ttagtacgga agacaatgct aataaataag agggtaataa taatattatt aatcggcaaa    780
aaagattaaa cgccaagcgt ttaattatca gaaagcaaac gtcgtaccaa tccttgaatg    840
cttcccaatt gtatattaag agtcatcaca gcaacatatt cttgttatta aattaattat    900
tattgatttt tgatattgta taaaaaaacc aaatatgtat aaaaaaagtg aataaaaaat    960
accaagtatg gagaaatata ttagaagtct atacgttaaa                         1000
```

<210> SEQ ID NO 130
<211> LENGTH: 16387
<212> TYPE: DNA
<213> ORGANISM: Artificial Sequence
<220> FEATURE:
<223> OTHER INFORMATION: Plasmid

<400> SEQUENCE: 130

```
gatcctctag tttctcggta ctatgcatat gatccaatat caaaggaaat gatagcattg     60
aaggatgaga ctaatccaat tgaggagtgg cagcatatag aacagctaaa gggtagtgct    120
gaaggaagca tacgataccc cgcatggaat gggataatat cacaggaggt actagactac    180
ctttcatcct acataaatag acgcatataa gtacgcattt aagcataaac acgcactatg    240
ccgttcttct catgtatata tatatacagg caacacgcag atataggtgc gacgtgaaca    300
gtgagctgta tgtgcgcagc tcgcgttgca ttttcggaag cgctcgtttt cggaaacgct    360
```

```
ttgaagttcc tattccgaag ttcctattct ctagaaagta taggaacttc agagcgcttt      420 tgaaaccaa aagcgctctg aagacgcact ttcaaaaaac caaaaacgca ccggactgta       480
acgagctact aaaatattgc gaataccgct tccacaaaca ttgctcaaaa gtatctcttt      540
gctatatatc tctgtgctat atccctatat aacctaccca tccacctttc gctccttgaa     600
cttgcatcta aactcgacct ctacattttt tatgtttatc tctagtatta ctctttagac     660
aaaaaaattg tagtaagaac tattcataga gtgaatcgaa aacaatacga aaatgtaaac     720
atttcctata cgtagtatat agagacaaaa tagaagaaac cgttcataat tttctgacca    780
atgaagaatc atcaacgcta tcactttctg ttcacaaagt atgcgcaatc cacatcggta    840
tagaatataa tcggggatgc ctttatcttg aaaaaatgca cccgcagctt cgctagtaat    900
cagtaaacgc gggaagtgga gtcaggcttt ttttatggaa gagaaaatag acaccaaagt    960
agccttcttc taaccttaac ggacctacag tgcaaaaagt tatcaagaga ctgcattata   1020
gagcgcacaa aggagaaaaa aagtaatcta agatgctttg ttagaaaaat agcgctctcg   1080
ggatgcattt ttgtagaaca aaaagaagt atagattctt tgttggtaaa atagcgctct    1140
cgcgttgcat ttctgttctg taaaaatgca gctcagattc tttgtttgaa aaattagcgc   1200
tctcgcgttg cattttttgtt ttacaaaaat gaagcacaga ttcttcgttg gtaaaatagc   1260
gctttcgcgt tgcattttctg ttctgtaaaa atgcagctca gattctttgt ttgaaaaatt   1320
agcgctctcg cgttgcattt ttgttctaca aaatgaagca cagatgcttc gttaacaaag   1380
atatgctatt gaagtgcaag atggaaacgc agaaaatgaa ccggggatgc gacgtgcaag   1440
attacctatg caatagatgc aatagtttct ccaggaaccg aaatacatac attgtcttcc   1500
gtaaagcgct agactatata ttattataca ggttcaaata tactatctgt ttcagggaaa   1560
actcccaggt tcggatgttc aaaattcaat gatgggtaac aagtacgatc gtaaatctgt   1620
aaaacagttt gtcggatatt aggctgtatc tcctcaaagc gtattcgaat atcattgaga   1680
agctgcattt tttttttttt ttttttttt tttttttata tatatttcaa ggatatacca   1740
ttgtaatgtc tgcccctaag aagatcgtcg ttttgccagg tgaccacgtt ggtcaagaaa   1800
tcacagccga agccattaag gttcttaaag ctatttctga tgttcgttcc aatgtcaagt   1860
tcgatttcga aaatcattta attggtggtg ctgctatcga tgctacaggt gttccacttc   1920
cagatgaggc gctggaagcc tccaagaagg ctgatgccgt tttgttaggt gctgtgggtg   1980
gtcctaaatg gggtaccggt agtgttagac ctgaacaagg tttactaaaa atccgtaaag   2040
aacttcaatt gtacgccaac ttaagaccat gtaactttgc atccgactct cttttagact   2100
tatctccaat caagccacaa tttgctaaag gtactgactt cgttgttgtt agagaattag   2160
tgggaggtat ttactttggt aagagaaagg aagacgatgg tgatggtgtc gcttgggata   2220
gtgaacaata caccgttcca gaagtgcaaa gaatcacaag aatggccgct tcatggccc    2280 tacaacatga gccaccattg cctatttggt ccttggataa agctaatgtt ttggcctctt   2340
caagattatg gagaaaaact gtggaggaaa ccatcaagaa cgaattccct acattgaaag   2400
ttcaacatca attgattgat tctgccgcca tgatcctagt taagaaccca acccacctaa   2460
atggtattat aatcaccagc aacatgtttg gtgatatcat ctccgatgaa gcctccgtta   2520
tcccaggctc cttgggtttg ttgccatctg cgtccttggc ctcttcgcca gacaagaaca   2580
ccgcatttgg tttgtacgaa ccatgccatg gttccgctcc agatttgcca aagaataagg   2640
tcaaccctat cgccactatc ttgtctgctg caatgatgtt gaaattgtca ttgaacttgc   2700
```

```
ctgaagaagg taaagccatt gaagatgcag ttaaaaaggt tttggatgca ggtatcagaa    2760
ctggtgattt aggtggttcc aacagtacca ccgaagtcgg tgatgctgtc gccgaagaag    2820
ttaagaaaat ccttgcttaa aaagattctc ttttttttatg atatttgtac aaaaaaaaaa    2880
aaaaaaaaaa aaaaaaaaaa aaaaaaaaaa aaaaaaaaaa aatgcagcgt cacatcggat    2940
aataatgatg gcagccattg tagaagtgcc ttttgcattt ctagtctctt tctcggtcta    3000
gctagtttta ctacatcgcg aagatagaat cttagatcac actgcctttg ctgagctgga    3060
tcaatagagt aacaaaagag tggtaaggcc tcgttaaagg acaaggacct gagcggaagt    3120
gtatcgtaca gtagacggag tatactagag tcgacctgca ggcatgcaag cttttcaatt    3180
catcattttt tttttattct ttttttttgat ttcggttttcc ttgaaatttt tttgattcgg    3240
taatctccga acagaaggaa gaacgaagga aggagcacag acttagattg gtatatatac    3300
gcatatgtag tgttgaagaa acatgaaatt gcccagtatt cttaacccaa ctgcacagaa    3360
caaaaacctg caggaaacga agataaatca tgtcgaaagc tacatataag gaacgtgctg    3420
ctactcatcc tagtcctgtt gctgccaagc tatttaatat catgcacgaa aagcaaacaa    3480
acttgtgtgc ttcattggat gttcgtacca ccaaggaatt actggagtta gttgaagcat    3540
taggtcccaa aatttgttta ctaaaaacac atgtggatat cttgactgat ttttccatgg    3600
agggcacagt taagccgcta aaggcattat ccgccaagta caattttttta ctcttcgaag    3660 acagaaaatt tgctgacatt ggtaatacag tcaaattgca gtactctgcg ggtgtataca    3720
gaatagcaga atgggcagac attacgaatg cacacggtgt ggtgggccca ggtattgtta    3780
gcggtttgaa gcaggcggca gaagaagtaa caaaggaacc tagaggcctt ttgatgttag    3840
cagaattgtc atgcaagggc tccctatcta ctggagaata tactaagggt actgttgaca    3900
ttgcgaagag cgacaaagat tttgttatcg gctttattgc tcaaagagac atgggtggaa    3960
gagatgaagg ttacgattgg ttgattatga cacccggtgt gggtttagat gacaagggag    4020
acgcattggg tcaacagtat agaaccgtgg atgatgtggc tctctacagga tctgacatta    4080 ttattgttgg aagaggacta tttgcaaagg aagggatgc taaggtagag ggtgaacgtt    4140
acagaaaagc aggctgggaa gcatatttga gaagatgcgg ccagcaaaac taaaaaactg    4200
tattataagt aaatgcatgt atactaaact cacaaattag agcttcaatt taattatatc    4260
agttattacc cgggaatctc ggtcgtaatg attttttataa tgacgaaaaa aaaaaaattg    4320
gaaagaaaaa gcttggcgta atcatggtca tagctgtttc ctgtgtgaaa ttgttatccg    4380
ctcacaattc cacacaacat acgagccgga agcataaagt gtaaagcctg gggtgcctaa    4440
tgagtgagct aactcacatt aattgcgttg cgctcactgc ccgcttttcca gtcgggaaac    4500 ctgtcgtgcc agctgcatta tgaatcggc caacgcgcgg ggagaggcgg tttgcgtatt    4560
gggcgctctt ccgcttcctc gctcactgac tcgctgcgct cggtcgttcg gctgcggcga    4620
gcggtatcag ctcactcaaa ggcggtaata cggttatcca cagaatcagg ggataacgca    4680
ggaaagaaca tgtgagcaaa aggccagcaa aaggccagga accgtaaaaa ggccgcgttg    4740
ctggcgtttt tccataggct ccgcccccct gacgagcatc acaaaaatcg acgctcaagt    4800
cagaggtggc gaaacccgac aggactataa agataccagg cgtttccccc tggaagctcc    4860
ctcgtgcgct ctcctgttcc gaccctgccg cttaccggat acctgtccgc ctttctccct    4920
tcgggaagcg tggcgctttc tcatagctca cgctgtaggt atctcagttc ggtgtaggtc    4980
gttcgctcca agctgggctg tgtgcacgaa ccccccgttc agcccgaccg ctgcgcctta    5040
tccggtaact atcgtcttga gtccaacccg gtaagacacg acttatcgcc actggcagca    5100
```

```
gccactggta acaggattag cagagcgagg tatgtaggcg gtgctacaga gttcttgaag    5160
tggtggccta actacggcta cactagaaga acagtatttg gtatctgcgc tctgctgaag    5220
ccagttacct tcggaaaaag agttggtagc tcttgatccg gcaaacaaac caccgctggt    5280
agcggtggtt ttttttgtttg caagcagcag attacgcgca gaaaaaaagg atctcaagaa    5340
gatcctttga tcttttctac ggggtctgac gctcagtgga acgaaaactc acgttaaggg    5400
attttggtca tgagattatc aaaaaggatc ttcacctaga tccttttaaa ttaaaaatga    5460
agttttaaat caatctaaag tatatatgag taaacttggt ctgacagtta ccaatgctta    5520
atcagtgagg cacctatctc agcgatctgt ctatttcgtt catccatagt tgcctgactc    5580
cccgtcgtgt agataactac gatacgggag ggcttaccat ctggccccag tgctgcaatg    5640
ataccgcgag acccacgctc accggctcca gatttatcag caataaacca gccagccgga    5700
agggccgagc gcagaagtgg tcctgcaact ttatccgcct ccatccagtc tattaattgt    5760
tgccgggaag ctagagtaag tagttcgcca gttaatagtt tgcgcaacgt tgttgccatt    5820
gctacaggca tcgtggtgtc acgctcgtcg tttggtatgg cttcattcag ctccggttcc    5880
caacgatcaa ggcgagttac atgatccccc atgttgtgca aaaaagcggt tagctccttc    5940
ggtcctccga tcgttgtcag aagtaagttg gccgcagtgt tatcactcat ggttatggca    6000
gcactgcata attctcttac tgtcatgcca tccgtaagat gcttttctgt gactggtgag    6060
tactcaacca agtcattctg agaatagtgt atgcggcgac cgagttgctc ttgcccggcg    6120
tcaatacggg ataataccgc gccacatagc agaactttaa aagtgctcat cattggaaaa    6180
cgttcttcgg ggcgaaaact ctcaaggatc ttaccgctgt tgagatccag ttcgatgtaa    6240
cccactcgtg cacccaactg atcttcagca tcttttactt tcaccagcgt ttctgggtga    6300
gcaaaaacag gaaggcaaaa tgccgcaaaa aagggaataa gggcgacacg gaaatgttga    6360
atactcatac tcttcctttt tcaatattat tgaagcattt atcagggtta ttgtctcatg    6420
agcggataca tatttgaatg tatttagaaa aataaacaaa taggggttcc gcgcacattt    6480
ccccgaaaag tgccacctga cgtctaagaa accattatta tcatgacatt aacctataaa    6540
aataggcgta tcacgaggcc ctttcgtctc gcgcgtttcg gtgatgacgg tgaaaacctc    6600
tgacacatgc agctcccgga gacggtcaca gcttgtctgt aagcggatgc cgggagcaga    6660
caagcccgtc agggcgcgtc agcgggtgtt ggcgggtgtc ggggctggct taactatgcg    6720
gcatcagagc agattgtact gagagtgcac cataaaattg taaacgttaa tattttgtta    6780
aaattcgcgt taaattttg ttaaatcagc tcattttta accaatagac cgaaatcggc    6840
aaaatccctt ataaatcaaa agaatagccc gagatagagt tgagtgttgt tccagtttgg    6900
aacaagagtc cactattaaa gaacgtggac tccaacgtca aagggcgaaa aaccgtctat    6960
cagggcgatg gcccactacg tgaaccatca cccaaatcaa gttttttggg gtcgaggtgc    7020
cgtaaagcac taaatcggaa ccctaaaggg agcccccgat ttagagcttg acggggaaag    7080
ccggcgaacg tggcgagaaa ggaagggaag aaagcgaaag gagcgggcgc taaggcgctg    7140
gcaagtgtag cggtcacgct gcgcgtaacc accacacccg ccgcgcttaa tgcgccgcta    7200
cagggcgcgt actatggttg ctttgacgta tgcggtgtga ataccgcac agatgcgtaa    7260 ggagaaaata ccgcatcagg cgccattcgc cattcaggct gcgcaactgt tgggaagggc    7320
gatcggtgcg ggcctcttcg ctattacgcc agctggcgaa aggggatgt gctgcaaggc    7380 gattaagttg ggtaacgcca gggttttccc agtcacgacg ttgtaaaacg acggccagtg    7440
```

```
aattcgagct ccaccgcgga tagatctgaa atgaataaca atactgacag tactaaataa    7500
ttgcctactt ggcttcacat acgttgcata cgtcgatata gataataatg ataatgacag    7560
caggattatc gtaatacgta atagttgaaa atctcaaaaa tgtgtgggtc attacgtaaa    7620
taatgatagg aatgggattc ttctattttt ccttttttcca ttctagcagc cgtcgggaaa    7680
acgtggcatc ctctctttcg ggctcaattg gagtcacgct gccgtgagca tcctctcttt    7740
ccatatctaa caactgagca cgtaaccaat ggaaaagcat gagcttagcg ttgctccaaa    7800
aaagtattgg atggttaata ccatttgtct gttctcttct gactttgact cctcaaaaaa    7860
aaaaaatcta caatcaacag atcgcttcaa ttacgccctc acaaaaactt ttttccttct    7920
tcttcgccca cgttaaattt tatccctcat gttgtctaac ggatttctgc acttgattta    7980
ttataaaaag acaaagacat aatacttctc tatcaatttc agttattgtt cttccttgcg    8040
ttattcttct gttcttcttt ttcttttgtc atatataacc ataaccaagt aatacatatt    8100
caaatctaga gctgaggatg ttgaagcaaa tcaacttcgg tggtactgtt gaaaccgtct    8160
acgaaagagc tgactggcca agagaaaagt tgttggacta cttcaagaac gacacttttg    8220
ctttgatcgg ttacggttcc caaggttacg tcaaggtttt gaacttgaga gacaacggtt    8280
tgaacgttat cattggtgtc cgtaaagatg gtgcttcttg gaaggctgcc atcgaagacg    8340
gttgggttcc aggcaagaac ttgttcactg ttgaagatgc tatcaagaga ggtagttacg    8400
ttatgaactt gttgtccgat gccgctcaat cagaaacctg gctgctatc aagccattgt    8460 tgaccaaggg taagactttg tacttctccc acggtttctc cccagtcttc aaggacttga    8520
ctcacgttga accaccaaag gacttagatg ttatcttggt tgctccaaag ggttccggta    8580
gaactgtcag atctttgttc aaggaaggtc gtggtattaa ctcttcttac gccgtctgga    8640
acgatgtcac cggtaaggct cacgaaaagg cccaagcttt ggccgttgcc attggttccg    8700
gttacgttta ccaaaccact ttcgaaagag aagtcaactc tgacttgtac ggtgaaagag    8760
gttgtttaat gggtggtatc cacggtatgt tcttggctca atacgacgtc ttgagagaaa    8820
acggtcactc cccatctgaa gctttcaacg aaaccgtcga agaagctacc caatctctat    8880
acccattgat cggtaagtac ggtatggatt acatgtacga tgcttgttcc accaccgcca    8940
gaagaggtgc tttggactgg tacccaatct tcaagaatgc tttgaagcct gttttccaag    9000
acttgtacga atctaccaag aacgtaccg aaaccaagag atctttggaa ttcaactctc    9060
aacctgacta cagagaaaag ctagaaaagg aattagacac catcagaaac atggaaatct    9120
ggaaggttgg taaggaagtc agaaagttga gaccagaaaa ccaataatta attaatcatg    9180
taattagtta tgtcacgctt acattcacgc cctcccccca catccgctct aaccgaaaag    9240
gaaggagtta gacaacctga agtctaggtc cctatttatt ttttatagt tatgttagta    9300 ttaagaacgt tatttatatt tcaaattttt cttttttttc tgtacagacg cgtgtacgca    9360
tgtaacatta tactgaaaac cttgcttgag aaggttttgg gacgctcgaa ggctttaatt    9420
tgcgggcggc cgctctagag agttgttagc aacctttttgt ttcttttgag ctggttcaga    9480
cattatgtac acgtatatgt gacgagttcg agaagtattt tactatcgta ctaaattta    9540 cctgaaaaat tatatactcg agaagagga agccaagaat tgagaaaaaa gaaaacccg    9600 cgagtaagga aattaaatac aggtgtacac atacacgcac acatatatat atatatatat    9660
atgtatatgt gtatataggaa agcgcgcgca tgttagtata tacgattcgt tggaaggggg    9720
ccgtccacca aacgtgactt gacgagttga caaattgacc tcaatatggc tcagtcagta    9780 attttagtt ccgctttatt cccgccatct ttcaggccac gagggtagct cataacgccg    9840
```

```
cgctaatgcc gctgcgtcac agcaaccagt agctcagcca aaaccgaaag agaaatcgta    9900
gctgtcccga tgaggactta tacacttgtc accatctaaa taaattattt attcgcgttt    9960
cggttcttgt tttcgattta attagattgt tcattgaatc ataataaata tgtaaaaaat   10020
atatatattt gaagctgctt cagaaaaaca gggcttccta gtgtacagat gtatgtcgga   10080
tgaaaaaaaa aaaatcttaa atgtgaaatt gggtcaattc aattgactat gacttgatgt   10140
tgcaaaaatt ccaagagaaa aagtttccag cacttgatat tattttcctc tttaattttt   10200
cgccttgtct acgatcttat tagcaccgat ccagggcatc atagaccttat actgttcacc   10260
aataatttcg ataccatgtg ctgcattgtt tcttctttta gcagtcatac tcgggtaacc   10320
cgtagcgcct tcacttatga acatcttagc gtattcaccg tcctggatac gtttcaaggc   10380
atttctcatg gcttgtcttg attctgcgtt aatgacttca ggtccggtga catactcacc   10440
atattctgca ttatttgaaa tggaatagtt catattagct ataccacctt catacattaa   10500
gtctactatc aacttcaatt catgtagaca ttcgaagtat gccatttcgg gagcgtaccc   10560
tgcttcgaca agcgtctcaa agcctgcttt aaccaattca acagttcctc cgcacagaac   10620
cgcttgttct ccaaataaat ctgtctcagt ctcgtcttta aaagtggttt ctattatacc   10680
cgttctcccg ccaccaactc ctgctgcgta gcttaaagct acattcttag cgtttccgct   10740
tgcgtcttgg tatatagcga tcaaatctgg aataccacca cccttaacaa attcgctcct   10800
aacagtatgc cccggagcct taggtgcaat cataataacg tccaaatctg ccctggggac   10860
tacttgattg taatgaatgg caaatccatg actgaaggcc aaggtagcgc ccttcttaat   10920
gtttggttct atttcatttt tgtacaattg cgattgaaat tcatctggcg ttaaaatcat   10980
gactaaatca gcgccggcaa cagccgctgc aacatctgtg actttcaagc catgtgcttc   11040
agcctttgca acggtagcac tacctttttct cagacctact gtcacgtcga ccccagaatc   11100
tttcaagtta caggcttgtg cgtgtccttg ggaaccatat cctataatag caaccttctt   11160
tccctggatg atgctcagat cgcagtcttt atcgtaaaac accttcatgt tttatttttt   11220
acttatattg ctggtagggt aaaaaaatat aactcctagg aataggttgt ctatatgttt   11280
ttgtcttgct tctataattg taacaaacaa ggaaagggaa aatactgggt gtaaaagcca   11340
ttgagtcaag ttaggtcatc cctttttatac aaaattttc aattttttt ccaagattct   11400
tgtacgatta attatttttt ttttgcgtcc tacagcgtga tgaaaatttc cgcctgctgc   11460
aagatgagcg ggaacgggcg aaatgtgcac gcgcacaact tacgaaacgc ggatgagtca   11520
ctgacagcca ccgcagaggt tctgactcct actgagctct attggaggtg gcagaaccgg   11580
taccggagga gaccgctata accggtttga atttattgtc acagtgtcac atcagcggca   11640
actcagaagt ttgacagcaa gcaagttcat cattcgaact agccttattg ttttagttca   11700
gtgacagcga actgccgtac tcgatgcttt atttctcacg gtagagcgga agaacagata   11760
ggggcagcgt gagaagagtt agaaagtaaa tttttatcac gtctgaagta ttcttattca   11820
taggaaattt tgcaaggttt tttagctcaa taacgggcta agttatataa ggtgttcacg   11880
cgattttctt gttatgtata cctcttctct gaggaatggt actactgtcc tgatgtaggc   11940
tccttaaatt ggtgggcaag aataacttat cgatattttg tatattggtc ttggagttca   12000
ccacgtaatg cctgtttaag accatcagtt aactctagta ttatttggtc ttggctactg   12060
gccgtttgct attattcaag tcttttgtgc ctttcccgtcg ggtaagggag ttatttaggg   12120
atacagaatc taacgaaaac taaatctcaa tgattaactc catttaatcc ttttttgaaa   12180
```

```
ggcaaaagag gtcccttgtt cacttacaac gttcttagcc aaattcgctt atcacttact   12240
acttcacgat atacagaagt aaaaacatat aaaaagatgt ctgtttgttt agccatcaca   12300
aaaggtatcg cagtttcttc tataggcctc tactctggtc ttttggcttc cgcttcattg   12360
attacatcta ctactccact agaggtttta acaggatctc taaaaacatc gatatcgtct   12420
ctgcgttcca atcctacggt gaatatattt ccaagcaatt cactgaagaa gaaagagaag   12480
atgttgtgga acatgcatgc ccaggtcctg gttcttgtgg tggtatgtat actgccaaca   12540
caatggcttc tgccgctgaa gtgctaggtt tgaccattcc aaactcctct tccttcccag   12600
ccgtttccaa ggagaagtta gctgagtgtg acaacattgg tgaatacatc aagaagacaa   12660
tggaattggg tattttacct cgtgatatcc tcacaaaaga ggcttttgaa aacgccatta   12720
cttatgtcgt tgcaaccggt gggtccacta atgctgtttt gcatttggtg gctgttgctc   12780
actctgcggg tgtcaagttg tcaccagatg atttccaaag aatcagtgat actacaccat   12840
tgatcggtga cttcaaacct tctggtaaat acgtcatggc cgatttgatt aacgttggtg   12900
gtacccaatc tgtgattaag tatctatatg aaaacaacat gttgcacggt aacacaatga   12960
ctgttaccgg tgacactttg gcagaacgtg caaagaaagc accaagccta cctgaaggac   13020
aagagattat taagccactc tcccacccaa tcaaggccaa cggtcacttg caaattctgt   13080
acggttcatt ggcaccaggt ggagctgtgg gtaaaattac cggtaaggaa ggtacttact   13140
tcaagggtag agcacgtgtg ttcgaagagg aaggtgcctt tattgaagcc ttggaaagag   13200
gtgaaatcaa gaagggtgaa aaaaccgttg ttgttatcag atatgaaggt ccaagaggtg   13260
caccaggtat gcctgaaatg ctaaagcctt cctctgctct gatgggttac ggtttgggta   13320
aagatgttgc attgttgact gatggtagat tctctggtgg ttctcacggg ttcttaatcg   13380
gccacattgt tcccgaagcc gctgaaggtg gtcctatcgg gttggtcaga gacggcgatg   13440
agattatcat tgatgctgat aataacaaga ttgacctatt agtctctgat aaggaaatgg   13500
ctcaacgtaa acaaagttgg gttgcacctc cacctcgtta cacaagaggt actctatcca   13560
agtatgctaa gttggtttcc aacgcttcca acggttgtgt tttagatgct tgattaatta   13620
agagtaagcg aatttcttat gatttatgat ttttattatt aaataagtta taaaaaaaat   13680
aagtgtatac aaattttaaa gtgactctta ggttttaaaa cgaaaattct tattcttgag   13740
taactctttc ctgtaggtca ggttgctttc tcaggtatag catgaggtcg ctcttattga   13800
ccacacctct accggcatgc cgagcaaatg cctgcaaatc gctccccatt tcacccaatt   13860
gtagatatgc taactccagc aatgagttga tgaatctcgg tgtgtatttt atgtcctcag   13920
aggacaacac ctgtggtact agttctagag cggccgcccg caaattaaag ccttcgagcg   13980
tcccaaaacc ttctcaagca aggttttcag tataatgtta catgcgtaca cgcgtctgta   14040
cagaaaaaaa agaaaaattt gaaatataaa taacgttctt aatactaaca taactataaa   14100
aaaataaata gggacctaga cttcaggttg tctaactcct tccttttcgg ttagagcgga   14160
tgtgggggga gggcgtgaat gtaagcgtga cataactaat tacatgatta attaactaga   14220
gagctttcgt tttcatgagt tccccgaatt cttttcggaag cttgtcactt gctaaattaa   14280
tgttatcact gtagtcaacc gggacatcga tgatgacagg accttcagcg ttcatgcctt   14340
gacgcagaac atctgccagc tggtctggtg attctacgcg caagccagtt gctccgaagc   14400
tttccgcata tttcacgata tcgatatttc cgaaatcgac cgcagatgta cggttatatt   14460
ttttcaattg ctggaatgca accatgtcat atgtgctgtc gttccataca atgtgtacaa   14520
ttggtgcttt tagtcgaact gctgtctcta attccattgc tgagaataag aaaccgccgt   14580
```

```
caccagagac agaaaccact ttttctcccg gtttcaccaa tgaagcgccg attgcccaag    14640
gaagcgcaac gccgagtgtt tgcataccgt tactgatcat taatgttaac ggctcgtagc    14700
tgcggaaata acgtgacatc caaatggcgt gcgaaccgat atcgcaagtt actgtaacat    14760
gatcatcgac tgcattacgc aactctttaa cgatttcaag agggtgcgct ctgtctgatt    14820
tccaatctgc aggcacctgc tcaccttcat gcatatattg ttttaaatca gaaaggattt    14880
tctgctcacg ctctgcaaat tccactttca cagcatcgtg ttcgatatga ttgatcgtgg    14940
acggaatgtc accgatcaat tcaagatcag gctggtaagc atgatcaatg tcagcgataa    15000
tctcgtctaa atggataatt gtccggtctc cattgatatt ccagaatttc ggatcatatt    15060
caatcgggtc atagccgatc gtcagaacaa catctgcctg ctctagcagt aaatcgccag    15120
gctggttgcg gaacaaaccg atacggccaa aatattgatc ctctaaatct ctagaaaggg    15180
taccggcagc ttgatatgtt tcaacaaatg gaagctgaac cttttcaaa agcttgcgaa    15240 ccgctttaat tgcttccggt cttccgcctt tcatgccgac caaaacgaca ggaagttttg    15300
ctgtttggat ttttgctatg ccgcactga ttgcatcatc tgctgcagga ccgagttttg    15360
gcgctgcaac agcacgcacg ttttcgtat ttgtgacttc attcacaaca tcttgcggaa    15420
agctcacaaa agcggcccca gcctgccctg ctgacgctat cctaaatgca tttgtaacag    15480
cttccggtat attttttaca tcttgaactt ctacactgta ttttgtaatc ggctggaata    15540
gcgccgcatt atccaaagat tgatgtgtcc gttttaaacg atctgcacgg atcacgtttc    15600
cagcaagcgc aacgacaggg tctccttcag tgttcgctgt cagcaggcct gttgccaagt    15660
tagaggcacc cggtcctgat gtgactaaca cgactcccgg ttttccagtt aaacggccga    15720
ctgcttgggc catgaatgct gcgttttgtt cgtgccgggc aacgataatt tcaggtcctt    15780
tatcttgtaa agcgtcaaat accgcatcaa ttttgcacc tggaatgcca aatacatgtg    15840
tgacaccttg ctccactaag caatcaacaa caagctccgc ccctctgttt ttcacaaggg    15900 attttgttc ttttgttgct tttgtcaaca tcctcagcga tgattgattg attgattgta    15960
cagtttgttt ttcttaatat ctatttcgat gacttctata tgatattgca ctaacaagaa    16020
gatattataa tgcaattgat acaagacaag gagttatttg cttctctttt atatgattct    16080
gacaatccat attgcgttgg tagtctttt tgctggaacg gttcagcgga aaagacgcat    16140
cgctcttttt gcttctagaa gaaatgccag caaaagaatc tcttgacagt gactgacagc    16200
aaaaatgtct ttttctaact agtaacaagg ctaagatatc agcctgaaat aaagggtggt    16260
gaagtaataa ttaaatcatc cgtataaacc tatacacata tatgaggaaa ataatacaa     16320 aagtgtttta aatacagata catacatgaa catatgcacg tatagcgccc aaatgtcggt    16380
aatggga                                                             16387
```

<210> SEQ ID NO 131
<211> LENGTH: 1188
<212> TYPE: DNA
<213> ORGANISM: Saccharomyces cerevisiae

<400> SEQUENCE: 131

```
atgttgagaa ctcaagccgc cagattgatc tgcaactccc gtgtcatcac tgctaagaga      60
acctttgctt tggccaccccg tgctgctgct tacagcagac cagctgcccg tttcgttaag    120
ccaatgatca ctaccgtgg tttgaagcaa atcaacttcg gtggtactgt tgaaaccgtc      180
tacgaaagag ctgactggcc aagagaaaag ttgttggact acttcaagaa cgacactttt     240
```

```
gctttgatcg gttacggttc ccaaggttac ggtcaaggtt tgaacttgag agacaacggt      300
ttgaacgtta tcattggtgt ccgtaaagat ggtgcttctt ggaaggctgc catcgaagac      360
ggttgggttc caggcaagaa cttgttcact gttgaagatg ctatcaagag aggtagttac      420
gttatgaact tgttgtccga tgccgctcaa tcagaaacct ggcctgctat caagccattg      480
ttgaccaagg gtaagacttt gtacttctcc cacggtttct ccccagtctt caaggacttg      540
actcacgttg aaccaccaaa ggacttagat gttatcttgg ttgctccaaa gggttccggt      600
agaactgtca gatctttgtt caaggaaggt cgtggtatta actcttctta cgccgtctgg      660
aacgatgtca ccggtaaggc tcacgaaaag gcccaagctt tggccgttgc cattggttcc      720
ggttacgttt accaaaccac tttcgaaaga gaagtcaact ctgacttgta cggtgaaaga      780
ggttgtttaa tgggtggtat ccacggtatg ttcttggctc aatacgacgt cttgagagaa      840
aacggtcact ccccatctga agctttcaac gaaaccgtcg aagaagctac ccaatctcta      900
tacccattga tcggtaagta cggtatggat tacatgtacg atgcttgttc caccaccgcc      960
agaagaggtg ctttggactg gtacccaatc ttcaagaatg ctttgaagcc tgttttccaa     1020
gacttgtacg aatctaccaa gaacggtacc gaaaccaaga gatctttgga attcaactct     1080
caacctgact acagagaaaa gctagaaaag gaattagaca ccatcagaaa catggaaatc     1140
tggaaggttg gtaaggaagt cagaaagttg agaccagaaa accaataa                 1188

<210> SEQ ID NO 132
<211> LENGTH: 1014
<212> TYPE: DNA
<213> ORGANISM: Pseudomonas fluorescens

<400> SEQUENCE: 132
atgaaagttt tctacgataa agactgcgac ctgtcgatca tccaaggtaa gaaagttgcc       60
atcatcggct acggttccca gggccacgct caagcatgca acctgaagga ttccggcgta      120
gacgtgactt tggcctgcg taaaggctcg gctaccgttg ccaaggctga agcccacggc      180
ttgaaagtga ccgacgttgc tgcagccgtt gccggtgccg acttggtcat gatcctgacc      240
ccggacgagt tccagtccca gctgtacaag aacgaaatcg agccgaacat caagaagggc      300
gccactctgg ccttctccca cggcttcgcg atccactaca accaggttgt gcctcgtgcc      360
gacctcgacg tgatcatgat cgcgccgaag gctccaggcc acaccgtacg ttccgagttc      420
gtcaagggcg gtggtattcc tgacctgatc gcgatctacc aggacgcttc cggcaacgcc      480
aagaacgttg ccctgtccta cgccgcaggc gtgggcggcg ccgtaccggg catcatcgaa      540
accaccttca aggacgagac tgaaaccgac ctgttcggtg agcaggctgt tctgtgtggc      600
ggtaccgtcg agctggtcaa agccggtttc gaaaccctgg ttgaagctgg ctacgctcca      660
gaaatggcct acttcgagtg cctgcacgaa ctgaagctga tcgttgacct catgtacgaa      720
ggcggtatcg ccaacatgaa ctactcgatc tccaacaacg ctgaatacgg cgagtacgtg      780
actggtccag aagtcatcaa cgccgaatcc cgtcaggcca tgcgcaatgc tctgaagcgc      840
atccaggacg gcgaatacgc gaagatgttc atcagcgaag gcgctaccgg ctacccatcg      900
atgaccgcca agcgtcgtaa caacgctgct cacggtatcg aaatcatcgg cgagcaactg      960
cgctcgatga tgccttggat cggtgccaac aaaatcgtcg acaaagccaa gaac           1014

<210> SEQ ID NO 133
<211> LENGTH: 250
<212> TYPE: DNA
<213> ORGANISM: Saccharomyces cerevisiae
```

<400> SEQUENCE: 133

```
ccgcaaatta aagccttcga gcgtcccaaa accttctcaa gcaaggtttt cagtataatg      60
ttacatgcgt acacgcgtct gtacagaaaa aaagaaaaa tttgaaatat aaataacgtt     120
cttaatacta acataactat aaaaaaataa atagggacct agacttcagg ttgtctaact     180
ccttcctttt cggttagagc ggatgtgggg ggagggcgtg aatgtaagcg tgacataact     240
aattacatga                                                           250
```

<210> SEQ ID NO 134
<211> LENGTH: 1181
<212> TYPE: DNA
<213> ORGANISM: Saccharomyces cerevisiae

<400> SEQUENCE: 134

```
taaaacctct agtggagtag tagatgtaat caatgaagcg gaagccaaaa gaccagagta      60
gaggcctata gaagaaactg cgatacccttt tgtgatggct aaacaaacag acatctttttt    120 atatgttttt acttctgtat atcgtgaagt agtaagtgat aagcgaattt ggctaagaac     180
gttgtaagtg aacaagggac ctcttttgcc tttcaaaaaa ggattaaatg gagttaatca     240
ttgagattta gttttcgtta gattctgtat ccctaaataa ctcccttacc cgacgggaag     300
gcacaaaaga cttgaataat agcaaacggc cagtagccaa gaccaaataa tactagagtt     360
aactgatggt cttaaacagg cattacgtgg tgaactccaa gaccaatata caaaatatcg     420
ataagttatt cttgcccacc aatttaagga gcctacatca ggacagtagt accattcctc     480
agagaagagg tatacataac aagaaaatcg cgtgaacacc ttatataact tagcccgtta     540
ttgagctaaa aaaccttgca aaatttccta tgaataagaa tacttcagac gtgataaaaa     600
tttactttct aactcttctc acgctgcccc tatctgttct tccgctctac cgtgagaaat     660
aaagcatcga gtacggcagt tcgctgtcac tgaactaaaa caataaggct agttcgaatg     720
atgaacttgc ttgctgtcaa acttctgagt tgccgctgat gtgacactgt gacaataaat     780
tcaaaccggt tatagcggtc tcctccggta ccggttctgc cacctccaat agagctcagt     840
aggagtcaga acctctgcgg tggctgtcag tgactcatcc gcgtttcgta agttgtgcgc     900
gtgcacattt cgcccgttcc cgctcatctt gcagcaggcg gaaattttca tcacgctgta     960
ggacgcaaaa aaaaaataat taatcgtaca agaatcttgg aaaaaaaatt gaaaatttt     1020 gtataaaagg gatgacctaa cttgactcaa tggcttttac acccagtatt ttcccttttcc    1080 ttgtttgtta caattataga agcaagacaa aaacatatag acaacctatt cctaggagtt     1140 atatttttttt accctaccag caatataagt aaaaaactag t                        1181
```

<210> SEQ ID NO 135
<211> LENGTH: 759
<212> TYPE: DNA
<213> ORGANISM: Saccharomyces cerevisiae

<400> SEQUENCE: 135

```
ggccctgcag gcctatcaag tgctggaaac ttttttctctt ggaattttg caacatcaag      60 tcatagtcaa ttgaattgac ccaatttcac atttaagatt ttttttttttt catccgacat    120 acatctgtac actaggaagc cctgtttttc tgaagcagct tcaaatatat atattttttta   180 catatttatt atgattcaat gaacaatcta attaaatcga aaacaagaac cgaaacgcga     240
ataaataatt tatttagatg gtgacaagtg tataagtcct catcgggaca gctacgattt     300
```

| | |
|---|---:|
| ctctttcggt tttggctgag ctactggttg ctgtgacgca gcggcattag cgcggcgtta | 360 |
| tgagctaccc tcgtggcctg aaagatggcg ggaataaagc ggaactaaaa attactgact | 420 |
| gagccatatt gaggtcaatt tgtcaactcg tcaagtcacg tttggtggac ggcccctttc | 480 |
| caacgaatcg tatatactaa catgcgcgcg cttcctatat acacatatac atatatatat | 540 |
| atatatatat gtgtgcgtgt atgtgtacac ctgtatttaa tttccttact cgcgggtttt | 600 |
| tcttttttct caattcttgg cttcctcttt ctcgagtata taattttttca ggtaaaattt | 660 |
| agtacgatag taaaatactt ctcgaactcg tcacatatac gtgtacataa tgtctgaacc | 720 |
| agctcaaaag aaacaaaagg ttgctaacaa ctctctaga | 759 |

<210> SEQ ID NO 136
<211> LENGTH: 643
<212> TYPE: DNA
<213> ORGANISM: Saccharomyces cerevisiae
<400> SEQUENCE: 136

| | |
|---|---:|
| gaaatgaata caatactga cagtactaaa taattgccta cttggcttca catacgttgc | 60 |
| atacgtcgat atagataata atgataatga cagcaggatt atcgtaatac gtaatagttg | 120 |
| aaaatctcaa aaatgtgtgg gtcattacgt aaataatgat aggaatggga ttcttctatt | 180 |
| tttccttttt ccattctagc agccgtcggg aaaacgtggc atcctctctt tcgggctcaa | 240 |
| ttggagtcac gctgccgtga gcatcctctc tttccatatc taacaactga gcacgtaacc | 300 |
| aatggaaaag catgagctta gcgttgctcc aaaaagtat tggatggtta ataccatttg | 360 |
| tctgttctct tctgactttg actcctcaaa aaaaaaaat ctacaatcaa cagatcgctt | 420 |
| caattacgcc ctcacaaaaa ctttttttcct tcttcttcgc ccacgttaaa ttttatccct | 480 |
| catgttgtct aacggatttc tgcacttgat ttattataaa aagacaaaga cataatactt | 540 |
| ctctatcaat ttcagttatt gttcttcctt gcgttattct tctgttcttc ttttctttt | 600 |
| gtcatatata accataacca agtaatacat attcaaatct aga | 643 |

<210> SEQ ID NO 137
<211> LENGTH: 1716
<212> TYPE: DNA
<213> ORGANISM: Bacillus subtilis
<400> SEQUENCE: 137

| | |
|---|---:|
| atgttgacaa aagcaacaaa agaacaaaaa tcccttgtga aaacagagg ggcggagctt | 60 |
| gttgttgatt gcttagtgga gcaaggtgtc acacatgtat ttggcattcc aggtgcaaaa | 120 |
| attgatgcgg tatttgacgc tttacaagat aaaggacctg aaattatcgt tgcccggcac | 180 |
| gaacaaaacg cagcattcat ggcccaagca gtcggccgtt taactggaaa accgggagtc | 240 |
| gtgttagtca catcaggacc gggtgcctct aacttggcaa caggcctgct gacagcgaac | 300 |
| actgaaggag accctgtcgt tgcgcttgct ggaaacgtga ccgtgcaga tcgtttaaaa | 360 |
| cggacacatc aatctttgga taatgcgcg ctattccagc cgattacaaa atacagtgta | 420 |
| gaagttcaag atgtaaaaaa ataccggaa gctgttacaa atgcatttag atagcgtca | 480 |
| gcagggcagg ctggggccgc ttttgtgagc tttccgcaag atgttgtgaa tgaagtcaca | 540 |
| aatacgaaaa acgtgcgtgc tgttcagcg ccaaaactcg gtcctgcagc agatgatgca | 600 |
| atcagtgcgg ccatagcaaa aatccaaaca gcaaaacttc ctgtcgtttt ggtcggcatg | 660 |
| aaaggcggaa gaccggaagc aattaaagcg gttcgcaagc ttttgaaaaa ggttcagctt | 720 |
| ccatttgttg aaacatatca agctgccggt accctttcta gagattaga ggatcaatat | 780 |

```
tttggccgta tcggtttgtt ccgcaaccag cctggcgatt tactgctaga gcaggcagat    840
gttgttctga cgatcggcta tgacccgatt gaatatgatc cgaaattctg gaatatcaat    900
ggagaccgga caattatcca tttagacgag attatcgctg acattgatca tgcttaccag    960
cctgatcttg aattgatcgg tgacattccg tccacgatca atcatatcga acacgatgct   1020
gtgaaagtgg aatttgcaga gcgtgagcag aaaatccttt ctgatttaaa acaatatatg   1080
catgaaggtg agcaggtgcc tgcagattgg aaatcagaca gagcgcaccc tcttgaaatc   1140
gttaaagagt tgcgtaatgc agtcgatgat catgttacag taacttgcga tatcggttcg   1200
cacgccattt ggatgtcacg ttatttccgc agctacgagc cgttaacatt aatgatcagt   1260
aacggtatgc aaacactcgg cgttgcgctt ccttgggcaa tcggcgcttc attggtgaaa   1320
ccgggagaaa aagtggtttc tgtctctggt gacggcggtt tcttattctc agcaatggaa   1380
ttagagacag cagttcgact aaaagcacca attgtacaca ttgtatggaa cgacagcaca   1440
tatgacatgg ttgcattcca gcaattgaaa aaatataacc gtacatctgc ggtcgatttc   1500
ggaaatatcg atatcgtgaa atatgcggaa agcttcggag caactggctt gcgcgtagaa   1560
tcaccagacc agctggcaga tgttctgcgt caaggcatga acgctgaagg tcctgtcatc   1620
atcgatgtcc cggttgacta cagtgataac attaatttag caagtgacaa gcttccgaaa   1680
gaattcgggg aactcatgaa aacgaaagct ctctag                             1716
```

<210> SEQ ID NO 138
<211> LENGTH: 571
<212> TYPE: PRT
<213> ORGANISM: Bacillus subtilis

<400> SEQUENCE: 138

```
Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205
```

Gln Thr Ala Lys Leu Pro Val Leu Val Gly Met Lys Gly Gly Arg
    210                 215                 220
Pro Glu Ala Ile Lys Ala Val Arg Lys Leu Lys Lys Val Gln Leu
225                 230                 235                 240
Pro Phe Val Glu Thr Tyr Gln Ala Ala Gly Thr Leu Ser Arg Asp Leu
                245                 250                 255
Glu Asp Gln Tyr Phe Gly Arg Ile Gly Leu Phe Arg Asn Gln Pro Gly
            260                 265                 270
Asp Leu Leu Leu Glu Gln Ala Asp Val Val Leu Thr Ile Gly Tyr Asp
        275                 280                 285
Pro Ile Glu Tyr Asp Pro Lys Phe Trp Asn Ile Asn Gly Asp Arg Thr
    290                 295                 300
Ile Ile His Leu Asp Glu Ile Ile Ala Asp Ile Asp His Ala Tyr Gln
305                 310                 315                 320
Pro Asp Leu Glu Leu Ile Gly Asp Ile Pro Ser Thr Ile Asn His Ile
                325                 330                 335
Glu His Asp Ala Val Lys Val Glu Phe Ala Glu Arg Glu Gln Lys Ile
            340                 345                 350
Leu Ser Asp Leu Lys Gln Tyr Met His Glu Gly Glu Gln Val Pro Ala
        355                 360                 365
Asp Trp Lys Ser Asp Arg Ala His Pro Leu Glu Ile Val Lys Glu Leu
    370                 375                 380
Arg Asn Ala Val Asp Asp His Val Thr Val Thr Cys Asp Ile Gly Ser
385                 390                 395                 400
His Ala Ile Trp Met Ser Arg Tyr Phe Arg Ser Tyr Glu Pro Leu Thr
                405                 410                 415
Leu Met Ile Ser Asn Gly Met Gln Thr Leu Gly Val Ala Leu Pro Trp
            420                 425                 430
Ala Ile Gly Ala Ser Leu Val Lys Pro Gly Glu Lys Val Val Ser Val
        435                 440                 445
Ser Gly Asp Gly Gly Phe Leu Phe Ser Ala Met Glu Leu Glu Thr Ala
    450                 455                 460
Val Arg Leu Lys Ala Pro Ile Val His Ile Val Trp Asn Asp Ser Thr
465                 470                 475                 480
Tyr Asp Met Val Ala Phe Gln Gln Leu Lys Lys Tyr Asn Arg Thr Ser
                485                 490                 495
Ala Val Asp Phe Gly Asn Ile Asp Ile Val Lys Tyr Ala Glu Ser Phe
            500                 505                 510
Gly Ala Thr Gly Leu Arg Val Glu Ser Pro Asp Gln Leu Ala Asp Val
        515                 520                 525
Leu Arg Gln Gly Met Asn Ala Glu Gly Pro Val Ile Ile Asp Val Pro
    530                 535                 540
Val Asp Tyr Ser Asp Asn Ile Asn Leu Ala Ser Asp Lys Leu Pro Lys
545                 550                 555                 560
Glu Phe Gly Glu Leu Met Lys Thr Lys Ala Leu
                565                 570

<210> SEQ ID NO 139
<211> LENGTH: 448
<212> TYPE: DNA
<213> ORGANISM: Saccharomyces cerevisiae

<400> SEQUENCE: 139
cccattaccg acatttgggc gctatacgtg catatgttca tgtatgtatc tgtatttaaa    60

```
acacttttgt attattttc ctcatatatg tgtataggtt tatacggatg atttaattat    120
tacttcacca ccctttattt caggctgata tcttagcctt gttactagtt agaaaaagac    180 attttgctg tcagtcactg tcaagagatt cttttgctgg catttcttct agaagcaaaa    240
agagcgatgc gtcttttccg ctgaaccgtt ccagcaaaaa agactaccaa cgcaatatgg    300
attgtcagaa tcatataaaa gagaagcaaa taactccttg tcttgtatca attgcattat    360
aatatcttct tgttagtgca atatcatata gaagtcatcg aaatagatat taagaaaaac    420
aaactgtaca atcaatcaat caatcatc                                      448
```

<210> SEQ ID NO 140
<211> LENGTH: 16387
<212> TYPE: DNA
<213> ORGANISM: Artificial Sequence
<220> FEATURE:
<223> OTHER INFORMATION: plasmid construct

<400> SEQUENCE: 140

```
tcccattacc gacatttggg cgctatacgt gcatatgttc atgtatgtat ctgtatttaa     60 aacactttg tattattttt cctcatatat gtgtataggt ttatacggat gatttaatta    120
ttacttcacc acccttttatt tcaggctgat atcttagcct tgttactagt tagaaaaaga    180 cattttgct gtcagtcact gtcaagagat tcttttgctg gcatttcttc tagaagcaaa    240
aagagcgatg cgtcttttcc gctgaaccgt tccagcaaaa aagactacca acgcaatatg    300
gattgtcaga atcatataaa agagaagcaa taactccttg tcttgtatc aattgcatta    360 taatatcttc ttgttagtgc aatatcatat agaagtcatc gaaatagata ttaagaaaaa    420
caaactgtac aatcaatcaa tcaatcatcg ctgaggatgt tgacaaaagc aacaaaagaa    480
caaaaatccc ttgtgaaaaa cagaggggcg gagcttgttg ttgattgctt agtggagcaa    540
ggtgtcacac atgtatttgg cattccaggt gcaaaaattg atgcggtatt tgacgcttta    600
caagataaag gacctgaaat tatcgttgcc cggcacgaac aaaacgcagc attcatggcc    660
caagcagtcg gccgtttaac tggaaaaccg ggagtcgtgt tagtcacatc aggacccggt    720
gcctctaact tggcaacagg cctgctgaca gcgaacactg aaggagaccc tgtcgttgcg    780
cttgctggaa acgtgatccg tgcagatcgt ttaaaacgga cacatcaatc tttggataat    840
gcggcgctat tccagccgat tacaaaatac agtgtagaag ttcaagatgt aaaaaatata    900
ccggaagctg ttacaaatgc atttaggata gcgtcagcag ggcaggctgg ggccgctttt    960
gtgagctttc gcaagatgt tgtgaatgaa gtcacaaata cgaaaaacgt gcgtgctgtt   1020
gcagcgccaa aactcggtcc tgcagcagat gatgcaatca gtgcggccat agcaaaaatc   1080
caaacagcaa aacttcctgt cgttttggtc ggcatgaaag gcggaagacc ggaagcaatt   1140
aaagcggttc gcaagctttt gaaaaaggtt cagcttccat tgttgaaac atatcaagct   1200 gccggtaccc tttctagaga tttagaggat caatattttg gccgtatcgg tttgttccgc   1260
aaccagcctg gcgatttact gctagagcag gcagatgttg ttctgacgat cggctatgac   1320
ccgattgaat atgatccgaa attctggaat atcaatggag accggacaat tatccattta   1380
gacgagatta tcgctgacat tgatcatgct taccagcctg atcttgaatt gatcggtgac   1440
attccgtcca cgatcaatca tatcgaacac gatgctgtga agtggaatt tgcagagcgt   1500 gagcagaaaa tcctttctga tttaaaacaa tatatgcatg aaggtgagca ggtgcctgca   1560
gattggaaat cagacagagc gcaccctctt gaaatcgtta aagagttgcg taatgcagtc   1620
```

```
gatgatcatg ttacagtaac ttgcgatatc ggttcgcacg ccatttggat gtcacgttat   1680
ttccgcagct acgagccgtt aacattaatg atcagtaacg gtatgcaaac actcggcgtt   1740
gcgcttcctt gggcaatcgg cgcttcattg gtgaaaccgg gagaaaaagt ggtttctgtc   1800
tctggtgacg gcggtttctt attctcagca atggaattag agacagcagt tcgactaaaa   1860
gcaccaattg tacacattgt atggaacgac agcacatatg acatggttgc attccagcaa   1920
ttgaaaaaat ataaccgtac atctgcggtc gatttcggaa atatcgatat cgtgaaatat   1980
gcggaaagct tcggagcaac tggcttgcgc gtagaatcac cagaccagct ggcagatgtt   2040
ctgcgtcaag gcatgaacgc tgaaggtcct gtcatcatcg atgtcccggt tgactacagt   2100
gataacatta atttagcaag tgacaagctt ccgaaagaat cggggaact catgaaaacg    2160 aaagctctct agttaattaa tcatgtaatt agttatgtca cgcttacatt cacgccctcc   2220
ccccacatcc gctctaaccg aaaaggaagg agttagacaa cctgaagtct aggtccctat   2280 ttatttttt atagttatgt tagtattaag aacgttattt atatttcaaa ttttctttt     2340 ttttctgtac agacgcgtgt acgcatgtaa cattatactg aaaaccttgc ttgagaaggt   2400
tttgggacgc tcgaaggctt taatttgcgg gcggccgctc tagaactagt accacaggtg   2460
ttgtcctctg aggacataaa atacacaccg agattcatca actcattgct ggagttagca   2520
tatctacaat tgggtgaaat ggggagcgat ttgcaggcat ttgctcggca tgccggtaga   2580
ggtgtggtca ataagagcga cctcatgcta tacctgagaa agcaacctga cctacaggaa   2640
agagttactc aagaataaga attttcgttt taaaacctaa gagtcacttt aaaatttgta   2700
tacacttatt tttttataa cttatttaat aataaaaatc ataaatcata agaaattcgc     2760
ttactcttaa ttaatcaagc atctaaaaca caaccgttgg aagcgttgga aaccaactta   2820
gcatacttgg atagagtacc tcttgtgtaa cgaggtggag gtgcaaccca actttgttta   2880
cgttgagcca tttccttatc agagactaat aggtcaatct tgttattatc agcatcaatg   2940
ataatctcat cgccgtctct gaccaacccg ataggaccac cttcagcggc ttcgggaaca   3000
atgtggccga ttaagaaccc gtgagaacca ccagagaatc taccatcagt caacaatgca   3060
acatctttac ccaaaccgta acccatcaga gcagaggaag ctttagcat ttcaggcata    3120 cctggtgcac ctcttggacc ttcatatctg ataacaacaa cggttttttc acccttcttg   3180
atttcacctc tttccaaggc ttcaataaag gcaccttcct cttcgaacac acgtgctcta   3240
cccttgaagt aagtaccttc cttaccggta attttaccca cagctccacc tggtgccaat   3300
gaaccgtaca gaatttgcaa gtgaccgttg gccttgattg ggtgggagag tggcttaata   3360
atctcttgtc cttcaggtag gcttggtgct ttctttgcac gttctgccaa agtgtcaccg   3420
gtaacagtca ttgtgttacc gtgcaacatg ttgttttcat atagatactt aatcacagat   3480
tgggtaccac caacgttaat caaatcggcc atgacgtatt taccagaagg tttgaagtca   3540
ccgatcaatg gtgtagtatc actgattctt tggaaatcat ctggtgacaa cttgacaccc   3600
gcagagtgag caacagccac caaatgcaaa acagcattag tggacccacc ggttgcaacg   3660
acataagtaa tggcgttttc aaaagcctct tttgtgagga tatcacgagg taaaataccc   3720
aattccattg tcttcttgat gtattcacca atgttgtcac actcagctaa cttctccttg   3780
gaaacggctg ggaaggaaga ggagtttgga atggtcaaac ctagcacttc agcggcagaa   3840
gccattgtgt tggcagtata cataccacca caagaaccag gacctgggca tgcatgttcc   3900
acaacatctt ctctttcttc ttcagtgaat tgcttggaaa tatattcacc gtaggattgg   3960
aacgcagaga cgatatcgat gttttagag atcctgttaa aacctctagt ggagtagtag    4020
```

-continued

```
atgtaatcaa tgaagcggaa gccaaaagac cagagtagag gcctatagaa gaaactgcga    4080 tacctttgt gatggctaaa caaacagaca tctttttata tgtttttact tctgtatatc     4140
gtgaagtagt aagtgataag cgaatttggc taagaacgtt gtaagtgaac aagggacctc    4200
ttttgccttt caaaaaagga ttaaatgagg ttaatcattg agatttagtt ttcgttagat    4260
tctgtatccc taaataactc ccttacccga cgggaaggca caaaagactt gaataatagc    4320
aaacggccag tagccaagac caaataatac tagagttaac tgatggtctt aaacaggcat    4380
tacgtggtga actccaagac caatatacaa aatatcgata agttattctt gcccaccaat    4440
ttaaggagcc tacatcagga cagtagtacc attcctcaga gaagaggtat acataacaag    4500
aaaatcgcgt gaacacctta tataacttag cccgttattg agctaaaaaa ccttgcaaaa    4560
tttcctatga ataagaatac ttcagacgtg ataaaaattt actttctaac tcttctcacg    4620
ctgcccctat ctgttcttcc gctctaccgt gagaaataaa gcatcgagta cggcagttcg    4680
ctgtcactga actaaaacaa taaggctagt tcgaatgatg aacttgcttg ctgtcaaact    4740
tctgagttgc cgctgatgtg acactgtgac aataaattca aaccggttat agcggtctcc    4800
tccggtaccg gttctgccac ctccaataga gctcagtagg agtcagaacc tctgcggtgg    4860
ctgtcagtga ctcatccgcg tttcgtaagt tgtgcgcgtg cacatttcgc ccgttcccgc    4920
tcatcttgca gcaggcggaa attttcatca cgctgtagga cgcaaaaaaa aaataattaa    4980
tcgtacaaga atcttggaaa aaaaattgaa aaattttgta taaagggat gacctaactt      5040 gactcaatgg cttttacacc cagtattttc cctttccttg tttgttacaa ttatagaagc    5100
aagacaaaaa catatagaca acctattcct aggagttata tttttttacc ctaccagcaa    5160
tataagtaaa aaactagtat gaaggtgttt tacgataaag actgcgatct gagcatcatc    5220
cagggaaaga aggttgctat tataggatat ggttcccaag gacacgcaca agccttgaac    5280
ttgaaagatt ctggggtcga cgtgacagta ggtctgtata aaggtgctgc tgatgcagca    5340
aaggctgaag cacatggctt taaagtcaca gatgttgcag cggctgttgc tggcgctgat    5400
ttagtcatga tttttaattcc agatgaattt caatcgcaat tgtacaaaaa tgaaatagaa    5460
ccaaacatta agaagggcgc taccttggcc ttcagtcatg gatttgccat tcattacaat    5520
caagtagtcc ccagggcaga tttgacgtt attatgattg cacctaaggc tccggggcat    5580
actgttagga gcgaatttgt taagggtggt ggtattccag atttgatcgc tatataccaa    5640
gacgttagcg gaaacgctaa gaatgtagct ttaagctacg cagcaggagt tggtggcggg    5700
agaacgggta taatagaaac cacttttaaa gacgagactg agacagattt atttggagaa    5760
caagcggttc tgtgcggagg aactgttgaa ttggttaaag caggctttga gacgcttgtc    5820
gaagcagggt acgctcccga aatggcatac ttcgaatgtc tacatgaatt gaagttgata    5880
gtagacttaa tgtatgaagg tggtatagct aatatgaact attccatttc aaataatgca    5940
gaatatggtg agtatgtcac cggacctgaa gtcattaacg cagaatcaag acaagccatg    6000
agaaatgcct tgaaacgtat ccaggacggt gaatacgcta agatgttcat aagtgaaggc    6060
gctacgggtt acccgagtat gactgctaaa agaagaaaca atgcagcaca tggtatcgaa    6120
attattggtg aacagttaag gtctatgatg ccctggatcg gtgctaataa gatcgtagac    6180
aaggcgaaaa attaaggccc tgcaggccta tcaagtgctg gaaactttt ctcttggaat     6240 ttttgcaaca tcagtcata gtcaattgaa ttgacccaat ttcacattta agatttttt      6300 tttttcatcc gacatacatc tgtacactag gaagccctgt ttttctgaag cagcttcaaa    6360
```

```
tatatatatt ttttacatat ttattatgat tcaatgaaca atctaattaa atcgaaaaca    6420
agaaccgaaa cgcgaataaa taatttattt agatggtgac aagtgtataa gtcctcatcg    6480
ggacagctac gatttctctt tcggttttgg ctgagctact ggttgctgtg acgcagcggc    6540
attagcgcgg cgttatgagc taccctcgtg gcctgaaaga tggcgggaat aaagcggaac    6600
taaaaattac tgactgagcc atattgaggt caatttgtca actcgtcaag tcacgtttgg    6660
tggacggccc ctttccaacg aatcgtatat actaacatgc gcgcgcttcc tatatacaca    6720
tatacatata tatatatata tatatgtgtg cgtgtatgtg tacacctgta tttaatttcc    6780
ttactcgcgg gttttctttt tttctcaatt cttggcttcc tctttctcga gtatataatt    6840
tttcaggtaa aatttagtac gatagtaaaa tacttctcga actcgtcaca tatacgtgta    6900
cataatgtct gaaccagctc aaaagaaaca aaaggttgct aacaactctc tagagcggcc    6960
gcccgcaaat taaagccttc gagcgtccca aaaccttctc aagcaaggtt ttcagtataa    7020
tgttacatgc gtacacgcgt ctgtacagaa aaaaagaaa aatttgaaat ataaataacg    7080
ttcttaatac taacataact ataaaaaaat aaataggggac ctagacttca ggttgtctaa    7140
ctccttcctt tcggttaga gcggatgtgg ggggagggcg tgaatgtaag cgtgacataa    7200
ctaattcat gattaattaa ttattggttt tctggtctca acttcctgac ttccttacca    7260
accttccaga tttccatgtt tctgatggtg tctaattcct tttctagctt ttctctgtag    7320
tcaggttgag agttgaattc caaagatctc ttggtttcgg taccgttctt ggtagattcg    7380
tacaagtctt ggaaaacagg cttcaaagca ttcttgaaga ttgggtacca gtccaaagca    7440
cctcttctgg cggtggtgga acaagcatcg tacatgtaat ccataccgta cttaccgatc    7500
aatgggtata gagattgggt agcttcttcg acggtttcgt tgaaagcttc agatggggag    7560
tgaccgtttt ctctcaagac gtcgtattga gccaagaaca taccgtggat accacccatt    7620
aaacaacctc tttcaccgta caagtcagag ttgacttctc tttcgaaagt ggtttggtaa    7680
acgtaaccgg aaccaatggc aacggccaaa gcttgggcct tttcgtgagc cttaccggtg    7740
acatcgttcc agacggcgta agaagagtta ataccacgac cttccttgaa caaagatctg    7800
acagttctac cggaaccctt tggagcaacc aagataacat ctaagtcctt tggtggttca    7860
acgtgagtca agtccttgaa gactggggag aaaccgtggg agaagtacaa agtcttaccc    7920
ttggtcaaca atggcttgat agcaggccag gtttctgatt gagcggcatc ggacaacaag    7980
ttcataacgt aactacctct cttgatagca tcttcaacag tgaacaagtt cttgcctgga    8040
acccaaccgt cttcgatggc agccttccaa gaagcaccat ctttacggac accaatgata    8100
acgttcaaac cgttgtctct caagttcaaa ccttgaccgt aaccttggga accgtaaccg    8160
atcaaagcaa aagtgtcgtt cttgaagtag tccaacaact tttctcttgg ccagtcagct    8220
ctttcgtaga cggtttcaac agtaccaccg aagttgattt gcttcaacat cctcagctct    8280
agatttgaat atgtattact tggttatggt tatatatgac aaaagaaaaa gaagaacaga    8340
agaataacgc aaggaagaac aataactgaa attgatagag aagtattatg tctttgtctt    8400
tttataataa atcaagtgca gaaatccgtt agacaacatg agggataaaa tttaacgtgg    8460
gcgaagaaga aggaaaaaag ttttgtgag gcgtaattg aagcgatctg ttgattgtag    8520
attttttttt tttgaggagt caaagtcaga agagaacaga caaatggtat taaccatcca    8580
atactttttt ggagcaacgc taagctcatg cttttccatt ggttacgtgc tcagttgtta    8640
gatatgaaa gagaggatgc tcacggcagc gtgactccaa ttgagcccga aagagaggat    8700
gccacgtttt cccgacggct gctagaatgg aaaaaggaaa aatagaagaa tcccattcct    8760
```

```
atcattattt acgtaatgac ccacacattt ttgagatttt caactattac gtattacgat   8820
aatcctgctg tcattatcat tattatctat atcgacgtat gcaacgtatg tgaagccaag   8880
taggcaatta tttagtactg tcagtattgt tattcatttc agatctatcc gcggtggagc   8940
tcgaattcac tggccgtcgt tttacaacgt cgtgactggg aaaaccctgg cgttacccaa   9000
cttaatcgcc ttgcagcaca tccccctttc gccagctggc gtaatagcga gaggcccgc    9060 accgatcgcc cttcccaaca gttgcgcagc ctgaatggcg aatggcgcct gatgcggtat   9120
tttctcctta cgcatctgtg cggtatttca caccgcatac gtcaaagcaa ccatagtacg   9180
cgccctgtag cggcgcatta agcgcggcgg gtgtggtggt tacgcgcagc gtgaccgcta   9240
cacttgccag cgccttagcg cccgctcctt tcgctttctt cccttccttt ctcgccacgt   9300
tcgccggctt ccccgtcaa  gctctaaatc ggggctccc  tttagggttc cgatttagtg   9360
ctttacggca cctcgacccc aaaaaacttg atttgggtga tggttcacgt agtgggccat   9420
cgccctgata  acggttttt  cgcccttttga cgttggagtc cacgttcttt aatagtggac   9480
tcttgttcca aactggaaca acactcaact ctatctcggg ctattctttt gatttataag   9540
ggattttgcc gatttcggtc tattggttaa aaaatgagct gatttaacaa aaatttaacg   9600 cgaatttta  caaaatatta acgtttacaa ttttatggtg cactctcagt acaatctgct   9660
ctgatgccgc atagttaagc cagccccgac acccgccaac acccgctgac gcgccctgac   9720
gggcttgtct gctcccggca tccgcttaca gacaagctgt gaccgtctcc gggagctgca   9780
tgtgtcagag gttttcaccg tcatcaccga aacgcgcgag acgaaagggc ctcgtgatac   9840
gcctattttt ataggttaat gtcatgataa taatggtttc ttagacgtca ggtggcactt   9900
ttcggggaaa tgtgcgcgga acccctattt gtttattttt ctaaatacat tcaaatatgt   9960
atccgctcat gagacaataa ccctgataaa tgcttcaata atattgaaaa aggaagagta  10020
tgagtattca acatttccgt gtcgccctta ttcccttttt tgcggcattt tgccttcctg  10080 ttttgctca  cccagaaacg ctggtgaaag taaaagatgc tgaagatcag ttgggtgcac  10140
gagtgggtta catcgaactg gatctcaaca gcggtaagat ccttgagagt tttcgccccg  10200
aagaacgttt tccaatgatg agcactttta aagttctgct atgtggcgcg gtattatccc  10260
gtattgacgc cgggcaagag caactcggtc gccgcataca ctattctcag aatgacttgg  10320
ttgagtactc accagtcaca gaaaagcatc ttacggatgg catgacagta agagaattat  10380
gcagtgctgc cataaccatg agtgataaca ctgcggccaa cttacttctg acaacgatcg  10440
gaggaccgaa ggagctaacc gcttttttgc acaacatggg gatcatgta  actcgccttg  10500 atcgttggga accggagctg aatgaagcca taccaaacga cgagcgtgac accacgatgc  10560
ctgtagcaat ggcaacaacg ttgcgcaaac tattaactgg cgaactactt actctagctt  10620
cccggcaaca attaatagac tggatggagg cggataaagt tgcaggacca cttctgcgct  10680
cggcccttcc ggctggctgg tttattgctg ataaatctgg agccggtgag cgtgggtctc  10740
gcggtatcat tgcagcactg gggccagatg gtaagccctc ccgtatcgta gttatctaca  10800
cgacggggag tcaggcaact atggatgaac gaaatagaca gatcgctgag ataggtgcct  10860
cactgattaa gcattggtaa ctgtcagacc aagtttactc atatatactt tagattgatt  10920
taaaacttca ttttttaattt aaaaggatct aggtgaagat cctttttgat aatctcatga  10980
ccaaaatccc ttaacgtgag ttttcgttcc actgagcgtc agaccccgta gaaaagatca  11040
aaggatcttc ttgagatcct ttttttctgc gcgtaatctg ctgcttgcaa acaaaaaaac  11100
```

```
caccgctacc agcggtggtt tgtttgccgg atcaagagct accaactctt tttccgaagg    11160
taactggctt cagcagagcg cagataccaa atactgttct tctagtgtag ccgtagttag    11220
gccaccactt caagaactct gtagcaccgc ctacatacct cgctctgcta atcctgttac    11280
cagtggctgc tgccagtggc gataagtcgt gtcttaccgg gttggactca agacgatagt    11340
taccggataa ggcgcagcgg tcgggctgaa cggggggttc gtgcacacag cccagcttgg    11400
agcgaacgac ctacaccgaa ctgagatacc tacagcgtga gctatgagaa agcgccacgc    11460
ttcccgaagg gagaaaggcg gacaggtatc cggtaagcgg cagggtcgga acaggagagc    11520
gcacgaggga gcttccaggg ggaaacgcct ggtatcttta tagtcctgtc gggtttcgcc    11580
acctctgact tgagcgtcga ttttgtgat gctcgtcagg gggcggagc ctatggaaaa     11640 acgccagcaa cgcggccttt ttacggttcc tggccttttg ctggccttt gctcacatgt     11700 tctttcctgc gttatcccct gattctgtgg ataaccgtat taccgccttt gagtgagctg    11760
ataccgctcg ccgcagccga acgaccgagc gcagcgagtc agtgagcgag gaagcggaag    11820
agcgcccaat acgcaaaccg cctctccccg cgcgttggcc gattcattaa tgcagctggc    11880
acgacaggtt tcccgactgg aaagcgggca gtgagcgcaa cgcaattaat gtgagttagc    11940
tcactcatta ggcaccccag gctttacact ttatgcttcc ggctcgtatg ttgtgtggaa    12000
ttgtgagcgg ataacaattt cacacaggaa acagctatga ccatgattac gccaagcttt    12060
ttctttccaa ttttttttt ttcgtcatta taaaaatcat tacgaccgag attcccgggt     12120 ataactgat ataattaaat tgaagctcta atttgtgagt ttagtataca tgcatttact     12180
tataatacag ttttttagtt ttgctggccg catcttctca aatatgcttc ccagcctgct    12240
tttctgtaac gttcaccctc taccttagca tcccttccct ttgcaaatag tcctcttcca    12300
acaataataa tgtcagatcc tgtagagacc acatcatcca cggttctata ctgttgaccc    12360
aatgcgtctc ccttgtcatc taaacccaca ccgggtgtca taatcaacca atcgtaacct    12420
tcatctcttc cacccatgtc tctttgagca ataaagccga taacaaaatc tttgtcgctc    12480
ttcgcaatgt caacagtacc cttagtatat tctccagtag atagggagcc cttgcatgac    12540
aattctgcta acatcaaaag gcctctaggt tcctttgtta cttcttctgc cgcctgcttc    12600
aaaccgctaa caatacctgg gcccaccaca ccgtgtgcat tcgtaatgtc tgcccattct    12660
gctattctgt atacacccgc agagtactgc aatttgactg tattaccaat gtcagcaaat    12720
tttctgtctt cgaagagtaa aaaattgtac ttggcggata atgcctttag cggcttaact    12780
gtgccctcca tggaaaaatc agtcaagata tccacatgtg tttttagtaa acaaattttg    12840
ggacctaatg cttcaactaa ctccagtaat tccttggtgg tacgaacatc caatgaagca    12900
cacaagtttg tttgcttttc gtgcatgata ttaaatagct tggcagcaac aggactagga    12960
tgagtagcag cacgttcctt atatgtagct ttcgacatga tttatcttcg tttcctgcag    13020 gttttttgttc tgtgcagttg ggttaagaat actgggcaat ttcatgtttc ttcaacacta    13080
catatgcgta tatataccaa tctaagtctg tgctccttcc ttcgttcttc cttctgttcg    13140
gagattaccg aatcaaaaaa atttcaagga aaccgaaatc aaaaaaaaga ataaaaaaaa    13200
aatgatgaat tgaaaagctt gcatgcctgc aggtcgactc tagtatactc cgtctactgt    13260
acgatacact tccgctcagg tccttgtcct ttaacgaggc cttaccactc ttttgttact    13320
ctattgatcc agctcagcaa aggcagtgtg atctaagatt ctatcttcgc gatgtagtaa    13380
aactagctag accgagaaag agactagaaa tgcaaaaggc acttctacaa tggctgccat    13440
cattattatc cgatgtgacg ctgcattttt tttttttttt ttttttttt ttttttttt    13500
```

```
tttttttttt ttttttttgta caaatatcat aaaaaaagag aatctttta agcaaggatt   13560 ttcttaactt cttcggcgac agcatcaccg acttcggtgg tactgttgga accacctaaa   13620
tcaccagttc tgatacctgc atccaaaacc ttttaactg catcttcaat ggctttacct   13680
tcttcaggca agttcaatga caatttcaac atcattgcag cagacaagat agtggcgata   13740
gggttgacct tattctttgg caaatctgga gcggaaccat ggcatggttc gtacaaacca   13800
aatgcggtgt tcttgtctgg caaagaggcc aaggacgcag atggcaacaa acccaaggag   13860
cctgggataa cggaggcttc atcggagatg atatcaccaa acatgttgct ggtgattata   13920
ataccattta ggtgggttgg gttcttaact aggatcatgg cggcagaatc aatcaattga   13980
tgttgaactt tcaatgtagg gaattcgttc ttgatggttt cctccacagt ttttctccat   14040
aatcttgaag aggccaaaac attagcttta tccaaggacc aaataggcaa tggtggctca   14100
tgttgtaggg ccatgaaagc ggccattctt gtgattcttt gcacttctgg aacggtgtat   14160
tgttcactat cccaagcgac accatcacca tcgtcttcct ttctcttacc aaagtaaata   14220
cctcccacta attctctaac aacaacgaag tcagtacctt tagcaaattg tggcttgatt   14280
ggagataagt ctaaaagaga gtcggatgca aagttacatg gtcttaagtt ggcgtacaat   14340
tgaagttctt tacggatttt tagtaaacct tgttcaggtc taacactacc ggtacccat   14400 ttaggaccac ccacagcacc taacaaaacg gcatcagcct tcttggaggc ttccagcgcc   14460
tcatctggaa gtggaacacc tgtagcatcg atagcagcac caccaattaa atgattttcg   14520
aaatcgaact tgacattgga acgaacatca gaaatagctt taagaacctt aatggcttcg   14580
gctgtgattt cttgaccaac gtggtcacct ggcaaaacga cgatcttctt aggggcagac   14640
attacaatgg tatatccttg aaatatatat aaaaaaaaaa aaaaaaaaaa aaaaaaaaaaa   14700 tgcagcttct caatgatatt cgaatacgct ttgaggagat acagcctaat atccgacaaa   14760
ctgttttaca gatttacgat cgtacttgtt acccatcatt gaatttttgaa catccgaacc   14820 tgggagtttt ccctgaaaca gatagtatat ttgaacctgt ataataatat atagtctagc   14880
gctttacgga agacaatgta tgtatttcgg ttcctggaga aactattgca tctattgcat   14940
aggtaatctt gcacgtcgca tccccggttc attttctgcg tttccatctt gcacttcaat   15000
agcatatctt tgttaacgaa gcatctgtgc ttcattttgt agaacaaaaa tgcaacgcga   15060
gagcgctaat ttttcaaaca aagaatctga gctgcatttt tacagaacag aaatgcaacg   15120
cgaaagcgct attttaccaa cgaagaatct gtgcttcatt tttgtaaaac aaaaatgcaa   15180
cgcgagagcg ctaattttc aaacaaagaa tctgagctgc attttacag aacagaaatg   15240 caacgcgaga gcgctatttt accaacaaag aatctatact tcttttttgt tctacaaaaa   15300
tgcatcccga gagcgctatt tttctaacaa agcatcttag attactttt ttctcctttg   15360 tgcgctctat aatgcagtct cttgataact ttttgcactg taggtccgtt aaggttagaa   15420
gaaggctact ttggtgtcta ttttctcttc cataaaaaaa gcctgactcc acttcccgcg   15480
tttactgatt actagcgaag ctgcgggtgc attttttcaa gataaaggca tccccgatta   15540
tattctatac cgatgtggat tgcgcatact ttgtgaacag aaagtgatag cgttgatgat   15600
tcttcattgg tcagaaaatt atgaacggtt tcttctattt tgtctctata tactacgtat   15660
aggaaatgtt tacattttcg tattgttttc gattcactct atgaatagtt cttactacaa   15720 ttttttttgtc taaagagtaa tactagagat aaacataaaa aatgtagagg tcagtttag   15780 atgcaagttc aaggagcgaa aggtggatgg gtaggttata tagggatata gcacagagat   15840
```

```
atatagcaaa gagatacttt tgagcaatgt ttgtggaagc ggtattcgca atattttagt    15900
agctcgttac agtccggtgc gttttttggtt ttttgaaagt gcgtcttcag agcgcttttg    15960
gttttcaaaa gcgctctgaa gttcctatac tttctagaga ataggaactt cggaatagga    16020
acttcaaagc gtttccgaaa acgagcgctt ccgaaaatgc aacgcgagct gcgcacatac    16080
agctcactgt tcacgtcgca cctatatctg cgtgttgcct gtatatatat atacatgaga    16140
agaacggcat agtgcgtgtt tatgcttaaa tgcgtactta tatgcgtcta tttatgtagg    16200
atgaaaggta gtctagtacc tcctgtgata ttatcccatt ccatgcgggg tatcgtatgc    16260
ttccttcagc actacccttt agctgttcta tatgctgcca ctcctcaatt ggattagtct    16320
catccttcaa tgctatcatt tcctttgata ttggatcata tgcatagtac cgagaaacta    16380
gaggatc                                                             16387
```

```
<210> SEQ ID NO 141
<211> LENGTH: 2237
<212> TYPE: DNA
<213> ORGANISM: Artificial Sequence
<220> FEATURE:
<223> OTHER INFORMATION: PDC1 Fragment A-ilvDSm

<400> SEQUENCE: 141
ttatgtatgc tcttctgact tttcgtgtga tgaggctcgt ggaaaaaatg aataatttat      60
gaatttgaga acaattttgt gttgttacgg tattttacta tggaataatc aatcaattga     120
ggattttatg caaatatcgt ttgaatattt ttccgaccct ttgagtactt ttcttcataa     180
ttgcataata ttgtccgctg ccccttttttc tgttagacgg tgtcttgatc tacttgctat    240
cgttcaacac caccttattt tctaactatt ttttttttag ctcatttgaa tcagcttatg     300
gtgatggcac atttttgcat aaacctagct gtcctcgttg aacataggaa aaaaaatat     360 ataaacaagg ctcttttcact ctccttgcaa tcagatttgg gtttgttccc tttattttca    420
tatttcttgt catattcctt tctcaattat tattttctac tcataacctc acgcaaaata     480
acacagtcaa atcaatcaaa atgactgaca aaaaaactct taaagactta agaaatcgta    540
gttctgttta cgattcaatg gttaaatcac ctaatcgtgc tatgttgcgt gcaactggta    600
tgcaagatga agactttgaa aaacctatcg tcggtgtcat ttcaacttgg gctgaaaaca    660
caccttgtaa tatccactta catgactttg gtaaactagc caaagtcggt gttaaggaag    720
ctggtgcttg gccagttcag tccggaacaa tcacggtttc tgatggaatc gccatgggaa    780
cccaaggaat gcgtttctcc ttgacatctc gtgatattat tgcagattct attgaagcag    840
ccatgggagg tcataatgcg gatgcttttg tagccattgg cggttgtgat aaaaacatgc    900
ccggttctgt tatcgctatg gctaacatgg atatcccagc catttttgct tacggcggaa    960
caattgcacc tggtaattta gacggcaaag atatcgattt agtctctgtc tttgaaggtg    1020
tcggccattg gaaccacggc gatatgacca agaagaagt taaagctttg gaatgtaatg    1080
cttgtcccgg tcctggaggc tgcggtggta tgtatactgc taacacaatg gcgacagcta    1140
ttgaagtttt gggacttagc cttccggggtt catcttctca cccggctgaa tccgcagaaa    1200
agaaagcaga tattgaagaa gctggtcgcg ctgttgtcaa aatgctcgaa atgggcttaa    1260
aaccttctga cattttaacg cgtgaagctt ttgaagatgc tattactgta actatggctc    1320
tgggaggttc aaccaactca acccttcacc tcttagctat tgcccatgct gctaatgtgg    1380
aattgacact tgatgatttc aatacttttcc aagaaaaagt tcctcatttg gctgatttga    1440
aaccttctgg tcaatatgta ttccaagacc tttacaaggt cggagggta ccagcagtta    1500
```

-continued

```
tgaaatatct ccttaaaaat ggcttccttc atggtgaccg tatcacttgt actggcaaaa    1560
cagtcgctga aaatttgaag gcttttgatg atttaacacc tggtcaaaag gttattatgc    1620
cgcttgaaaa tcctaaacgt gaagatggtc cgctcattat tctccatggt aacttggctc    1680
cagacggtgc cgttgccaaa gtttctggtg taaaagtgcg tcgtcatgtc ggtcctgcta    1740
aggtctttaa ttctgaagaa gaagccattg aagctgtctt gaatgatgat attgttgatg    1800
gtgatgttgt tgtcgtacgt tttgtaggac caaagggcgg tcctggtatg cctgaaatgc    1860 tttcccttc atcaatgatt gttggtaaag ggcaaggtga aaaagttgcc cttctgacag    1920
atggccgctt ctcaggtggt acttatggtc ttgtcgtggg tcatatcgct cctgaagcac    1980
aagatggcgg tccaatcgcc tacctgcaaa caggagacat agtcactatt gaccaagaca    2040
ctaaggaatt acactttgat atctccgatg aagagttaaa acatcgtcaa gagaccattg    2100
aattgccacc gctctattca cgcggtatcc ttggtaaata tgctcacatc gtttcgtctg    2160
cttctagggg agccgtaaca gacttttgga agcctgaaga aactggcaaa aaatgagcga    2220
tttaatctct aattatt                                                  2237
```

<210> SEQ ID NO 142
<211> LENGTH: 4420
<212> TYPE: DNA
<213> ORGANISM: Artificial Sequence
<220> FEATURE:
<223> OTHER INFORMATION: PDC1 A-ilvDSm-BUC cassette

<400> SEQUENCE: 142

```
ttatgtatgc tcttctgact tttcgtgtga tgaggctcgt ggaaaaaatg aataatttat      60
gaatttgaga acaattttgt gttgttacgg tatttacta tggaataatc aatcaattga     120
ggattttatg caaatatcgt ttgaatattt ttccgaccct ttgagtactt tcttcataa     180 ttgcataata ttgtccgctg cccctttttc tgttagacgg tgtcttgatc tacttgctat     240
cgttcaacac caccttattt tctaactatt ttttttttag ctcatttgaa tcagcttatg     300
gtgatggcac attttgcat aaacctagct gtcctcgttg aacataggaa aaaaaaatat     360
ataaacaagg ctctttcact ctccttgcaa tcagatttgg gtttgttccc tttattttca     420
tatttcttgt catattcctt tctcaattat tattttctac tcataacctc acgcaaaata     480
acacagtcaa atcaatcaaa atgactgaca aaaaaactct aaagacttag agaaatcgta     540
gttctgttta cgattcaatg gttaaatcac ctaatcgtgc tatgttgcgt gcaactggta     600
tgcaagatga agactttgaa aaacctatcg tcggtgtcat ttcaacttgg gctgaaaaca     660
caccttgtaa tatccactta catgactttg gtaaactagc caaagtcggt gttaaggaag     720
ctggtgcttg gccagttcag ttcggaacaa tcacggtttc tgatggaatc gccatgggaa     780
cccaaggaat gcgtttctcc ttgacatctc gtgatattat tgcagattct attgaagcag     840
ccatgggagg tcataatgcg gatgcttttg tagccattgg cggttgtgat aaaaacatgc     900
ccggttctgt tatcgctatg gctaacatgg atatcccagc catttttgct tacggcggaa     960
caattgcacc tggtaattta gacggcaaag atatcgattt agtctctgtc tttgaaggtg    1020
tcggccattg gaaccacggc gatatgacca agaagaagt taaagctttg gaatgtaatg    1080 cttgtccccgg tcctggaggc tgcggtggta tgtatactgc taacacaatg gcgacagcta    1140
ttgaagtttt gggacttagc cttccgggtt catcttctca cccggctgaa tccgcagaaa    1200
agaaagcaga tattgaagaa gctggtcgcg ctgttgtcaa aatgctcgaa atgggcttaa    1260
```

```
aaccttctga cattttaacg cgtgaagctt ttgaagatgc tattactgta actatggctc    1320
tgggaggttc aaccaactca acccttcacc tcttagctat tgcccatgct gctaatgtgg    1380
aattgacact tgatgatttc aatactttcc aagaaaaagt tcctcatttg gctgatttga    1440
aaccttctgg tcaatatgta ttccaagacc tttacaaggt cggaggggta ccagcagtta    1500
tgaaatatct ccttaaaaat ggcttccttc atggtgaccg tatcacttgt actggcaaaa    1560
cagtcgctga aaatttgaag cttttgatg atttaacacc tggtcaaaag gttattatgc     1620
cgcttgaaaa tcctaaacgt gaagatggtc cgctcattat tctccatggt aacttggctc    1680
cagacggtgc cgttgccaaa gtttctggtg taaaagtgcg tcgtcatgtc ggtcctgcta    1740
aggtctttaa ttctgaagaa gaagccattg aagctgtctt gaatgatgat attgttgatg    1800
gtgatgttgt tgtcgtacgt tttgtaggac caagggcgg tcctggtatg cctgaaatgc     1860
tttccctttc atcaatgatt gttggtaaag gcaaggtga aaaagttgcc cttctgacag     1920
atggccgctt ctcaggtggt acttatggtc ttgtcgtggg tcatatcgct cctgaagcac    1980
aagatggcgg tccaatcgcc tacctgcaaa caggagacat agtcactatt gaccaagaca    2040
ctaaggaatt acactttgat atctccgatg aagagttaaa acatcgtcaa gagaccattg    2100
aattgccacc gctctattca cgcggtatcc ttggtaaata tgctcacatc gtttcgtctg    2160
cttctagggg agccgtaaca gacttttgga agcctgaaga aactggcaaa aaatgagcga    2220
tttaatctct aattattagt taaagtttta taagcatttt tatgtaacga aaataaatt     2280
ggttcatatt attactgcac tgtcacttac catggaaaga ccagacaaga agttgccgac    2340
agtctgttga attggcctgg ttaggcttaa gtctgggtcc gcttctttac aaatttggag    2400
aatttctctt aaacgatatg tatattcttt tcgttggaaa agatgtcttc caaaaaaaa    2460
accgatgaat tagtggaacc aaggaaaaaa aagaggtat ccttgattaa ggaacactgt     2520
ttaaacagtg tggtttccaa aaccctgaaa ctgcattagt gtaatagaag actagacacc    2580
tcgatacaaa taatggttac tcaattcaaa actgccagcg aattcgactc tgcaattgct    2640
caagacaagc tagttgtcgt agatttctac gccacttggt gcggtccatg taaaatgatt    2700
gctccaatga ttgaaaaatg tggctgtggt ttcagggtcc ataaagcttt tcaattcatc    2760
ttttttttt ttgttctttt ttttgattcc ggtttctttg aaatttttt gattcggtaa       2820
tctccgagca gaaggaagaa cgaaggaagg agcacagact tagattggta tatatacgca    2880
tatgtggtgt tgaagaaaca tgaaattgcc cagtattctt aacccaactg cacagaacaa    2940
aaacctgcag gaaacgaaga taatcatgt cgaaagctac atataaggaa cgtgctgcta     3000
ctcatcctag tcctgttgct gccaagctat ttaatatcat gcacgaaaag caaacaaact    3060
tgtgtgcttc attggatgtt cgtaccacca aggaattact ggagttagtt gaagcattag    3120
gtcccaaaat ttgtttacta aaaacacatg tggatatctt gactgatttt tccatggagg    3180
gcacagttaa gccgctaaag gcattatccg ccaagtacaa ttttttactc ttcgaagaca    3240
gaaaatttgc tgacattggt aatacagtca aattgcagta ctctgcgggt gtatacagaa    3300
tagcagaatg ggcagacatt acgaatgcac acggtgtggt gggcccaggt attgttagcg    3360
gtttgaagca ggcggcggaa gaagtaacaa aggaacctag aggccttttg atgttagcag    3420
aattgtcatg caagggctcc ctagctactg agaatatac taagggtact gttgacattg      3480
cgaagagcga caaagatttt gttatcggct ttattgctca agagacatg gtggaagag      3540
atgaaggtta cgattggttg attatgacac ccggtgtggg tttagatgac aagggagacg    3600
cattgggtca acagtataga accgtggatg atgtggtctc tacaggatct gacattatta    3660
```

```
ttgttggaag aggactattt gcaaagggaa gggatgctaa ggtagagggt gaacgttaca      3720
gaaaagcagg ctgggaagca tatttgagaa gatgcggcca gcaaaactaa aaaactgtat      3780
tataagtaaa tgcatgtata ctaaactcac aaattagagc ttcaatttaa ttatatcagt      3840
tattacccgg gaatctcggt cgtaatgatt tctataatga cgaaaaaaaa aaaattggaa      3900
agaaaaagct tcatggcctt ccactttccc aaacaacacc tacggtatct ctcaagtctt      3960
atggggttcc attggtttca ccactggtgc taccttgggt gctgctttcg ctgctgaaga      4020
aattgatcca agaagagag ttatcttatt cattggtgac ggttctttgc aattgactgt       4080
tcaagaaatc tccaccatga tcagatgggg cttgaagcca tacttgttcg tcttgaacaa      4140
cgatggttac accattgaaa agttgattca cggtccaaag gctcaataca cgaaattca       4200 aggttgggac cacctatcct tgttgccaac tttcggtgct aaggactatg aaacccacag      4260
agtcgctacc accggtgaat gggacaagtt gacccaagac aagtctttca cgacaactc      4320 taagatcaga atgattgaaa tcatgttgcc agtcttcgat gctccacaaa acttggttga     4380
acaagctaag ttgactgctg ctaccaacgc taagcaataa                           4420
```

<210> SEQ ID NO 143
<211> LENGTH: 2686
<212> TYPE: DNA
<213> ORGANISM: Artificial Sequence
<220> FEATURE:
<223> OTHER INFORMATION: pUC19

<400> SEQUENCE: 143

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcgggctgg cttaactatg cggcatcaga gcagattgta ctgagagtgc       180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt cgagctcggt acccggggat      420
cctctagagt cgacctgcag gcatgcaagc ttggcgtaat catggtcata gctgtttcct      480
gtgtgaaatt gttatccgct cacaattcca cacaacatac gagccggaag cataaagtgt      540
aaagcctggg gtgcctaatg agtgagctaa ctcacattaa ttgcgttgcg ctcactgccc      600
gctttccagt cgggaaacct gtcgtgccag ctgcattaat gaatcggcca acgcgcgggg      660
agaggcggtt tgcgtattgg gcgctcttcc gcttcctcgc tcactgactc gctgcgctcg      720
gtcgttcggc tgcggcgagc ggtatcagct cactcaaagg cggtaatacg gttatccaca      780
gaatcagggg ataacgcagg aaagaacatg tgagcaaaag gccagcaaaa ggccaggaac      840
cgtaaaaagg ccgcgttgct ggcgtttttc cataggctcc gcccccctga cgagcatcac      900
aaaaatcgac gctcaagtca gaggtggcga aacccgacag gactataaag ataccaggcg      960
tttccccctg gaagctccct cgtgcgctct cctgttccga ccctgccgct taccggatac     1020
ctgtccgcct ttctcccttc gggaagcgtg gcgctttctc atagctcacg ctgtaggtat     1080
ctcagttcgg tgtaggtcgt tcgctccaag ctgggctgtg tgcacgaacc ccccgttcag     1140
cccgaccgct gcgccttatc cggtaactat cgtcttgagt ccaacccggt aagacacgac     1200
ttatcgccac tggcagcagc cactggtaac aggattagca gagcgaggta tgtaggcggt     1260
```

```
gctacagagt tcttgaagtg gtggcctaac tacggctaca ctagaaggac agtatttggt   1320
atctgcgctc tgctgaagcc agttaccttc ggaaaaagag ttggtagctc ttgatccggc   1380
aaacaaacca ccgctggtag cggtggtttt tttgtttgca agcagcagat tacgcgcaga   1440
aaaaaaggat ctcaagaaga tcctttgatc ttttctacgg ggtctgacgc tcagtggaac   1500
gaaaactcac gttaagggat tttggtcatg agattatcaa aaaggatctt cacctagatc   1560
cttttaaatt aaaaatgaag ttttaaatca atctaaagta tatatgagta aacttggtct   1620
gacagttacc aatgcttaat cagtgaggca cctatctcag cgatctgtct atttcgttca   1680
tccatagttg cctgactccc cgtcgtgtag ataactacga tacgggaggg cttaccatct   1740
ggccccagtg ctgcaatgat accgcgagac ccacgctcac cggctccaga tttatcagca   1800
ataaaccagc cagccggaag ggccgagcgc agaagtggtc ctgcaacttt atccgcctcc   1860
atccagtcta ttaattgttg ccgggaagct agagtaagta gttcgccagt taatagtttg   1920
cgcaacgttg ttgccattgc tacaggcatc gtggtgtcac gctcgtcgtt tggtatggct   1980
tcattcagct ccggttccca acgatcaagg cgagttacat gatcccccat gttgtgcaaa   2040
aaagcggtta gctccttcgg tcctccgatc gttgtcagaa gtaagttggc cgcagtgtta   2100
tcactcatgg ttatggcagc actgcataat tctcttactg tcatgccatc cgtaagatgc   2160
ttttctgtga ctggtgagta ctcaaccaag tcattctgag aatagtgtat gcggcgaccg   2220
agttgctctt gcccggcgtc aatacgggat aataccgcgc cacatagcag aactttaaaa   2280
gtgctcatca ttggaaaacg ttcttcgggg cgaaaactct caaggatctt accgctgttg   2340
agatccagtt cgatgtaacc cactcgtgca cccaactgat cttcagcatc ttttactttc   2400
accagcgttt ctgggtgagc aaaaacagga aggcaaaatg ccgcaaaaaa gggaataagg   2460
gcgacacgga aatgttgaat actcatactc ttcctttttc aatattattg aagcatttat   2520
cagggttatt gtctcatgag cggatacata tttgaatgta tttagaaaaa taaacaaata   2580
ggggttccgc gcacatttcc ccgaaaagtg ccacctgacg tctaagaaac cattattatc   2640
atgacattaa cctataaaaa taggcgtatc acgaggccct ttcgtc                 2686
```

<210> SEQ ID NO 144
<211> LENGTH: 3521
<212> TYPE: DNA
<213> ORGANISM: Artificial Sequence
<220> FEATURE:
<223> OTHER INFORMATION: PDC5 A-sadB-BUC cassette

<400> SEQUENCE: 144

```
aaggaaataa agcaaataac aataacacca ttatttttaat ttttttttcta ttactgtcgc    60
taacacctgt atggttgcaa ccaggtgaga atccttctga tgcatacttt atgcgtttat   120
gcgttttgcg ccccttggaa aaaaattgat tctcatcgta aatgcatact acatgcgttt   180
atgggaaaag cctccatatc caaggtcgc gtttcttta gaaaactaa tacgtaaacc      240
tgcattaagg taagattata tcagaaaatg tgttgcaaga aatgcattat gcaatttttt   300
gattatgaca atctctcgaa agaaatttca tatgatgaga cttgaataat gcagcggcgc   360
ttgctaaaag aacttgtata taagagctgc cattctcgat caatatactg tagtaagtcc   420
tttcctctct ttcttattac acttatttca cataatcaat ctcaaagaga acaacacaat   480
acaataacaa gaagaacaaa atgaaagctc tggtttatca cggtgaccac aagatctcgc   540
ttgaagacaa gcccaagccc acccttcaaa agcccacgtg tgtagtagta cgggttttga   600
agaccacgat ctgcggcacg gatctcggca tctacaaagg caagaatcca gaggtcgccg   660
```

```
acgggcgcat cctgggccat gaaggggtag gcgtcatcga ggaagtgggc gagagtgtca    720
cgcagttcaa gaaaggcgac aaggtcctga tttcctgcgt cacttcttgc ggctcgtgcg    780
actactgcaa gaagcagctt tactcccatt gccgcgacgg cgggtggatc ctgggttaca    840
tgatcgatgg cgtgcaggcc gaatacgtcc gcatcccgca tgccgacaac agcctctaca    900
agatccccca gacaattgac gacgaaatcg ccgtcctgct gagcgacatc ctgcccaccg    960
gccacgaaat cggcgtccag tatgggaatg tccagccggg cgatgcggtg gctattgtcg   1020
gcgcgggccc cgtcggcatg tccgtactgt tgaccgccca gttctactcc ccctcgacca   1080
tcatcgtgat cgacatggac gagaatcgcc tccagctcgc caaggagctc ggggcaacgc   1140
acaccatcaa ctccggcacg gagaacgttg tcgaagccgt gcataggatt gcggcagagg   1200
gagtcgatgt tgcgatcgag gcggtgggca taccggcgac ttgggacatc tgccaggaga   1260
tcgtcaagcc cggcgcgcac atcgccaacg tcggcgtgca tggcgtcaag gttgacttcg   1320
agattcagaa gctctggatc aagaacctga cgatcaccac gggactggtg aacacgaaca   1380
cgacgcccat gctgatgaag gtcgcctcga ccgacaagct tccgttgaag aagatgatta   1440
cccatcgctt cgagctggcc gagatcgagc acgcctatca ggtattcctc aatggcgcca   1500
aggagaaggc gatgaagatc atcctctcga acgcaggcgc tgcctgagct aattaacata   1560
aaactcatga ttcaacgttt gtgtattttt ttacttttga aggttataga tgtttaggta   1620
aataattggc atagatatag ttttagtata ataaatttct gatttggttt aaaatatcaa   1680
ctattttttt tcacatatgt tcttgtaatt acttttctgt cctgtcttcc aggttaaaga   1740
ttagcttcta atattttagg tggtttatta tttaatttta tgctgattaa tttatttact   1800
tgtttaaacg gccggccaat gtggctgtgg tttcagggtc cataaagctt ttcaattcat   1860
ctttttttt tttgttcttt ttttttgattc cggtttcttt gaaatttttt tgattcggta   1920
atctccgagc agaaggaaga acgaaggaag gagcacagac ttagattggt atatatacgc   1980
atatgtggtg ttgaagaaac atgaaattgc ccagtattct taacccaact gcacagaaca   2040
aaaacctgca ggaaacgaag ataaatcatg tcgaaagcta catataagga acgtgctgct   2100
actcatccta gtcctgttgc tgccaagcta tttaatatca tgcacgaaaa gcaaacaaac   2160
ttgtgtgctt cattggatgt tcgtaccacc aaggaattac tggagttagt tgaagcatta   2220
ggtcccaaaa tttgtttact aaaaacacat gtggatatct tgactgattt ttccatggag   2280
ggcacagtta agccgctaaa ggcattatcc gccaagtaca atttttttact cttcgaagac   2340
agaaaatttg ctgacattgg taatacagtc aaattgcagt actctgcggg tgtatacaga   2400
atagcagaat gggcagacat tacgaatgca cacggtgtgg tgggcccagg tattgttagc   2460
ggtttgaagc aggcggcgga agaagtaaca aaggaaccta gaggcctttt gatgttagca   2520
gaattgtcat gcaagggctc cctagctact ggagaatata ctaagggtac tgttgacatt   2580
gcgaagagcg acaaagattt tgttatcggc tttattgctc aaagagacat gggtggaaga   2640
gatgaaggtt acgattggtt gattatgaca cccggtgtgg gtttagatga caagggagac   2700
gcattgggtc aacagtatag aaccgtggat gatgtggtct ctacaggatc tgacattatt   2760
attgttggaa gaggactatt tgcaagggaa agggatgcta aggtagaggg tgaacgttac   2820
agaaaagcag gctgggaagc atatttgaga agatgcggcc agcaaaacta aaaaactgta   2880
ttataagtaa atgcatgtat actaaactca caaattagag cttcaatttta attatatcag   2940
ttattacccg ggaatctcgg tcgtaatgat ttctataatg acgaaaaaaa aaaaattgga   3000
```

```
aagaaaaagc ttcatggcct tctactttcc aacagatgt atacgctatc gtccaagtct   3060 tgtgggttc cattggtttc acagtcggcg ctctattggg tgctactatg gccgctgaag   3120
aacttgatcc aaagaagaga gttatttat tcattggtga cggttctcta caattgactg   3180
ttcaagaaat ctctaccatg attagatggg gtttgaagcc atacattttt gtcttgaata   3240
acaacggtta caccattgaa aaattgattc acggtcctca tgccgaatat aatgaaattc   3300
aaggttggga ccacttggcc ttattgccaa cttttggtgc tagaaactac gaaacccaca   3360
gagttgctac cactggtgaa tgggaaaagt tgactcaaga caaggacttc aagacaact    3420 ctaagattag aatgattgaa gttatgttgc cagtctttga tgctccacaa aacttggtta   3480
aacaagctca attgactgcc gctactaacg ctaaacaata a                       3521
```

<210> SEQ ID NO 145
<211> LENGTH: 1685
<212> TYPE: DNA
<213> ORGANISM: Artificial Sequence
<220> FEATURE:
<223> OTHER INFORMATION: gpd2::loxP-URA3-loxP cassette

<400> SEQUENCE: 145

```
gtatttggt agattcaatt ctctttccct ttccttttcc ttcgctcccc ttccttatca     60
gcattgcgga ttacgtattc taatgttcag ataacttcgt atagcataca ttatacgaag   120
ttatgcagat tgtactgaga gtgcaccata ccacagcttt tcaattcaat tcatcatttt   180 tttttattc ttttttttga tttcggtttc tttgaaattt ttttgattcg gtaatctccg    240
aacagaagga agaacgaagg aaggagcaca gacttagatt ggtatatata cgcatatgta   300
gtgttgaaga acatgaaat tgcccagtat tcttaaccca actgcacaga acaaaaacct    360
gcaggaaacg aagataaatc atgtcgaaag ctacatataa ggaacgtgct gctactcatc   420
ctagtcctgt tgctgccaag ctatttaata tcatgcacga aaagcaaaca aacttgtgtg   480
cttcattgga tgttcgtacc accaaggaat tactggagtt agttgaagca ttaggtccca   540
aaatttgttt actaaaaaca catgtggata tcttgactga ttttttccatg gagggcacag  600 ttaagccgct aaaggcatta tccgccaagt acaatttttt actcttcgaa gacagaaaat   660
ttgctgacat tggtaataca gtcaaattgc agtactctgc gggtgtatac agaatagcag   720
aatgggcaga cattacgaat gcacacgtg tggtgggccc aggtattgtt agcggtttga    780
agcaggcggc agaagaagta acaaaggaac ctagaggcct tttgatgtta gcagaattgt   840
catgcaaggg ctccctatct actggagaat atactaaggg tactgttgac attgcgaaga   900
gcgacaaaga ttttgttatc ggcttttattg ctcaaagaga catgggtgga agagatgaag   960
gttacgattg gttgattatg acacccggtg tgggtttaga tgacaaggga gacgcattgg   1020
gtcaacagta tagaaccgtg gatgatgtgg tctctacagg atctgacatt attattgttg   1080
gaagaggact atttgcaaag ggaagggat ctaaggtaga gggtgaacgt tacagaaaag   1140
caggctggga agcatatttg agaagatgcg gccagcaaaa ctaaaaaact gtattataag   1200
taaatgcatg tatactaaac tcacaaatta gagcttcaat ttaattatat cagttattac   1260
cctatgcggt gtgaaatacc gcacagatgc gtaaggagaa ataccgcat caggaaattg   1320 taaacgttaa tattttgtta aaattcgcgt taaattttg ttaaatcagc tcatttttta    1380
accaataggc cgaaatcggc aaaatcccct ataaatcaaa agaatagacc gagatagggt   1440
tgagtgttgt tccagtttgg aacaagagtc cactattaaa gaacgtggac tccaacgtca   1500
aagggcgaaa aaccgtctat cagggcgatg gcccactacg tgaaccatca ccctaatcaa   1560
```

```
gataacttcg tatagcatac attatacgaa gttatccagt gatgatacaa cgagttagcc    1620
aaggtgacac tctccccccc cctcccccctc tgatctttcc tgttgcctct ttttccccca   1680
accaa                                                                1685
```

EXTRACTION SOLVENTS DERIVED FROM OIL FOR ALCOHOL REMOVAL IN EXTRACTIVE FERMENTATION

This application is a continuation of U.S. patent application Ser. No. 13/894,894, filed on May 15, 2013, which is a continuation of U.S. patent application Ser. No. 13/692,254, filed on Dec. 3, 2012, now U.S. Pat. No. 8,476,047, which is a continuation of U.S. patent application Ser. No. 13/162,643, filed on Jun. 17, 2011, now U.S. Pat. No. 8,409,834, which claims the benefit of U.S. Provisional Application No. 61/356,290, filed on Jun. 18, 2010; U.S. Provisional Application No. 61/368,451, filed on Jul. 28, 2010; U.S. Provisional Application No. 61/368,436, filed on Jul. 28, 2010; U.S. Provisional Application No. 61/368,444, filed on Jul. 28, 2010; U.S. Provisional Application No. 61/368,429, filed on Jul. 28, 2010; U.S. Provisional Application No. 61/379,546, filed on Sep. 2, 2010; and U.S. Provisional Application No. 61/440,034, filed on Feb. 7, 2011; U.S. patent application Ser. No. 13/160,766, filed on Jun. 15, 2011; the entire contents of which are all herein incorporated by reference.

The Sequence Listing associated with this application is filed in electronic form via EFS-Web and hereby incorporated by reference into the specification in its entirety.

FIELD OF THE INVENTION

The present invention relates the production of fermentative alcohols such as butanol, and in particular to extraction solvents for extractive fermentation and processes for converting oil derived from biomass into the extraction solvents.

BACKGROUND OF THE INVENTION

Alcohols have a variety of applications in industry and science such as a beverage (i.e., ethanol), fuel, reagents, solvents, and antiseptics. For example, butanol is an alcohol that is an important industrial chemical with a variety of applications including use as a fuel additive, as a feedstock chemical in the plastics industry, and as a food-grade extractant in the food and flavor industry. Accordingly, there is a high demand for alcohols such as butanol, as well as for efficient and environmentally-friendly production methods.

Production of alcohol utilizing fermentation by microorganisms is one such environmentally-friendly production method. In the production of butanol, in particular, some microorganisms that produce butanol in high yields also have low butanol toxicity thresholds. Removal of butanol from the fermentation vessel as it is being produced is a means to manage these low butanol toxicity thresholds.

In situ product removal (ISPR) (also referred to as extractive fermentation) can be used to remove butanol (or other fermentative alcohol) from the fermentation vessel as it is produced, thereby allowing the microorganism to produce butanol at high yields. One ISPR method for removing fermentative alcohol that has been described in the art is liquid-liquid extraction (U.S. Patent Application Publication No. 2009/0305370). In order to be technically and economically viable, liquid-liquid extraction calls for good contact between the extractant and the fermentation broth for efficient mass transfer of the product alcohol into the extractant; good phase separation of the extractant from the fermentation broth (during and/or after fermentation); efficient recovery and recycle of the extractant; minimal degradation of the ability of the extractant to extract the product alcohol (e.g., by preventing the lowering of the partition coefficient for the product alcohol into the extractant); and minimal contamination of the extractant by lipids that lower the partition coefficient over a long-term operation.

The partition coefficient of the extractant can be degraded over time with each recycle, for example, by the build-up of lipids present in the biomass that is fed to the fermentation vessel as feedstock of hydrolysable starch. As an example, a liquefied corn mash loaded to a fermentation vessel at 30 wt % dry corn solids can result in a fermentation broth that contains about 1.2 wt % corn oil during conversion of glucose to butanol by simultaneous saccharification and fermentation (SSF) (with saccharification of the liquefied mash occurring during fermentation by the addition of glucoamylase to produce glucose). The dissolution of the corn oil lipids in oleyl alcohol (OA) serving as an extractant during ISPR can result in build-up of lipid concentration with each OA recycle, decreasing the partition coefficient for the product alcohol in OA as the lipid concentration in OA increases with each recycle of OA.

In addition, the presence of the undissolved solids during extractive fermentation can negatively affect the efficiency of alcohol production. For example, the presence of the undissolved solids may lower the mass transfer coefficient inside the fermentation vessel, impede phase separation in the fermentation vessel, result in the accumulation of corn oil from the undissolved solids in the extractant leading to reduced extraction efficiency over time, increase the loss of solvent because it becomes trapped in solids and ultimately removed as Dried Distillers' Grains with Solubles (DDGS), slow the disengagement of extractant drops from the fermentation broth, and/or result in a lower fermentation vessel volume efficiency.

Several approaches for reducing the degradation of the extractant used in extractive fermentation with lipid have included biomass wet milling, fractionation, and removal of solids. Wet milling is an expensive, multi-step process that separates a biomass (e.g., corn) into its key components (germ, pericarp fiber, starch, and gluten) in order to capture value from each co-product separately. This process gives a purified starch stream; however, it is costly and includes the separation of the biomass into its non-starch components which is unnecessary for fermentative alcohol production. Fractionation removes fiber and germ which contains a majority of the lipids present in ground whole grain such as corn, resulting in corn that has a higher starch (endosperm) content. Dry fractionation does not separate the germ and fiber and therefore, it is less expensive than wet milling. However, fractionation does not remove the entirety of the fiber or germ, and does not result in total elimination of solids. Furthermore, there is some loss of starch in fractionation. Wet milling of corn is more expensive than dry fractionation, but dry fractionation is more expensive than dry grinding of unfractionated corn. Removal of solids including germ containing lipids, from liquefied mash prior to use in fermentation can substantially eliminate undissolved solids as described, for example, in co-pending, commonly owned U.S. Provisional Application Ser. No. 61/356,290, filed Jun. 18, 2010. However, it would be advantageous if the degradation of the partition coefficient of the extractant can be reduced even without fractionation or removal of undissolved solids. Thus, there is a continuing need to develop more efficient methods and systems for producing product alcohols, such as butanol, through extractive fermentation in which the degradation of the partition coefficient of the extractant is reduced.

Moreover, the extractant (e.g., oleyl alcohol) is typically added to the fermentation process, rather than produced at a step in the process and therefore, the extractant is a raw material expense. Since extractant can be lost by adsorption on non-fermentable solids and/or diluted by lipids introduced into the fermentation process, the economics of an alcohol production process can be affected by the efficiency of the extractant recovery and recycle. Thus, there exists a continuing need for alternative extractants for ISPR that can result in a more economical process by reducing capital and/or operating costs.

BRIEF SUMMARY OF THE INVENTION

The present invention satisfies the above needs by providing methods for producing product alcohols such as butanol, in which the lipids in a biomass are converted into an extractant that can be used in ISPR, and in which the amount of lipids that are fed to the fermentation vessel with the feedstock and/or upon extractant recycle, are decreased. The present invention offers a solution to the degradation of the ability of the extractant to extract a product alcohol (e.g., butanol) by preventing the lowering of the partition coefficient for the product alcohol into the extractant. The application offers a solution to the contamination of the extractant by triglycerides that lower the partition coefficient of the extractant for a product alcohol. The present invention provides further related advantages as will be made apparent by the description of the embodiments that follow.

Catalytic (e.g., enzymatic) hydrolysis of lipids derived from biomass into fatty acids can decrease the rate of undesirable build-up of lipids in the ISPR extractant. The fatty acids can be obtained from hydrolysis of lipids found in the biomass which supplies the fermentable carbon for fermentation. Fatty acids would not be expected to decrease the partition coefficient of the product alcohol such as a butanol into the extractant phase as much as the lipids, as the partition coefficient for butanol from water to fatty acids has been determined to be significantly greater than the partition coefficient for butanol from water to fatty acid esters or triglycerides. Moreover, the fatty acids can be used as an ISPR extractant which can be produced at a step in the alcohol production process and can be used in place of, or in addition to, a supplied, exogenous ISPR extractant that is not produced in the process (such as, but not limited to, oleyl alcohol or oleic acid), thereby reducing the raw material expense for the ISPR extractant.

In one embodiment, the present invention is directed to a method comprising contacting biomass comprising water, fermentable carbon source, and oil with one or more catalyst whereby at least a portion of the oil is hydrolyzed by one or more catalyst to form an extractant, wherein the fermentable carbon source and the oil are both derived from the biomass. The biomass may comprises corn grain, corn cobs, crop residues, corn husks, corn stover, grasses, wheat, rye, wheat straw, barley, barley straw, hay, rice straw, switchgrass, waste paper, sugar cane bagasse, sorghum, sugar cane, soy, grains, cellulosic material, lignocellulosic material, trees, branches, roots, leaves, wood chips, sawdust, shrubs and bushes, vegetables, fruits, flowers, animal manure, and mixtures thereof. In a further embodiment, the oil may comprise glycerides and one or more catalysts may hydrolyze the glycerides to form fatty acids. In another embodiment, the one or more catalysts may be selected from esterase, lipase, phospholipase, and lysophospholipase.

In another embodiment, the extractant may comprise fatty acids, fatty amides, fatty alcohols, fatty esters, triglycerides, or mixtures thereof. In a further embodiment, the extractant may comprise a mixture of fatty acids or a mixture of fatty acids and fatty amides. In a further embodiment, a partition coefficient of the extractant for the product alcohol may be greater than a partition coefficient of the oil of the biomass for the product alcohol.

The method of the present invention may further comprise the step of inactivating the catalyst after at least a portion of the oil is hydrolyzed. In another embodiment, the method may further comprise the step of separating the oil from the biomass prior to hydrolysis by one or more catalyst. The claimed method may also further comprise the steps of contacting the biomass with a fermentation broth in a fermentation vessel; fermenting the carbon source of the biomass to produce a product alcohol; and removing in situ the product alcohol from the fermentation broth by contacting the broth with the extractant. The product alcohol may be butanol.

In another embodiment, the present invention is directed to a method for producing an alcohol comprising (a) providing biomass comprising water, fermentable carbon source, and oil; (b) liquefying the biomass to produce a liquefied biomass; (c) contacting the liquefied biomass with one or more catalysts whereby at least a portion of the oil is hydrolyzed to form an extractant; (d) contacting the liquefied biomass with a saccharification enzyme capable of converting oligosaccharides into fermentable sugar; (e) contacting the liquefied biomass with a fermentation broth in a fermentation vessel; (f) fermenting the carbon source of the liquefied biomass to produce a product alcohol; (g) removing in situ the product alcohol from the fermentation broth by contacting the broth with the extractant; and optionally steps (c) and (d) occur concurrently. The biomass may comprises corn grain, corn cobs, crop residues, corn husks, corn stover, grasses, wheat, rye, wheat straw, barley, barley straw, hay, rice straw, switchgrass, waste paper, sugar cane bagasse, sorghum, sugar cane, soy, grains, cellulosic material, lignocellulosic material, trees, branches, roots, leaves, wood chips, sawdust, shrubs and bushes, vegetables, fruits, flowers, animal manure, and mixtures thereof. In a further embodiment, the oil may comprise glycerides and one or more catalysts may hydrolyze the glycerides to form fatty acids. In another embodiment, the one or more catalysts may be selected from esterase, lipase, phospholipase, and lysophospholipase. In another embodiment, the extractant may comprise fatty acids, fatty amides, fatty alcohols, fatty esters, triglycerides, or mixtures thereof. In a further embodiment, the extractant may comprise a mixture of fatty acids or a mixture of fatty acids or fatty amides. In a further embodiment, a partition coefficient of the extractant for the product alcohol may be greater than a partition coefficient of the oil of the biomass for the product alcohol. The method of the present invention may further comprise the step of inactivating the catalyst after at least a portion of the oil is hydrolyzed. The product alcohol may be butanol.

The present invention is also directed to a composition comprising a recombinant microorganism capable of producing an alcohol; fermentable carbon source; one or more catalysts capable of hydrolyzing glycerides into fatty acids; oil comprising glycerides; and fatty acids. The one or more catalysts may be selected from esterase, lipase, phospholipase, and lysophospholipase, and the oil may be corn, tallow, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha and vegetable oil blends. In a further embodiment, the fermentable carbon source and the oil are derived from biomass. The biomass may comprise corn grain, corn cobs, crop residues, corn husks, corn stover, grasses, wheat, rye, wheat straw, barley, barley straw, hay, rice straw, switchgrass, waste paper, sugar cane bagasse, sorghum, sugar cane, soy, grains, cellulosic material, lignocellulosic material, trees, branches, roots, leaves, wood chips, sawdust, shrubs and bushes, vegetables, fruits, flowers, animal manure, and mixtures thereof. The composition may further comprise a saccharification enzyme and/or undissolved solids. The composition may also comprise at least one or more of monoglycerides, diglycerides, triglycerides, glycerol, monosaccharides, oligosaccharides, or alcohol. In addition, the alcohol may be butanol.

In some embodiments, a method of removing oil derived from biomass from a fermentation process includes contacting an aqueous biomass feedstream with a catalyst. The feedstream includes water, fermentable carbon and an amount of oil, and the fermentable carbon and the oil are both derived from the biomass. At least a portion of the oil is hydrolyzed according to methods described in the present invention into fatty acids to form a catalyst-treated biomass feedstream including the fatty acids.

In some embodiments, a method of producing an extractant for in situ removal of a product alcohol includes providing biomass which includes sugar and oil, the oil having an amount of triglycerides, and contacting the oil with a composition including one or more enzymes capable of hydrolyzing the triglycerides into fatty acids. The triglycerides in the oil are hydrolyzed to form a fermentation product extractant having a partition coefficient for the product alcohol greater than a partition coefficient of the oil of the biomass for the product alcohol.

In some embodiments, a method for producing butanol includes (a) providing biomass having starch and oil, the oil including an amount of glycerides; (b) liquefying the biomass to produce a liquefied biomass, the liquefied biomass including oligosaccharides hydrolyzed from the starch; (c) contacting the biomass of step (a) or the liquefied biomass of step (b) with a composition having one or more enzymes capable of converting the glycerides into free fatty acids whereby the free fatty acids form a fermentation product extractant; (d) contacting the liquefied biomass with a saccharification enzyme capable of converting oligosaccharides into fermentable sugar including monomeric glucose; (e) contacting the liquefied biomass with a biocatalyst capable of converting the fermentable sugar to butanol whereby a fermentation product comprising butanol is produced; and (f) contacting the fermentation product with the fermentation product extractant whereby the butanol is separated from the fermentation product, the fermentation product extractant having a partition coefficient for the butanol greater than a partition coefficient of the oil of the biomass for the butanol.

In some embodiments, a method includes, at a step during a process to produce a product alcohol from a feedstock, contacting the product alcohol with an extractant comprising free fatty acids obtained from enzymatic hydrolysis of a native oil wherein the oil comprises glycerides. The extractant has a partition coefficient for the product alcohol greater than a partition coefficient of the native oil for the product alcohol.

In some embodiments, the process to produce a product alcohol from a feedstock includes (a) liquefying the feedstock to create a feedstock slurry; (b) centrifuging the feedstock slurry of (a) to produce a centrifuge product including (i) an aqueous layer comprising sugar, (ii) a plant-derived oil layer, and (iii) a solids layer; (c) feeding the aqueous layer of (b) to a fermentation vessel; and (d) fermenting the sugar of the aqueous layer to produce the product alcohol.

In some embodiments, the process to produce a product alcohol from a feedstock further includes adding the extractant to the fermentation vessel to form a two-phase mixture comprising an aqueous phase and a product alcohol-containing organic phase.

In some embodiments, the native oil is a plant-derived oil, and in some embodiments, the process to produce a product alcohol from a feedstock further includes obtaining the plant-derived oil from the plant-derived oil layer; and converting the plant-derived oil into the extractant by contacting the oil with one or more enzymes that hydrolyze the glycerides into free fatty acids.

In some embodiments, the process to produce a product alcohol from a feedstock further includes inactivating the one or more enzymes after at least a portion of the glycerides have been hydrolyzed into free fatty acids.

In some embodiments, the process to produce a product alcohol from a feedstock further includes feeding the plant-derived oil to the fermentation vessel prior to the step of converting the plant-derived oil into the extractant.

In some embodiments, the process to produce a product alcohol from a feedstock further includes adding a second extractant to the fermentation vessel to form a two-phase mixture comprising an aqueous phase and a product alcohol-containing organic phase.

In some embodiments, the plant-derived oil is converted to the extractant after the step of adding a second extractant.

In some embodiments, a method of removing oil derived from biomass from a fermentation process, includes (a) providing a fermentation broth comprising a product alcohol and oil derived from biomass, the oil including glycerides; (b) contacting the fermentation broth with a first extractant to form a two-phase mixture comprising an aqueous phase and an organic phase, wherein the product alcohol and the oil partition into the organic phase to form a product alcohol-containing organic phase; (c) separating the product alcohol-containing organic phase from the aqueous phase; (d) separating the product alcohol from the organic phase to produce a lean organic phase; and (e) contacting the lean organic phase with a composition comprising one or more catalysts capable of hydrolyzing the glycerides into free fatty acids to produce a second extractant comprising at least a portion of the first extractant and free fatty acids.

In some embodiments, the method further includes repeating step (b) by contacting the fermentation broth with the second extractant of step (e).

In some embodiments, an in situ fermentation extractant-forming composition includes (a) mash formed from biomass and including water, starch and oil, (b) a catalyst capable of hydrolyzing at least a portion of the triglycerides into free fatty acids, and (c) free fatty acids. The starch and the oil are both derived from the biomass, and the oil includes an amount of triglycerides.

In some embodiments, a fermentation broth includes (a) a recombinant microorganism capable of producing butanol, (b) oligosaccharides, (c) a catalyst for hydrolyzing glycerides into free fatty acids, (d) glycerides, and (e) free fatty acids.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

FIG. 1 schematically illustrates an exemplary method and system of the present invention, in which a liquefied biomass is contacted with a catalyst for lipid hydrolysis before fermentation.

FIG. 2 schematically illustrates an exemplary method and system of the present invention, in which a liquefied and saccharified biomass is contacted with a catalyst for lipid hydrolysis before fermentation.

FIG. 3 schematically illustrates an exemplary method and system of the present invention, in which lipids in a biomass feedstream are contacted with a catalyst for lipid hydrolysis before or during liquefaction.

FIG. 4 schematically illustrates an exemplary method and system of the present invention, in which undissolved solids and lipids are removed from a liquefied biomass before fermentation, and in which the removed lipids are hydrolyzed into free fatty acids using a catalyst, and the free fatty acids are supplied to the fermentation vessel.

FIG. 5 schematically illustrates an exemplary method and system of the present invention, in which lipids derived from native oil are hydrolyzed into free fatty acids using a catalyst, and the free fatty acids are supplied to the fermentation vessel.

FIG. 6 schematically illustrates an exemplary method and system of the present invention, in which biomass lipids present in a first extractant exiting a fermentation vessel are converted into free fatty acids that are supplied to a fermentation vessel as a second extractant.

DETAILED DESCRIPTION OF THE INVENTION

Figure 1:
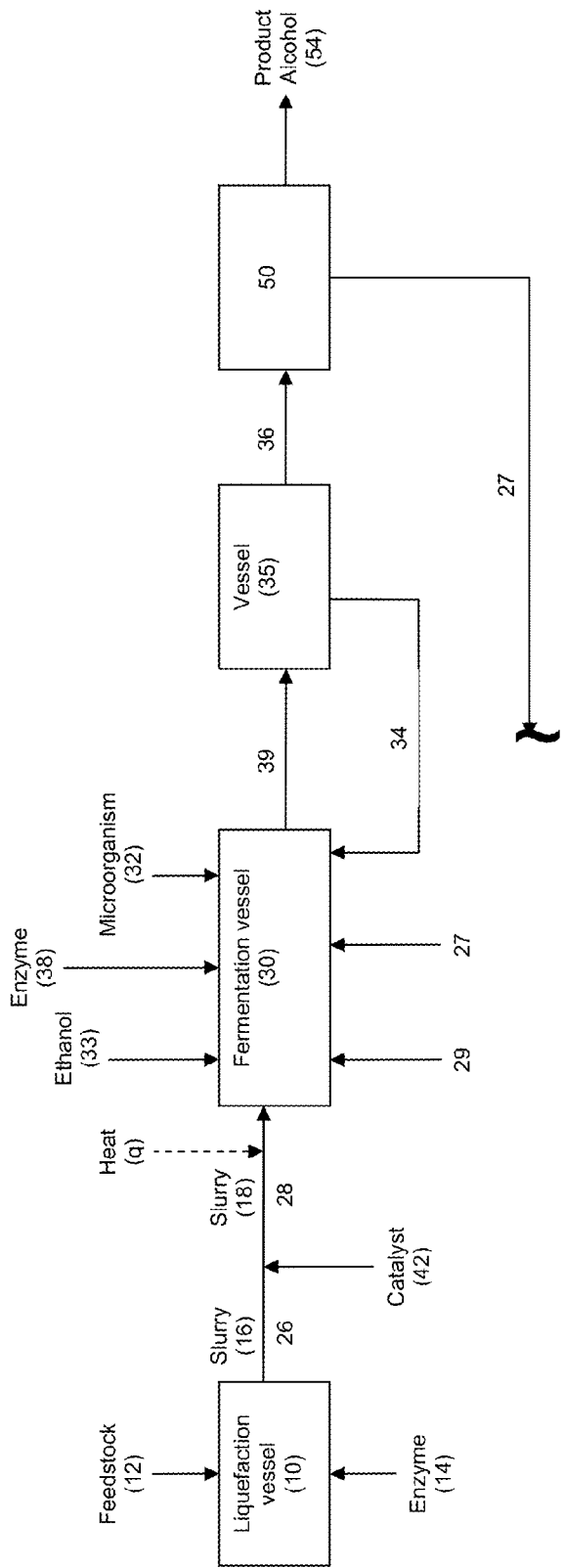

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes.

In order to further define this invention, the following terms and definitions are herein provided.

As used herein, the terms "comprises," "comprising," "includes," "including," "has," "having," "contains," or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, that is, occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, alternatively within 5% of the reported numerical value.

"Biomass" as used herein refers to a natural product containing hydrolyzable polysaccharides that provide fermentable sugars including any sugars and starch derived from natural resources such as corn, cane, wheat, cellulosic or lignocellulosic material and materials comprising cellulose, hemicellulose, lignin, starch, oligosaccharides, disaccharides and/or monosaccharides, and mixtures thereof. Biomass may also comprise additional components such as protein and/or lipids. Biomass may be derived from a single source or biomass can comprise a mixture derived from more than one source. For example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, trees, branches, roots, leaves, wood chips, sawdust, shrubs and bushes, vegetables, fruits, flowers, animal manure, and mixtures thereof. For example, mash, juice, molasses, or hydrolysate may be formed from biomass by any processing known in the art for processing the biomass for purposes of fermentation such as by milling, treating, and/or liquefying and comprises fermentable sugar and may comprise water. For example, cellulosic and/or lignocellulosic biomass may be processed to obtain a hydrolysate containing fermentable sugars by any method known to one skilled in the art. A low ammonia pretreatment is disclosed in U.S. Patent Application Publication No. 2007/0031918A1, which is herein incorporated by reference. Enzymatic saccharification of cellulosic and/or lignocellulosic biomass typically makes use of an enzyme consortium for breaking down cellulose and hemicellulose to produce a hydrolysate containing sugars including glucose, xylose, and arabinose. (Saccharification enzymes suitable for cellulosic and/or lignocellulosic biomass are reviewed in Lynd, et al. (Microbiol. Mol. Biol. Rev. 66:506-577, 2002).

Mash, juice, molasses, or hydrolysate may include feedstock 12 and hydrolysate 16 as described herein. An aqueous feedstream may be derived or formed from biomass by any processing known in the art for processing the biomass for purposes of fermentation such as by milling, treating, and/or liquefying and comprises fermentable carbon substrate (e.g., sugar) and may comprise water. An aqueous feedstream may include feedstock 12 and feedstock slurry 16 as described herein.

"Feedstock" as used herein means a feed in a fermentation process, the feed containing a fermentable carbon source with or without undissolved solids, and where applicable, the feed containing the fermentable carbon source before or after the fermentable carbon source has been liberated from starch or obtained from the break down of complex sugars by further processing such as by liquefaction, saccharification, or other process. Feedstock includes or is derived from a biomass. Suitable feedstocks include, but are not limited to, rye, wheat, corn, cane, barley, cellulosic material, lignocellulosic material, or mixtures thereof.

"Fermentation broth" as used herein means the mixture of water, sugars, dissolved solids, optionally microorganisms producing alcohol, product alcohol, and all other constituents of the material held in the fermentation vessel in which product alcohol is being made by the reaction of sugars to alcohol, water, and carbon dioxide ($CO_2$) by the microorganisms present. From time to time, as used herein the term "fermentation medium" and "fermented mixture" can be used synonymously with "fermentation broth."

"Fermentable carbon source" or "fermentable carbon substrate" as used herein means a carbon source capable of being metabolized by the microorganisms disclosed herein for the production of fermentative alcohol. Suitable fermentable carbon sources include, but are not limited to, monosaccharides such as glucose or fructose; disaccharides such as lactose or sucrose; oligosaccharides; polysaccharides such as starch or cellulose; C5 sugars such as xylose and arabinose; one carbon substrates including methane; and mixtures thereof.

"Fermentable sugar" as used herein refers to one or more sugars capable of being metabolized by the microorganisms disclosed herein for the production of fermentative alcohol.

"Fermentation vessel" as used herein means the vessel in which the fermentation reaction is carried out whereby product alcohol such as butanol is made from sugars.

"Liquefaction vessel" as used herein means the vessel in which liquefaction is carried out. Liquefaction is the process in which oligosaccharides are liberated from the feedstock. In some embodiments where the feedstock is corn, oligosaccharides are liberated from the corn starch content during liquefaction.

"Saccharification vessel" as used herein means the vessel in which saccharification (i.e., the break down of oligosaccharides into monosaccharides) is carried out. Where fermentation and saccharification occur simultaneously, the saccharification vessel and the fermentation vessel may be one in the same vessel.

"Sugar" as used herein refers to oligosaccharides, disaccharides, monosaccharides, and/or mixtures thereof. The term "saccharide" also includes carbohydrates including starches, dextrans, glycogens, cellulose, pentosans, as well as sugars.

As used herein, "saccharification enzyme" means one or more enzymes that are capable of hydrolyzing polysaccharides and/or oligosaccharides, for example, alpha-1,4-glucosidic bonds of glycogen, or starch. Saccharification enzymes may include enzymes capable of hydrolyzing cellulosic or lignocellulosic materials as well.

"Undissolved solids" as used herein means non-fermentable portions of feedstock, for example, germ, fiber, and gluten.

"Product alcohol" as used herein refers to any alcohol that can be produced by a microorganism in a fermentation process that utilizes biomass as a source of fermentable carbon substrate. Product alcohols include, but are not limited to, $C_1$ to $C_8$ alkyl alcohols. In some embodiments, the product alcohols are $C_2$ to $C_8$ alkyl alcohols. In other embodiments, the product alcohols are $C_2$ to $C_5$ alkyl alcohols. It will be appreciated that $C_1$ to $C_8$ alkyl alcohols include, but are not limited to, methanol, ethanol, propanol, butanol, and pentanol. Likewise $C_2$ to $C_8$ alkyl alcohols include, but are not limited to, ethanol, propanol, butanol, and pentanol. "Alcohol" is also used herein with reference to a product alcohol.

"Butanol" as used herein refers with specificity to the butanol isomers 1-butanol (1-BuOH), 2-butanol (2-BuOH), tert-butanol, and/or isobutanol (iBuOH or i-BuOH or I-BUOH, also known as 2-methyl-1-propanol), either individually or as mixtures thereof. From time to time, when referring to esters of butanol, the terms "butyl esters" and "butanol esters" may be used interchangeably.

"Propanol" as used herein refers to the propanol isomers isopropanol or 1-propanol.

"Pentanol" as used herein refers to the pentanol isomers 1-pentanol, 3-methyl-1-butanol, 2-methyl-1-butanol, 2,2-dimethyl-1-propanol, 3-pentanol, 2-pentanol, 3-methyl-2-butanol, or 2-methyl-2-butanol.

The term "alcohol equivalent" as used herein refers to the weight of alcohol that would be obtained by a perfect hydrolysis of an alcohol ester and the subsequent recovery of the alcohol from an amount of alcohol ester.

The term "aqueous phase titer" as used herein refers to the concentration of a particular alcohol (e.g., butanol) in the fermentation broth.

The term "effective titer" as used herein refers to the total amount of a particular alcohol (e.g., butanol) produced by fermentation or alcohol equivalent of the alcohol ester produced by alcohol esterification per liter of fermentation medium. For example, the effective titer of butanol in a unit volume of a fermentation includes: (i) the amount of butanol in the fermentation medium; (ii) the amount of butanol recovered from the organic extractant; (iii) the amount of butanol recovered from the gas phase, if gas stripping is used; and (iv) the alcohol equivalent of the butanol ester in either the organic or aqueous phase.

"In Situ Product Removal (ISPR)" as used herein means the selective removal of a specific fermentation product from a biological process such as fermentation, to control the product concentration in the biological process as the product is produced.

"Extractant" or "ISPR extractant" as used herein means an organic solvent used to extract any product alcohol such as butanol or used to extract any product alcohol ester produced by a catalyst from a product alcohol and a carboxylic acid or lipid. From time to time, as used herein the term "solvent" may be used synonymously with "extractant." For the processes described herein, extractants are water-immiscible.

The terms "water-immiscible" or "insoluble" refer to a chemical component such as an extractant or solvent, which is incapable of mixing with an aqueous solution such as a fermentation broth, in such a manner as to form one liquid phase.

The term "aqueous phase" as used herein refers to the aqueous phase of a biphasic mixture obtained by contacting a fermentation broth with a water-immiscible organic extractant. In an embodiment of a process described herein that includes fermentative extraction, the term "fermentation broth" then specifically refers to the aqueous phase in biphasic fermentative extraction.

The term "organic phase" as used herein refers to the non-aqueous phase of a biphasic mixture obtained by contacting a fermentation broth with a water-immiscible organic extractant.

The term "carboxylic acid" as used herein refers to any organic compound with the general chemical formula —COOH in which a carbon atom is bonded to an oxygen atom by a double bond to make a carbonyl group (—C=O) and to a hydroxyl group (—OH) by a single bond. A carboxylic acid may be in the form of the protonated carboxylic acid, in the form of a salt of a carboxylic acid (e.g., an ammonium, sodium, or potassium salt), or as a mixture of protonated carboxylic acid and salt of a carboxylic acid. The term carboxylic acid may describe a single chemical species (e.g., oleic acid) or a mixture of carboxylic acids as can be produced, for example, by the hydrolysis of biomass-derived fatty acid esters or triglycerides, diglycerides, monoglycerides, and phospholipids.

The term "fatty acid" as used herein refers to a carboxylic acid (e.g., aliphatic monocarboxylic acid) having $C_4$ to $C_{28}$ carbon atoms (most commonly $C_{12}$ to $C_{24}$ carbon atoms), which is either saturated or unsaturated. Fatty acids may also be branched or unbranched. Fatty acids may be derived from, or contained in esterified form, in an animal or vegetable fat, oil, or wax. Fatty acids may occur naturally in the form of glycerides in fats and fatty oils or may be obtained by hydrolysis of fats or by synthesis. The term fatty acid may describe a single chemical species or a mixture of fatty acids. In addition, the term fatty acid also encompasses free fatty acids.

The term "fatty alcohol" as used herein refers to an alcohol having an aliphatic chain of $C_4$ to $C_{22}$ carbon atoms, which is either saturated or unsaturated.

The term "fatty aldehyde" as used herein refers to an aldehyde having an aliphatic chain of $C_4$ to $C_{22}$ carbon atoms, which is either saturated or unsaturated.

The term "fatty amide" as used herein refers to an amide having a long, aliphatic chain of $C_4$ to $C_{22}$ carbon atoms, which is either saturated or unsaturated.

The term "fatty ester" as used herein refers to an ester having a long aliphatic chain of $C_4$ to $C_{22}$ carbon atoms, which is either saturated or unsaturated.

"Native oil" as used herein refers to lipids obtained from plants (e.g., biomass) or animals. "Plant-derived oil" as used herein refers to lipids obtain from plants in particular. From time to time, "lipids" may be used synonymously with "oil" and "acyl glycerides." Native oils include, but are not limited to, tallow, corn, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha, and vegetable oil blends.

The term "separation" as used herein is synonymous with "recovery" and refers to removing a chemical compound from an initial mixture to obtain the compound in greater purity or at a higher concentration than the purity or concentration of the compound in the initial mixture.

As used herein, "recombinant microorganism" refers to microorganisms such as bacteria or yeast, that are modified by use of recombinant DNA techniques, for example, by engineering a host cell to comprise a biosynthetic pathway such as a biosynthetic pathway to produce an alcohol such as butanol.

The present invention provides extractants obtained by catalytic hydrolysis of oil glycerides derived from biomass and methods of producing the extractants. In particular, the glycerides in biomass oil can be catalytically hydrolyzed into fatty acids using a catalyst such as an enzyme. The fatty acids can serve as extractants for in situ removal of a product alcohol such as butanol from a fermentation broth. Thus, the present invention also provides methods for producing a product alcohol such as butanol through extractive fermentation using the extractants that were produced from the biomass oil. The present invention also provides methods for catalytically hydrolyzing the oil present in a feedstock slurry into fatty acids prior to fermentation, whereby the oil is converted to fatty acids and the degradation of the partition coefficient of the ISPR extractant over time that is attributable to the presence of the oil in the fermentation vessel can be reduced. Moreover, the fatty acids obtained by hydrolysis of the feedstock oil can serve as an ISPR extractant having a partition coefficient for a fermentative alcohol greater than a partition coefficient of the feedstock oil for the fermentative alcohol. The feedstock oil can be separated from the feedstock slurry prior to hydrolysis and used as an ISPR extractant, or the oil can be hydrolyzed into fatty acids while in the feedstock slurry. Further, fatty acids as ISPR extractant can be used in place of or in addition to a conventional exogenous extractant, such as oleyl alcohol or oleic acid, thereby reducing the raw material expense associated with the exogenous extractant.

The present invention will be described with reference to the Figures. FIG. 1 illustrates an exemplary process flow diagram for production of fermentative alcohol according to an embodiment of the present invention. As shown, a feedstock 12 can be introduced to an inlet in a liquefaction vessel 10 and liquefied to produce a feedstock slurry 16. Feedstock 12 contains hydrolysable starch that supplies a fermentable carbon source (e.g., fermentable sugar such as glucose), and can be a biomass such as, but not limited to, rye, wheat, corn, cane, barley, cellulosic material, lignocellulosic material, or mixtures thereof, or can otherwise be derived from a biomass. In some embodiments, feedstock 12 can be one or more components of a fractionated biomass and in other embodiments, feedstock 12 can be a milled, unfractionated biomass. In some embodiments, feedstock 12 can be corn such as dry milled, unfractionated corn kernels, and the undissolved solids can include germ, fiber, and gluten. The undissolved solids are non-fermentable portions of feedstock 12. For purposes of the discussion herein with reference to the embodiments shown in the Figures, feedstock 12 will often be described as constituting milled, unfractionated corn in which the undissolved solids have not been separated therefrom. However, it should be understood that the exemplary methods and systems described herein can be modified for different feedstocks whether fractionated or not, as apparent to one of skill in the art. In some embodiments, feedstock 12 can be high-oleic corn, such that corn oil derived therefrom is a high-oleic corn oil having an oleic acid content of at least about 55 wt % oleic acid. In some embodiments, the oleic acid content in high-oleic corn oil can be up to about 65 wt %, as compared with the oleic acid content in normal corn oil which is about 24 wt %. High-oleic oil can provide some advantages for use in the methods of the present invention, as hydrolysis of the oil provides fatty acids having a high oleic acid content for contacting with a fermentation broth. In some embodiments, the fatty acids or mixtures thereof comprise unsaturated fatty acids. The presence of unsaturated fatty acids decreases the melting point, providing advantages for handling. Of the unsaturated fatty acids, those which are monounsaturated, that is, possessing a single carbon-carbon double bond, may provide advantages with respect to melting point without sacrificing suitable thermal and oxidative stability for process considerations.

The process of liquefying feedstock 12 involves hydrolysis of starch in feedstock 12 into sugars including, for example, dextrins and oligosaccharides, and is a conventional process. Any known liquefying processes, as well as the corresponding liquefaction vessel, normally utilized by the industry can be used including, but not limited to, the acid process, the acid-enzyme process, or the enzyme process. Such processes can be used alone or in combination. In some embodiments, the enzyme process can be utilized and an appropriate enzyme 14, for example, alpha-amylase, is introduced to an inlet in liquefaction vessel 10. Water can also be introduced to liquefaction vessel 10. In some embodiments, a saccharification enzyme, for example, glucoamylase, may also be introduced to liquefaction vessel 10. In additional embodiments, a lipase may also be introduced to liquefaction vessel 10 to catalyze the conversion of one or more components of the oil to fatty acids.

Feedstock slurry 16 produced from liquefying feedstock 12 includes sugar, oil 26, and undissolved solids derived from the biomass from which feedstock 12 was formed. In some embodiments, the oil is in an amount of about 0 wt % to at least about 2 wt % of the fermentation broth composition. In some embodiments, the oil is in an amount of at least about 0.5 wt % of the feedstock. Feedstock slurry 16 can be discharged from an outlet of liquefaction vessel 10. In some embodiments, feedstock 12 is corn or corn kernels and therefore, feedstock slurry 16 is a corn mash slurry.

A catalyst 42 can be added to feedstock slurry 16. Catalyst 42 is capable of hydrolyzing glycerides in oil 26 to free fatty acids (FFA) 28. For example, when feedstock 12 is corn, then oil 26 is the feedstock's constituent corn oil, and the free fatty acids 28 are corn oil fatty acids (COFA). Thus, after introduction of catalyst 42 to feedstock slurry 16, at least a portion of the glycerides in oil 26 are hydrolyzed to FFA 28, resulting in a feedstock slurry 18 having FFA 28 and catalyst 42. The resulting acid/oil composition from hydrolyzing oil 26 is typically at least about 17 wt % FFA. In some embodiments, the resulting acid/oil composition from hydrolyzing oil 26 is at least about 20 wt % FFA, at least about 25 wt % FFA, at least about 30 wt % FFA, at least about 35 wt % FFA, at least about 40 wt % FFA, at least about 45 wt % FFA, at least about 50 wt % FFA, at least about 55 wt % FFA, at least about 60 wt % FFA, at least about 65 wt % FFA, at least about 70 wt % FFA, at least about 75 wt % FFA, at least about 80 wt % FFA, at least about 85 wt % FFA, at least about 90 wt % FFA, at least about 95 wt % FFA, or at least about 99 wt % FFA. In some embodiments, the concentration of the fatty acid (such as carboxylic acid) in the fermentation vessel exceeds the solubility limit in the aqueous phase and results in the production a two-phase fermentation mixture comprising an organic phase and an aqueous phase. In some embodiments, the concentration of carboxylic acid (or fatty acid) in the fermentation broth is typically not greater than about 0.8 g/L and is limited by the solubility of the carboxylic acid (or fatty acid) in the broth.

In some embodiments, catalyst 42 can be one or more enzymes, for example, hydrolase enzymes such as lipase enzymes. Lipase enzymes used may be derived from any source including, for example, *Absidia, Achromobacter, Aeromonas, Alcaligenes, Alternaria, Aspergillus, Achromobacter, Aureobasidium, Bacillus, Beauveria, Brochothrix, Candida, Chromobacter, Coprinus, Fusarium, Geotricum, Hansenula, Humicola, Hyphozyma, Lactobacillus, Metarhizium, Mucor, Nectria, Neurospora, Paecilomyces, Penicillium, Pseudomonas, Rhizoctonia, Rhizomucor, Rhizopus, Rhodosporidium, Rhodotorula, Saccharomyces, Sus, Sporobolomyces, Thermomyces, Thiarosporella, Trichoderma, Verticillium*, and/or a strain of *Yarrowia*. In a preferred aspect, the source of the lipase is selected from the group consisting of *Absidia blakesleena, Absidia corymbifera, Achromobacter iophagus, Alcaligenes* sp., *Alternaria brassiciola, Aspergillus flavus, Aspergillus niger, Aspergillus tubingensis, Aureobasidium pullulans, Bacillus pumilus, Bacillus strearothermophilus, Bacillus subtilis, Brochothrix thermosohata, Candida cylindracea (Candida rugosa), Candida paralipolytica, Candida Antarctica* lipase A, *Candida antartica* lipase B, *Candida emobii, Candida deformans, Chromobacter viscosum, Coprinus cinerius, Fusarium oxysporum, Fusarium solani, Fusarium solani pisi, Fusarium roseum culmorum, Geotricum penicillatum, Hansenula anomala, Humicola brevispora, Humicola brevis* var. thermoidea, *Humicola insolens, Lactobacillus curvatus, Rhizopus oryzae, Penicillium cyclopium, Penicillium crustosum, Penicillium expansum, Penicillium* sp. I, *Penicillium* sp. II, *Pseudomonas aeruginosa, Pseudomonas alcaligenes, Pseudomonas cepacia* (syn. *Burkholderia cepacia), Pseudomonas fluorescens, Pseudomonas fragi, Pseudomonas maltophilia, Pseudomonas mendocina, Pseudomonas mephitica lipolytica, Pseudomonas alcaligenes, Pseudomonas plantari, Pseudomonas pseudoalcaligenes, Pseudomonas putida, Pseudomonas stutzeri*, and *Pseudomonas wisconsinensis, Rhizoctonia solani, Rhizomucor miehei, Rhizopus japonicus, Rhizopus microsporus, Rhizopus nodosus, Rhodosporidium toruloides, Rhodotorula glutinis, Saccharomyces cerevisiae, Sporobolomyces shibatanus, Sus scrofa, Thermomyces lanuginosus* (formerly *Humicola lanuginose), Thiarosporella phaseolina, Trichoderma harzianum, Trichoderma reesei*, and *Yarrowia lipolytica*. In a further preferred aspect, the lipase is selected from the group consisting of *Thermomcyces lanuginosus* lipase, *Aspergillus* sp. lipase, *Aspergillus niger* lipase, *Aspergillus tubingensis* lipase, *Candida antartica* lipase B, *Pseudomonas* sp. lipase, *Penicillium roqueforti* lipase, *Penicillium camembertii* lipase, *Mucor javanicus* lipase, *Burkholderia cepacia* lipase, *Alcaligenes* sp. lipase, *Candida rugosa* lipase, *Candida parapsilosis* lipase, *Candida deformans* lipase, lipases A and B from *Geotrichum candidum, Neurospora crassa* lipase, *Nectria haematococca* lipase, *Fusarium heterosporum* lipase *Rhizopus delemar* lipase, *Rhizomucor miehei* lipase, *Rhizopus arrhizus* lipase, and *Rhizopus oryzae* lipase. Suitable commercial lipase preparations suitable as enzyme catalyst 42 include, but are not limited to Lipolase® 100 L, Lipex® 100 L, Lipoclean® 2000T, Lipozyme® CALB L, Novozyme® CALA L, and Palatase 20000L, available from Novozymes, or from *Pseudomonas fluorescens, Pseudomonas cepacia, Mucor miehei*, hog pancreas, *Candida cylindracea, Rhizopus niveus, Candida antarctica, Rhizopus arrhizus* or *Aspergillus* available from SigmaAldrich.

Phospholipases are enzymes that hydrolyze the ester bonds of phospholipids, but many phospholipases also can hydrolyze triglycerides, diglycerides, and monoglycerides (lipid acyl hydrolase (LAH) activity). As used herein, the term "phospholipase" encompasses enzymes having any phospholipase activity, for example, cleaving a glycerolphosphate ester linkage (catalyzing hydrolysis of a glycerolphosphate ester linkage), for example, in an oil, such as a crude oil or a vegetable oil. The phospholipase activity of the invention can generate a water extractable phosphorylated base and a diglyceride. The phospholipase activity can comprise a phospholipase C (PLC) activity; a PI-PLC activity, a phospholipase A (PLA) activity such as a phospholipase AI or phospholipase A2 activity; a phospholipase B (PLB) activity such as a phospholipase B1 or phospholipase B2 activity, including lysophospholipase (LPL) activity and/or lysophospholipase-transacylase (LPT A) activity; a phospholipase D (PLD) activity such as a phospholipase DI or a phospholipase D2 activity; and/or a patatin activity or any combination thereof. The term "phospholipase" also encompasses enzymes having lysophospholipase activity, where the two substrates of this enzyme are 2-lysophosphatidylcholine and $H_2O$, and where its two products are glycerophosphocholine and carboxylate. Phospholipase AI (PLA1) enzymes remove the 1-position fatty acid to produce free fatty acid and 1-lyso-2-acylphospholipid. Phospholipase A2 (PLA2) enzymes remove the 2-position fatty acid to produce free fatty acid and l-acyl-2-lysophospholipid. PLA1 and PLA2 enzymes can be intra- or extra-cellular, membrane-bound or soluble. Phospholipase C (PLC) enzymes remove the phosphate moiety to produce 1,2 diacylglycerol and a phosphate ester. Phospholipase D (PLD) enzymes produce 1,2-diacylglycerophosphate and base group. A phospholipase useful in the present invention may be obtained from a variety of biological sources, for example, but not limited to, filamentous fungal species within the genus *Fusarium*, such as a strain of *F. culmorum, F. heterosporum, F. solani*, or *F. oxysporum*; or a filamentous fungal species within the genus *Aspergillus*, such as a strain of *Aspergillus awamori, Aspergillus foetidus, Aspergillus japonicus, Aspergillus niger* or *Aspergillus oryzae*. Also useful in the present invention are *Thermomyces lanuginosus* phospholipase variants such as the commercial product Lecitase® Ultra (Novozymes A'S, Denmark). One or more phospholipases may be applied as lyophilized powder, immobilized or in aqueous solution.

After at least a portion of the glycerides are hydrolyzed, in some embodiments, catalyst 42 can be inactivated. Any method known in the art can be used to render catalyst 42 inactive. For example, in some embodiments, catalyst 42 can be inactivated by the application of heat, by adjusting the pH of the reaction mass to a pH where catalyst 42 is irreversibly inactivated, and/or by adding a chemical or biochemical species capable of selectively inactivating the catalyst activity. As shown, for example, in the embodiment of FIG. 1, heat q is applied to feedstock slurry 18, whereby catalyst 42 becomes inactive. The application of heat q can be applied to feedstock slurry 18 before feedstock slurry 18 is fed to a fermentation vessel 30. Heat-treated feedstock slurry 18 (with inactive catalyst 42) is then introduced into a fermentation vessel 30 along with a microorganism 32 to be included in a fermentation broth held in fermentation vessel 30. Alternatively, feedstock slurry 18 can be fed to fermentation vessel 30 and subjected to heat q while in the fermentation vessel, before fermentation vessel inoculation of microorganism 32. For example, in some embodiments, catalyst inactivation treatment can be achieved by heating feedstock slurry 18 with heat q to temperature of at least about 75° C. for at least about 5 minutes, at least about 75° C. for at least about 10 minutes, at least about 75° C. for at least about 15 minutes, at least about 80° C. for at least about 5 minutes, at least about 80° C. for at least about 10 minutes, at least about 80° C. for at least about 15 minutes, at least about 85° C. for at least about 5 minutes, at least about 85° C. for at least about 10 minutes, or at least about 85° C. for at least about 15 minutes. In some embodiments, after being subject to heat q, feedstock slurry 18 is cooled to an appropriate temperature for fermentation prior to introduction to fermentation vessel 30 (or prior to fermentation vessel inoculation in the case that the application of heat q is conducted in the fermentation vessel). For example, in some embodiments, the temperature of feedstock slurry 18 is about 30° C. prior to contacting with a fermentation broth.

Inactivation of catalyst 42 is preferred when it is desirable to prevent catalyst 42 from esterifying alcohol with fatty acids 28 in the fermentation vessel. In some embodiments, production of an alcohol ester by esterification of product alcohol in a fermentation medium with an organic acid (e.g., fatty acid) and a catalyst (e.g., lipase) is desirable, as further described in co-pending, commonly owned U.S. Provisional Application Ser. No. 61/368,429, filed on Jul. 28, 2010; U.S. Provisional Application Ser. No. 61/379,546, filed on Sep. 2, 2010; and U.S. Provisional Application Ser. No. 61/440,034, filed on Feb. 7, 2011, all incorporated herein in its entirety by reference thereto. For example, for butanol production, active catalyst 42 in fermentation vessel (introduced via slurry 18) can catalyze the esterification of the butanol with fatty acids 28 (introduced via slurry 18) to form fatty acid butyl esters (FABE) in situ.

Fermentation vessel 30 is configured to ferment slurry 18 to produce a product alcohol such as butanol. In particular, microorganism 32 metabolizes the fermentable sugar in slurry 18 and excretes a product alcohol. Microorganism 32 is selected from the group of bacteria, cyanobacteria, filamentous fungi, and yeasts. In some embodiments, microorganism 32 can be a bacteria such as *E. coli*. In some embodiments, microorganism 32 can be a fermentative recombinant microorganism. The slurry can include sugar, for example, in the form of oligosaccharides, and water, and can comprise less than about 20 g/L of monomeric glucose, more preferably less than about 10 g/L or less than about 5 g/L of monomeric glucose. Suitable methodology to determine the amount of monomeric glucose is well known in the art. Such suitable methods known in the art include HPLC.

In some embodiments, slurry 18 is subjected to a saccharification process in order to break the complex sugars (e.g., oligosaccharides) in slurry 18 into monosaccharides that can be readily metabolized by microorganism 32. Any known saccharification process that is routinely utilized by the industry can be used including, but not limited to, the acid process, the acid-enzyme process, or the enzyme process. In some embodiments, simultaneous saccharification and fermentation (SSF) can occur inside fermentation vessel 30, as shown in FIG. 1. In some embodiments, an enzyme 38, such as glucoamylase, can be introduced to an inlet in fermentation vessel 30 in order to breakdown the starch or oligosaccharides to glucose capable of being metabolized by microorganism 32.

Optionally, ethanol 33 may be supplied to fermentation vessel 30 to be included in the fermentation broth. In some embodiments, when a recombinant microorganism having a butanol biosynthetic pathway is used as microorganism 32 for butanol production, microorganism 32 may require supplementation of a 2-carbon substrate (e.g., ethanol) to survive and grow. Thus, in some embodiments, ethanol 33 may be supplied to fermentation vessel 30.

However, it has been surprisingly found that methods of the present invention, in which free fatty acid (e.g., FFA 28) is present in the fermentation vessel, can allow reduction of the amount of ethanol 33 typically supplied for a given recombinant microorganism without detriment to the vitality of the recombinant microorganism. Further, in some embodiments, the methods of the present invention provide that the alcohol (e.g., butanol) production rate without ethanol supplementation to be comparable with the production rate that can be realized when ethanol 33 is supplemented. As further demonstrated by the comparative examples presented in Examples 1-14 below, the butanol production rate when fatty acid but not ethanol is in the fermentation vessel can be greater than the butanol production rate when neither fatty acid nor ethanol is in the fermentation vessel. Thus, in some embodiments, the amount of ethanol 33 supplementation is reduced compared to conventional processes. For example, a typical amount of ethanol added to a fermentation vessel for microorganisms requiring supplementation of a 2-carbon substrate is about 5 g/L anhydrous ethanol (i.e., 5 g anhydrous ethanol per liter of fermentation medium). In some embodiments, the butanol fermentation is not supplemented with any ethanol 33. In the latter case, the stream of ethanol 33 is entirely omitted from the fermentation vessel. Thus, in some embodiments of the present invention, it is possible to reduce or eliminate the cost associated with supplemental ethanol 33, as well as the inconvenience associated with storing vats of ethanol 33 and supplying it to the fermentation vessel during butanol fermentation.

Moreover, regardless of ethanol supplementation, in some embodiments, the methods of the present invention can provide a higher rate of glucose uptake by microorganism 32 by virtue of the presence of fatty acids during the fermentation. The fatty acids can be introduced into fermentation vessel 30 as carboxylic acid 28, hydrolyzed from supplied oil 26, and/or derived from hydrolysis of constituent biomass oil of slurry 16. Methods for producing a product alcohol from a fermentation process in which fatty acids are produced at a step in the process and are contacted with microorganism cultures in a fermentation vessel for improving microorganism growth rate and glucose consumption are described in co-pending, commonly owned U.S. Provisional Application Ser. No. 61/368,451, filed on Jul. 28, 2010, which is incorporated herein in its entirety by reference thereto.

In fermentation vessel 30, alcohol is produced by microorganism 32. In situ product removal (ISPR) can be utilized to remove the product alcohol from the fermentation broth. In some embodiments, ISPR includes liquid-liquid extraction. Liquid-liquid extraction can be performed according to the processes described in U.S. Patent Application Publication No. 2009/0305370, the disclosure of which is hereby incorporated in its entirety. U.S. Patent Application Publication No. 2009/0305370 describes methods for producing and recovering butanol from a fermentation broth using liquid-liquid extraction, the methods comprising the step of contacting the fermentation broth with a water-immiscible extractant to form a two-phase mixture comprising an aqueous phase and an organic phase. Typically, the extractant can be an organic extractant selected from the group consisting of saturated, mono-unsaturated, poly-unsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, triglycerides, and mixtures thereof, which contacts a fermentation broth and to form a two-phase mixture comprising an aqueous phase and an organic phase. The extractant may also be an organic extractant selected from the group consisting of saturated, mono-unsaturated, poly-unsaturated (and mixtures thereof) $C_4$ to $C_{22}$ fatty alcohols, $C_4$ to $C_{28}$ fatty acids, esters of $C_4$ to $C_{28}$ fatty acids, $C_4$ to $C_{22}$ fatty aldehydes, $C_4$ to $C_{22}$ fatty amides, and mixtures thereof, which contacts a fermentation broth and to form a two-phase mixture comprising an aqueous phase and an organic phase. Free fatty acids 28 from slurry 18 can also serve as an ISPR extractant 28. For example, when free fatty acids 28 are corn oil fatty acids (COFA), ISPR extractant 28 is COFA. ISPR extractant (FFA) 28 contacts the fermentation broth and forms a two-phase mixture comprising an aqueous phase 34 and an organic phase. The product alcohol present in the fermentation broth preferentially partitions into the organic phase to form an alcohol-containing organic phase 36. In some embodiments, fermentation vessel 30 has one or more inlets for receiving one or more additional ISPR extractants 29 which form a two-phase mixture comprising an aqueous phase and an organic phase, with the product alcohol partitioning into the organic phase.

The biphasic mixture can be removed from fermentation vessel 30 as stream 39 and introduced into a vessel 35, in which the alcohol-containing organic phase 36 is separated from the aqueous phase 34. The alcohol-containing organic phase 36 is separated from the aqueous phase 34 of the biphasic mixture stream 39 using methods known in the art including, but not limited to, siphoning, aspiration, decantation, centrifugation, using a gravity settler, membrane-assisted phase splitting, and the like. All or part of the aqueous phase 34 can be recycled into fermentation vessel 30 as fermentation medium (as shown), or otherwise discarded and replaced with fresh medium, or treated for the removal of any remaining product alcohol and then recycled to fermentation vessel 30. Then, the alcohol-containing organic phase 36 is treated in a separator 50 to recover product alcohol 54, and the resulting alcohol-lean extractant 27 can then be recycled back into fermentation vessel 30, usually in combination with fresh FFA 28 from slurry 18 and/or with fresh extractant 29 for further extraction of the product alcohol. Alternatively, fresh FFA 28 (from slurry 18) and/or extractant 29 can be continuously added to the fermentation vessel to replace the ISPR extractant(s) removed in biphasic mixture stream 39.

In some embodiments, any additional ISPR extractant 29 can be an exogenous organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof. In some embodiments, ISPR extractant 29 can be a carboxylic acid and in some embodiments, ISPR extractant 29 can be a fatty acid. In some embodiments, the carboxylic acid or fatty acid can have 4 to 28 carbons, 4 to 22 carbons in other embodiments, 8 to 22 carbons in other embodiments, 10 to 28 carbons in other embodiments, 7 to 22 carbons in other embodiments, 12 to 22 carbons in other embodiments, 4 to 18 carbons in other embodiments, 12 to 22 carbons in other embodiments, and 12 to 18 carbons in still other embodiments. In some embodiments, ISPR extractant 29 is one or more of the following fatty acids: azaleic, capric, caprylic, castor, coconut (i.e., as a naturally-occurring combination of fatty acids, including lauric, myrisitic, palmitic, caprylic, capric, stearic, caproic, arachidic, oleic, and linoleic, for example), dimer, isostearic, lauric, linseed, myristic, oleic, olive, palm oil, palmitic, palm kernel, peanut, pelargonic, ricinoleic, sebacic, soya, stearic acid, tall oil, tallow, #12 hydroxy stearic, or any seed oil. In some embodiments, ISPR extractant 29 is one or more of diacids, azelaic, dimer and sebacic acid. Thus, in some embodiments, ISPR extractant 29 can be a mixture of two or more different fatty acids. In some embodiments, ISPR extractant 29 can be a fatty acid derived from chemical or enzymatic hydrolysis of glycerides derived from native oil. For example, in some embodiments, ISPR extractant 29 can be free fatty acids 28' obtained by enzymatic hydrolysis of native oil such as biomass lipids as later described with reference to the embodiment of FIG. 5. In some embodiments, ISPR extractant 29 can be a fatty acid extractant selected from the group consisting of fatty acids, fatty alcohols, fatty amides, fatty acid methyl esters, lower alcohol esters of fatty acids, fatty acid glycol esters, hydroxylated triglycerides, and mixtures thereof, obtained from chemical conversion of native oil such as biomass lipids as described for example in co-pending, commonly owned U.S. Provisional Application Ser. No. 61/368,436, filed on Jul. 28, 2010. In such embodiments, the biomass lipids for producing extractant 29 can be from a same or different biomass source from which feedstock 12 is obtained. For example, in some embodiments, the biomass lipids for producing extractant 29 can be derived from soya, whereas the biomass source of feedstock 12 is corn. Any possible combination of different biomass sources for extractant 29 versus feedstock 12 can be used, as should be apparent to one of skill in the art. In some embodiments, additional ISPR extractant 29 includes COFA.

In situ extractive fermentation can be carried out in a batch mode or a continuous mode in fermentation vessel 30. For in situ extractive fermentation, the organic extractant can contact the fermentation medium at the start of the fermentation forming a biphasic fermentation medium. Alternatively, the organic extractant can contact the fermentation medium after the microorganism has achieved a desired amount of growth, which can be determined by measuring the optical density of the culture. Further, the organic extractant can contact the fermentation medium at a time at which the product alcohol level in the fermentation medium reaches a preselected level. In the case of butanol production, for example, the ISPR extractant can contact the fermentation medium at a time before the butanol concentration reaches a level which would be toxic to the microorganism. After contacting the fermentation medium with the ISPR extractant, the butanol product partitions into the extractant, decreasing the concentration in the aqueous phase containing the microorganism, thereby limiting the exposure of the production microorganism to the inhibitory butanol product.

The volume of the ISPR extractant to be used depends on a number of factors including the volume of the fermentation medium, the size of the fermentation vessel, the partition coefficient of the extractant for the butanol product, and the fermentation mode chosen, as described below. The volume of the extractant can be about 3% to about 60% of the fermentation vessel working volume. Depending on the efficiency of the extraction, the aqueous phase titer of butanol in the fermentation medium can be, for example, from about 1 g/L to about 85 g/L, from about 10 g/L to about 40 g/L, from about 10 g/L to about 20 g/L, from about 15 g/L to about 50 g/L or from about 20 g/L to about 60 g/L. In some embodiments, the resulting fermentation broth after alcohol esterification can comprise free (i.e., unesterified) alcohol and in some embodiments, the concentration of free alcohol in the fermentation broth after alcohol esterification is not greater than 1, 3, 6, 10, 15, 20, 25, 30 25, 40, 45, 50, 55, or 60 g/L when the product alcohol is butanol, or when the product alcohol is ethanol, the concentration of free alcohol in the fermentation broth after alcohol esterification is not greater than 15, 20, 25, 30 25, 40, 45, 50, 55, 60, 65, 70, 75, 80, 85, 90, 95, or 100 g/L. Without being held to theory, it is believed that higher butanol titer may obtained with the extractive fermentation method, in part, from the removal of the toxic butanol product from the fermentation medium, thereby keeping the level below that which is toxic to the microorganism.

In a batchwise mode of in situ extractive fermentation, a volume of organic extractant is added to the fermentation vessel and the extractant is not removed during the process. This mode requires a larger volume of organic extractant to minimize the concentration of the inhibitory butanol product in the fermentation medium. Consequently, the volume of the fermentation medium is less and the amount of product produced is less than that obtained using the continuous mode. For example, the volume of the extractant in the batchwise mode can be 20% to about 60% of the fermentation vessel working volume in one embodiment, and about 30% to about 60% in another embodiment.

Gas stripping (not shown) can be used concurrently with the ISPR extractant to remove the product alcohol from the fermentation medium.

In the embodiment of FIG. 1, the product alcohol is extracted from the fermentation broth in situ, with the separation of the biphasic mixture 39 occurring in a separate vessel 35. In some embodiments, separation of the biphasic mixture 39 can occur in the fermentation vessel, as shown in the embodiments of later described FIGS. 2 and 3 in which the alcohol-containing organic phase stream 36 exits directly from fermentation vessel 30. Aqueous phase stream 34 can also exit directly from fermentation vessel 30, be treated for the removal of any remaining product alcohol and recycled, or discarded and replaced with fresh fermentation medium. The extraction of the product alcohol by the organic extractant(s) can be done with or without the removal of the microorganism from the fermentation broth. The microorganism can be removed from the fermentation broth by means known in the art including, but not limited to, filtration or centrifugation. For example, aqueous phase stream 34 can include microorganism 32 such as yeast. Microorganism 32 can be easily separated from the aqueous phase stream, for example, in a centrifuge (not shown). Microorganism 32 can then be recycled to fermentation vessel 30 which over time can increase the production rate of alcohol production, thereby resulting in an increase in the efficiency of the alcohol production.

In a continuous mode of in situ extractive fermentation, the volume of the extractant can be about 3% to about 50% of the fermentation vessel working volume in one embodiment, about 3% to about 30% in another embodiment, 3% to about 20% in another embodiment; and 3% to about 10% in another embodiment. Because the product is continually removed from the reactor, a smaller volume of extractant is required enabling a larger volume of the fermentation medium to be used.

As an alternative to in situ extractive fermentation, the product alcohol can be extracted from the fermentation broth downstream of fermentation vessel 30. In such an instance, the fermentation broth can be removed from fermentation vessel 30 and introduced into vessel 35. Extractant 28 can then be introduced into vessel 35 and contacted with the fermentation broth to obtain biphasic mixture 39 in vessel 35, which is then separated into the organic and aqueous phases 36 and 34. Alternatively, extractant 28 can be added to the fermentation broth in a separate vessel (not shown) prior to introduction to vessel 35.

As a non-limiting prophetic example, with reference to the embodiment of FIG. 1, an aqueous suspension of ground whole corn (as feedstock 12), which can nominally contain about 4 wt % corn oil, can be treated with amylase (as liquefaction enzyme 14) at about 85° C. to 120° C. for 30 minutes to 2 hours, and the resulting liquefied mash 16 cooled to between 65° C. and 30° C. and treated with 0.1 ppm to 10 ppm (in some embodiments, 0.5 ppm to 1.0 ppm) of lipase (as catalyst 42) at pH 4.5 to 7.5 (in some embodiments, between pH 5.5 and 6.5) for sufficient time to produce from at least 30% to as high as at least 99% conversion of the available fatty acid content in lipids to free fatty acids. Optionally, the liquefied and lipase-treated mash 18 can be heated to inactivate lipase 42 prior to fermentation. Mash 18 can be cooled to about 30° C. (e.g., using a heat-exchanger) and loaded to fermentation vessel 30 at about 25% to 30 wt % dry corn solids. Saccharification of the liquefied mash 18 during fermentation by the addition of glucoamylase (as saccharification enzyme 38) can result in the production of glucose. The resulting fermentation broth can contain significantly less than the amount of corn oil (e.g., about 1.2 wt % corn oil) that can be present in a fermentation broth using a liquefied mash that has not been treated with lipase 42. In particular, the lipase 42 treatment can result in the conversion of corn oil lipids 26 (triglycerides (TG)) into COFA as FFA 28 (and some diglycerides (DG) or monoglycerides (MG)), decreasing the rate of build-up of lipids 26 in any ISPR extractant 29 (e.g., oleyl alcohol), and dissolution of COFA 28 into organic phase 36 during ISPR should not decrease the partition coefficient of butanol in organic phase 36 as much as would the dissolution of lipids (TG) into the organic phase 36.

In some embodiments, the system and processes of FIG. 1 can be modified such that feedstock slurry 16 (having oil 26) and catalyst 42 are introduced and contacted in fermentation vessel 30 so as to produce slurry 18 (having FFA 28). The fermentation vessel temperature can then be raised to heat inactivate catalyst 42. The fermentation vessel temperature can then be reduced, and the fermentation vessel can be inoculated with microorganism 32, whereby the sugars of slurry 18 can be fermented to produce a product alcohol.

In some embodiments, the system and processes of FIG. 1 can be modified such that simultaneous saccharification and fermentation (SSF) in fermentation vessel 30 is replaced with a separate saccharification vessel 60 (see FIG. 2) prior to fermentation vessel 30, as should be apparent to one of skill in the art. Thus, slurry 18 can be saccharified either before fermentation or during fermentation in an SSF process. It should also be apparent that catalyst 42 for hydrolysis of feedstock oil 26 can be introduced before, after, or contemporaneously with saccharification enzyme 38. Thus, in some embodiments, addition of enzyme 38 and catalyst 42 can be stepwise (e.g., catalyst 42, then enzyme 38, or vice versa), or substantially simultaneous (i.e., at exactly the same time as in the time it takes for a person or a machine to perform the addition in one stroke, or one enzyme/catalyst immediately following the other catalyst/enzyme as in the time it takes for a person or a machine to perform the addition in two strokes).

Figure 2:
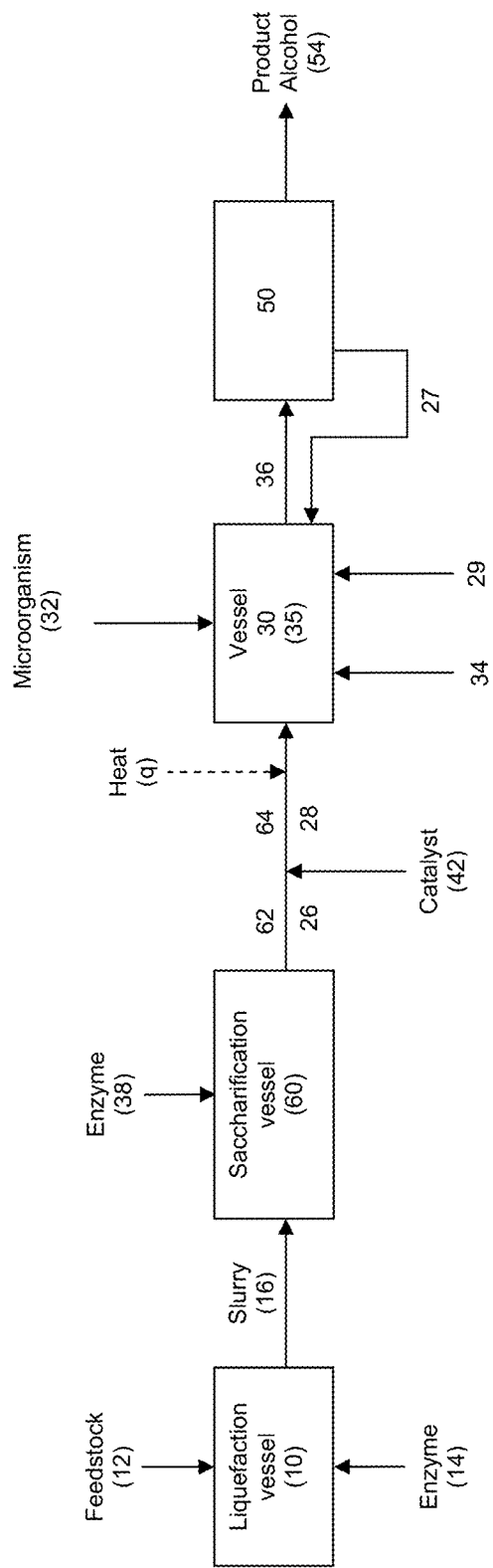

For example, as shown in the embodiment of FIG. 2, the system and processes of FIG. 1 can be modified such that simultaneous saccharification and fermentation (SSF) in fermentation vessel 30 is replaced with a separate saccharification vessel 60 prior to fermentation vessel 30. FIG. 2 is substantially identical to FIG. 1 except for the inclusion of a separate saccharification vessel 60 receiving enzyme 38, with catalyst 42 being introduced to a liquefied, saccharified feedstock stream 62. Feedstock slurry 16 is introduced into saccharification vessel 60 along with enzyme 38 such as glucoamylase, whereby sugars in the form of oligosaccharides in slurry 16 can be broken down into monosaccharides. A liquefied, saccharified feedstock stream 62 exits saccharification vessel 60 to which catalyst 42 is introduced. Feedstock stream 62 includes monosaccharides, oil 26, and undissolved solids derived from the feedstock. Oil 26 is hydrolyzed by the introduction of catalyst 42 resulting in a liquefied, saccharified feedstock slurry 64 having free fatty acids 28 and catalyst 42.

Alternatively, in some embodiments, catalyst 42 can be added with saccharification enzyme 38 to simultaneously produce glucose and hydrolyze oil lipids 26 to free fatty acids 28. The addition of enzyme 38 and catalyst 42 can be stepwise (e.g., catalyst 42, then enzyme 38, or vice versa) or simultaneous. Alternatively, in some embodiments, slurry 62 can be introduced to fermentation vessel with catalyst 42 being added directly to the fermentation vessel 30.

In the embodiment of FIG. 2, heat q is applied to feedstock slurry 64, whereby catalyst 42 becomes inactive, and heat-treated slurry 64 is then introduced to fermentation vessel 30 along with alcohol-producing microorganism 32, which metabolizes the monosaccharides to produce a product alcohol (e.g., butanol). Alternatively, slurry 64 can be fed to fermentation vessel 30 and subjected to heat q while in the fermentation vessel, before inoculation of microorganism 32.

As described above with reference to FIG. 1, free fatty acids 28 can also serve as an ISPR extractant for preferentially partitioning the product alcohol from the aqueous phase. In some embodiments, one or more additional ISPR extractants 29 can also be introduced into fermentation vessel 30. Separation of the biphasic mixture occurs in fermentation vessel 30, whereby alcohol-containing organic phase stream 36 and aqueous phase stream 34 exit directly from fermentation vessel 30. Alternatively, separation of the biphasic mixture can be conducted in a separate vessel 35 as provided in the embodiments of FIG. 1. The remaining process operations of the embodiment of FIG. 2 are identical to FIG. 1 and therefore, will not be described in detail again.

In still other embodiments of the present invention, oil 26 derived from feedstock 12 can be catalytically hydrolyzed into FFA 28 either prior to or during liquefaction. For example, in the embodiment of FIG. 3, feedstock 12 having oil 26 is fed to liquefaction vessel 10, along with catalyst 42 for hydrolysis of at least a portion of the glycerides in oil 26 into FFA 28. Enzyme 14 (e.g., alpha-amylase) for hydrolyzing the starch in feedstock 12 can also be introduced to vessel 10 to produce a liquefied feedstock. The addition of enzyme 14 and catalyst 42 can be stepwise or simultaneous. For example, catalyst 42 can be introduced, and then enzyme 14 can be introduced after at least a portion of oil 26 has been hydrolyzed. Alternatively, enzyme 14 can be introduced, and then catalyst 42 can be introduced. The liquefaction process can involve the application of heat q. In such embodiments, it is preferred that catalyst 42 is introduced prior to or during liquefaction when the process temperature is below that which inactivates catalyst 42, so that oil 26 can be hydrolyzed. Thereafter, application of heat q can provide a two-fold purpose of liquefaction and inactivation of catalyst 42.

In any case, oil 26 in feedstock 12 is converted to FFA 28 in liquefaction vessel 10, such that biphasic feedstock slurry 18 exits liquefaction vessel 10. Biphasic slurry 18 includes both an organic phase of FFA 28 as well as sugar, water, and undissolved solids of an aqueous phase. In some embodiments, the aqueous phase can include glycerol (glycerin) from converting the glycerides in the oil to fatty acids. In some embodiments, such glycerol, if present, can be removed from the stream 18 prior to introduction into fermentation vessel 30.

Figure 3:
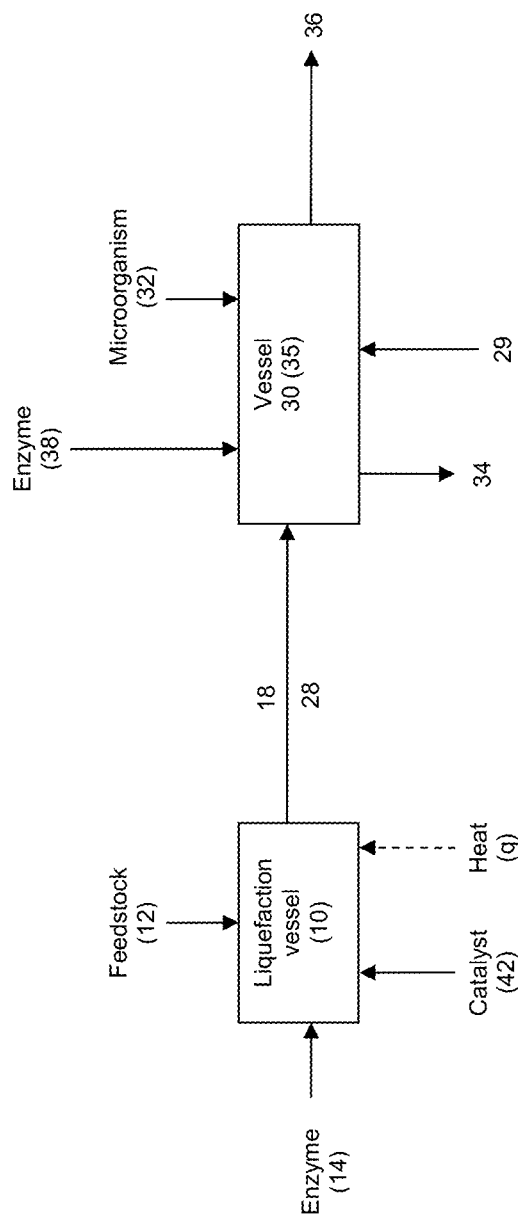

With reference to FIG. 3, biphasic stream 18 is contacted with the fermentation broth in fermentation vessel 30 to form a biphasic mixture. In fermentation vessel 30, product alcohol produced by SSF partitions into the organic phase including FFA 28. Alternatively, in some embodiments, the process can be modified to include a separate saccharification vessel as discussed in connection with FIG. 2. Separation of the biphasic mixture occurs in fermentation vessel 30, whereby alcohol-containing organic phase stream 36 and aqueous phase stream 34 exit directly from fermentation vessel 30. Alternatively, separation of the biphasic mixture can be conducted in a separate vessel 35 as provided in the embodiments of FIG. 1. Optionally, one or more additional extractants 29 can be introduced into fermentation vessel 30 to form an organic phase that preferentially partitions the product alcohol from the aqueous phase. Alcohol-containing organic phase 36 can be introduced to separator 50 for recovery of product alcohol 54 and optional recycle of recovered extractant 27 as shown in FIG. 1. The remaining process operations of the embodiment of FIG. 3 can be identical to the previously described figures and therefore, will not be described in detail again.

Figure 4:
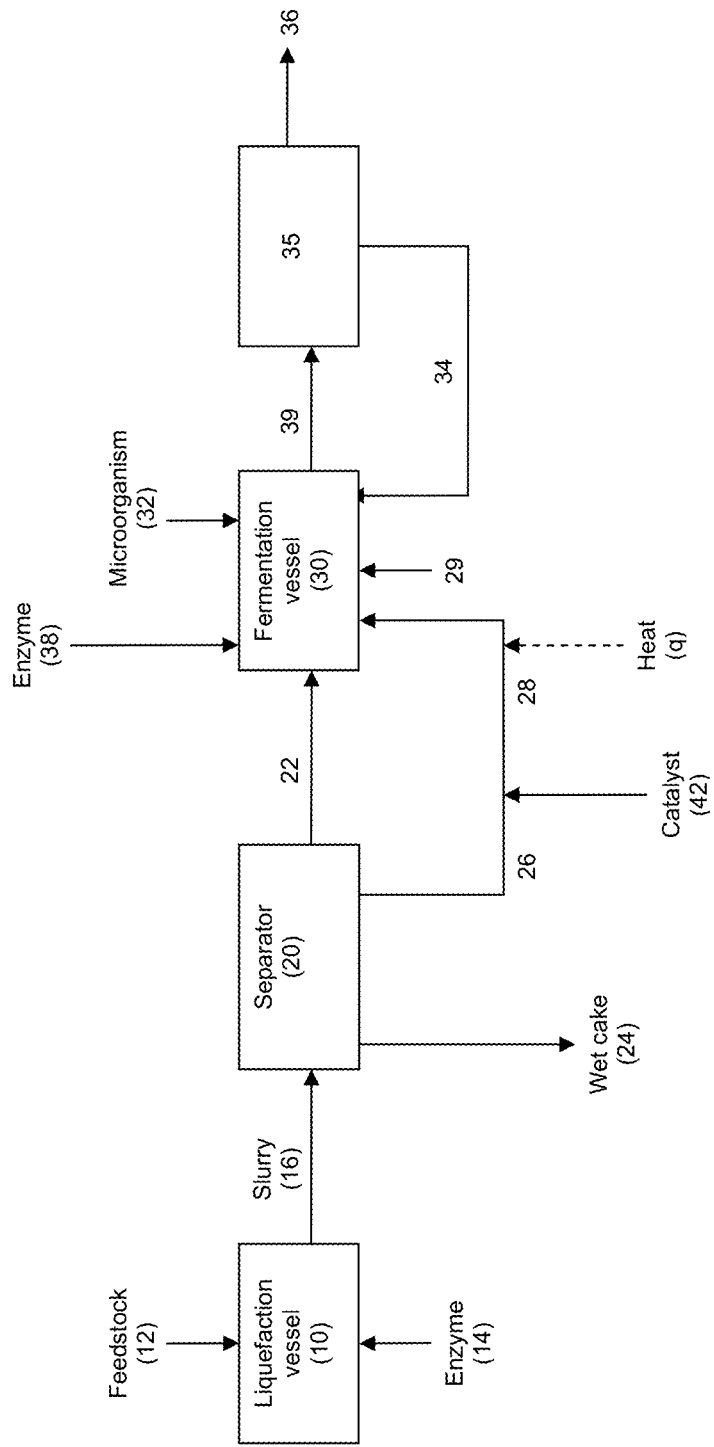

In some embodiments, including any of the earlier described embodiments with respect to FIGS. 1-3, undissolved solids can be removed from the feedstock slurry prior to introduction into fermentation vessel 30. For example, as shown in the embodiment of FIG. 4, feedstock slurry 16 is introduced into an inlet of a separator 20 which is configured to discharge the undissolved solids as a solid phase or wet cake 24. For example, in some embodiments, separator 20 may include a filter press, vacuum filtration, or a centrifuge for separating the undissolved solids from feedstock slurry 16. Optionally, in some embodiments, separator 20 can also be configured to remove some, or substantially all, of oil 26 present in feedstock slurry 16. In such embodiments, separator 20 can be any suitable separator known in the art for removing oil from an aqueous feedstream including, but not limited to, siphoning, decantation, aspiration, centrifugation, using a gravity settler, membrane-assisted phase splitting, and the like. The remaining feedstock including the sugar and water is discharged as an aqueous stream 22 to fermentation vessel 30.

In some embodiments, separator 20 removes oil 26 but not undissolved solids. Thus, aqueous stream 22 fed to fermentation vessel 30 includes undissolved solids. For example, in some embodiments, separator 20 includes a Tricanter® (three-phase centrifuge) centrifuge 20 that agitates or spins feedstock slurry 16 to produces a centrifuge product comprising an aqueous layer containing the sugar and water (i.e., stream 22), a solids layer containing the undissolved solids (i.e., wet cake 24), and an oil layer (i.e., oil stream 26). In such a case, catalyst 42 can be contacted with the removed oil 26 to produce a stream of FFA 28 including catalyst 42, as shown in FIG. 4. Heat q can then be applied to the stream of FFA 28, whereby catalyst 42 becomes inactive. The stream of FFA 28 and inactive catalyst 42 can then be introduced into fermentation vessel 30, along with stream 22 and microorganism 32. Alternatively, FFA 28 and active catalyst 42 can be fed to fermentation vessel 30 from vessel 40, and active catalyst 42 can thereafter be subjected to heat q and inactivated while in the fermentation vessel, before inoculation of microorganism 32.

FFA 28 can serve as ISPR extractant 28 and forms a biphasic mixture in fermentation vessel 30. Product alcohol produced by SSF partitions into organic phase 36 constituted by FFA 28. In some embodiments, one or more additional ISPR extractants 29 can also be introduced into fermentation vessel 30. Thus, oil 26 (e.g., from feedstock) can be catalytically hydrolyzed to FFA 28, thereby decreasing the rate of build-up of lipids in an ISPR extractant while also producing an ISPR extractant. The organic phase 36 can be separated from the aqueous phase 34 of the biphasic mixture 39 at vessel 35. In some embodiments, separation of the biphasic mixture 39 can occur in the fermentation vessel, as shown in the embodiments described in FIGS. 2 and 3 in which the alcohol-containing organic phase stream 36 exits directly from fermentation vessel 30. Organic phase 36 can be introduced to separator 50 for recovery of product alcohol 54 and optional recycle of recovered extractant 27 as shown in FIG. 1. The remaining process operations of the embodiment of FIG. 4 are identical to FIG. 1 and therefore, will not be described in detail again.

When wet cake 24 is removed via centrifuge 20, in some embodiments, a portion of the oil from feedstock 12, such as corn oil when the feedstock is corn, remains in wet cake 24. Wet cake 24 can be washed with additional water in the centrifuge once aqueous solution 22 has been discharged from the centrifuge 20. Washing wet cake 24 will recover the sugar (e.g., oligosaccharides) present in the wet cake and the recovered sugar and water can be recycled to the liquefaction vessel 10. After washing, wet cake 20 can be dried to form Dried Distillers' Grains with Solubles (DDGS) through any suitable known process. The formation of the DDGS from wet cake 24 formed in centrifuge 20 has several benefits. Since the undissolved solids do not go to the fermentation vessel, DDGS does not have trapped extractant and/or product alcohol such as butanol, it is not subjected to the conditions of the fermentation vessel, and it does not contact the microorganisms present in the fermentation vessel. All these benefits make it easier to process and sell DDGS, for example, as animal feed. In some embodiments, oil 26 is not discharged separately from wet cake 24, but rather oil 26 is included as part of wet cake 24 and is ultimately present in the DDGS. In such instances, the oil can be separated from the DDGS and converted to an ISPR extractant 29 for subsequent use in the same or different alcohol fermentation process. Methods and systems for removing undissolved solids from feedstock 16 via centrifugation are described in detail in co-pending, commonly owned U.S. Patent Application No. 61/356,290, filed Jun. 18, 2010, which is incorporated herein in its entirety by reference thereto.

In still other embodiments (not shown), saccharification can occur in a separate saccharification vessel 60 (see FIG. 2) which is located between separator 20 and liquefaction vessel 10, as should be apparent to one of skill in the art.

Figure 5:
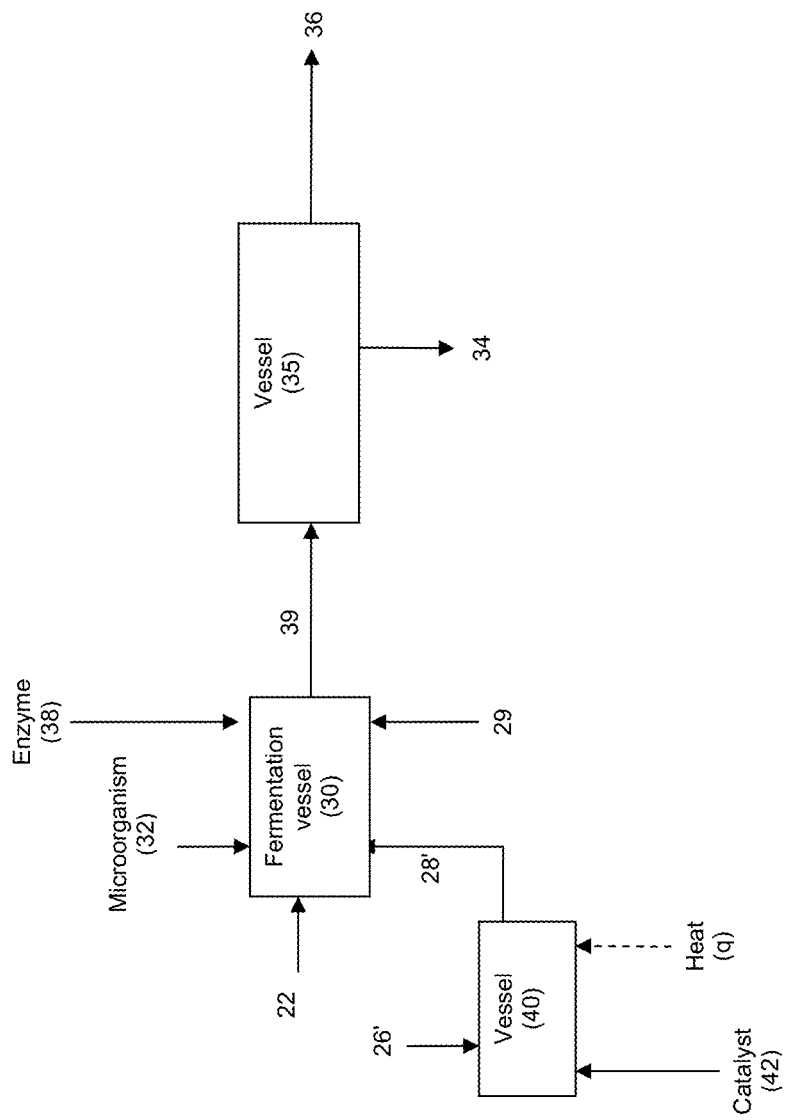

In still other embodiments, as shown, for example, in the embodiment of FIG. 5, a native oil 26' is supplied to a vessel 40 to which catalyst 42 is also supplied, whereby at least a portion of glycerides in oil 26' are hydrolyzed to form FFA 28'. Catalyst 42 can be subsequently inactivated, such as by the application of heat q. A product stream from vessel 40 containing FFA 28' and inactive catalyst 42 are then introduced into fermentation vessel 30, along with aqueous feedstock stream 22 in which feedstock oil 26, and in some embodiments, the undissolved solids have been previously removed by means of separator 20 (see, e.g., the embodiment of FIG. 4). Saccharification enzyme 38 and microorganism 32 are also introduced into fermentation vessel 30, whereby a product alcohol is produced by SSF.

Alternatively, oil 26' and catalyst 42 can be fed directly to fermentation vessel 30 in which oil 26' is hydrolyzed to FFA 28' rather than using vessel 40. Thereafter, active catalyst 42 can be subjected to heat q and inactivated while in the fermentation vessel before inoculation of microorganism 32. Alternatively, FFA 28' and active catalyst 42 can be fed to fermentation vessel 30 from vessel 40, and active catalyst 42 can thereafter be subjected to heat q and inactivated while in the fermentation vessel before inoculation of microorganism 32. In such embodiments, feedstock slurry 16 including oil 26, rather than stream 22 in which oil 26 was removed, can be fed to fermentation vessel 30 and contacted with active catalyst 42. Active catalyst 42 can therefore be used to hydrolyze oil 26 into FFA 28, thereby reducing the loss and/or degradation of the partition coefficient of the extractant over time that is attributable to the presence of the oil in the fermentation vessel.

In some embodiments, the system and processes of FIG. 5 can be modified such that simultaneous saccharification and fermentation in fermentation vessel 30 is replaced with a separate saccharification vessel 60 prior to fermentation vessel 30, as should be apparent to one of skill in the art (see, e.g., the embodiment of FIG. 2).

In some embodiments, native oil 26' can be tallow, corn, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha, vegetable oil blends, and mixtures thereof. In some embodiments, native oil 26' is a mixture of two or more native oils, for example, a mixture of palm and soybean oils. In some embodiments, native oil 26' is a plant-derived oil. In some embodiments, the plant-derived oil can be, though not necessarily, derived from biomass that can be used in a fermentation process. The biomass can be the same or different source from which feedstock 12 (shown in FIG. 5 as stream 22) is obtained. Thus, for example, in some embodiments, oil 26' can be derived from corn, whereas feedstock 12 can be cane. For example, in some embodiments, oil 26' can be derived from corn, and the biomass source of feedstock 12 is also corn. Any possible combination of different biomass sources for oil 26' versus feedstock 12 can be used, as should be apparent to one of skill in the art.

FFA 28' can serve as an ISPR extractant 28' to form a two-phase mixture including an aqueous phase and an organic phase, with the product alcohol produced in the fermentation medium preferentially partitioning into the organic phase constituted by ISPR extractant 28'. In some embodiments, one or more additional ISPR extractants 29 can be introduced into fermentation vessel 30 as described above with reference to FIG. 1. The organic phase 36 can be separated from the aqueous phase 34 of the biphasic mixture 39 at vessel 35. In some embodiments, separation of the biphasic mixture 39 can occur in the fermentation vessel, as shown in the embodiments described in FIGS. 2 and 3 in which the alcohol-containing organic phase stream 36 exits directly from fermentation vessel 30. Organic phase 36 can be introduced in separator 50 for recovery of product alcohol 54 and optional recycle of recovered extractant 27 as shown in FIG. 1. The remaining process operations of the embodiment of FIG. 5 are identical to FIG. 1 and therefore, will not be described in detail again.

Figure 6:
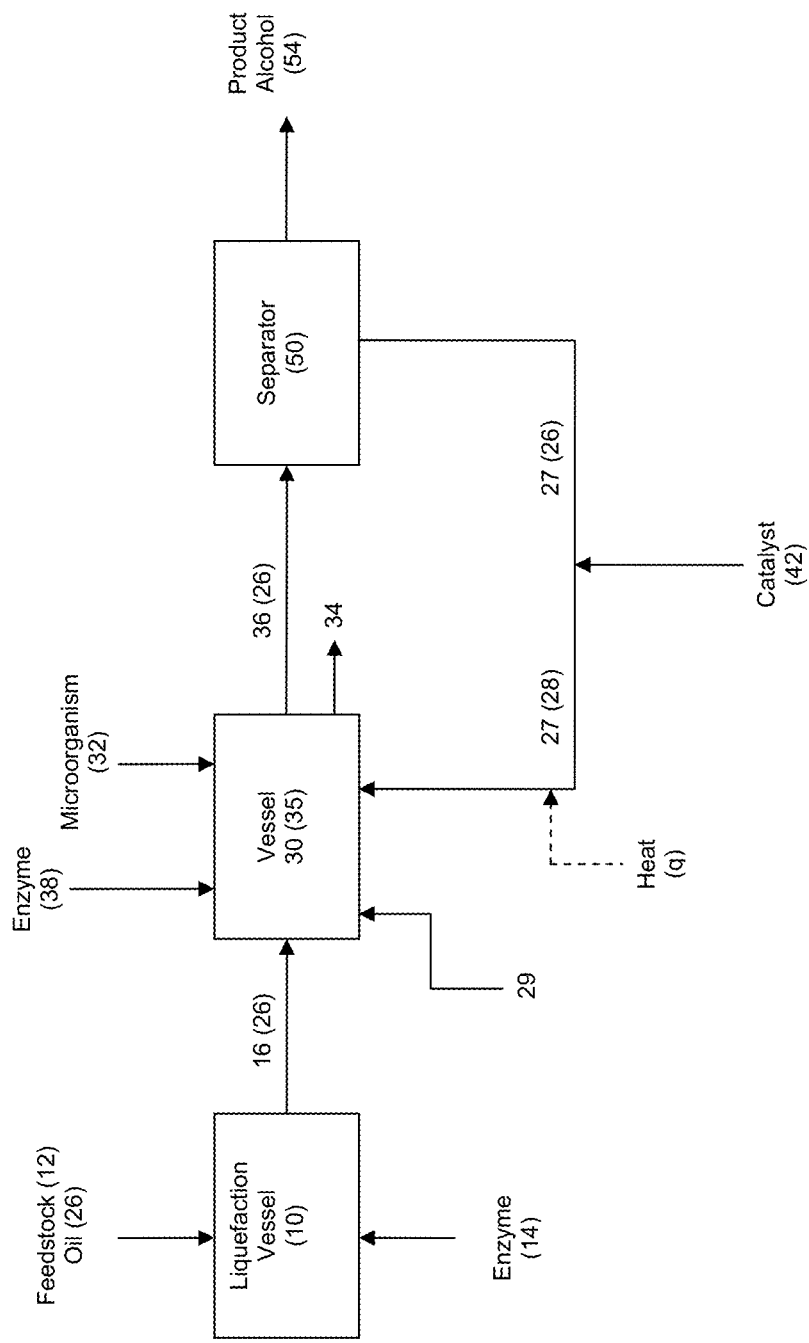

In some embodiments of the present invention, biomass oil present in feedstock 12 can be converted to FFA 28 at a step following alcoholic fermentation. FFA 28 can then be introduced as ISPR extractant 28 in the fermentation vessel. For example, in the embodiment of FIG. 6, feedstock 12 is liquefied to produced feedstock slurry 16 which includes oil 26 derived from the feedstock. Feedstock slurry 16 can also include undissolved solids from the feedstock. Alternatively, the undissolved solids can be separated from slurry 16 via a separator, such as a centrifuge (not shown). Feedstock slurry 16 containing oil 26 is introduced directly to fermentation vessel 30 containing a fermentation broth including saccharification enzyme 38 and microorganism 32. A product alcohol is produced by SSF in fermentation vessel 30. Alternatively, in some embodiments, the process can be modified to include a separate saccharification vessel as discussed in connection with FIG. 2.

ISPR extractant 29 is introduced to fermentation vessel 30 to form a biphasic mixture, and the product alcohol is removed by partitioning into the organic phase of the ISPR extractant 29. Oil 26 also partitions into the organic phase. Separation of the biphasic mixture occurs in fermentation vessel 30, whereby alcohol-containing organic phase stream 36 and aqueous phase stream 34 exit directly from fermentation vessel 30. Alternatively, separation of the biphasic mixture can be conducted in a separate vessel 35 as provided in the embodiments of FIG. 1. Organic phase stream 36 including oil 26 is introduced into separator 50 to recover product alcohol 54 from extractant 29. The resulting alcohol-lean extractant 27 includes recovered extractant 29 and oil 26. Extractant 27 is contacted with catalyst 42, whereby at least a portion of glycerides in oil 26 are hydrolyzed to form FFA 28. Heat q can then be applied to extractant 27 including FFA 28 so as to inactivate catalyst 42 before being recycled back into fermentation vessel 30. Such recycled extractant stream 27 can be a separate stream or a combined stream with fresh, make-up extractant stream 29. The subsequent withdrawal of alcohol-containing organic phase 36 from fermentation vessel 30 can then include FFA 28 and ISPR extractant 29 (as fresh extractant 29 and recycled extractant 27), in addition to the product alcohol and additional oil 26 from newly introduced feedstock slurry 16. Organic phase 36 can then be treated to recover the product alcohol, and recycled back into fermentation vessel 30 after contacting with catalyst 42 for hydrolysis of additional oil 26, in the same manner as just described. In some embodiments, use of make-up ISPR extractant 29 can be phased out as the fermentation process is operated over time because the process itself can produce FFA 28 as a make-up ISPR extractant for extracting the product alcohol. Thus, the ISPR extractant can be the stream of recycled extractant 27 with FFA 28.

Thus, FIGS. 1-5 provide various non-limiting embodiments of methods and systems involving fermentation processes and FFAs 28 produced from catalytic hydrolysis of biomass derived oil 26, and FFAs 28' produced from catalytic hydrolysis of native oil 26' such as plant-derived oil that can be used as ISPR extractants 28 and 28' to remove product alcohol in extractive fermentation.

In some embodiments, including any of the aforementioned embodiments described with reference to FIGS. 1-6, the fermentation broth in fermentation vessel 30 includes at least one recombinant microorganism 32 which is genetically modified (that is, genetically engineered) to produce butanol via a biosynthetic pathway from at least one fermentable carbon source. In particular, recombinant microorganisms can be grown in a fermentation broth which contains suitable carbon substrates. Additional carbon substrates may include, but are not limited to, monosaccharides such as fructose; oligosaccharides such as lactose, maltose, or sucrose; polysaccharides such as starch or cellulose; or mixtures thereof, and unpurified mixtures from renewable feedstocks such as cheese whey permeate, cornsteep liquor, sugar beet molasses, and barley malt. Other carbon substrates may include ethanol, lactate, succinate, or glycerol.

Additionally the carbon substrate may also be one-carbon substrates such as carbon dioxide or methanol for which metabolic conversion into key biochemical intermediates has been demonstrated. In addition to one and two carbon substrates, methylotrophic organisms are also known to utilize a number of other carbon containing compounds such as methylamine, glucosamine, and a variety of amino acids for metabolic activity. For example, methylotrophic yeasts are known to utilize the carbon from methylamine to form trehalose or glycerol (Bellion, et al., *Microb. Growth C1 Compd.*, [Int. Symp.], 7th (1993), 415-32, Editor(s): Murrell, J. Collin; Kelly, Don P. Publisher: Intercept, Andover, UK). Similarly, various species of *Candida* will metabolize alanine or oleic acid (Sulter, et al., Arch. Microbiol. 153:485-489, 1990). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable, in some embodiments, the carbon substrates are glucose, fructose, and sucrose, or mixtures of these with C5 sugars such as xylose and/or arabinose for yeasts cells modified to use C5 sugars. Sucrose may be derived from renewable sugar sources such as sugar cane, sugar beets, cassava, sweet sorghum, and mixtures thereof. Glucose and dextrose may be derived from renewable grain sources through saccharification of starch based feedstocks including grains such as corn, wheat, rye, barley, oats, and mixtures thereof. In addition, fermentable sugars may be derived from renewable cellulosic or lignocellulosic biomass through processes of pretreatment and saccharification, as described in, for example, in U.S. Patent Application Publication No. 2007/0031918 A1, which is herein incorporated by reference. In addition to an appropriate carbon source (from aqueous stream 22), fermentation broth must contain suitable minerals, salts, cofactors, buffers and other components, known to those skilled in the art, suitable for the growth of the cultures and promotion of an enzymatic pathway comprising a dihydroxyacid dehydratase (DHAD).

Recombinant microorganisms that produce butanol via a biosynthetic pathway can include a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Candida, Hansenula,* or *Saccharomyces*. In one embodiment, recombinant microorganisms can be selected from the group consisting of *Escherichia coli, Lactobacillus plantarum*, and *Saccharomyces cerevisiae*. In one embodiment, the recombinant microorganism is a crabtree-positive yeast selected from *Saccharomyces, Zygosaccharomyces, Schizosaccharomyces, Dekkera, Torulopsis, Brettanomyces,* and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Zygosaccharomyces rouxii,* and *Candida glabrata*. For example, the production of butanol utilizing fermentation with a microorganism, as well as which microorganisms produce butanol, is known and is disclosed, for example, in U.S. Patent Application Publication No. 2009/0305370, herein incorporated by reference. In some embodiments, microorganisms comprise a butanol biosynthetic pathway. Suitable isobutanol biosynthetic pathways are known in the art (see, e.g., U.S. Patent Application Publication No. 2007/0092957, herein incorporated by reference). In some embodiments, at least one, at least two, at least three, or at least four polypeptides catalyzing substrate to product conversions of a pathway are encoded by heterologous polynucleotides in the microorganism. In some embodiments, all polypeptides catalyzing substrate to product conversions of a pathway are encoded by heterologous polynucleotides in the microorganism. In some embodiments, the microorganism comprises a reduction or elimination of pyruvate decarboxylase activity. Microorganisms substantially free of pyruvate decarboxylase activity are described in U.S. Patent Application Publication No. 2009/0305363, herein incorporated by reference.

Construction of certain strains, including those used in the Examples, is provided herein.
Construction of *Saccharomyces cerevisiae* Strain BP1083 ("NGCI-070")

The strain BP1064 was derived from CEN.PK 113-7D (CBS 8340; Centraalbureau voor Schimmelcultures (CBS) Fungal Biodiversity Centre, Netherlands) and contains deletions of the following genes: URA3, HIS3, PDC1, PDC5, PDC6, and GPD2. BP1064 was transformed with plasmids pYZ090 (SEQ ID NO: 1, described in U.S. Provisional Application Ser. No. 61/246,844) and pLH468 (SEQ ID NO: 2) to create strain NGCI-070 (BP1083, PNY1504).

Deletions, which completely removed the entire coding sequence, were created by homologous recombination with PCR fragments containing regions of homology upstream and downstream of the target gene and either a G418 resistance marker or URA3 gene for selection of transformants. The G418 resistance marker, flanked by loxP sites, was removed using Cre recombinase. The URA3 gene was removed by homologous recombination to create a scarless deletion or if flanked by loxP sites, was removed using Cre recombinase.

The scarless deletion procedure was adapted from Akada, et al., (Yeast 23:399-405, 2006). In general, the PCR cassette for each scarless deletion was made by combining four fragments, A-B-U-C, by overlapping PCR. The PCR cassette contained a selectable/counter-selectable marker, URA3 (Fragment U), consisting of the native CEN.PK 113-7D URA3 gene, along with the promoter (250 bp upstream of the URA3 gene) and terminator (150 bp downstream of the URA3 gene). Fragments A and C, each 500 bp long, corresponded to the 500 bp immediately upstream of the target gene (Fragment A) and the 3' 500 bp of the target gene (Fragment C). Fragments A and C were used for integration of the cassette into the chromosome by homologous recombination. Fragment B (500 bp long) corresponded to the 500 bp immediately downstream of the target gene and was used for excision of the URA3 marker and Fragment C from the chromosome by homologous recombination, as a direct repeat of the sequence corresponding to Fragment B was created upon integration of the cassette into the chromosome. Using the PCR product ABUC cassette, the URA3 marker was first integrated into and then excised from the chromosome by homologous recombination. The initial integration deleted the gene, excluding the 3' 500 bp. Upon excision, the 3' 500 bp region of the gene was also deleted. For integration of genes using this method, the gene to be integrated was included in the PCR cassette between fragments A and B.
URA3 Deletion To delete the endogenous URA3 coding region, a ura3::loxP-kanMX-loxP cassette was PCR-amplified from pLA54 template DNA (SEQ ID NO: 3). pLA54 contains the *K. lactis* TEF1 promoter and kanMX marker, and is flanked by loxP sites to allow recombination with Cre recombinase and removal of the marker. PCR was done using Phusion® DNA polymerase (New England BioLabs Inc., Ipswich, Mass.) and primers BK505 and BK506 (SEQ ID NOs: 4 and 5). The URA3 portion of each primer was derived from the 5' region upstream of the URA3 promoter and 3' region downstream of the coding region such that integration of the loxP-kanMX-loxP marker resulted in replacement of the URA3 coding region. The PCR product was transformed into CEN.PK 113-7D using standard genetic techniques (Methods in Yeast Genetics, 2005, Cold Spring Harbor Laboratory Press, Cold Spring Harbor, N.Y., pp. 201-202) and transformants were selected on YPD containing G418 (100 µg/mL) at 30° C. Transformants were screened to verify correct integration by PCR using primers LA468 and LA492 (SEQ ID NOs: 6 and 7) and designated CEN.PK 113-7D Δura3::kanMX.

HIS3 Deletion

The four fragments for the PCR cassette for the scarless HIS3 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). HIS3 Fragment A was amplified with primer oBP452 (SEQ ID NO: 14) and primer oBP453 (SEQ ID NO: 15) containing a 5' tail with homology to the 5' end of HIS3 Fragment B. HIS3 Fragment B was amplified with primer oBP454 (SEQ ID NO: 16) containing a 5' tail with homology to the 3' end of HIS3 Fragment A, and primer oBP455 (SEQ ID NO: 17) containing a 5' tail with homology to the 5' end of HIS3 Fragment U. HIS3 Fragment U was amplified with primer oBP456 (SEQ ID NO: 18) containing a 5' tail with homology to the 3' end of HIS3 Fragment B, and primer oBP457 (SEQ ID NO: 19) containing a 5' tail with homology to the 5' end of HIS3 Fragment C. HIS3 Fragment C was amplified with primer oBP458 (SEQ ID NO: 20) containing a 5' tail with homology to the 3' end of HIS3 Fragment U, and primer oBP459 (SEQ ID NO: 21). PCR products were purified with a PCR Purification kit (Qiagen, Valencia, Calif.). HIS3 Fragment AB was created by overlapping PCR by mixing HIS3 Fragment A and HIS3 Fragment B and amplifying with primers oBP452 (SEQ ID NO: 14) and oBP455 (SEQ ID NO: 17). HIS3 Fragment UC was created by overlapping PCR by mixing HIS3 Fragment U and HIS3 Fragment C and amplifying with primers oBP456 (SEQ ID NO: 18) and oBP459 (SEQ ID NO: 21). The resulting PCR products were purified on an agarose gel followed by a Gel Extraction kit (Qiagen, Valencia, Calif.). The HIS3 ABUC cassette was created by overlapping PCR by mixing HIS3 Fragment AB and HIS3 Fragment UC and amplifying with primers oBP452 (SEQ ID NO: 14) and oBP459 (SEQ ID NO: 21). The PCR product was purified with a PCR Purification kit (Qiagen, Valencia, Calif.).

Competent cells of CEN.PK 113-7D Δura3::kanMX were made and transformed with the HIS3 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a his3 knockout were screened for by PCR with primers oBP460 (SEQ ID NO: 22) and oBP461 (SEQ ID NO: 23) using genomic DNA prepared with a Gentra® Puregene® Yeast/Bact. kit (Qiagen, Valencia, Calif.). A correct transformant was selected as strain CEN.PK 113-7D Δura3::kanMX Δhis3::URA3.

KanMX Marker Removal from the Δura3 Site and URA3 Marker Removal from the Δhis3 Site The KanMX marker was removed by transforming CEN.PK 113-7D Δura3::kanMX Δhis3::URA3 with pRS423::PGAL1-cre (SEQ ID NO: 66, described in U.S. Provisional Application No. 61/290,639) using a Frozen-EZ Yeast Transformation II™ kit (Zymo Research Corporation, Irvine, Calif.) and plating on synthetic complete medium lacking histidine and uracil supplemented with 2% glucose at 30° C. Transformants were grown in YP supplemented with 1% galactose at 30° C. for ~6 hours to induce the Cre recombinase and KanMX marker excision and plated onto YPD (2% glucose) plates at 30° C. for recovery. An isolate was grown overnight in YPD and plated on synthetic complete medium containing 5-fluoro-orotic acid (5-FOA, 0.1%) at 30° C. to select for isolates that lost the URA3 marker. 5-FOA resistant isolates were grown in and plated on YPD for removal of the pRS423::PGAL1-cre plasmid. Isolates were checked for loss of the KanMX marker, URA3 marker, and pRS423::PGAL1-cre plasmid by assaying growth on YPD+ G418 plates, synthetic complete medium lacking uracil plates, and synthetic complete medium lacking histidine plates. A correct isolate that was sensitive to G418 and auxotrophic for uracil and histidine was selected as strain CEN.PK 113-7D Δura3::loxP Δhis3 and designated as BP857. The deletions and marker removal were confirmed by PCR and sequencing with primers oBP450 (SEQ ID NO: 24) and oBP451 (SEQ ID NO: 25) for Δura3 and primers oBP460 (SEQ ID NO: 22) and oBP461 (SEQ ID NO: 23) for Δhis3 using genomic DNA prepared with a Gentra® Puregene® Yeast/Bact. kit (Qiagen, Valencia, Calif.).

PDC6 Deletion

The four fragments for the PCR cassette for the scarless PDC6 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC6 Fragment A was amplified with primer oBP440 (SEQ ID NO: 26) and primer oBP441 (SEQ ID NO: 27) containing a 5' tail with homology to the 5' end of PDC6 Fragment B. PDC6 Fragment B was amplified with primer oBP442 (SEQ ID NO: 28), containing a 5' tail with homology to the 3' end of PDC6 Fragment A, and primer oBP443 (SEQ ID NO: 29) containing a 5' tail with homology to the 5' end of PDC6 Fragment U. PDC6 Fragment U was amplified with primer oBP444 (SEQ ID NO: 30) containing a 5' tail with homology to the 3' end of PDC6 Fragment B, and primer oBP445 (SEQ ID NO: 31) containing a 5' tail with homology to the 5' end of PDC6 Fragment C. PDC6 Fragment C was amplified with primer oBP446 (SEQ ID NO: 32) containing a 5' tail with homology to the 3' end of PDC6 Fragment U, and primer oBP447 (SEQ ID NO: 33). PCR products were purified with a PCR Purification kit (Qiagen, Valencia, Calif.). PDC6 Fragment AB was created by overlapping PCR by mixing PDC6 Fragment A and PDC6 Fragment B and amplifying with primers oBP440 (SEQ ID NO: 26) and oBP443 (SEQ ID NO: 29). PDC6 Fragment UC was created by overlapping PCR by mixing PDC6 Fragment U and PDC6 Fragment C and amplifying with primers oBP444 (SEQ ID NO: 30) and oBP447 (SEQ ID NO: 33). The resulting PCR products were purified on an agarose gel followed by a Gel Extraction kit (Qiagen, Valencia, Calif.). The PDC6 ABUC cassette was created by overlapping PCR by mixing PDC6 Fragment AB and PDC6 Fragment UC and amplifying with primers oBP440 (SEQ ID NO: 26) and oBP447 (SEQ ID NO: 33). The PCR product was purified with a PCR Purification kit (Qiagen, Valencia, Calif.).

Competent cells of CEN.PK 113-7D Δura3::loxP Δhis3 were made and transformed with the PDC6 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc6 knockout were screened for by PCR with primers oBP448 (SEQ ID NO: 34) and oBP449 (SEQ ID NO: 35) using genomic DNA prepared with a Gentra® Puregene® Yeast/Bact. kit (Qiagen, Valencia, Calif.). A correct transformant was selected as strain CEN.PK 113-7D Δura3::loxP Δhis3 Δpdc6::URA3.

CEN.PK 113-7D Δura3::loxP Δhis3 Δpdc6::URA3 was grown overnight in YPD and plated on synthetic complete medium containing 5-fluoro-orotic acid (0.1%) at 30° C. to select for isolates that lost the URA3 marker. The deletion and marker removal were confirmed by PCR and sequencing with primers oBP448 (SEQ ID NO: 34) and oBP449 (SEQ ID NO: 35) using genomic DNA prepared with a Gentra® Puregene®

Yeast/Bact. kit (Qiagen, Valencia, Calif.). The absence of the PDC6 gene from the isolate was demonstrated by a negative PCR result using primers specific for the coding sequence of PDC6, oBP554 (SEQ ID NO: 36) and oBP555 (SEQ ID NO: 37). The correct isolate was selected as strain CEN.PK 113-7D Δura3::loxP Δhis3 Δpdc6 and designated as BP891.

PDC1 Deletion ilvDSm Integration

The PDC1 gene was deleted and replaced with the ilvD coding region from *Streptococcus mutans* ATCC No. 700610. The A fragment followed by the ilvD coding region from *Streptococcus mutans* for the PCR cassette for the PDC1 deletion-ilvDSm integration was amplified using Phusion® High Fidelity PCR Master Mix (New England BioLabs Inc., Ipswich, Mass.) and NYLA83 (described herein and in U.S. Provisional Application No. 61/246,709) genomic DNA as template, prepared with a Gentra® Puregene® Yeast/Bact. kit (Qiagen, Valencia, Calif.). PDC1 Fragment A-ilvDSm (SEQ ID NO: 141) was amplified with primer oBP513 (SEQ ID NO: 38) and primer oBP515 (SEQ ID NO: 39) containing a 5' tail with homology to the 5' end of PDC1 Fragment B. The B, U, and C fragments for the PCR cassette for the PDC1 deletion-ilvDSm integration were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC1 Fragment B was amplified with primer oBP516 (SEQ ID NO: 40) containing a 5' tail with homology to the 3' end of PDC1 Fragment A-ilvDSm, and primer oBP517 (SEQ ID NO: 41) containing a 5' tail with homology to the 5' end of PDC1 Fragment U. PDC1 Fragment U was amplified with primer oBP518 (SEQ ID NO: 42) containing a 5' tail with homology to the 3' end of PDC1 Fragment B, and primer oBP519 (SEQ ID NO: 43) containing a 5' tail with homology to the 5' end of PDC1 Fragment C. PDC1 Fragment C was amplified with primer oBP520 (SEQ ID NO: 44), containing a 5' tail with homology to the 3' end of PDC1 Fragment U, and primer oBP521 (SEQ ID NO: 45). PCR products were purified with a PCR Purification kit (Qiagen, Valencia, Calif. PDC1 Fragment A-ilvDSm-B was created by overlapping PCR by mixing PDC1 Fragment A-ilvDSm and PDC1 Fragment B and amplifying with primers oBP513 (SEQ ID NO: 38) and oBP517 (SEQ ID NO: 41). PDC1 Fragment UC was created by overlapping PCR by mixing PDC1 Fragment U and PDC1 Fragment C and amplifying with primers oBP518 (SEQ ID NO: 42) and oBP521 (SEQ ID NO: 45). The resulting PCR products were purified on an agarose gel followed by a Gel Extraction kit (Qiagen, Valencia, Calif.). The PDC1 A-ilvDSm-BUC cassette (SEQ ID NO: 142) was created by overlapping PCR by mixing PDC1 Fragment A-ilvDSm-B and PDC1 Fragment UC and amplifying with primers oBP513 (SEQ ID NO: 38) and oBP521 (SEQ ID NO: 45). The PCR product was purified with a PCR Purification kit (Qiagen, Valencia, Calif.).

Competent cells of CEN.PK 113-7D Δura3::loxP Δhis3 Δpdc6 were made and transformed with the PDC1 A-ilvDSm-BUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc1 knockout ilvDSm integration were screened for by PCR with primers oBP511 (SEQ ID NO: 46) and oBP512 (SEQ ID NO: 47) using genomic DNA prepared with a Gentra® Puregene® Yeast/Bact. kit (Qiagen, Valencia, Calif.). The absence of the PDC1 gene from the isolate was demonstrated by a negative PCR result using primers specific for the coding sequence of PDC1, oBP550 (SEQ ID NO: 48) and oBP551 (SEQ ID NO: 49). A correct transformant was selected as strain CEN.PK 113-7D Δura3::loxP Δhis3 Δpdc6 Δpdc1::ilvDSm-URA3.

CEN.PK 113-7D Δura3::loxP Δhis3 Δpdc6 Δpdc1::ilvDSm-URA3 was grown overnight in YPD and plated on synthetic complete medium containing 5-fluoro-orotic acid (0.1%) at 30° C. to select for isolates that lost the URA3 marker. The deletion of PDC1, integration of ilvDSm, and marker removal were confirmed by PCR and sequencing with primers oBP511 (SEQ ID NO: 46) and oBP512 (SEQ ID NO: 47) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm and designated as BP907.

PDC5 Deletion sadB Integration

The PDC5 gene was deleted and replaced with the sadB coding region from *Achromobacter xylosoxidans*. A segment of the PCR cassette for the PDC5 deletion-sadB integration was first cloned into plasmid pUC19-URA3MCS.

pUC19-URA3MCS is pUC19 based and contains the sequence of the URA3 gene from Saccaromyces *cerevisiae* situated within a multiple cloning site (MCS). pUC19 contains the pMB1 replicon and a gene coding for beta-lactamase for replication and selection in *Escherichia coli*. In addition to the coding sequence for URA3, the sequences from upstream and downstream of this gene were included for expression of the URA3 gene in yeast. The vector can be used for cloning purposes and can be used as a yeast integration vector.

The DNA encompassing the URA3 coding region along with 250 bp upstream and 150 bp downstream of the URA3 coding region from Saccaromyces *cerevisiae* CEN.PK 113-7D genomic DNA was amplified with primers oBP438 (SEQ ID NO: 12) containing BamHI, AscI, PmeI, and FseI restriction sites, and oBP439 (SEQ ID NO: 13) containing XbaI, PacI, and NotI restriction sites, using Phusion® High Fidelity PCR Master Mix (New England BioLabs Inc., Ipswich, Mass.). Genomic DNA was prepared using a Gentra® Puregene® Yeast/Bact. kit (Qiagen, Valencia, Calif.). The PCR product and pUC19 (SEQ ID NO: 143) were ligated with T4 DNA ligase after digestion with BamHI and XbaI to create vector pUC19-URA3MCS. The vector was confirmed by PCR and sequencing with primers oBP264 (SEQ ID NO: 10) and oBP265 (SEQ ID NO: 11).

The coding sequence of sadB and PDC5 Fragment B were cloned into pUC19-URA3MCS to create the sadB-BU portion of the PDC5 A-sadB-BUC PCR cassette. The coding sequence of sadB was amplified using pLH468-sadB (SEQ ID NO: 67) as template with primer oBP530 (SEQ ID NO: 50) containing an AscI restriction site, and primer oBP531 (SEQ ID NO: 51) containing a 5' tail with homology to the 5' end of PDC5 Fragment B. PDC5 Fragment B was amplified with primer oBP532 (SEQ ID NO: 52) containing a 5' tail with homology to the 3' end of sadB, and primer oBP533 (SEQ ID NO: 53) containing a PmeI restriction site. PCR products were purified with a PCR Purification kit (Qiagen, Valencia, Calif.). sadB-PDC5 Fragment B was created by overlapping PCR by mixing the sadB and PDC5 Fragment B PCR products and amplifying with primers oBP530 (SEQ ID NO: 50) and oBP533 (SEQ ID NO: 53). The resulting PCR product was digested with AscI and PmeI and ligated with T4 DNA ligase into the corresponding sites of pUC19-URA3MCS after digestion with the appropriate enzymes. The resulting plasmid was used as a template for amplification of sadB-Fragment B-Fragment U using primers oBP536 (SEQ ID NO: 54) and oBP546 (SEQ ID NO: 55) containing a 5' tail with homology to the 5' end of PDC5 Fragment C. PDC5 Fragment C was amplified with primer oBP547 (SEQ ID NO: 56) containing a 5' tail with homology to the 3' end of PDC5 sadB-Fragment B-Fragment U, and primer oBP539 (SEQ ID NO: 57). PCR products were purified with a PCR Purification kit (Qiagen, Valencia, Calif.). PDC5 sadB-Fragment B-Fragment U-Fragment C was created by overlapping PCR by mixing PDC5 sadB-Fragment B-Fragment U and PDC5 Fragment C and amplifying with primers oBP536 (SEQ ID NO: 54) and oBP539 (SEQ ID NO: 57). The resulting PCR product was purified on an agarose gel followed by a Gel Extraction kit (Qiagen, Valencia, Calif.). The PDC5 A-sadB-BUC cassette (SEQ ID NO: 144) was created by amplifying PDC5 sadB-Fragment B-Fragment U-Fragment C with primers oBP542 (SEQ ID NO: 58) containing a 5' tail with homology to the 50 nucleotides immediately upstream of the native PDC5 coding sequence, and oBP539 (SEQ ID NO: 57). The PCR product was purified with a PCR Purification kit (Qiagen, Valencia, Calif.).

Competent cells of CEN.PK 113-7D Δura3::loxP Δhis3 Δpdc6 Δpdc1::ilvDSm were made and transformed with the PDC5 A-sadB-BUC PCR cassette using a Frozen-EZ Yeast Transformation II™ kit (Zymo Research Corporation, Irvine, Calif.). Transformation mixtures were plated on synthetic complete media lacking uracil supplemented with 1% ethanol (no glucose) at 30° C. Transformants with a pdc5 knockout sadB integration were screened for by PCR with primers oBP540 (SEQ ID NO: 59) and oBP541 (SEQ ID NO: 60) using genomic DNA prepared with a Gentra® Puregene® Yeast/Bact. kit (Qiagen, Valencia, Calif.). The absence of the PDC5 gene from the isolate was demonstrated by a negative PCR result using primers specific for the coding sequence of PDC5, oBP552 (SEQ ID NO: 61) and oBP553 (SEQ ID NO: 62). A correct transformant was selected as strain CEN.PK 113-7D Δura3::loxP Δhis3 Δpdc6 Δpdc1::ilvDSm Δpdc5::sadB-URA3.

CEN.PK 113-7D Δura3::loxP Δhis3 Δpdc6 Δpdc1::ilvDSm Δpdc5::sadB-URA3 was grown overnight in YPE (1% ethanol) and plated on synthetic complete medium supplemented with ethanol (no glucose) and containing 5-fluoro-orotic acid (0.1%) at 30° C. to select for isolates that lost the URA3 marker. The deletion of PDC5, integration of sadB, and marker removal were confirmed by PCR with primers oBP540 (SEQ ID NO: 59) and oBP541 (SEQ ID NO: 60) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm Δpdc5::sadB and designated as BP913.

GPD2 Deletion

To delete the endogenous GPD2 coding region, a gpd2::loxP-URA3-loxP cassette (SEQ ID NO: 145) was PCR-amplified using loxP-URA3-loxP (SEQ ID NO: 68) as template DNA. loxP-URA3-loxP contains the URA3 marker from (ATCC No. 77107) flanked by loxP recombinase sites. PCR was done using Phusion® DNA polymerase (New England BioLabs Inc., Ipswich, Mass.) and primers LA512 and LA513 (SEQ ID NOs: 8 and 9). The GPD2 portion of each primer was derived from the 5' region upstream of the GPD2 coding region and 3' region downstream of the coding region such that integration of the loxP-URA3-loxP marker resulted in replacement of the GPD2 coding region. The PCR product was transformed into BP913 and transformants were selected on synthetic complete media lacking uracil supplemented with 1% ethanol (no glucose). Transformants were screened to verify correct integration by PCR using primers oBP582 and AA270 (SEQ ID NOs: 63 and 64).

The URA3 marker was recycled by transformation with pRS423::PGAL1-cre (SEQ ID NO: 66) and plating on synthetic complete media lacking histidine supplemented with 1% ethanol at 30° C. Transformants were streaked on synthetic complete medium supplemented with 1% ethanol and containing 5-fluoro-orotic acid (0.1%) and incubated at 30° C. to select for isolates that lost the URA3 marker. 5-FOA resistant isolates were grown in YPE (1% ethanol) for removal of the pRS423::PGAL1-cre plasmid. The deletion and marker removal were confirmed by PCR with primers oBP582 (SEQ ID NO: 63) and oBP591 (SEQ ID NO: 65). The correct isolate was selected as strain CEN.PK 113-7D Δura3::loxP Δhis3 Δpdc6 Δpdc1::ilvDSm Δpdc5::sadB Δgpd2::loxP and designated as PNY1503 (BP1064).

BP1064 was transformed with plasmids pYZ090 (SEQ ID NO: 1) and pLH468 (SEQ ID NO: 2) to create strain NGCI-070 (BP1083; PNY1504).

Construction of Strains NYLA74, NYLA83, and NYLA84

Insertion-inactivation of endogenous PDC1 and PDC6 genes of S. cerevisiae. PDC1, PDC5, and PDC6 genes encode the three major isozymes of pyruvate decarboxylase is described as follows:

Construction of pRS425::GPM-sadB

A DNA fragment encoding a butanol dehydrogenase (SEQ ID NO: 70) from *Achromobacter xylosoxidans* (disclosed in U.S. Patent Application Publication No. 2009/0269823) was cloned. The coding region of this gene called sadB for secondary alcohol dehydrogenase (SEQ ID NO: 69) was amplified using standard conditions from *A. xylosoxidans* genomic DNA, prepared using a Gentra® Puregene® kit (Qiagen, Valencia, Calif.) following the recommended protocol for gram negative organisms using forward and reverse primers N473 and N469 (SEQ ID NOs: 74 and 75), respectively. The PCR product was TOPO®-Blunt cloned into pCR®4 BLUNT (Invitrogen™, Carlsbad, Calif.) to produce pCR4Blunt::sadB, which was transformed into *E. coli* Mach-1 cells. Plasmid was subsequently isolated from four clones, and the sequence verified.

The sadB coding region was PCR amplified from pCR4Blunt::sadB. PCR primers contained additional 5' sequences that would overlap with the yeast GPM1 promoter and the ADH1 terminator (N583 and N584, provided as SEQ ID NOs: 76 and 77). The PCR product was then cloned using "gap repair" methodology in *Saccharomyces cerevisiae* (Ma, et al., Gene 58:201-216, 1987) as follows. The yeast-*E. coli* shuttle vector pRS425::GPM::kivD::ADH which contains the GPM1 promoter (SEQ ID NO: 72), kivD coding region from *Lactococcus lactis* (SEQ ID NO: 71), and ADH1 terminator (SEQ ID NO: 73) (described in U.S. Patent Application Publication No. 2007/0092957 A1, Example 17) was digested with BbvCI and PacI restriction enzymes to release the kivD coding region. Approximately 1 μg of the remaining vector fragment was transformed into *S. cerevisiae* strain BY4741 along with 1 μg of sadB PCR product. Transformants were selected on synthetic complete medium lacking leucine. The proper recombination event, generating pRS425::GPM-sadB, was confirmed by PCR using primers N142 and N459 (SEQ ID NOs: 108 and 109).

Construction of pdc6:: PGPM1-sadB Integration Cassette and PDC6 Deletion:

A pdc6::PGPM1-sadB-ADH1t-URA3r integration cassette was made by joining the GPM-sadB-ADHt segment (SEQ ID NO: 79) from pRS425::GPM-sadB (SEQ ID NO: 78) to the URA3r gene from pUC19-URA3r. pUC19-URA3r (SEQ ID NO:80) contains the URA3 marker from pRS426 (ATCC No. 77107) flanked by 75 bp homologous repeat sequences to allow homologous recombination in vivo and removal of the URA3 marker. The two DNA segments were joined by SOE PCR (as described by Horton, et al., Gene 77:61-68, 1989) using as template pRS425::GPM-sadB and pUC19-URA3r plasmid DNAs, with Phusion® DNA polymerase (New England BioLabs Inc., Ipswich, Mass.) and primers 114117-11A through 114117-11D (SEQ ID NOs: 81, 82, 83, and 84), and 114117-13A and 114117-13B (SEQ ID NOs: 85 and 86).

The outer primers for the SOE PCR (114117-13A and 114117-13B) contained 5' and 3' ~50 bp regions homologous to regions upstream and downstream of the PDC6 promoter and terminator, respectively. The completed cassette PCR fragment was transformed into BY4700 (ATCC No. 200866) and transformants were maintained on synthetic complete media lacking uracil and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 112590-34G and 112590-34H (SEQ ID NOs: 87 and 88), and 112590-34F and 112590-49E (SEQ ID NOs: 89 and 90) to verify integration at the PDC6 locus with deletion of the PDC6 coding region. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain has the genotype: BY4700 pdc6::PGPM1-sadB-ADH1t.

Construction of pdc1::PPDC1-ilvD Integration Cassette and PDC1 Deletion:

A pdc1::PPDC1-ilvD-FBA1t-URA3r integration cassette was made by joining the ilvD-FBA1 t segment (SEQ ID NO: 91) from pLH468 (SEQ ID NO: 2) to the URA3r gene from pUC19-URA3r by SOE PCR (as described by Horton, et al., Gene 77:61-68, 1989) using as template pLH468 and pUC19-URA3r plasmid DNAs, with Phusion® DNA polymerase (New England BioLabs Inc., Ipswich, Mass.) and primers 114117-27A through 114117-27D (SEQ ID NOs: 111, 112, 113, and 114).

The outer primers for the SOE PCR (114117-27A and 114117-27D) contained 5' and 3' ~50 bp regions homologous to regions downstream of the PDC1 promoter and downstream of the PDC1 coding sequence. The completed cassette PCR fragment was transformed into BY4700 pdc6::PGPM1-sadB-ADH1t and transformants were maintained on synthetic complete media lacking uracil and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 114117-36D and 135 (SEQ ID NOs: 92 and 93), and primers 112590-49E and 112590-30F (SEQ ID NOs: 90 and 94) to verify integration at the PDC1 locus with deletion of the PDC1 coding sequence. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA67" has the genotype: BY4700 pdc6::PGPM1-sadB-ADH1t pdc1::PPDC1-ilvD-FBA1t.

HIS3 Deletion

To delete the endogenous HIS3 coding region, a his3::URA3r2 cassette was PCR-amplified from URA3r2 template DNA (SEQ ID NO: 95). URA3r2 contains the URA3 marker from pRS426 (ATCC No. 77107) flanked by 500 bp homologous repeat sequences to allow homologous recombination in vivo and removal of the URA3 marker. PCR was done using Phusion® DNA polymerase (New England BioLabs Inc., Ipswich, Mass.) and primers 114117-45A and 114117-45B (SEQ ID NOs: 96 and 97) which generated a ~2.3 kb PCR product. The HIS3 portion of each primer was derived from the 5' region upstream of the HIS3 promoter and 3' region downstream of the coding region such that integration of the URA3r2 marker results in replacement of the HIS3 coding region. The PCR product was transformed into NYLA67 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened to verify correct integration by replica plating of transformants onto synthetic complete media lacking histidine and supplemented with 2% glucose at 30° C. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain, called NYLA73, has the genotype: BY4700 pdc6::PGPM1-sadB-ADH1t pdc1::PPDC1-ilvD-FBA1t Δhis3.

Construction of pdc5::kanMX Integration Cassette and PDC5 Deletion:

A pdc5::kanMX4 cassette was PCR-amplified from strain YLR134W chromosomal DNA (ATCC No. 4034091) using Phusion® DNA polymerase (New England BioLabs Inc., Ipswich, Mass.) and primers PDC5::KanMXF and PDC5::KanMXR (SEQ ID NOs: 98 and 99) which generated a ~2.2 kb PCR product. The PDC5 portion of each primer was derived from the 5' region upstream of the PDC5 promoter and 3' region downstream of the coding region such that integration of the kanMX4 marker results in replacement of the PDC5 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on YP media supplemented with 1% ethanol and geneticin (200 µg/mL) at 30° C. Transformants were screened by PCR to verify correct integration at the PDC locus with replacement of the PDC5 coding region using primers PDC5kofor and N175 (SEQ ID NOs: 100 and 101). The identified correct transformants have the genotype: BY4700 pdc6::PGPM1-sadB-ADH1t pdc1::PPDC1-ilvD-FBA1t Δhis3 pdc5::kanMX4. The strain was named NYLA74.

Plasmid vectors pRS423::CUP1-alsS+FBA-budA and pRS426::FBA-budC+GPM-sadB were transformed into NYLA74 to create a butanediol producing strain (NGCI-047).

Plasmid vectors pLH475-Z4B8 (SEQ ID NO: 140) and pLH468 were transformed into NYLA74 to create an isobutanol producing strain (NGCI-049).

Deletion of HXK2 (hexokinase II):

A hxk2::URA3r cassette was PCR-amplified from URA3r2 template (described above) using Phusion® DNA polymerase (New England BioLabs Inc., Ipswich, Mass.) and primers 384 and 385 (SEQ ID NOs: 102 and 103) which generated a ~2.3 kb PCR product. The HXK2 portion of each primer was derived from the 5' region upstream of the HXK2 promoter and 3' region downstream of the coding region such that integration of the URA3r2 marker results in replacement of the HXK2 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened by PCR to verify correct integration at the HXK2 locus with replacement of the HXK2 coding region using primers N869 and N871 (SEQ ID NOs: 104 and 105). The URA3r2 marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth, and by PCR to verify correct marker removal using primers N946 and N947 (SEQ ID NOs: 106 and 107). The resulting identified strain named NYLA83 has the genotype: BY4700 pdc6::PGPM1-sadB-ADH1t pdc1::PPDC1-ilvD-FBA1t Δhis3 Δhxk2.

Construction of pdc5::kanMX Integration Cassette and PDC5 Deletion:

A pdc5::kanMX4 cassette was PCR-amplified as described above. The PCR fragment was transformed into NYLA83, and transformants were selected and screened as described above. The identified correct transformants named NYLA84 have the genotype: BY4700 pdc6::PGPM1-sadB-ADH1t pdc1::PPDC1-ilvD-FBA1t Δhis3 Δhxk2 pdc5::kanMX4.

Plasmid vectors pLH468 and pLH532 were simultaneously transformed into strain NYLA84 (BY4700 pdc6::PGPM1-sadB-ADH1t pdc1::PPDC1-ilvD-FBA1t Δhis3 Δhxk2 pdc5::kanMX4) using standard genetic techniques (Methods in Yeast Genetics, 2005, Cold Spring Harbor Laboratory Press, Cold Spring Harbor, N.Y.) and the resulting "butanologen NYLA84" was maintained on synthetic complete media lacking histidine and uracil, and supplemented with 1% ethanol at 30° C.

Expression Vector pLH468

The pLH468 plasmid (SEQ ID NO: 2) was constructed for expression of DHAD, KivD, and HADH in yeast and is described in U.S. Patent Application Publication No. 2009/0305363, herein incorporated by reference. pLH486 was constructed to contain: a chimeric gene having the coding region of the ilvD gene from *Streptococcus mutans* (nt position 3313-4849) expressed from the *S. cerevisiae* FBA1 promoter (nt 2109-3105) followed by the FBA1 terminator (nt 4858-5857) for expression of DHAD; a chimeric gene having the coding region of codon optimized horse liver alcohol dehydrogenase (nt 6286-7413) expressed from the *S. cerevisiae* GPM1 promoter (nt 7425-8181) followed by the ADH1 terminator (nt 5962-6277) for expression of ADH; and a chimeric gene having the coding region of the codon-optimized kivD gene from *Lactococcus lactis* (nt 9249-10895) expressed from the TDH3 promoter (nt 10896-11918) followed by the TDH3 terminator (nt 8237-9235) for expression of KivD.

Coding regions for *Lactococcus lactis* ketoisovalerate decarboxylase (KivD) and horse liver alcohol dehydrogenase (HADH) were synthesized by DNA2.0, Inc. (Menlo Park, Calif.) based on codons that were optimized for expression in *Saccharomyces cerevisiae* (SEQ ID NO: 71 and 118, respectively) and provided in plasmids pKivDy-DNA2.0 and pHadhy-DNA2.0. The encoded proteins are SEQ ID NOs: 117 and 119, respectively. Individual expression vectors for KivD and HADH were constructed. To assemble pLH467 (pRS426::PTDH3-kivDy-TDH3t), vector pNY8 (SEQ ID NO: 121; also named pRS426.GPD-ald-GPDt, described in U.S. Patent Application Publication No. 2008/0182308, Example 17, which is herein incorporated by reference) was digested with AscI and SfiI enzymes, thus excising the GPD promoter and the ald coding region. A TDH3 promoter fragment (SEQ ID NO: 122) from pNY8 was PCR amplified to add an AscI site at the 5' end and an SpeI site at the 3' end, using 5' primer OT1068 and 3' primer OT1067 (SEQ ID NOs: 123 and 124). The AscI/SfiI digested pNY8 vector fragment was ligated with the TDH3 promoter PCR product digested with AscI and SpeI, and the SpeI-SfiI fragment containing the codon optimized kivD coding region isolated from the vector pKivD-DNA2.0. The triple ligation generated vector pLH467 (pRS426::PTDH3-kivDy-TDH3t). pLH467 was verified by restriction mapping and sequencing.

pLH435 (pRS425::PGPM1-Hadhy-ADH1t) was derived from vector pRS425::GPM-sadB (SEQ ID NO: 78) which is described in U.S. Provisional Application Ser. No. 61/058,970, Example 3, which is herein incorporated by reference. pRS425::GPM-sadB is the pRS425 vector (ATCC No. 77106) with a chimeric gene containing the GPM1 promoter (SEQ ID NO:72), coding region from a butanol dehydrogenase of *Achromobacter xylosoxidans* (sadB; DNA SEQ ID NO: 69; protein SEQ ID NO:70: disclosed in U.S. Patent Application Publication No. 2009/0269823), and ADH1 terminator (SEQ ID NO: 73). pRS425::GPMp-sadB contains BbvI and PacI sites at the 5' and 3' ends of the sadB coding region, respectively. A NheI site was added at the 5' end of the sadB coding region by site-directed mutagenesis using primers OT1074 and OT1075 (SEQ ID NOs: 126 and 127) to generate vector pRS425-GPMp-sadB-NheI, which was verified by sequencing. pRS425::PGPM1-sadB-NheI was digested with NheI and PacI to drop out the sadB coding region, and ligated with the NheI-PacI fragment containing the codon optimized HADH coding region from vector pHadhy-DNA2.0 to create pLH435.

To combine KivD and HADH expression cassettes in a single vector, yeast vector pRS411 (ATCC No. 87474) was digested with SacI and NotI, and ligated with the SacI-SalI fragment from pLH467 that contains the PTDH3-kivDy-TDH3t cassette together with the SalI-NotI fragment from pLH435 that contains the PGPM1-Hadhy-ADH1t cassette in a triple ligation reaction. This yielded the vector pRS411::PTDH3-kivDy-PGPM1-Hadhy (pLH441) which was verified by restriction mapping.

In order to generate a co-expression vector for all three genes in the lower isobutanol pathway: ilvD, kivDy, and Hadhy, pRS423 FBA ilvD(Strep) (SEQ ID NO: 128) which is described in U.S. Patent Application Publication No. 2010/0081154 as the source of the IlvD gene, was used. This shuttle vector contains an F1 origin of replication (nt 1423 to 1879) for maintenance in *E. coli* and a 2 micron origin (nt 8082 to 9426) for replication in yeast. The vector has an FBA1 promoter (nt 2111 to 3108; SEQ ID NO: 120) and FBA terminator (nt 4861 to 5860; SEQ ID NO: 129). In addition, it carries the His marker (nt 504 to 1163) for selection in yeast and ampicillin resistance marker (nt 7092 to 7949) for selection in *E. coli*. The ilvD coding region (nt 3116 to 4828; SEQ ID NO: 115; protein SEQ ID NO: 116) from *Streptococcus mutans* UA159 (ATCC No. 700610) is between the FBA promoter and FBA terminator forming a chimeric gene for expression. In addition, there is a lumio tag fused to the ilvD coding region (nt 4829-4849).

The first step was to linearize pRS423 FBA ilvD(Strep) (also called pRS423-FBA(SpeI)-IlvD(*Streptococcus mutans*)-Lumio) with SacI and SacII (with SacII site blunt ended using T4 DNA polymerase), to give a vector with total length of 9,482 bp. The second step was to isolate the kivDy-hADHy cassette from pLH441 with SacI and KpnI (with KpnI site blunt ended using T4 DNA polymerase), which gives a 6,063 bp fragment. This fragment was ligated with the 9,482 bp vector fragment from pRS423-FBA(SpeI)-IlvD(*Streptococcus mutans*)-Lumio. This generated vector pLH468 (pRS423::PFBA1-ilvD(Strep) Lumio-FBA1t-

PTDH3-kivDy-TDH3t-PGPM1-hadhy-ADH1t) which was confirmed by restriction mapping and sequencing.

pLH532 Construction

The pLH532 plasmid (SEQ ID NO: 130) was constructed for expression of ALS and KARI in yeast. pLH532 is a pHR81 vector (ATCC No. 87541) containing the following chimeric genes: 1) the CUP1 promoter (SEQ ID NO: 139), acetolactate synthase coding region from *Bacillus subtilis* (AlsS; SEQ ID NO: 137; protein SEQ ID NO: 138) and CYC1 terminator2 (SEQ ID NO: 133); 2) an ILV5 promoter (SEQ ID NO: 134), Pf5.IvC coding region (SEQ ID NO: 132) and ILV5 terminator (SEQ ID NO: 135); and 3) the FBA1 promoter (SEQ ID NO: 136), *S. cerevisiae* KARI coding region (ILV5; SEQ ID NO: 131); and CYC1 terminator.

The Pf5.IlvC coding region is a sequence encoding KARI derived from *Pseudomonas fluorescens* that was described in U.S. Patent Application Publication No. 2009/0163376, which is herein incorporated by reference.

The Pf5.IlvC coding region was synthesized by DNA2.0, Inc. (Menlo Park, Calif.; SEQ ID NO: 132) based on codons that were optimized for expression in *Saccharomyces cerevisiae*.

pYZ090 Construction pYZ090 (SEQ ID NO: 1) is based on the pHR81 (ATCC No. 87541) backbone and was constructed to contain a chimeric gene having the coding region of the alsS gene from *Bacillus subtilis* (nt position 457-2172) expressed from the yeast CUP1 promoter (nt 2-449) and followed by the CYC1 terminator (nt 2181-2430) for expression of ALS, and a chimeric gene having the coding region of the ilvC gene from *Lactococcus lactis* (nt 3634-4656) expressed from the yeast ILV5 promoter (2433-3626) and followed by the ILV5 terminator (nt 4682-5304) for expression of KARI.

pYZ067 Construction pYZ067 was constructed to contain the following chimeric genes: 1) the coding region of the ilvD gene from *S. mutans* UA159 (nt position 2260-3971) expressed from the yeast FBA1 promoter (nt 1161-2250) followed by the FBA terminator (nt 4005-4317) for expression of dihydroxy acid dehydratase (DHAD), 2) the coding region for horse liver ADH (nt 4680-5807) expressed from the yeast GPM promoter (nt 5819-6575) followed by the ADH1 terminator (nt 4356-4671) for expression of alcohol dehydrogenase, and 3) the coding region of the KivD gene from *Lacrococcus lactis* (nt 7175-8821) expressed from the yeast TDH3 promoter (nt 8830-9493) followed by the TDH3 terminator (nt 5682-7161) for expression of ketoisovalerate decarboxylase.

pRS423::CUP1-alsS+FBA-budA and pRS426::FBA-budC+GPM-sadB and pLH475-Z4B8 construction Construction of pRS423::CUP1-alsS+FBA-budA and pRS426::FBA-budC+GPM-sadB and pLH475-Z4B8 is described in U.S. Patent Application Publication No. 2009/0305363, incorporated herein by reference.

Further, while various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the claims and their equivalents.

All publications, patents, and patent applications mentioned in this specification are indicative of the level of skill of those skilled in the art to which this invention pertains, and are herein incorporated by reference to the same extent as if each individual publication, patent, or patent application was specifically and individually indicated to be incorporated by reference.

EXAMPLES

The following nonlimiting examples will further illustrate the invention. It should be understood that, while the following examples involve corn as feedstock and COFA as carboxylic acid, other biomass sources can be used for feedstock and acids other than COFA can serve as carboxylic acid, without departing from the present invention. Moreover, while the following examples involve butanol and butyl ester production, other alcohols including ethanol, and alcohol esters can be produced without departing from the present invention.

As used herein, the meaning of abbreviations used was as follows: "g" means gram(s), "kg" means kilogram(s), "L" means liter(s), "mL" means milliliter(s), "µL" means microliter(s), "mL/L" means milliliter(s) per liter, "mL/min" means milliliter(s) per min, "DI" means deionized, "uM" means micrometer(s), "nm" means nanometer(s), "w/v" means weight/volume, "OD" means optical density, "$OD_{600}$" means optical density at a wavelength of 600 nM, "dcw" means dry cell weight, "rpm" means revolutions per minute, "° C." means degree(s) Celsius, "° C./min" means degrees Celsius per minute, "slpm" means standard liter(s) per minute, "ppm" means part per million, "pdc" means pyruvate decarboxylase enzyme followed by the enzyme number.

General Methods

Seed Flask Growth

A *Saccharomyces cerevisiae* strain that was engineered to produce isobutanol from a carbohydrate source, with pdc1 deleted, pdc5 deleted, and pdc6 deleted, was grown to 0.55-1.1 g/L dcw ($OD_{600}$ 1.3-2.6—Thermo Helios α Thermo Fisher Scientific Inc., Waltham, Mass.) in seed flasks from a frozen culture. The culture was grown at 26° C. in an incubator rotating at 300 rpm. The frozen culture was previously stored at −80° C. The composition of the first seed flask medium was:
- 3.0 g/L dextrose
- 3.0 g/L ethanol, anhydrous
- 3.7 g/L ForMedium™ Synthetic Complete Amino Acid (Kaiser) Drop-Out: without HIS, without URA (Reference No. DSCK162CK)
- 6.7 g/L Difco Yeast Nitrogen Base without amino acids (No. 291920)

Twelve milliliters from the first seed flask culture was transferred to a 2 L flask and grown at 30° C. in an incubator rotating at 300 rpm. The second seed flask has 220 mL of the following medium:
- 30.0 g/L dextrose
- 5.0 g/L ethanol, anhydrous
- 3.7 g/L ForMedium™ Synthetic Complete Amino Acid (Kaiser) Drop-Out: without HIS, without URA (Reference No. DSCK162CK)
- 6.7 g/L Difco Yeast Nitrogen Base without amino acids (No. 291920)
- 0.2 M MES Buffer titrated to pH 5.5-6.0

The culture was grown to 0.55-1.1 g/L dcw ($OD_{600}$ 1.3-2.6). An addition of 30 mL of a solution containing 200 g/L peptone and 100 g/L yeast extract was added at this cell concentration. Then, an addition of 300 mL of 0.2 uM filter sterilized Cognis, 90-95% oleyl alcohol was added to the flask. The culture continues to grow to >4 g/L dcw ($OD_{600}$>10) before being harvested and added to the fermentation.

Fermentation Preparation
Initial Fermentation Vessel Preparation

A glass jacked, 2 L fermentation vessel (Sartorius AG, Goettingen, Germany) was charged with house water to 66% of the liquefaction weight. A pH probe (Hamilton Easyferm Plus K8, part number: 238627, Hamilton Bonaduz AG, Bonaduz, Switzerland) was calibrated through the Sartorius DCU-3 Control Tower Calibration menu. The zero was calibrated at pH=7. The span was calibrated at pH=4. The probe was then placed into the fermentation vessel through the stainless steel head plate. A dissolved oxygen probe ($pO_2$ probe) was also placed into the fermentation vessel through the head plate. Tubing used for delivering nutrients, seed culture, extracting solvent, and base were attached to the head plate and the ends were foiled. The entire fermentation vessel was placed into a Steris (Steris Corporation, Mentor, Ohio) autoclave and sterilized in a liquid cycle for 30 minutes.

The fermentation vessel was removed from the autoclave and placed on a load cell. The jacket water supply and return line was connected to the house water and clean drain, respectively. The condenser cooling water in and water out lines were connected to a 6-L recirculating temperature bath running at 7° C. The vent line that transfers the gas from the fermentation vessel was connected to a transfer line that was connected to a Thermo mass spectrometer (Prima dB, Thermo Fisher Scientific Inc., Waltham, Mass.). The sparger line was connected to the gas supply line. The tubing for adding nutrients, extract solvent, seed culture, and base was plumbed through pumps or clamped closed.

The fermentation vessel temperature was controlled at 55° C. with a thermocouple and house water circulation loop. Wet corn kernels (#2 yellow dent) were ground using a hammer mill with a 1.0 mm screen, and the resulting ground whole corn kernels were then added to the fermentation vessel at a charge that was 29-30% (dry corn solids weight) of the liquefaction reaction mass.

Lipase Treatment Pre-Liquefaction

A lipase enzyme stock solution was added to the fermentation vessel to a final lipase concentration of 10 ppm. The fermentation vessel was held at 55° C., 300 rpm, and 0.3 slpm $N_2$ overlay for >6 hrs. After the lipase treatment was complete, liquefaction was performed as described below (Liquefaction).

Liquefaction

An alpha-amylase was added to the fermentation vessel per its specification sheet while the fermentation vessel was mixing at 300-1200 rpm, with sterile, house $N_2$ being added at 0.3 slpm through the sparger. The temperature set-point was changed from 55° C. to 85° C. When the temperature was >80° C., the liquefaction cook time was started and the liquefaction cycle was held at >80° C. for 90-120 minutes. The fermentation vessel temperature set-point was set to the fermentation temperature of 30° C. after the liquefaction cycle was complete. $N_2$ was redirected from the sparger to the head space to prevent foaming without the addition of a chemical antifoaming agent.

Lipase Treatment Post-Liquefaction

The fermentation vessel temperature was set to 55° C. instead of 30° C. after the liquefaction cycle was complete (Liquefaction). The pH was manually controlled at pH=5.8 by making bolus additions of acid or base when needed. A lipase enzyme stock solution was added to the fermentation vessel to a final lipase concentration of 10 ppm. The fermentation vessel was held at 55° C., 300 rpm, and 0.3 slpm $N_2$ overlay for >6 hrs. After the Lipase Treatment was complete, the fermentation vessel temperature was set to 30° C.

Lipase Heat Inactivation Treatment (Heat Kill Treatment Method)

The fermentation vessel temperature was held at >80° C. for >15 minutes to inactivate the lipase. After the Heat Inactivation Treatment was complete, the fermentation vessel temperature was set to 30° C.

Nutrient Addition Prior to Inoculation

Ethanol (6.36 mL/L, post-inoculation volume, 200 proof, anhydrous) was added to the fermentation vessel just prior to inoculation. Thiamine was added to a final concentration of 20 mg/L and 100 mg/L nicotinic acid was also added just prior to inoculation.

Oleyl Alcohol or Corn Oil Fatty Acids Addition Prior to Inoculation

Added 1 L/L (post-inoculation volume) of oleyl alcohol or corn oil fatty acids immediately after inoculation.

Fermentation Vessel Inoculation

The fermentation vessels $pO_2$ probe was calibrated to zero while $N_2$ was being added to the fermentation vessel. The fermentation vessels $pO_2$ probe was calibrated to its span with sterile air sparging at 300 rpm. The fermentation vessel was inoculated after the second seed flask with >4 g/L dcw. The shake flask was removed from the incubator/shaker for 5 minutes allowing a phase separation of the oleyl alcohol phase and the aqueous phase. The aqueous phase (110 mL) was transferred to a sterile, inoculation bottle. The inoculum was pumped into the fermentation vessel through a peristaltic pump.

Fermentation Vessel Operating Conditions

The fermentation vessel was operated at 30° C. for the entire growth and production stages. The pH was allowed to drop from a pH between 5.7-5.9 to a control set-point of 5.2 without adding any acid. The pH was controlled for the remainder of the growth and production stage at a pH=5.2 with ammonium hydroxide. Sterile air was added to the fermentation vessel, through the sparger, at 0.3 slpm for the remainder of the growth and production stages. The $pO_2$ was set to be controlled at 3.0% by the Sartorius DCU-3 Control Box PID control loop, using stir control only, with the stirrer minimum being set to 300 rpm and the maximum being set to 2000 rpm. The glucose was supplied through simultaneous saccharification and fermentation of the liquified corn mash by adding a α-amylase (glucoamylase). The glucose was kept excess (1-50 g/L) for as long as starch was available for saccharification.

Analytical
Gas Analysis

Process air was analyzed on a Thermo Prima (Thermo Fisher Scientific Inc., Waltham, Mass.) mass spectrometer. This was the same process air that was sterilized and then added to each fermentation vessel. Each fermentation vessel's off-gas was analyzed on the same mass spectrometer. This Thermo Prima dB has a calibration check run every Monday morning at 6:00 am. The calibration check was scheduled through the Gas Works v1.0 (Thermo Fisher Scientific Inc., Waltham, Mass.) software associated with the mass spectrometer. The gas calibrated for were:

| GAS | Calibration Concentration mole % | Cal Frequency |
| --- | --- | --- |
| Nitrogen | 78% | weekly |
| Oxygen | 21% | weekly |
| Isobutanol | 0.2% | yearly |
| Argon | 1% | weekly |
| Carbon Dioxide | 0.03% | weekly |

Carbon dioxide was checked at 5% and 15% during calibration cycle with other known bottled gases. Oxygen was checked at 15% with other known bottled gases. Based on the analysis of the off-gas of each fermentation vessel, the amount of isobutanol stripped, oxygen consumed, and carbon dioxide respired into the off-gas was measured by using the mass spectrometer's mole fraction analysis and gas flow rates (mass flow controller) into the fermentation vessel. Calculate the gassing rate per hour and then integrating that rate over the course of the fermentation.

Biomass Measurement

A 0.08% Trypan Blue solution was prepared from a 1:5 dilution of 0.4% Trypan Blue in NaCl (VWR BDH8721-0) with 1×PBS. A 1.0 mL sample was pulled from a fermentation vessel and placed in a 1.5 mL Eppendorf centrifuge tube and centrifuged in an Eppendorf, 5415C at 14,000 rpm for 5 minutes. After centrifugation, the top solvent layer was removed with an m200 Variable Channel BioHit pipette with 20-200 μL BioHit pipette tips. Care was made not to remove the layer between the solvent and aqueous layers. Once the solvent layer was removed, the sample was re-suspended using a Vortex-Genie® set at 2700 rpm.

A series of dilutions was required to prepare the ideal concentration for hemacytometer counts. If the OD was 10, a 1:20 dilution would be performed to achieve 0.5 OD which would give the ideal amount of cells to be counted per square, 20-30. In order to reduce inaccuracy in the dilution due to corn solids, multiple dilutions with cut 100-1000 μL BioHit pipette tips were required. Approximately, 1 cm was cut off the tips to increase the opening which prevented the tip from clogging. For a 1:20 final dilution, an initial 1:1 dilution of fermentation sample and 0.9% NaCl solution was prepared. Then, a 1:1 dilution of the previous solution (i.e., the initial 1:1 dilution) and 0.9% NaCl solution (the second dilution) was generated followed by a 1:5 dilution of the second dilution and Trypan Blue Solution. Samples were vortexed between each dilution and cut tips were rinsed into the 0.9% NaCl and Trypan Blue solutions.

The cover slip was carefully placed on top of the hemacytometer (Hausser Scientific Bright-Line 1492). An aliquot (10 μL) was drawn of the final Trypan Blue dilution with an m20 Variable Channel BioHit pipette with 2-20 μL BioHit pipette tips and injected into the hemacytometer. The hemacytometer was placed on the Zeis Axioskop 40 microscope at 40× magnification. The center quadrant was broken into 25 squares and the four corner and center squares in both chambers were then counted and recorded. After both chambers were counted, the average was taken and multiplied by the dilution factor (20), then by 25 for the number for squares in the quadrant in the hemacytometer, and then divided by 0.0001 mL which is the volume of the quadrant that was counted. The sum of this calculation is the number cells per mL.

LC Analysis of Fermentation Products in the Aqueous Phase

Samples were refrigerated until ready for processing. Samples were removed from refrigeration and allowed to reach room temperature (about one hour). Approximately 300 μL of sample was transferred with a m1000 Variable Channel BioHit pipette with 100-1000 μL BioHit pipette tips into a 0.2 um centrifuge filter (Nanosep® MF modified nylon centrifuge filter), then centrifuged using a Eppendorf, 5415C for five minutes at 14,000 rpm. Approximately 200 μL of filtered sample was transferred into a 1.8 auto sampler vial with a 250 μL glass vial insert with polymer feet. A screw cap with PTFE septa was used to cap the vial before vortexing the sample with a Vortex-Genie® set at 2700 rpm.

Sample was then run on Agilent 1200 series LC equipped with binary, isocratic pumps, vacuum degasser, heated column compartment, sampler cooling system, UV DAD detector and RI detector. The column used was an Aminex HPX-87H, 300×7.8 with a Bio-Rad Cation H refill, 30×4.6 guard column. Column temperature was 40° C., with a mobile phase of 0.01 N sulfuric acid, at a flow rate of 0.6 mL/min for 40 minutes. Results are shown in Table 1.

TABLE 1

| Retention times of fermentation products in aqueous phase | | | | |
|---|---|---|---|---|
| HPLC 302/310 Normalized to 10 μL injections | FW | RID Retention Time, min | Range of Standards, g/L | UV Retention Time, min |
| citric acid | 192.12 | 8.025 | 0.3-17 | 7.616 |
| glucose | 180.16 | 8.83 | 0.5-71 | |
| pyruvic acid (Na) | 110.04 | 9.388 | 0.1-5.2 | 8.5 |
| A-Kiv (Na) | 138.1 | 9.91 | 0.07-5.0 | 8.55 |
| 2,3-dihydroxyisovaleric acid (Na) | 156.1 | 10.972 | 0.2-8.8 | 10.529 |
| succinic acid | 118.09 | 11.561 | 0.3-16 | 11.216 |
| lactic acid (Li) | 96.01 | 12.343 | 0.3-17 | 11.948 |
| glycerol | 92.09 | 12.974 | 0.8-39 | |
| formic acid | 46.03 | 13.686 | 0.2-13 | 13.232 |
| acetate (Na) | 82.03 | 14.914 | 0.5-16 | 14.563 |
| meso-butanediol | 90.12 | 17.583 | 0.1-19 | |
| (+/−)-2,3-butanediol | 90.12 | 18.4 | 0.2-19 | |
| isobutyric acid | 88.11 | 19.685 | 0.1-8.0 | 19.277 |
| ethanol | 46.07 | 21.401 | 0.5-34 | |
| isobutyraldehyde | 72.11 | 27.64 | 0.01-0.11 | |
| isobutanol | 74.12 | 32.276 | 0.2-15 | |
| 3-OH-2-butanone (acetoin) | 88.11 | | 0.1-11 | 17.151 |

GC Analysis of Fermentation Products in the Solvent Phase

Samples were refrigerated until ready for processing. Samples were removed from refrigeration and allowed to reach room temperature (about one hour). Approximately 150 μL of sample was transferred using a m1000 Variable Channel BioHit pipette with 100-1000 μL BioHit pipette tips into a 1.8 auto sampler vial with a 250 μL glass vial insert with polymer feet. A screw cap with PTFE septa was used to cap the vial.

Sample was then run on Agilent 7890A GC with a 7683B injector and a G2614A auto sampler. The column was a HP-InnoWax column (30 m×0.32 mm ID, 0.25 μm film). The carrier gas was helium at a flow rate of 1.5 mL/min measured at 45° C. with constant head pressure; injector split was 1:50 at 225° C.; oven temperature was 45° C. for 1.5 minutes, 45° C. to 160° C. at 10° C./min for 0 minutes, then 230° C. at 35° C./min for 14 minutes for a run time of 29 minutes. Flame ionization detection was used at 260° C. with 40 mL/min helium makeup gas. Results are shown in Table 2.

TABLE 2

| Retention times of fermentation products in solvent phase. | | | |
|---|---|---|---|
| GC 302/310 Normalized to 10 μL injections | FW | Solvent Retention Time, min | Range of Standards, g/L |
| isobutyraldehyde | 72.11 | 2.75 | 0.7-10.4 |
| ethanol | 46.07 | 3.62 | 0.5-34 |
| isobutanol | 74.12 | 5.53 | 0.2-16 |
| 3-OH-2-butanone (acetoin) | 88.11 | 8.29 | 0.1-11 |
| (+/−)-2,3-butanediol | 90.12 | 10.94 | 0.1-19 |
| isobutyric acid | 88.11 | 11.907 | 0.1-7.9 |
| meso-butanediol | 90.12 | 11.26 | 0.1-6.5 |
| glycerol | 92.09 | 16.99 | 0.8-9 |

Samples analyzed for fatty acid butyl esters were run on Agilent 6890 GC with a 7683B injector and a G2614A auto sampler. The column was a HP-DB-FFAP column (15 meters×0.53 mm ID (Megabore), 1-micron film thickness column (30 m×0.32 mm ID, 0.25 μm film). The carrier gas was helium at a flow rate of 3.7 mL/min measured at 45° C. with constant head pressure; injector split was 1:50 at 225° C.; oven temperature was 100° C. for 2.0 minutes, 100° C. to 250° C. at 10° C./min, then 250° C. for 9 minutes for a run time of 26 minutes. Flame ionization detection was used at 300° C. with 40 mL/min helium makeup gas. The following GC standards (Nu-Chek Prep; Elysian, Minn.) were used to confirm the identity of fatty acid isobutyl ester products: iso-butyl palmitate, iso-butyl stearate, iso-butyl oleate, iso-butyl linoleate, iso-butyl linolenate, iso-butyl arachidate.

Examples 1-14 describe various fermentation conditions that may be used for the claimed methods. As an example, some fermentations were subjected to Lipase Treatment pre-liquefaction and others were subjected to Lipase Treatment post-liquefaction. In other examples, the fermentation was subjected to Heat inactivation Treatment. Following fermentation, the effective isobutanol titer (Eff Iso Titer) was measured, that is, the total grams of isobutanol produced per liter aqueous volume. Results are shown in Table 3.

Example 1

Control

Experiment identifier 2010Y014 included: Seed Flask Growth method, Initial Fermentation Vessel Preparation method, Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 2

Experiment identifier 2010Y015 included: Seed Flask Growth method, Initial Fermentation Vessel Preparation method, Liquefaction method, Lipase Treatment Post-Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 3

Experiment identifier 2010Y016 included: Seed Flask Growth method, Initial Fermentation Vessel Preparation method, Liquefaction method, Lipase Treatment Post-Liquefaction method, Nutrient Addition Prior to Inoculation method with the exception of the exclusion of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 4

Experiment identifier 2010Y017 included: Seed Flask Growth method, Initial Fermentation Vessel Preparation method, Liquefaction method, Heat Kill Treatment method Post-Liquefaction, Nutrient Addition Prior to Inoculation method with the exception of the exclusion of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 5

Experiment identifier 2010Y018 included: Seed Flask Growth method, Initial Fermentation Vessel Preparation method, Liquefaction method, Lipase Treatment Post-Liquefaction method with the exception of only adding 7.2 ppm lipase after liquefaction, Heat Kill Treatment method Post-Liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 6

Control

Experiment identifier 2010Y019 included: Seed Flask Growth method, Initial Fermentation Vessel Preparation method, Liquefaction method, Heat Kill Treatment method Post-Liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 7

Control

Experiment identifier 2010Y021 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 8

Experiment identifier 2010Y022 included: Seed Flask Growth method, Initial Fermentation Vessel Preparation method, Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 9

Experiment identifier 2010Y023 included: Seed Flask Growth method, Initial Fermentation Vessel Preparation method, Liquefaction method, Lipase Treatment Post-Liquefaction method, no Heat Kill Treatment, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 10

Experiment identifier 2010Y024 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method with the exception of there being no addition of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 11

Experiment identifier 2010Y029 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 12

Experiment identifier 2010Y030 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method with the exception of there being no addition of ethanol, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 13

Control

Experiment identifier 2010Y031 included: Seed Flask Growth method, Initial Fermentation Vessel Preparation method, Liquefaction method, Lipase Treatment Post Liquefaction method, no Heat Kill Treatment, Nutrient Addition Prior to Inoculation method with the exception of there being no addition of ethanol, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 14

Experiment identifier 2010Y032 included: Seed Flask Growth method, Initial Fermentation Vessel Preparation method, Liquefaction method, Lipase Treatment Post-Liquefaction method, no Heat Kill Treatment, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

TABLE 3

Fermentation conditions for Examples 1-14.

| Example # | Experimental Identifier | Lipase | Max cell Count × $10^7$ | Ethanol g/L | Solvent | Heat Kill Lipase | Eff Iso Titer g/L* | max Eff Iso rate g/L/h |
|---|---|---|---|---|---|---|---|---|
| 1 | 2010Y014 | none | 27.2 | 5 | Oleyl alcohol | none | 56.0 | 0.79 |
| 2 | 2010Y015 | 10 ppm | 31.5 | 5 | Oleyl alcohol | none | 52.4 | 0.74 |
| 3 | 2010Y016 | 10 ppm | 6.7 | 0 | Oleyl alcohol | none | 25.9 | 0.36 |
| 4 | 2010Y017 | none | 7.9 | 0 | Oleyl alcohol | post-liquefaction | 17.2 | 0.25 |
| 5 | 2010Y018 | 7.2 ppm | 16.2 | 5 | Oleyl alcohol | post-liquefaction | 45.8 | 0.66 |
| 6 | 2010Y019 | none | 17.5 | 5 | Oleyl alcohol | post-liquefaction | 48.1 | 0.69 |
| 7 | 2010Y021 | 10 ppm | 21.2 | 5 | Oleyl alcohol | during liquefaction | 46.8 | 0.82 |
| 8 | 2010Y022 | none | 9 | 5 | Oleyl alcohol | during liquefaction | 56.2 | 0.87 |
| 9 | 2010Y023 | 10 ppm | 12.8 | 5 | Corn Oil Fatty Acids | none | 60.3 | 1.3 |
| 10 | 2010Y024 | 10 ppm | 25.3 | 0 | Oleyl alcohol | during liquefaction | 19.8 | 0.33 |
| 11 | 2010Y029 | 10 ppm | 21.2 | 5 | Corn Oil Fatty Acids | during liquefaction | 28.36 | 0.52 |
| 12 | 2010Y030 | 10 ppm | 9 | 0 | Corn Oil Fatty Acids | during liquefaction | 12.71 | 0.24 |

TABLE 3-continued

Fermentation conditions for Examples 1-14.

| Example # | Experimental Identifier | Lipase | Max cell Count × $10^7$ | Ethanol g/L | Solvent | Heat Kill Lipase | Eff Iso Titer g/L* | max Eff Iso rate g/L/h |
|---|---|---|---|---|---|---|---|---|
| 13 | 2010Y031 | 10 ppm | 12.8 | 0 | Corn Oil Fatty Acids | none | 18.86 | 0.35 |
| 14 | 2010Y032 | 10 ppm | 25.3 | 5 | Corn Oil Fatty Acids | none | 53.36 | 0.92 |

*The "Eff Iso Titer g/L" = total grams of isobutanol produced per liter aqueous volume Example 15

The experimental identifier was GLNOR432A. NYLA74 (a butanediol producer—NGCI-047) was grown in 25 mL of medium in a 250 mL flask from a frozen vial to ~1 OD. The pre-seed culture was transferred to a 2 L flask and grown to 1.7-1.8 OD. The medium for both flasks was:
3.0 g/L dextrose
3.0 g/L ethanol, anhydrous
6.7 g/L Difco Yeast Nitrogen Base without amino acids (No. 291920)
1.4 g/L Yeast Dropout Mix (Sigma Y2001)
10 mL/L 1% w/v L-Leucine stock solution
2 mL/L 1% w/v L-Tryptophan stock solution
A 1 L, Applikon fermentation vessel was inoculated with 60 mL of the seed flask. The fermentation vessel contained 700 mL of the following sterile medium:
20.0 g/L dextrose
8.0 mL/L ethanol, anhydrous
6.7 g/L Difco Yeast Nitrogen Base without amino acids (No. 291920)
2.8 g/L Yeast Dropout Mix (Sigma Y2001)
20 mL/L 1% w/v L-Leucine stock solution
4 mL/L 1% w/v L-Tryptophan stock solution
0.5 mL Sigma 204 Antifoam
0.8 mL/L 1% w/v Ergesterol solution in 1:1::Tween 80:Ethanol
The residual glucose was kept excess with a 50% w/w glucose solution. The dissolved oxygen concentration of the fermentation vessel was controlled at 30% with stir control. The pH was controlled at pH=5.5. The fermentation vessel was sparged with 0.3 slpm of sterile, house air. The temperature was controlled at 30° C.

Example 16

Figure 7:
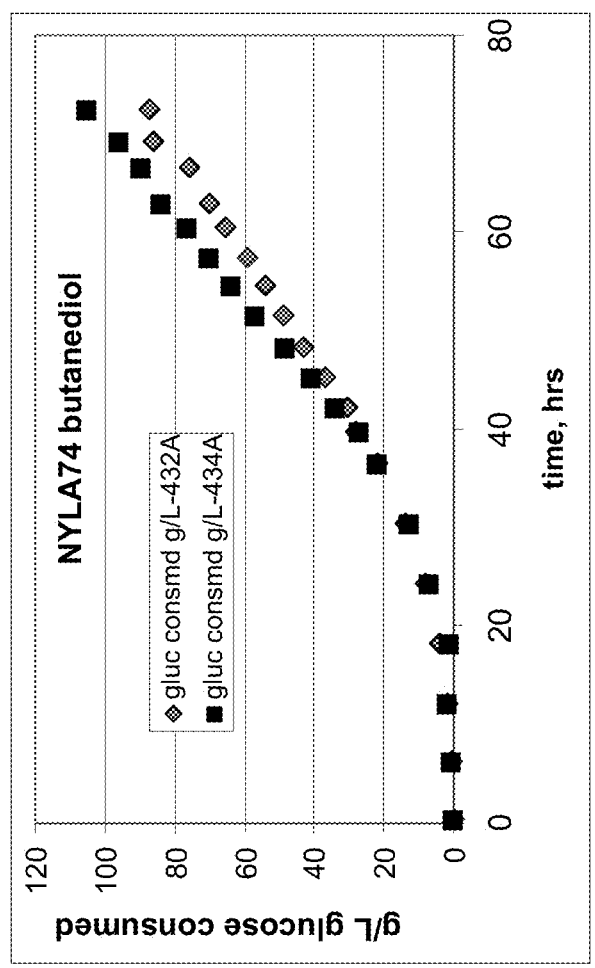
FIG. 7 is a chart illustrating the effect that the presence of fatty acids in a fermentation vessel has on glucose consumption for butanologen strain NGCI-047.

The experimental identifier was GLNOR434A. This example is the same as example 15 with the exception of the addition of 3 g of oleic acid and the addition of 3 g of palmitic acid prior to inoculation. NYLA74 (a butanediol producer—NGCI-047) was the biocatalyst.
FIG. 7 shows that there were more grams per liter of glucose consumed in the fermentation vessel that received the fatty acids. The squares represent the fermentation vessel that received oleic acid and palmitic acid. The circles represent the fermentation vessel that did not receive any extra fatty acids.

Example 17

The experimental identifier was GLNOR435A. This example was the same as example 15 except it was inoculated with NYLA74 (an isobutanol producer—NGCI-049).

Example 18

Figure 8:
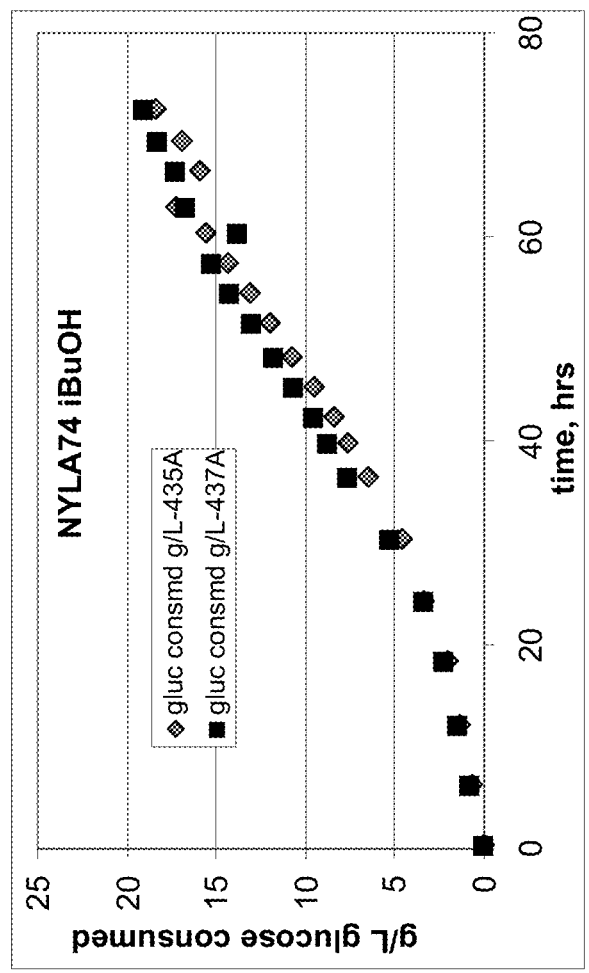
FIG. 8 is a chart illustrating the effect that the presence of fatty acids in a fermentation vessel has on glucose consumption for butanologen strain NGCI-049.

The experimental identifier was GLNOR437A. This example was the same as Example 16 except it was inoculated with NYLA74 (an isobutanol producer) (NGCI-049).
FIG. 8 shows that there were more grams per liter of glucose consumed in the fermentation vessel that received the fatty acids. The squares represent the fermentation vessel that received oleic acid and palmitic acid. The circles represent the fermentation vessel that did not receive any extra fatty acids.

Example 19

The experimental identifier was 090420_3212. This example was run similarly to Example 15 except it was inoculated with butanologen NYLA84 (an isobutanol producer). This fermentation was run in a 1 L Sartorius fermentation vessel.

Example 20

Figure 9:
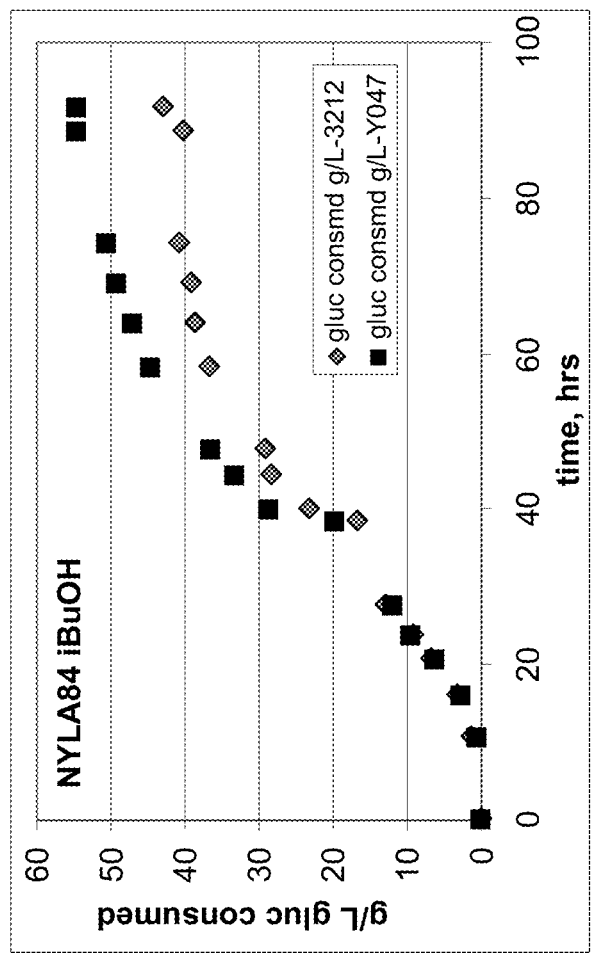
FIG. 9 is a chart illustrating the effect that the presence of fatty acids in a fermentation vessel has on glucose consumption for butanologen strain NYLA84.

The experimental identifier was 2009Y047. This example was run similarly to Example 16 except it was inoculated with butanologen NYLA84 (an isobutanol producer). This fermentation was run in a 1 L Sartorius fermentation.
FIG. 9 shows that there were more grams per liter of glucose consumed in the fermentation vessel that received the fatty acids. The squares represent the fermentation vessel that received oleic acid and palmitic acid. The circles represent the fermentation vessel that did not receive any extra fatty acids.
Table 4 shows +/− fatty acid addition, maximum optical density, and g/L glucose consumed.

TABLE 4

| Example # | Experimental Identifier | Strain | Fatty Acids Added | Product | 69 hours $OD_{600}$ | 69 hours g/L glucose consumed |
|---|---|---|---|---|---|---|
| 15 | GLNOR432A | NYLA74 | − | butanediol | 12.8 | 86.0 |
| 16 | GLNOR434A | NYLA74 | + | butanediol | 23.1 | 95.9 |
| 17 | GLNOR435A | NYLA74 | − | isobutanol | 2.4 | 16.9 |

TABLE 4-continued

| Example # | Experimental Identifier | Strain | Fatty Acids Added | Product | 69 hours OD$_{600}$ | 69 hours g/L glucose consumed |
|---|---|---|---|---|---|---|
| 18 | GLNOR437A | NYLA74 | + | isobutanol | 4.5 | 18.3 |
| 19 | 090420_3212 | NYLA84 | − | isobutanol | 9.6 | 39.3 |
| 20 | 2009Y047 | NYLA84 | + | isobutanol | 20.2 | 49.1 |

Example 21

Lipase Treatment of Liquefied Corn Mash for Simultaneous Saccharification and Fermentation with In-Situ Product Removal Using Oleyl Alcohol Samples of broth and oleyl alcohol taken from fermentations run as described above in Examples 1, 2, and 3 were analyzed for wt % lipid (derivatized as fatty acid methyl esters, FAME) and for wt % free fatty acid (FFA, derivatized as fatty acid methyl esters, FAME) according to the method described by E. G. Bligh and W. J. Dyer (Canadian Journal of Biochemistry and Physiology, 37:911-17, 1959, hereafter Reference 1). The liquefied corn mash that was prepared for each of the three fermentations was also analyzed for wt % lipid and for wt % FFA after treatment with Lipolase® 100 L (Novozymes) (10 ppm of Lipolase® total soluble protein (BCA protein analysis, Sigma Aldrich)) per kg of liquefaction reaction mass containing 30 wt % ground corn kernels). No lipase was added to the liquefied corn mash in Example 1 (control), and the fermentations described in Examples 2 and 3 containing liquefied corn mash treated with lipase (no heat inactivation of lipase) were identical except that no ethanol was added to the fermentation described in Example 3.

The % FFA in lipase-treated liquefied corn mash prepared for fermentations run as described in Examples 2 and 3 was 88% and 89%, respectively, compared to 31% without lipase treatment (Example 1). At 70 h (end of run (EOR)), the concentration of FFA in the OA phase of fermentations run as described in Examples 2 and 3 (containing active lipase) was 14% and 20%, respectively, and the corresponding increase in lipids (measured as corn oil fatty acid methyl ester derivatives) was determined by GC/MS to be due to the lipase-catalyzed esterification of COFA by OA, where COFA was first produced by lipase-catalyzed hydrolysis of corn oil in the liquefied corn mash. Results are shown in Table 5.

TABLE 5

Lipid and free fatty acid content of fermentations containing oleyl alcohol as ISPR solvent and active lipase

| fermentation | lipase | time (h), sample | lipids (wt %) | FFA (wt %) | lipids (g) | FFA (g) | lipids + FFA (g) | % FFA |
|---|---|---|---|---|---|---|---|---|
| Example 1 | none | liq. mash | 0.61 | 0.28 | 5.3 | 2.4 | 7.7 | 31 |
| Example 1 | none | 0.8 h, broth | 0.49 | 0.22 | 5.5 | 2.5 | 8.0 | 31 |
| Example 1 | none | 31 h, broth | 0.19 | 0.03 | 2.1 | 0.3 | 2.4 | 13 |
| Example 1 | none | 31 h, OA | 0.36 | 0.21 | 3.4 | 2.0 | 5.3 | 37 |
| Example 1 | none | 70 h, broth | 0.15 | 0.03 | 1.7 | 0.3 | 2.0 | 15 |
| Example 1 | none | 70 h, OA | 0.57 | 0.25 | 5.3 | 2.3 | 7.7 | 31 |
| Example 2 | 10 ppm | liq. mash | 0.13 | 0.97 | 1.1 | 8.5 | 9.6 | 88 |
| Example 2 | 10 ppm | 0.8 h, broth | 0.15 | 0.62 | 1.7 | 7.0 | 8.7 | 81 |
| Example 2 | 10 ppm | 31 h, broth | 0.16 | 0.05 | 1.8 | 0.5 | 2.3 | 23 |
| Example 2 | 10 ppm | 31 h, OA | 0.37 | 0.23 | 3.5 | 2.2 | 5.7 | 38 |
| Example 2 | 10 ppm | 70 h, broth | 0.17 | 0.02 | 1.9 | 0.3 | 2.2 | 13 |
| Example 2 | 10 ppm | 70 h, OA | 0.60 | 0.10 | 5.7 | 1.0 | 6.7 | 14 |
| Example 3 | 10 ppm | liq. mash | 0.12 | 0.97 | 1.0 | 8.5 | 9.5 | 89 |
| Example 3 | 10 ppm | 0.8 h, broth | 0.32 | 0.40 | 3.6 | 4.5 | 8.1 | 56 |
| Example 3 | 10 ppm | 31 h, broth | 0.17 | 0.05 | 1.9 | 0.6 | 2.5 | 24 |
| Example 3 | 10 ppm | 31 h, OA | 0.38 | 0.22 | 3.6 | 2.1 | 5.7 | 37 |
| Example 3 | 10 ppm | 70 h, broth | 0.15 | 0.02 | 1.7 | 0.2 | 1.9 | 13 |
| Example 3 | 10 ppm | 70 h, OA | 0.46 | 0.12 | 4.4 | 1.1 | 5.6 | 20 |

Example 22

Heat Inactivation of Lipase in Lipase-Treated Liquefied Corn Mash to Limit Production of Oleyl Alcohol Esters of Corn Oil Free Fatty Acids Tap water (918.4 g) was added to a jacketed 2-L resin kettle, then 474.6 g wet weight (417.6 g dry weight) of ground whole corn kernels (1.0 mm screen on hammer mill) was added with stirring. The mixture was heated to 55° C. with stirring at 300 rpm, and the pH adjusted to 5.8 with 2 N sulfuric acid. To the mixture was added 14.0 g of an aqueous solution containing 0.672 g of Spezyme®-FRED L (Genencor®, Palo Alto, Calif.), and the temperature of the mixture increased to 85° C. with stirring at 600 rpm and pH 5.8. After 120 minutes at 85° C., the mixture was cooled to 50° C. and 45.0 mL aliquots of the resulting liquefied corn mash were transferred to 50-mL polypropylene centrifuge tubes and stored frozen at −80° C.

In a first reaction, 50 g of liquefied corn mash prepared as described above was mixed with 10 ppm Lipolase® 100 L (Novozymes) for 6 h at 55° C. and with no inactivation of lipase at 85° C. for 1 h, the mixture was cooled to 30° C. In a second reaction, 50 g of liquefied corn mash was mixed with 10 ppm Lipolase® for 6 h at 55° C., then heated to 85° C. for 1 h (lipase inactivation), then cooled to 30° C. In a third reaction, 50 g of liquefied corn mash without added lipase was mixed for 6 h at 55° C., and with no heating at 85° C. for 1 h, the mixture was cooled to 30° C., 38 g of oleyl alcohol was added, and the resulting mixture stirred for 73 h at 30° C. In a fourth reaction, 50 g of liquefied corn mash without added lipase was mixed for 6 h at 55° C., then heated to 85° C. for 1 h, then cooled to 30° C. Each of the four reaction mixtures was sampled at 6 h, then 38 g of oleyl alcohol added, and the resulting mixtures stirred at 30° C. and sampled at 25 h and 73 h. Samples (both liquefied mash and oleyl alcohol (OA)) were analyzed for wt % lipid (derivatized as fatty acid methyl esters, FAME) and for wt % free fatty acid (FFA, derivatized as fatty acid methyl esters, FAME) according to the method described by Reference 1.

The % FFA in the OA phase of the second reaction run with heat inactivation of lipase prior to OA addition was 99% at 25 h and 95% at 73 h, compared to only 40% FFA and 21% FFA at 25 h and 73 h, respectively, when the lipase in lipase-treated liquefied corn mash was not heat inactivated (first reaction). No significant change in % FFA was observed in the two control reactions without added lipase. Results are shown in Table 6.

TABLE 6

Lipid and free fatty acid content of a mixture of liquefied corn mash and oleyl alcohol in the presence or absence of active or heat-inactivated lipase

| reaction conditions | time (h), sample | lipids (wt %) | FFA (wt %) | lipids (mg) | FFA (mg) | lipid + FFA (mg) | % FFA |
|---|---|---|---|---|---|---|---|
| 10 ppm active lipase, | 6 h, liq. mash | 0.08 | 0.71 | 41 | 345 | 386 | 89 |
| no 85° C. heat treatment | 25 h, liq. mash | 0.22 | 0.06 | 105 | 27 | 132 | 20 |
| | 25 h, OA | 0.58 | 0.39 | 212 | 143 | 355 | 40 |
| | 73 h, liq. mash | 0.25 | 0.05 | 121 | 22 | 143 | 18 |
| | 73 h, OA | 0.91 | 0.24 | 333 | 88 | 420 | 21 |
| 10 ppm inactive lipase, | 6 h, liq. mash | 0.06 | 0.45 | 28 | 224 | 252 | 89 |
| 85° C. heat treatment | 25 h, liq. mash | 0.10 | 0.11 | 49 | 54 | 103 | 53 |
| | 25 h, OA | 0.02 | 0.96 | 8 | 366 | 374 | 99 |
| | 73 h, liq. mash | 0.24 | 0.15 | 117 | 72 | 189 | 62 |
| | 73 h, OA | 0.06 | 1.11 | 23 | 424 | 447 | 95 |
| no lipase, | 6 h, liq. mash | 0.80 | 0.40 | 401 | 199 | 599 | 33 |
| no 85° C. heat treatment | 25 h, liq. mash | 0.30 | 0.05 | 147 | 25 | 173 | 15 |
| | 25 h, OA | 0.55 | 0.36 | 212 | 139 | 351 | 40 |
| | 73 h, liq. mash | 0.23 | 0.05 | 117 | 26 | 143 | 23 |
| | 73 h, OA | 0.79 | 0.42 | 305 | 162 | 467 | 34 |
| no lipase, | 6 h, liq. mash | 0.74 | 0.36 | 370 | 183 | 553 | 33 |
| 85° C. heat treatment | 25 h, liq. mash | 0.31 | 0.05 | 156 | 27 | 183 | 15 |
| | 25 h, OA | 0.60 | 0.35 | 233 | 136 | 369 | 37 |
| | 73 h, liq. mash | 0.20 | 0.05 | 99 | 23 | 121 | 23 |
| | 73 h, OA | 0.84 | 0.41 | 326 | 159 | 486 | 33 |

Example 23

Heat Inactivation of Lipase in Lipase-Treated Liquefied Corn Mash for Simultaneous Saccharification and Fermentation with In-Situ Product Removal Using Oleyl Alcohol Three fermentations were run as described above in Examples 4, 5, and 6. No lipase was added to the liquefied corn mash in Examples 4 and 6 prior to fermentation, and the Lipase Treatment of the liquefied corn mash in the fermentation described in Example 5 (using 7.2 ppm of Lipolase® total soluble protein) was followed immediately by Heat Inactivation Treatment (to completely inactivate the lipase), and subsequently followed by Nutrient Addition Prior to Inoculation and fermentation. The % FFA in liquefied corn mash prepared without lipase treatment for fermentations run as described in Examples 4 and 6 was 31% and 34%, respectively, compared to 89% with lipase treatment (Example 5). Over the course of the fermentations listed in Table 10, the concentration of FFA in the OA phase did not decrease in any of the three fermentations, including that containing heat-inactivated lipase. The % FFA in the OA phase of the fermentation run according to Example 5 (with heat inactivation of lipase prior to fermentation) was 95% at 70 h (end of run (EOR)), compared to only 33% FFA for the remaining two fermentations (Examples 4 and 6) where liquefied corn mash was not treated with lipase. Results are shown in Table 7.

Example 24

Lipase Treatment of Ground Whole Corn Kernels Prior to Liquefaction

Tap water (1377.6 g) was added into each of two jacketed 2-L resin kettles, then 711.9 g wet weight (625.8 g dry weight) of ground whole corn kernels (1.0 mm screen on hammer mill) was added to each kettle with stirring. Each mixture was heated to 55° C. with stirring at 300 rpm, and the pH adjusted to 5.8 with 2 N sulfuric acid. To each mixture was added 21.0 g of an aqueous solution containing 1.008 g of Spezyme®-FRED L (Genencor®, Palo Alto, Calif.). To one mixture was then added 10.5 mL of aqueous solution of Lipolase® 100 L Solution (21 mg total soluble protein, 10 ppm lipase final concentration) and to the second mixture was added 1.05 mL of aqueous solution of Lipolase® 100 L Solution (2.1 mg total soluble protein, 1.0 ppm lipase final concentration). Samples were withdrawn from each reaction mixture at 1 h, 2 h, 4 h and 6 h at 55° C., then the temperature of the mixture was increased to 85° C. with stirring at 600 rpm and pH 5.8, and a sample was taken when the mixture first reached 85° C. After 120 minutes at 85° C., a sample was taken and the mixtures were cooled to 50° C. and final samples of the resulting liquefied corn mash were transferred to 50-mL polypropylene centrifuge tubes; all samples were stored frozen at −80° C.

TABLE 7

Lipid and free fatty acid content of fermentations containing oleyl alcohol as ISPR solvent and heat-inactivated lipase (after lipase treatment of liquefied mash)

| fermentation | lipase | time (h), sample | lipids (wt %) | FFA (wt %) | lipids (g) | FFA (g) | lipid + FFA (g) | % FFA |
|---|---|---|---|---|---|---|---|---|
| Example 4 | none | liquefied mash | 0.65 | 0.30 | 7.2 | 3.3 | 10.4 | 31 |
| Example 4 | none | 0.2 h, broth | 0.56 | 0.28 | 6.6 | 3.3 | 9.9 | 33 |
| Example 4 | none | 4.3 h, broth | 0.28 | 0.09 | 3.3 | 1.0 | 4.4 | 24 |
| Example 4 | none | 4.3 h, OA | 0.45 | 0.27 | 4.0 | 2.4 | 6.4 | 37 |
| Example 4 | none | 30 h, broth | 0.17 | 0.05 | 2.0 | 0.6 | 2.7 | 24 |
| Example 4 | none | 30 h, OA | 0.63 | 0.29 | 5.7 | 2.6 | 8.3 | 32 |
| Example 4 | none | 53 h, broth | 0.13 | 0.04 | 1.5 | 0.5 | 2.0 | 23 |
| Example 4 | none | 53 h, OA | 0.67 | 0.32 | 6.0 | 2.9 | 8.9 | 32 |
| Example 4 | none | 70 h, broth | 0.13 | 0.04 | 1.5 | 0.4 | 1.9 | 23 |
| Example 4 | none | 70 h, OA | 0.64 | 0.31 | 5.8 | 2.8 | 8.5 | 33 |
| Example 5 | 7.2 ppm | liquefied mash | 0.11 | 0.89 | 1.3 | 9.9 | 11.2 | 89 |
| Example 5 | 7.2 ppm | 0.2 h, broth | 0.25 | 0.83 | 2.9 | 9.8 | 12.8 | 77 |
| Example 5 | 7.2 ppm | 4.3 h, broth | 0.14 | 0.17 | 1.6 | 2.1 | 3.7 | 56 |
| Example 5 | 7.2 ppm | 4.3 h, OA | 0.02 | 0.84 | 0.2 | 7.9 | 8.1 | 97 |
| Example 5 | 7.2 ppm | 30 h, broth | 0.08 | 0.18 | 1.0 | 2.1 | 3.1 | 68 |
| Example 5 | 7.2 ppm | 30 h, OA | 0.04 | 0.92 | 0.3 | 8.6 | 8.9 | 96 |
| Example 5 | 7.2 ppm | 53 h, broth | 0.07 | 0.11 | 0.9 | 1.3 | 2.2 | 61 |
| Example 5 | 7.2 ppm | 53 h, OA | 0.08 | 0.95 | 0.7 | 8.9 | 9.6 | 93 |
| Example 5 | 7.2 ppm | 70 h, broth | 0.08 | 0.10 | 0.9 | 1.2 | 2.1 | 55 |
| Example 5 | 7.2 ppm | 70 h, OA | 0.05 | 0.94 | 0.4 | 8.8 | 9.2 | 95 |
| Example 6 | none | liquefied mash | 0.66 | 0.34 | 7.3 | 3.8 | 11.1 | 34 |
| Example 6 | none | 0.2 h, broth | 0.63 | 0.34 | 7.6 | 4.0 | 11.6 | 34 |
| Example 6 | none | 4.3 h, broth | 0.33 | 0.10 | 3.9 | 1.2 | 5.1 | 23 |
| Example 6 | none | 4.3 h, OA | 0.45 | 0.27 | 4.0 | 2.4 | 6.4 | 38 |
| Example 6 | none | 30 h, broth | 0.17 | 0.06 | 2.1 | 0.8 | 2.8 | 26 |
| Example 6 | none | 30 h, OA | 0.69 | 0.33 | 6.2 | 3.0 | 9.1 | 32 |
| Example 6 | none | 53 h, broth | 0.14 | 0.05 | 1.6 | 0.5 | 2.2 | 25 |
| Example 6 | none | 53 h, OA | 0.72 | 0.35 | 6.4 | 3.1 | 9.5 | 33 |
| Example 6 | none | 70 h, broth | 0.15 | 0.05 | 1.8 | 0.6 | 2.4 | 25 |
| Example 6 | none | 70 h, OA | 0.70 | 0.34 | 6.2 | 3.0 | 9.2 | 33 |

In two separate reactions, a 50 g sample of the 10 ppm lipase-treated liquefied corn mash or a 55 g sample of the 1.0 ppm lipase-treated liquefied corn mash prepared as described above was mixed with oleyl alcohol (OA) (38 g) at 30° C. for 20 h, then the liquefied mash and OA in each reaction mixture were separated by centrifugation and each phase analyzed for wt % lipid (derivatized as fatty acid methyl esters, FAME) and for wt % free fatty acid (FFA, derivatized as fatty acid methyl esters, FAME) according to the method described by Reference 1. The % FFA in the OA phase of the liquefied mash/OA mixture prepared using heat inactivation of 10 ppm lipase during liquefaction was 98% at 20 h, compared to only 62% FFA in the OA phase of the liquefied mash/OA mixture prepared using heat inactivation of 1.0 ppm lipase during liquefaction. Results are shown in Table 8.

TABLE 8

Lipid and free fatty acid content of a mixture of liquefied corn mash and oleyl alcohol, using lipase treatment of ground corn suspension prior to liquefaction (heat inactivation of lipase during liquefaction)

| reaction conditions | time (h), sample | lipids (wt %) | FFA (wt %) | lipids (mg) | FFA (mg) | lipid + FFA (mg) | % FFA |
|---|---|---|---|---|---|---|---|
| 10 ppm lipase at 55° C. prior to liquefaction at 85° C., mix with OA for 20 h | 1 h, pre-liquefaction | 0.226 | 0.627 | 112 | 311 | 424 | 74 |
| | 2 h, pre-liquefaction | 0.199 | 0.650 | 99 | 323 | 422 | 77 |
| | 4 h, pre-liquefaction | 0.151 | 0.673 | 75 | 334 | 410 | 82 |
| | 6 h, pre-liquefaction | 0.101 | 0.700 | 50 | 348 | 398 | 87 |
| | 0 h, 85° C., liq. mash | 0.129 | 0.764 | 64 | 380 | 444 | 86 |
| | 2 h, 85° C., liq. mash | 0.129 | 0.751 | 64 | 373 | 437 | 85 |
| | 20 h, 30° C., liq. mash | 0.074 | 0.068 | 37 | 34 | 71 | 48 |
| | 20 h, 30° C., OA | 0.015 | 1.035 | 5.7 | 394 | 400 | 98 |
| 1.0 ppm lipase at 55° C. prior to liquefaction at 85° C., mix with OA for 20 h | 1 h, pre-liquefaction | 0.408 | 0.480 | 226 | 266 | 492 | 54 |
| | 2 h, pre-liquefaction | 0.401 | 0.424 | 222 | 235 | 457 | 51 |
| | 4 h, pre-liquefaction | 0.299 | 0.433 | 165 | 240 | 405 | 58 |
| | 6 h, pre-liquefaction | 0.346 | 0.453 | 192 | 251 | 442 | 57 |
| | 0 h, 85° C., liq. mash | 0.421 | 0.407 | 233 | 225 | 458 | 49 |
| | 2 h, 85° C., liq. mash | 0.424 | 0.429 | 235 | 237 | 472 | 50 |
| | 20 h, 30° C., liq. mash | 0.219 | 0.054 | 121 | 30 | 151 | 20 |
| | 20 h, 30° C., OA | 0.344 | 0.573 | 140 | 233 | 373 | 62 |

TABLE 9

Percent free fatty acid content (% FFA) of a mixture of ground whole corn kernels using lipase treatment at 55° C. prior to liquefaction

| | % FFA | | | | |
|---|---|---|---|---|---|
| time | 0 h | 1 h | 2 h | 4 h | 6 h |
| Lipolase ® 100L | 33 | 56 | 74 | 76 | 79 |
| Lipex ® 100L | 34 | 66 | 81 | 83 | 83 |
| Lipoclean ® 2000T | 38 | 55 | 73 | 69 | 65 |
| Lipozyme ® CALB L | 39 | 38 | 37 | 43 | 41 |
| Novozyme ® CALA L | 37 | 40 | 44 | 44 | 45 |
| Palatase ® 20000 L | 37 | 49 | 59 | 62 | 66 |
| no enzyme | 38 | 33 | 37 | 41 | 42 |

Example 25

Lipase Screening for Treatment of Ground Whole Corn Kernels Prior to Liquefaction Seven reaction mixtures containing tap water (67.9 g) and ground whole corn kernels (35.1 g wet wt., ground with 1.0 mm screen using a hammer mill) at pH 5.8 were stirred at 55° C. in stoppered flasks. A 3-mL sample (t=0 h) was removed from each flask and the sample immediately frozen on dry ice, then ca. 0.5 mL of 10 mM sodium phosphate buffer (pH 7.0) containing 1 mg total soluble protein (10 ppm final concentration in reaction mixture) of one of the following lipases (Novozymes) were added to one of each flask: Lipolase® 100 L, Lipex® 100 L, Lipoclean® 2000T, Lipozyme® CALB L, Novozyme® CALA L, and Palatase 20000L; no lipase was added to the seventh flask. The resulting mixtures were stirred at 55° C. in stoppered flasks, and 3-mL samples were withdrawn from each reaction mixture at 1 h, 2 h, 4 h and 6 h and immediately frozen in dry ice until analyzed for wt % lipid (derivatized as fatty acid methyl esters, FAME) and for wt % free fatty acid (FFA, derivatized as fatty acid methyl esters, FAME) according to the method described by Reference 1, and the percent free fatty acid content was calculated relative to the total combined concentrations of lipid and free fatty acid was determined for each sample. Results are shown in Table 9.

Example 26

Lipase Treatment of Ground Whole Corn Kernels Prior to Simultaneous Saccharification and Fermentation with In-Situ Product Removal Using Oleyl Alcohol Three fermentations were run as described above in Examples 7, 8, and 10. For fermentations run as described in Examples 7 and 10, lipase (10 ppm of Lipolase® total soluble protein) was added to the suspension of ground corn and heated at 55° C. for 6 h prior to Liquefaction to produce a liquefied corn mash containing heat-inactivated lipase. No lipase was added to the suspension of ground corn used to prepare liquefied corn mash for the fermentation described in Example 8, but the suspension was subjected to the same heating step at 55° C. prior to liquefaction. The % FFA in lipase-treated liquefied corn mash prepared for fermentations run as described in Examples 7 and 10 was 83% and 86%, respectively, compare to 41% without lipase treatment (Example 8). Over the course of the fermentations, the concentration of FFA did not decrease in any of the fermentations, including that containing heat-inactivated lipase. The % FFA in the OA phase of the fermentation run according to Examples 7 and 10 (with heat inactivation of lipase prior to fermentation) was 97% at 70 h (end of run (EOR)), compared to only 49% FFA for the fermentation run according to Example 8 where ground whole corn kernels had not been treated with lipase prior to liquefaction. Results are shown in Table 10.

TABLE 10

Lipid and free fatty acid content of fermentations containing oleyl alcohol as ISPR solvent and heat-inactivated lipase (lipase treatment of ground corn suspension prior to liquefaction)

| fermentation | lipase | time (h), sample | lipids (wt %) | FFA (wt %) | lipids (g) | FFA (g) | lipid + FFA (g) | % FFA |
|---|---|---|---|---|---|---|---|---|
| Example 7 | 10 ppm | pre-lipase/pre-liq. | 0.65 | 0.22 | 7.1 | 2.4 | 9.4 | 25 |
| Example 7 | 10 ppm | post-lipase/pre-liq. | 0.22 | 0.65 | 2.4 | 7.0 | 9.5 | 74 |
| Example 7 | 10 ppm | liquefied mash | 0.17 | 0.79 | 1.8 | 8.5 | 10.3 | 83 |
| Example 7 | 10 ppm | 0.3 h, broth | 0.16 | 0.79 | 1.8 | 8.9 | 10.7 | 83 |
| Example 7 | 10 ppm | 4.8 h, broth | 0.14 | 0.31 | 1.6 | 3.5 | 5.1 | 69 |
| Example 7 | 10 ppm | 4.8 h, OA | 0.04 | 0.68 | 0.3 | 5.4 | 5.6 | 95 |
| Example 7 | 10 ppm | 29 h, broth | 0.10 | 0.12 | 1.2 | 1.3 | 2.5 | 53 |
| Example 7 | 10 ppm | 29 h, OA | 0.03 | 1.05 | 0.2 | 8.2 | 8.4 | 98 |
| Example 7 | 10 ppm | 53 h, broth | | | | | | |
| Example 7 | 10 ppm | 53 h, OA | 0.07 | 1.14 | 0.5 | 9.0 | 9.5 | 95 |
| Example 7 | 10 ppm | 70 h, broth | 0.11 | 0.07 | 1.2 | 0.8 | 2.0 | 39 |
| Example 7 | 10 ppm | 70 h, OA | 0.03 | 1.10 | 0.2 | 8.7 | 8.9 | 97 |
| Example 8 | none | pre-lipase/pre-liq. | 0.62 | 0.23 | 6.7 | 2.5 | 9.2 | 27 |
| Example 8 | none | post-lipase/pre-liq. | 0.57 | 0.26 | 6.2 | 2.8 | 9.0 | 31 |
| Example 8 | none | liquefied mash | 0.52 | 0.36 | 5.6 | 4.0 | 9.6 | 41 |
| Example 8 | none | 0.3 h, broth | 0.50 | 0.33 | 5.7 | 3.8 | 9.4 | 40 |
| Example 8 | none | 4.8 h, broth | 0.47 | 0.14 | 5.3 | 1.6 | 6.9 | 24 |
| Example 8 | none | 4.8 h, OA | 0.12 | 0.32 | 1.0 | 2.9 | 3.9 | 73 |
| Example 8 | none | 29 h, broth | 0.30 | 0.05 | 3.4 | 0.6 | 4.0 | 16 |
| Example 8 | none | 29 h, OA | 0.31 | 0.46 | 2.7 | 4.1 | 6.9 | 60 |
| Example 8 | none | 53 h, broth | | | | | | |
| Example 8 | none | 53 h, OA | 0.47 | 0.50 | 4.2 | 4.4 | 8.6 | 51 |
| Example 8 | none | 70 h, broth | 0.22 | 0.04 | 2.5 | 0.5 | 3.0 | 17 |
| Example 8 | none | 70 h, OA | 0.40 | 0.39 | 3.6 | 3.5 | 7.0 | 49 |
| Example 10 | 10 ppm | pre-lipase/pre-liq. | 0.67 | 0.23 | 7.4 | 2.5 | 9.9 | 25 |
| Example 10 | 10 ppm | post-lipase/pre-liq. | 0.19 | 0.69 | 2.1 | 7.6 | 9.7 | 78 |
| Example 10 | 10 ppm | liquefied mash | 0.14 | 0.85 | 1.6 | 9.4 | 11.0 | 86 |
| Example 10 | 10 ppm | 0.3 h, broth | 0.13 | 0.82 | 1.5 | 9.4 | 10.9 | 86 |
| Example 10 | 10 ppm | 4.8 h, broth | 0.11 | 0.29 | 1.3 | 3.3 | 4.6 | 72 |
| Example 10 | 10 ppm | 4.8 h, OA | 0.04 | 0.60 | 0.3 | 5.2 | 5.6 | 94 |
| Example 10 | 10 ppm | 29 h, broth | 0.09 | 0.14 | 1.0 | 1.6 | 2.6 | 61 |
| Example 10 | 10 ppm | 29 h, OA | 0.01 | 0.96 | 0.1 | 8.4 | 8.5 | 99 |
| Example 10 | 10 ppm | 53 h, broth | | | | | | |
| Example 10 | 10 ppm | 53 h, OA | 0.02 | 0.95 | 0.2 | 8.3 | 8.4 | 98 |
| Example 10 | 10 ppm | 70 h, broth | 0.09 | 0.08 | 1.1 | 0.9 | 1.9 | 45 |
| Example 10 | 10 ppm | 70 h, OA | 0.03 | 0.99 | 0.3 | 8.7 | 9.0 | 97 |

Example 27

Lipase Treatment of Ground Whole Corn Kernels or Liquefied Corn Mash for Simultaneous Saccharification and Fermentation with In-Situ Product Removal Using Corn Oil Fatty Acids (COFA)

Five fermentations were run as described above in Examples 9, 11, 12, 13, and 14. For the fermentations run as described in Examples 9, 13, and 14, lipase (10 ppm of Lipolase® total soluble protein) was added after Liquefaction and there was no heat-inactivation of lipase. Fermentations run as described in Examples 9 and 14 had 5 g/L of ethanol added prior to inoculation, whereas the fermentation run as described in Example 13 had no added ethanol. The fermentations run as described in Examples 11 and 12 employed the addition of 10 ppm Lipolase® total soluble protein to the suspension of ground corn prior to liquefaction, resulting in heat inactivation of lipase during liquefaction. The fermentation run as described in Example 11 had 5 g/L of ethanol added prior to inoculation, whereas the fermentation run as described in Example 12 had no added ethanol. The final total grams of isobutanol (i-BuOH) present in the COFA phase of the fermentations containing active lipase was significantly greater than the final total grams of i-BuOH present in the COFA phase of the fermentations containing inactive lipase. The final total grams of isobutanol (i-BuOH) present in the fermentation broths containing active lipase were only slightly less than the final total grams of i-BuOH present in the fermentation broths containing inactive lipase, such that the overall production of i-BuOH (as a combination of free i-BuOH and isobutyl esters of COFA (FABE)) was significantly greater in the presence of active lipase when compared to that obtained in the presence of heat-inactivated lipase. Results are shown in Tables 11 and 12.

TABLE 11

Dependence of the production of free isobutanol (i-BuOH) and isobutyl esters of COFA (FABE) in fermentations containing corn oil fatty acids (COFA) as ISPR solvent on presence (Examples 9, 13, and 14) or absence (Examples 11 and 12) of active lipase (COFA phase analysis)

| fermentation | fermentation time (h) | g i-BuOH/ kg COFA | g FABE/ kg COFA | g i-BuOH from FABE/ kg COFA | total g i-BuOH/ kg COFA |
|---|---|---|---|---|---|
| Example 9 | 4.5 | 2.4 | 0.0 | 0 | 2.4 |
| Example 9 | 28.8 | 5.4 | 70.9 | 16.5 | 22.0 |
| Example 9 | 52.4 | 8.9 | 199.0 | 46.4 | 55.3 |
| Example 9 | 69.3 | 4.9 | 230.9 | 53.9 | 69.3 |
| Example 11 | 6.6 | 2.3 | 0.0 | 0.0 | 2.3 |
| Example 11 | 53.5 | 25.1 | 2.9 | 0.6 | 25.7 |
| Example 11 | 71.1 | 24.4 | 6.3 | 1.4 | 25.8 |
| Example 12 | 6.6 | 2.3 | 0.0 | 0.0 | 2.3 |
| Example 12 | 53.5 | 12.8 | 1.6 | 0.4 | 13.2 |

TABLE 11-continued

Dependence of the production of free isobutanol (i-BuOH) and isobutyl esters of COFA (FABE) in fermentations containing corn oil fatty acids (COFA) as ISPR solvent on presence (Examples 9, 13, and 14) or absence (Examples 11 and 12) of active lipase (COFA phase analysis)

| fermen-tation | fermen-tation time (h) | g i-BuOH/ kg COFA | g FABE/ kg COFA | g i-BuOH from FABE/ kg COFA | total g i-BuOH/ kg COFA |
|---|---|---|---|---|---|
| Example 12 | 71.1 | 12.8 | 3.0 | 0.7 | 13.5 |
| Example 13 | 6.6 | 2.3 | 0.0 | 0.0 | 2.3 |
| Example 13 | 53.5 | 4.9 | 72.1 | 16.0 | 20.9 |
| Example 13 | 71.1 | 4.6 | 91.4 | 20.3 | 24.9 |
| Example 14 | 6.6 | 2.1 | 0.0 | 0.0 | 2.1 |
| Example 14 | 53.5 | 9.8 | 197.2 | 43.8 | 53.6 |
| Example 14 | 71.1 | 4.9 | 244.5 | 54.3 | 59.2 |

TABLE 12

Dependence of the production of free isobutanol (i-BuOH) and isobutyl esters of COFA (FABE) in fermentations containing corn oil fatty acids (COFA) as ISPR solvent on presence (Examples 9, 13, and 14) or absence (Examples 11 and 12) of active lipase (fermentation broth analysis)

| sample | fermen-tation time (h) | g i-BuOH/ kg broth | g FABE/ kg broth | g i-BuOH from FABE/ kg broth | total g i-BuOH/ kg broth |
|---|---|---|---|---|---|
| Example 9 | 4.5 | 0.0 | 0.0 | 0 | 0 |
| Example 9 | 28.8 | 0.0 | 12.6 | 2.9 | 2.9 |
| Example 9 | 52.4 | 0.0 | 30.3 | 7.1 | 7.1 |
| Example 9 | 69.3 | 0.0 | 24.7 | 5.8 | 5.8 |
| Example 11 | 6.6 | 0.0 | 0.0 | 0 | 0.0 |
| Example 11 | 53.5 | 9.8 | 0.0 | 0 | 9.8 |
| Example 11 | 71.1 | 9.5 | 0.0 | 0 | 9.5 |
| Example 12 | 6.6 | 0.0 | 0.0 | 0 | 0 |
| Example 12 | 53.5 | 3.8 | 0.0 | 0.0 | 3.8 |
| Example 12 | 71.1 | 5.1 | 0.0 | 0.0 | 5.1 |
| Example 13 | 6.6 | 0.0 | 0.0 | 0 | 0 |
| Example 13 | 53.5 | 2.1 | 3.0 | 0.7 | 2.8 |
| Example 13 | 71.1 | 2.1 | 7.4 | 1.6 | 3.7 |
| Example 14 | 6.6 | 0.0 | 0.0 | 0 | 0.0 |
| Example 14 | 53.5 | 2.9 | 22.4 | 5.0 | 7.9 |
| Example 14 | 71.1 | 3.3 | 19.3 | 4.3 | 7.6 |

TABLE 13

Reaction conditions for conversion of isobutanol (i-BuOH) to isobutyl esters of corn oil fatty acids (i-BuO-COFA)

| reaction | MES (0.2M) (g) | i-BuOH (g) | COFA (g) | lipase (ppm) |
|---|---|---|---|---|
| 1 | 45.96 | 3.6 | 43.4 | 10 |
| 2 | 45.96 | 3.6 | 21.7 | 10 |
| 3 | 45.96 | 3.6 | 10.85 | 10 |
| 4 | 45.96 | 3.6 | 43.4 | 4 |
| 5 | 45.96 | 3.6 | 43.4 | 0 |

TABLE 14

Weights of isobutanol (i-BuOH) and isobutyl esters of corn oil fatty acids (i-BuO-COFA) present in the aqueous fraction (AQ) and organic fraction (ORG) for reactions described in Table 13

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 0.1 | 0.77 | 2.83 | 2.77 | 0.05 | 0.24 |
| 1 | 1 | 0.76 | 2.84 | 2.58 | 0.25 | 1.13 |
| 1 | 2 | 0.74 | 2.86 | 2.41 | 0.44 | 2.00 |
| 1 | 4 | 0.66 | 2.94 | 2.05 | 0.89 | 4.03 |
| 1 | 6 | 0.63 | 2.97 | 1.43 | 1.54 | 6.93 |
| 1 | 21.5 | 0.28 | 3.32 | 0.34 | 2.98 | 13.4 |
| 1 | 25.5 | 0.23 | 3.37 | 0.29 | 3.08 | 13.8 |
| 2 | 0.1 | 1.17 | 2.43 | 2.36 | 0.07 | 0.30 |
| 2 | 1 | 1.09 | 2.51 | 2.26 | 0.24 | 1.10 |
| 2 | 2 | 1.07 | 2.53 | 2.19 | 0.34 | 1.52 |
| 2 | 4 | 1.03 | 2.57 | 1.99 | 0.59 | 2.64 |
| 2 | 6 | 1.00 | 2.60 | 1.70 | 0.90 | 4.04 |
| 2 | 21.5 | 0.75 | 2.85 | 0.58 | 2.27 | 10.2 |
| 2 | 25.5 | 0.59 | 3.01 | 0.49 | 2.52 | 11.4 |
| 3 | 0.1 | 1.56 | 2.04 | 1.98 | 0.06 | 0.27 |
| 3 | 1 | 1.55 | 2.05 | 1.77 | 0.28 | 1.24 |
| 3 | 2 | 1.49 | 2.11 | 1.65 | 0.46 | 2.08 |
| 3 | 4 | 1.45 | 2.15 | 1.28 | 0.87 | 3.92 |
| 3 | 6 | 1.33 | 2.27 | 0.96 | 1.31 | 5.92 |
| 3 | 21.5 | 1.12 | 2.48 | 0.26 | 2.22 | 10.0 |
| 3 | 25.5 | 0.88 | 2.72 | 0.26 | 2.46 | 11.1 |
| 4 | 0.1 | 0.84 | 2.76 | 2.75 | 0.02 | 0.07 |
| 4 | 1 | 0.78 | 2.82 | 2.73 | 0.09 | 0.40 |
| 4 | 2 | 0.83 | 2.77 | 2.59 | 0.17 | 0.79 |
| 4 | 4 | 0.78 | 2.82 | 2.44 | 0.38 | 1.71 |
| 4 | 6 | 0.78 | 2.82 | 2.10 | 0.72 | 3.25 |
| 4 | 21.5 | 0.58 | 3.02 | 1.12 | 1.90 | 8.57 |
| 4 | 25.5 | 0.51 | 3.09 | 0.97 | 2.11 | 9.51 |
| 5 | 0.1 | 0.90 | 2.70 | 2.70 | 0.00 | 0.00 |
| 5 | 1 | 0.90 | 2.70 | 2.70 | 0.00 | 0.00 |
| 5 | 2 | 0.92 | 2.68 | 2.68 | 0.00 | 0.00 |
| 5 | 4 | 0.89 | 2.71 | 2.70 | 0.00 | 0.02 |
| 5 | 6 | 0.92 | 2.68 | 2.62 | 0.06 | 0.29 |
| 5 | 21.5 | 0.90 | 2.70 | 2.62 | 0.08 | 0.37 |
| 5 | 25.5 | 0.89 | 2.71 | 2.62 | 0.09 | 0.41 |

Example 28

Dependence of Isobutyl-COFA Ester Concentration on Aqueous/COFA Ratio in Lipase-Catalyzed Reactions Reaction mixtures containing aqueous 2-(N-morpholino) ethanesulfonic acid buffer (0.20 M, pH 5.2), isobutanol (2-methyl-1-propanol), lipase (Lipolase® 100 L; Novozymes) and corn oil fatty acids prepared from corn oil (Table 13) were stirred at 30° C., and samples were withdrawn from each reaction mixture at predetermined times, immediately centrifuged, and the aqueous and organic layers separated and analyzed for isobutanol (i-BuOH) and isobutyl esters of corn oil fatty acids (i-BuO-COFA) (Table 14).

Example 29

Dependence of Isobutyl-COFA Ester Concentration on Aqueous/COFA Ratio in Lipase-Catalyzed Reactions Reaction mixtures containing aqueous 2-(N-morpholino) ethanesulfonic acid buffer (0.20 M, pH 5.2), isobutanol (2-methyl-1-propanol) or n-butanol, lipase (Lipolase® 100 L; Novozymes) and corn oil fatty acids prepared from corn oil (Table 15) were stirred at 30° C., and samples were withdrawn from each reaction mixture at predetermined times, immediately centrifuged, and the aqueous and organic layers separated and analyzed for isobutanol (i-BuOH) or n-butanol (n-BuOH) and isobutyl- or butyl esters of corn oil fatty acids (BuO-COFA) (Table 16).

TABLE 15

Reaction conditions for conversion of isobutanol (i-BuOH) or n-butanol (n-BuOH) to butyl esters of corn oil fatty acids (BuO-COFA)

| reaction | butanol | MES(0.2M) (g) | butanol (g) | COFA (g) | lipase (ppm) |
|---|---|---|---|---|---|
| 6 | iso-butanol | 45.96 | 3.6 | 13.5 | 10 |
| 7 | n-butanol | 45.96 | 3.6 | 13.5 | 10 |
| 8 | iso-butanol | 45.96 | 3.6 | 13.5 | 0 |
| 9 | isobutanol | 45.96 | 3.6 | 13.5 | 4 |

TABLE 16

Weights of isobutanol (i-BuOH) or n-butanol (n-BuOH) and butyl esters of corn oil fatty acids (BuO-COFA) present in the aqueous fraction (AQ) and organic fraction (ORG) for reactions described in Table 15

| reaction | time (h) | total i-BuOH (g) (AQ) | total i-BuOH (g) (ORG) | total i-BuOH (g) (ORG) | i-BuOH (g) (ORG) | i-BuOH from i-BuO-COFA (g) (ORG) |
|---|---|---|---|---|---|---|
| 6 | 0 | 1.46 | 2.14 | 2.11 | 0.04 | 0.16 |
| 6 | 2 | 1.41 | 2.19 | 1.63 | 0.56 | 2.51 |
| 6 | 4 | 1.27 | 2.33 | 1.31 | 1.02 | 4.58 |
| 6 | 21 | 0.66 | 2.94 | 0.29 | 2.65 | 12.0 |
| 6 | 25 | 0.60 | 3.00 | 0.26 | 2.73 | 12.3 |
| 6 | 46 | 0.54 | 3.06 | 0.22 | 2.83 | 12.8 |

| reaction | time (h) | total n-BuOH (g) (AQ) | total n-BuOH (g) (ORG) | n-BuOH (g) (ORG) | n-BuOH from n-BuO-COFA (g) (ORG) | n-BuO-COFA (g) (ORG) |
|---|---|---|---|---|---|---|
| 7 | 0 | 1.31 | 2.29 | 2.26 | 0.03 | 0.11 |
| 7 | 2 | 1.26 | 2.34 | 1.89 | 0.45 | 2.03 |
| 7 | 4 | 1.20 | 2.40 | 1.66 | 0.74 | 3.35 |
| 7 | 21 | 0.81 | 2.79 | 0.50 | 2.29 | 10.3 |
| 7 | 25 | 0.77 | 2.83 | 0.40 | 2.43 | 11.0 |
| 7 | 46 | 0.50 | 3.10 | 0.23 | 2.87 | 12.9 |

| reaction | time (h) | total i-BuOH (g) (AQ) | total i-BuOH (g) (ORG) | i-BuOH (g) (ORG) | i-BuOH from i-BuO-COFA (g) (ORG) | i-BuO-COFA (g) (ORG) |
|---|---|---|---|---|---|---|
| 8 | 0 | 1.62 | 1.98 | 1.98 | 0.00 | 0.01 |
| 8 | 2 | 1.56 | 2.04 | 2.04 | 0.00 | 0.00 |
| 8 | 4 | 1.59 | 2.01 | 2.01 | 0.00 | 0.00 |
| 8 | 21 | 1.59 | 2.01 | 2.00 | 0.01 | 0.04 |
| 8 | 25 | 1.55 | 2.05 | 2.04 | 0.01 | 0.04 |
| 8 | 46 | 1.45 | 2.15 | 2.12 | 0.02 | 0.11 |
| 9 | 0 | 1.57 | 2.03 | 2.02 | 0.01 | 0.04 |
| 9 | 2 | 1.54 | 2.06 | 1.86 | 0.19 | 0.86 |
| 9 | 4 | 1.44 | 2.16 | 1.79 | 0.36 | 1.64 |
| 9 | 21 | 1.14 | 2.46 | 0.95 | 1.51 | 6.82 |
| 9 | 25 | 1.10 | 2.50 | 0.83 | 1.67 | 7.50 |
| 9 | 46 | 0.78 | 2.82 | 0.44 | 2.37 | 10.7 |

Example 30

Production of Iso-Butyl Oleate by Lipase-Catalyzed Reaction of Iso-Butanol and Oleic Acid Reaction mixtures containing aqueous 2-(N-morpholino) ethanesulfonic acid buffer (0.20 M, pH 5.2), isobutanol (2-methyl-1-propanol), lipase (0 ppm or 10 ppm Lipolase® 100 L; Novozymes) and oleic acid (Alfa Aesar) (Table 17) were stirred at 30° C., and samples were withdrawn from each reaction mixture at predetermined times, immediately centrifuged, and the aqueous and organic layers separated and analyzed for isobutanol (i-BuOH) and iso-butyl oleate (i-BuO-oleate) (Table 18).

TABLE 17

Reaction conditions for conversion of isobutanol
(i-BuOH) to iso-butyl oleate (i-BuO-oleate)

| reaction | MES (0.2M) (g) | i-BuOH (g) | oleic acid (g) | lipase (ppm) |
|---|---|---|---|---|
| 10 | 46.11 | 3.64 | 14.62 | 10 |
| 11 | 46.10 | 3.59 | 14.40 | 0 |

TABLE 18

Weights of isobutanol (i-BuOH) and iso-butyl oleate (i-BuO-COFA) present in the
aqueous fraction (AQ) and organic fraction (ORG) for reactions described in Table 17.

| reaction | time (h) | total i-BuOH (g) (AQ) | total i-BuOH (g) (ORG) | i-BuOH (g) (ORG) | i-BuOH from i-BuO-oleate (g) (ORG) | i-BuO-oleate (g) (ORG) |
|---|---|---|---|---|---|---|
| 10 | 0 | 1.37 | 2.28 | 2.24 | 0.04 | 0.18 |
| 10 | 2 | 1.30 | 2.34 | 1.95 | 0.40 | 1.81 |
| 10 | 4 | 1.28 | 2.37 | 1.82 | 0.55 | 2.53 |
| 10 | 6 | 1.22 | 2.42 | 1.71 | 0.72 | 3.27 |
| 10 | 23 | 0.92 | 2.72 | 0.71 | 2.01 | 9.20 |
| 10 | 27 | 0.89 | 2.75 | 0.65 | 2.11 | 9.62 |
| 10 | 47 | 0.81 | 2.84 | 0.55 | 2.29 | 10.5 |
| 10 | 51 | 0.82 | 2.83 | 0.54 | 2.29 | 10.5 |
| 11 | 0 | 1.44 | 2.16 | 2.16 | 0.00 | 0.00 |
| 11 | 2 | 1.45 | 2.15 | 2.15 | 0.00 | 0.00 |
| 11 | 4 | 1.44 | 2.16 | 2.16 | 0.00 | 0.00 |
| 11 | 6 | 1.43 | 2.16 | 2.16 | 0.00 | 0.00 |
| 11 | 23 | 1.49 | 2.10 | 2.10 | 0.01 | 0.02 |
| 11 | 27 | 1.46 | 2.14 | 2.13 | 0.01 | 0.04 |
| 11 | 47 | 1.48 | 2.12 | 2.09 | 0.02 | 0.10 |
| 11 | 51 | 1.52 | 2.07 | 2.05 | 0.02 | 0.11 |

Example 31

Production of Iso-Butyl Oleate by Lipase-Catalyzed Reaction of Iso-Butanol and Oleic Acid

Reaction mixtures containing aqueous 2-(N-morpholino) ethanesulfonic acid buffer (MES, 0.20 M, pH 5.2), isobutanol (2-methyl-1-propanol), oleic acid (Alfa Aesar), and lipase (10 ppm) from Lipolase® 100 L, Lipex® 100 L, Lipozyme® CALB L, Novozyme® CALA L, Palatase® from Novozymes, or lipase (10 ppm) from *Pseudomonas fluorescens*, *Pseudomonas cepacia*, *Mucor miehei*, hog pancreas, *Candida cylindracea*, *Rhizopus niveus*, *Candida antarctica*, *Rhizopus arrhizus* or *Aspergillus* from SigmaAldrich (Table 19), were stirred at 30° C., and samples were withdrawn from each reaction mixture at predetermined times, immediately centrifuged, and the aqueous and organic layers separated and analyzed for isobutanol (i-BuOH) and iso-butyl oleate (i-BuO-oleate) (Table 20).

TABLE 19

Reaction conditions for conversion of isobutanol
(i-BuOH) to iso-butyl oleate (i-BuO-oleate)

| MES (0.2M) (g) | i-BuOH (g) | oleic acid (g) | lipase (ppm) |
|---|---|---|---|
| 46.105 | 3.601 | 13.72 | 10 |

TABLE 20

Weights of isobutanol (i-BuOH) and iso-butyl oleate (i-BuO-oleate) present in the aqueous
fraction (AQ) and organic fraction (ORG) for reactions described in Table 19

| lipase | time (h) | total i-BuOH (g) (AQ) | total i-BuOH (g) (ORG) | i-BuOH (g) (ORG) | i-BuOH from i-BuO-oleate (g) (ORG) | i-BuO-oleate (g) (ORG) |
|---|---|---|---|---|---|---|
| Lipolase ® 100L | 23 | 1.55 | 2.05 | 1.47 | 0.59 | 2.68 |
| Lipex ® 100L | 23 | 0.65 | 2.95 | 0.30 | 2.65 | 12.09 |
| Lipozyme ® CALB L | 23 | 1.01 | 2.59 | 0.82 | 1.77 | 8.08 |
| Novozyme ® CALA L | 23 | 1.39 | 2.22 | 2.16 | 0.06 | 0.27 |
| Palatase ® | 23 | 1.27 | 2.33 | 1.43 | 0.91 | 4.14 |
| *Pseudomonas fluorescens* | 23 | 1.38 | 2.22 | 1.97 | 0.25 | 1.14 |
| *Pseudomonas cepacia* | 23 | 1.39 | 2.21 | 1.95 | 0.26 | 1.20 |
| *Mucor miehei* | 23 | 1.29 | 2.31 | 1.57 | 0.75 | 3.42 |
| hog pancreas | 23 | 1.40 | 2.20 | 2.19 | 0.01 | 0.04 |
| *Candida cylindracea* | 23 | 1.15 | 2.45 | 1.08 | 1.37 | 6.25 |
| *Rhizopus niveus* | 23 | 1.39 | 2.21 | 2.19 | 0.02 | 0.11 |
| *Candida antarctica* | 23 | 1.37 | 2.24 | 2.08 | 0.15 | 0.69 |
| *Rhizopus arrhizus* | 23 | 1.01 | 2.59 | 0.81 | 1.78 | 8.12 |
| *Aspergillus* | 23 | 1.36 | 2.24 | 2.06 | 0.18 | 0.82 |

Example 32

Production of Iso-Butyl COFA Esters by Phospholipase-Catalyzed Reaction of Iso-Butanol and Corn Oil Fatty Acids (COFA)

Reaction mixtures containing aqueous 2-(N-morpholino) ethanesulfonic acid buffer (0.20 M, pH 5.3), isobutanol (2-methyl-1-propanol), phospholipase (Phospholipase A; SigmaAldrich, L3295-250) and corn oil fatty acids prepared from corn oil were stirred at 30° C. (Table 21), and samples were withdrawn from each reaction mixture at predetermined times, immediately centrifuged, and the aqueous and organic layers separated and analyzed for isobutanol (i-BuOH) and isobutyl esters of corn oil fatty acids (i-BuO-COFA) (Table 22).

TABLE 21

Reaction conditions for conversion of isobutanol (i-BuOH) to isobutyl esters of corn oil fatty acids (i-BuO-COFA)

| reaction # | MES buffer (0.2M) (g) | i-BuOH (g) | COFA (g) | lipase (ppm) |
|---|---|---|---|---|
| 1 | 46.1 | 3.6 | 14.7 | 10 |
| 2 | 46.1 | 3.6 | 14.7 | 3 |
| 3 | 46.1 | 3.6 | 14.7 | 0 |

TABLE 22

Weights of isobutanol (i-BuOH) and isobutyl esters of corn oil fatty acids (i-BuO-COFA) present in the aqueous fraction (AQ) and organic fraction (ORG) for reactions described in Table 21

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 0.1 | 1.29 | 2.39 | 2.39 | 0.00 | 0.00 |
| 1 | 2 | 1.24 | 2.44 | 2.38 | 0.06 | 0.26 |
| 1 | 20 | 1.25 | 2.43 | 2.22 | 0.21 | 0.96 |
| 1 | 24 | 1.26 | 2.42 | 2.19 | 0.23 | 1.03 |
| 1 | 44 | 1.27 | 2.41 | 2.13 | 0.28 | 1.28 |
| 1 | 48 | 1.22 | 2.46 | 2.15 | 0.31 | 1.41 |
| 2 | 0.1 | 1.27 | 2.34 | 2.34 | 0.00 | 0.00 |
| 2 | 2 | 1.25 | 2.35 | 2.33 | 0.02 | 0.08 |
| 2 | 20 | 1.24 | 2.37 | 2.30 | 0.07 | 0.30 |
| 2 | 24 | 1.22 | 2.38 | 2.31 | 0.07 | 0.32 |
| 2 | 44 | 1.33 | 2.28 | 2.18 | 0.10 | 0.44 |
| 2 | 48 | 1.23 | 2.38 | 2.27 | 0.11 | 0.48 |
| 3 | 0.1 | 1.27 | 2.33 | 2.33 | 0.00 | 0.00 |
| 3 | 2 | 1.26 | 2.34 | 2.34 | 0.00 | 0.00 |
| 3 | 20 | 1.22 | 2.38 | 2.37 | 0.01 | 0.07 |
| 3 | 24 | 1.25 | 2.35 | 2.33 | 0.02 | 0.08 |
| 3 | 44 | 1.24 | 2.36 | 2.32 | 0.04 | 0.18 |
| 3 | 48 | 1.24 | 2.36 | 2.32 | 0.04 | 0.18 |

Example 33

Comparison of Partition Coefficients for Isobutanol Between Water and Extractant Aqueous solutions of isobutanol (30 g/L) were mixed with corn oil fatty acids (COFA), oleic acid, or corn oil triglycerides, and their measured partition coefficients reported in the table relative to the measured partition coefficient for oleyl alcohol. Results are shown in Table 23.

TABLE 23

Relative partition coefficients for isobutanol (30 g/L) between water and extractant

| extractant | isobutanol partition coefficient, relative to oleyl alcohol |
|---|---|
| oleyl alcohol | 100% |
| corn oil fatty acids | 91% |
| corn oil fatty acid isobutyl esters | 43% |
| corn oil triglycerides | 10% |

Example 34

Hydroxylated Triglycerides from Corn Oil

To a three-neck 500 mL flask equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for two hours, upon which time the reaction mixture was worked up: resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 48.9 g of yellow oil. The $^1H$ NMR analysis of the crude reaction product showed that 63% of double bonds were epoxidized.

A. Corn Oil Hydroxylation (63% Hydroxylation)

To a three-neck 500 mL flask equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for two hours, upon which time the reaction mixture was worked up: resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 48.9 g of yellow oil. The $^1H$ NMR analysis of the crude reaction product showed that 63% of double bonds were epoxidized.

To a 500 mL round bottom flask was added epoxidized corn oil (20.0 g), tetrahydrofuran (THF) (100.0 mL), and sulfuric acid (50 mL of 1.7 M aqueous solution). The cloudy mixture was stirred for two hours at 50° C., and then worked up by partitioning between water (100 mL) and ethyl acetate (200 mL). The organic layer was washed with water (3×50 mL) and then brine (50 mL). The organic layer was dried over anh. $Na_2SO_4$ and concentrated in vacuo to obtain 19.9 g of dark yellow oil (63% hydroxylation corn oil).

B. Corn Oil Hydroxylation (47% Hydroxylation)

To a three-neck 500 mL flask, equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for one hour, upon which time the reaction mixture was worked up: the resin was removed by filtration, and the filtrate partitioned between ethyl acetate (75 mL) and water (50 mL).

After the layers were separated, the organic layer was washed with sat. aq. $NaHCO_3$ solution (50 mL), and brine (50 mL). The organic layer was dried over anh. $Na_2SO_4$ and concentrated in vacuo to obtain 49.8 g of yellow oil. The $^1H$ NMR analysis of the crude reaction product showed that 47% of double bonds were epoxidized.

To a 500 mL round bottom flask was added epoxidized corn oil (20.0 g), THF (100.0 mL), and sulfuric acid (50 mL of 1.7M aqueous solution). The cloudy mixture was stirred for two hours at 50° C., and then worked up by partitioning between water (100 mL) and ethyl acetate (200 mL). The organic layer was washed with water (3×50 mL) and then brine (50 mL). The organic layer was dried over anh. $Na_2SO_4$ and concentrated in vacuo to obtain 19.2 g of dark yellow oil (47% hydroxylation corn oil).

C. Corn Oil Hydroxylation (28% Hydroxylation)

To a three-neck 500 mL flask, equipped with a mechanical stirrer and addition funnel was added corn oil (50.0 g), toluene (25.0 mL), Amberlyte IR-120 resin (12.5 g), and glacial acetic acid (7.5 g). The resulting mixture was heated to 60° C., and then hydrogen peroxide (41.8 g of 30% $H_2O_2$ in water) was added dropwise over one hour. The mixture was stirred at 60° C. for two hours, upon which time the reaction mixture was worked up: the resin was removed by filtration, and the filtrate partitioned between ethyl acetate (75 mL) and water (50 mL). After the layers were separated, the organic layer was washed with sat. aq. $NaHCO_3$ solution (50 mL), and brine (50 mL). The organic layer was dried over anh. $Na_2SO_4$ and concentrated in vacuo to obtain 47.2 g of yellow oil. The $^1H$ NMR analysis of the crude reaction product showed that 28% of double bonds were epoxidized.

To a 500 mL round bottom flask was added epoxidized corn oil (20.0 g), THF (100.0 mL), and sulfuric acid (50 mL of 1.7M aqueous solution). The cloudy mixture was stirred for two hours at 50° C., and then worked up by partitioning between water (100 mL) and ethyl acetate (200 mL). The organic layer was washed with water (3×50 mL) and then brine (50 mL). The organic layer was dried over anh. $Na_2SO_4$ and concentrated in vacuo to obtain 20.3 g of dark yellow oil (28% hydroxylation corn oil).

Partition Coefficient Measurement

To a 5 mL vial was added 0.910 g of the 67% hydroxylated corn oil, and 0.910 mL of 3 wt % i-BuOH water solution. The biphasic mixture was vigorously stirred using Vortex Genie® for 10 minutes. Upon mixing, the separation of layers was aided by centrifuging the mixture using Fisher Scientific Centrific 228 centrifuge (3300 rpm) for 10 minutes. 0.100 g of both layers were taken. The organic, upper layer was diluted to 1.00 mL with toluene solution of ethylene glycol diethylether (10.1 mg/mL), and the water layer was diluted to 1.00 mL with methanol solution of ethylene glycol diethylether (10.2 mg/mL). The concentrations of i-BuOH in both phases were measured using a calibrated gas chromatograph (GC). The same procedure was repeated for 47% and 28% hydroxylated corn oil. The partition coefficient thus measured was 3.2 for the 67% hydroxylated corn oil, 2.3 for the 47% hydroxylated corn oil, and 2.1 for the 28% hydroxylated corn oil.

The above outlined procedure was repeated with 6% i-BuOH water solution. The partition coefficients for 67%-, 47%-, and 28%-hydroxylated corn oils were 2.9, 2.9, and 2.0, respectively.

Example 34

Fatty Amides Plus Fatty Acids, and Pure Fatty Amides from Corn Oil

Corn oil was reacted with aqueous ammonium hydroxide in a manner similar to that described by Roe, et al., J. Am. Oil Chem. Soc. 29:18-22, 1952. Mazola® corn oil (0.818 L, 755 g) was placed in a 1 gallon stainless steel reactor to which was added 1.71 L (1540 g) of aqueous ammonium hydroxide (28% as $NH_3$). The reactor was heated with stirring to 160° C. and was maintained at that temperature with stirring for 7 h during which time the pressure reached 400 psi. The reactor was cooled and the product, a creamy white solid, was removed and the reactor rinsed with ethyl acetate. The product was dissolved in 5 L ethyl acetate and washed 5 times with 500 mL each of water which was neutralized with $H_2SO_4$. The ethyl acetate was then dried over anhydrous $Na_2SO_4$ and the solvent removed on a rotary evaporator leaving a light brown soft solid.

$^{13}C$ NMR in $CDC_3$ indicated that the product contained an approximate 2:1 ratio of fatty amide to fatty acid and that the conversion of the corn oil to product was quantitative. The product had a melting point of 57-58° C., but dropped about 11° C. when saturated with water.

Pure corn oil fatty amide was synthesized from corn oil according to Kohlhase, et al., J. Am. Oil Chem. Soc. 48:265-270, 1971 using anhydrous ammonia with ammonium acetate as a catalyst.

Three grams of ammonium acetate were placed in a 400 mL stainless steel shaker tube to which was added 51.8 g of corn oil. Anhydrous ammonia (89.7 g) was then added and the reactor sealed and heated for 7 h at 125° C. during which time the pressure reached 1300 psi. The reactor was cooled, the light colored solid removed and the reactor rinsed with ethyl acetate. The product dissolved in ethyl acetate was then worked up as in the case of the fatty amide/fatty acid mixture above.

Fatty acids were synthesized from corn oil by base hydrolysis using NaOH. Round bottom flask (5 L) was equipped with a mechanical stirrer, thermocouple, heating mantle, condenser, and nitrogen tee. Charged with 500 g of food grade corn oil, 1 L of water and 75 g of sodium hydroxide. Mixture was heated to 90° C. and held for three hours, during which time it became a single thick, emulsion-like single phase. At the end of this time, TLC shows no remaining corn oil in the mixture. The mixture was then cooled to 72° C. and 500 mL of 25% sulfuric acid was added to acidify the mixture. It was then cooled to room temperature and 2 L of diethyl ether was added. The ether layer was washed 3×1 L with 1% sulfuric acid, 1×1 L with saturated brine, dried over $MgSO_4$, and filtered. The ether was removed by rotovap and then the oil was purged with nitrogen overnight, obtaining 470 g of a yellow oil that partially crystallized overnight. Titration for free fatty acids via AOCS method Ca 5a-40 shows a fatty acid content of 95% expressed as oleic acid. A sample was silanized by reacting 104 mg with 100 µL of N-methyl-N-(trimethylsilyl)trifluoroacetamide in 1 mL of dry pyridine. Gas chromatography-mass spectrometry (GCMS) analysis of the silanized product shows the presence of the TMS derivatives of the 16:0, 18:2, 18:1, 18:0, and 20:0 acids Three preparations: (1) the 2:1 mixture of corn oil fatty amide and corn oil fatty acid from aqueous ammonia, (2) a 2:1 mixture of pure corn oil fatty amide:pure corn oil fatty acid, and (3) a 1:2 mixture of pure corn oil fatty amide:corn oil fatty acid, were all tested for their ability to extract isobutanol from a 3% solution in water. Seven hundred milligrams of each was added to 2.1 mL of water containing 3% isobutanol in a 20 mL scintillation vial and placed on a rotary shaker overnight at 30° C. In all three cases, the organic phase became liquid at this temperature, indicating a further lowering of the melting point with the uptake of isobutanol. Fifty microliters of the upper phase were diluted with either 200 µL of toluene containing ethylene glycol diethylether (10.068 mg/mL) as a GC standard or 200 µL of isopropanol containing the same concentration of ethylene glycol diethylether. Fifty microliters of the lower phase was diluted with 150 µL of methanol and 50 µL of isopropanol containing the same concentration of ethylene glycol diethylether. The concentrations of isobutanol in both phases were determined using a calibrated GC. The partition coefficients measured were as follows: 3.81 for (1), 4.31 for (2), and 3.58 for (3).

Fatty amide/fatty acid aqueous ammonia preparation (1), and a preparation (1a) constituted by preparation (1) mixed 1:1 with pure corn oil fatty acid (equivalent to 1:2 fatty amide: fatty acid) were incubated in shake flasks with fermentation broth containing the *Saccharomyces* butanologen NGCI-070 at a ratio of 3 parts broth to 1 part amide/acid mixture. Preparation (1) was a soft solid, while preparation (1a) was a liquid at 30° C. Starting at a glucose concentration of 8.35 g/L, the shake flasks were then incubated for 25 h on an incubator shaker and the consumption of glucose followed as a function of time. Table 24 indicates that the fatty amide/fatty acid mixtures at both ratios were not toxic to the butanologen and even showed higher rates of glucose uptake than with oleyl alcohol.

TABLE 24

| Flask | Glucose conc. (g/L) | | |
|---|---|---|---|
| | Time = 0 | 18 hrs | 25 hrs |
| Oleyl Alcohol | 8.35 | 4.26 | 0 |
| Oleyl Alcohol | 8.35 | 4.46 | 0 |
| 2:1 Synthesized Fatty Amide:Fatty Acid Mix (Preparation (1)) | 8.35 | 3.06 | 0 |
| 2:1 Synthesized Fatty Amide:Fatty Acid Mix (Preparation (1)) | 8.35 | 3.22 | 0 |
| 1:1 Synthesized Fatty Amide Fatty Acid Mix:Pure Fatty Acids (Preparation (1a)) | 8.35 | 2.73 | 0 |
| 1:1 Synthesized Fatty Amide Fatty Acid Mix:Pure Fatty Acids (Preparation (1a)) | 8.35 | 2.73 | 0 |

Example 35

Fatty Alcohols from Corn Oil

With reference to the reaction of Equation IV above for producing fatty alcohols from corn oil, a 22 L, round-bottom flask equipped with a mechanical stirrer, reflux condenser with $N_2$ source, addition funnel, internal thermocouple, and rubber septum was flame-dried under nitrogen. The flask was charged with 132 g (3.30 moles) of 95% lithium aluminum hydride powder that is weighed out in a dry box and loaded into a solids addition funnel. The 22 L flask was cooled with an ice bath, and 9.0 liters of anhydrous THF were added into the reactor via a cannula. The resulting slurry was cooled to 0-5° C. and a solution of 956 g (1.10 moles) of Wesson® corn oil in 1.00 liter of anhydrous THF was added dropwise over 2-3 hours while holding the reaction temperature at 5-20° C. After adding the corn oil, the slurry was stirred overnight at ambient temperature. When the reaction was done, as verified by TLC chromatography, it was quenched by the dropwise addition of a solution of 130 g of water dissolved in 370 mL of THF. Then 130 g of 15% aqueous NaOH solution was added followed by the addition of 400 g of water. The mixture was vigorously stirred while warming to room temperature and produced a white granular solid. The solids were filtered off using a fritted-glass filter funnel and washed with additional THF. The THF was removed on a rotary evaporator and the residue was taken up in 3.00 liters of ethyl acetate. The product solution was washed with 2×1.00 L of water, 1×1.00 L of brine, dried over $Na_2SO_4$, filtered, and concentrated in vacuo to give 836 g (97%) of fatty alcohols as yellow oil. The crude fatty alcohol mixture was then distilled (140° C./1 mmHg), and used in the following partition coefficients experiments.

Partition Coefficient Experiments

To each of the five 5-mL vials were added 1 mL of fatty alcohol mixture, and 1 mL of 3 wt % i-BuOH water solution. The biphasic mixture was vigorously stirred using Vortex Genie® for 10, 20, 30, 40, and 60 minutes, respectively. Upon mixing, the separation of layers was aided by centrifuging the mixture using Fisher Scientific Centrific 228 centrifuge (3300 rpm) for 10 minutes. 0.100 mL of both layers were taken. The organic, upper layer was diluted to 1.00 mL with toluene solution of ethylene glycol diethylether, and the water layer was diluted to 1.00 mL with methanol solution of ethylene glycol diethylether. The concentrations of i-BuOH in both phases were measured using a calibrated GC. The partition coefficient thus measured was 2.70.

The same partition coefficient measurement, as described above was run for 6 wt % i-BuOH concentration. The partition coefficient thus measured was 3.06.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for producing a product alcohol comprising
(a) providing biomass comprising fermentable sugar oil, and undissolved solids;
(b) liquefying the biomass to produce a feedstock slurry;
(c) separating the feedstock slurry to produce (i) aqueous stream comprising fermentable sugar, (ii) oil stream, and (iii) wet cake comprising undissolved solids;
(d) contacting the aqueous stream with a microorganism capable of converting the fermentable sugar to the product alcohol whereby the product alcohol is produced;
(e) hydrolyzing the oil stream to form an extractant, wherein the partition coefficient of the extractant for the product alcohol is greater than the partition coefficient of the oil for the product alcohol;
(f) recovering the product alcohol from the aqueous stream by contacting the product alcohol with the extractant.

2. The method of claim 1, wherein the feedstock is separated by siphoning, aspiration, decantation, centrifugation, membrane-assisted phase splitting, filtration, or combination thereof.

3. The method of claim 2, wherein centrifugation is three-phase centrifugation or centrifugation by gravity settler.

4. The method of claim 1, wherein the wet cake is washed to recover sugar.

5. The method of claim 4, wherein the wet cake is washed by centrifugation.

6. The method of claim 4, wherein the recovered sugar is recycled to a liquefaction vessel.

7. The method of claim 4, wherein the washed wet cake is dried to form Dried Distillers' Grains with Solubles.

8. The method of claim 1, wherein the oil is hydrolyzed by one or more esterases.

9. The method of claim 8, wherein the one or more enzymes is inactivated after hydrolysis of the oil stream.

10. The method of claim 8, wherein the one or more esterases is selected from lipases, phospholipases, and lyso-phosholipases.

11. The method of claim 1, wherein the aqueous stream is recycled to a fermentation vessel.

12. The method of claim 1, wherein the extractant is recycled.

13. The method of claim 12, wherein the extractant is recycled to a fermentation vessel.

14. The method of claim 1, wherein the biomass is selected from corn, wheat, rye, barley, sugar cane bagasse, sugar cane, and mixtures thereof.

15. The method of claim 1, wherein the microorganism comprises an isobutanol biosynthetic pathway.

16. The method of claim 15, wherein the microorganism is selected from *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Candida, Hansenula,* and *Saccharomyces.*

17. The method of claim 16, wherein the microorganism is *Saccharomyces cerevisiae.*

18. The method of claim 1, wherein the microorganism is recovered from the aqueous stream.

19. The method of claim 1, wherein the recovered microorganism is recycled to a fermentation vessel.

20. The method of claim 1, wherein the product alcohol is selected from ethanol, 1-butanol, 2-butanol, and isobutanol.

* * * * *